US011434208B2

(12) United States Patent
Zhang et al.

(10) Patent No.: US 11,434,208 B2
(45) Date of Patent: Sep. 6, 2022

(54) ORGANIC COMPOUND, ELECTRONIC COMPONENT AND ELECTRONIC APPARATUS

(71) Applicant: Shaanxi Lighte Optoelectronics Material Co., Ltd., Xi'an (CN)

(72) Inventors: Kongyan Zhang, Xi'an (CN); Tiantian Ma, Xi'an (CN); Jiamei Cao, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/622,372

(22) PCT Filed: Oct. 19, 2020

(86) PCT No.: PCT/CN2020/121974
§ 371 (c)(1),
(2) Date: Dec. 23, 2021

(87) PCT Pub. No.: WO2021/135516
PCT Pub. Date: Jul. 8, 2021

(65) Prior Publication Data
US 2022/0220084 A1 Jul. 14, 2022

(30) Foreign Application Priority Data

Dec. 30, 2019 (CN) .......................... 201911404312.8
Jul. 3, 2020 (CN) .......................... 202010635712.6

(51) Int. Cl.
*C07D 213/24* (2006.01)
*C07D 239/26* (2006.01)
(Continued)

(52) U.S. Cl.
CPC ......... *C07D 251/24* (2013.01); *C07D 239/26* (2013.01); *C07D 401/04* (2013.01);
(Continued)

(58) Field of Classification Search
CPC .. C07D 213/24; C07D 239/26; C07D 251/24; C07D 401/04; C07D 401/08;
(Continued)

(56) References Cited

FOREIGN PATENT DOCUMENTS

| CN | 105308026 A | | 2/2016 | |
| CN | 110028459 A | * | 7/2019 | ........... C07C 255/58 |

(Continued)

OTHER PUBLICATIONS

International Search Report from corresponding International Application No. PCT/CN2020/121974, dated Dec. 21, 2020, 6 pages.
(Continued)

*Primary Examiner* — Vu A Nguyen
(74) *Attorney, Agent, or Firm* — Tucker Ellis LLP

(57) ABSTRACT

Provided in the present disclosure is an organic compound, which relates to the technical field of organic materials. In the compound of the present disclosure, an electron-deficient nitrogen-containing heteroaryl and cyano are linked to adamantly, so that the LUMO energy level is deepened, thereby electron mobility is further improved. Further provided in the present disclosure are an electronic component and electronic apparatus comprising the described organic compound. The organic compound can improve the electron transport performance of electronic components. When used as an electron transport layer of an organic light-emitting electroluminescent device, the compound can improve the luminous efficiency and service life of the device and reduce the working voltage.

13 Claims, 2 Drawing Sheets

(51) Int. Cl.
| | |
|---|---|
| *C07D 251/24* | (2006.01) |
| *C07D 401/04* | (2006.01) |
| *C07D 401/08* | (2006.01) |
| *C07D 401/14* | (2006.01) |
| *C07D 405/04* | (2006.01) |
| *C07D 405/08* | (2006.01) |
| *C07D 405/14* | (2006.01) |
| *C07D 409/04* | (2006.01) |
| *C07D 409/08* | (2006.01) |
| *C07D 409/14* | (2006.01) |
| *H01L 51/00* | (2006.01) |
| *H01L 51/50* | (2006.01) |

(52) U.S. Cl.
CPC ......... *C07D 401/14* (2013.01); *C07D 405/04* (2013.01); *C07D 409/04* (2013.01); *C07D 409/14* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/5004* (2013.01); *H01L 51/5072* (2013.01); *H01L 2251/552* (2013.01)

(58) Field of Classification Search
CPC .. C07D 401/14; C07D 405/04; C07D 405/08; C07D 405/14; C07D 409/04; C07D 409/08; C07D 409/14
See application file for complete search history.

(56) References Cited

FOREIGN PATENT DOCUMENTS

| | | | | | |
|---|---|---|---|---|---|
| CN | 110156756 | A | * | 8/2019 | ......... H01L 51/0052 |
| CN | 110156756 | A | | 8/2019 | |
| CN | 110183333 | A | | 8/2019 | |
| CN | 110240546 | A | | 9/2019 | |
| CN | 110289361 | A | | 9/2019 | |
| CN | 110467536 | A | | 11/2019 | |
| CN | 110615759 | A | * | 12/2019 | ........... C07D 213/16 |
| CN | 110615759 | A | | 12/2019 | |
| CN | 111039882 | A | * | 4/2020 | ........... C07D 251/24 |
| CN | 111039882 | A | | 4/2020 | |
| CN | 111646951 | A | | 9/2020 | |
| CN | 111662241 | A | | 9/2020 | |

OTHER PUBLICATIONS

Yu Gu, "Synthesis and Properties of Adamantane-Based Host Materials with Wide Energy Gaps for Phosphorescent OLEDs," Ph. D. Theses, Wuhan University, Apr. 2015, 184 pages inclusive of English summery of relevancy.
First Office Action of China National Intellectual Property Administration for counterpart Chinese Application No. 202010635712.6, dated Jan. 11, 2021, 22 pages.
Second Office Action for counterpart Chinese Application No. 202010635712.6, dated Apr. 27, 2021, 10 pages.

* cited by examiner

ORGANIC COMPOUND, ELECTRONIC COMPONENT AND ELECTRONIC APPARATUS

CROSS REFERENCE TO RELATED APPLICATIONS

The present application claims the priority to Chinese Patent Application CN201911404312.8 filed on Dec. 30, 2019, which is incorporated herein by reference in its entirety. The present application claims the priority to Chinese Patent Application CN202010635712.6 filed on Jul. 3, 2020, which is incorporated herein by reference in its entirety.

TECHNICAL FIELD

The present application relates to the technical field of organic materials, in particular to an organic compound, an electronic component and an electronic apparatus.

BACKGROUND

As a new generation of display technology, organic electroluminescent materials (OLED) have the advantages of ultra-thinness, self-illumination, wide viewing angle, fast response, high luminous efficiency, good temperature adaptability, simple production process, low driving voltage, low energy consumption, etc., and therefore, have been widely used in industries such as flat panel displays, flexible displays, solid-state lighting and vehicle displays.

An organic electroluminescent device usually includes an anode, a cathode, and an organic material layer therebetween. The organic material layer is usually formed with a multi-layer structure composed of different materials to improve the brightness, efficiency and life of the organic electroluminescent device. The organic material layer is composed of a hole injection layer, a hole transport layer, a luminescent layer, an electron transport layer, an electron injection layer and the like. In the structure of the organic electroluminescent device, when a voltage is applied between the two electrodes, holes and electrons are injected into the organic material layer from the anode and the cathode respectively, excitons are formed when the injected holes and electrons meet, and light is emitted when these excitons return to a ground state.

In the existing organic electroluminescent devices, the most important issues are life and efficiency. As the area of displays becomes larger, the driving voltage also increases, and the luminous efficiency and power efficiency also need to be improved. Therefore, it is necessary to continue to develop new types of materials to further improve the performance of organic electroluminescent devices.

The above information in the background is only used to enhance the understanding of the background of the present application, so it may include information that does not constitute the prior art known to those of ordinary skill in the art.

SUMMARY

The objective of the present disclosure is to provide an organic compound, an electronic component and an electronic apparatus to improve the performance of an organic electroluminescent device.

In order to achieve the above objective of the disclosure, the present disclosure adopts the following technical solutions:

According to a first aspect of the present disclosure, an organic compound is provided, and the structural formula of the organic compound is as shown in chemical formula 1:

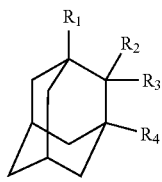

chemical formula 1

Wherein, any one of $R_1$, $R_2$, $R_3$, and $R_4$ is

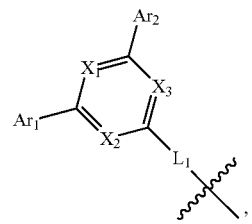

any other of $R_1$, $R_2$, $R_3$, and $R_4$ is

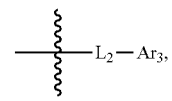

the other two of $R_1$, $R_2$, $R_3$, and $R_4$ are the same or different, each of them is independently selected from hydrogen, deuterium, fluorine, chlorine, alkyl with 1 to 12 carbon atoms, haloalkyl with 1 to 12 carbon atoms, alkoxy with 1 to 12 carbon atoms, cycloalkyl with 3 to 10 carbon atoms, aryl with 6 to 20 carbon atoms, and heteroaryl with 3 to 20 carbon atoms, and ⁓ represents a chemical bond;

$X_1$, $X_2$, and $X_3$ are the same or different, $X_1$ is $C(R^{X1})$ or N, $X_2$ is $C(R^{X2})$ or N, $X_3$ is $C(R^{X3})$ or N, and at least one of $X_1$, $X_2$, and $X_3$ is N;

$R^{X1}$, $R^{X2}$, and $R^{X3}$ are the same or different, and are each independently selected from hydrogen, deuterium, halogen, cyano, alkyl with 1 to 12 carbon atoms, haloalkyl with 1 to 12 carbon atoms, alkoxy with 1 to 12 carbon atoms, cycloalkyl with 3 to 10 carbon atoms, aryl with 6 to 20 carbon atoms, and heteroaryl with 3 to 20 carbon atoms;

$L_1$ and $L_2$ are the same or different, and are each independently selected from single bond, substituted or unsubstituted arylene with 6 to 30 carbon atoms, substituted or unsubstituted heteroarylene with 3 to 30 carbon atoms, and substituted or unsubstituted cycloalkylene with 3 to 10 carbon atoms;

$Ar_1$, $Ar_2$ and $Ar_3$ are the same or different, and are each independently selected from substituted or unsubstituted alkyl with 1 to 20 carbon atoms, substituted or unsubstituted aryl with 6 to 30 carbon atoms, substituted or unsubstituted heteroaryl with 3 to 30 carbon atoms, substituted or unsubstituted cycloalkyl with 3 to 20 carbon atoms, substituted or unsubstituted aralkyl with 7 to 30 carbon atoms, and substituted or unsubstituted heteroaralkyl with 2 to 30 carbon atoms;

substituents in $L_1$, $L_2$, $Ar_1$, $Ar_2$ and $Ar_2$ are the same or different from each other, and are each independently selected from the group consisting of deuterium, halogen, cyano, alkyl with 1 to 10 carbon atoms, haloalkyl with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms, and at least one substituent is cyano.

The compound of the present disclosure takes adamantyl as the core structure, is a compound formed by connecting electron-deficient nitrogen-containing heteroaryl and cyano to adamantyl. The compound composed of the adamantyl and the cyano has a strong dipole moment, so that the polarity of the compound is improved. In particular, the highly polar and electrically attracting cyano can deepen the LUMO energy level, thereby further improving the electron mobility. Therefore, after the cyano is combined with the electron-deficient nitrogen-containing heteroaryl, the electron-withdrawing ability of this part of the group is significantly improved, an organic material with high electron mobility can be obtained, and the electron transport efficiency can be improved. When used as an electron transport layer of an organic electroluminescent device, the material can improve the luminous efficiency and life of the device and reduce the working voltage. In addition, the large size and rigidity of the adamantyl also improve the film-forming ability and thermal stability of the material, making it easier for use for mass production.

According to a second aspect of the present disclosure, an electronic component is provided, including an anode and a cathode disposed oppositely, and a functional layer disposed between the anode and the cathode; the functional layer includes the above-mentioned organic compound.

According to a third aspect of the present disclosure, an electronic apparatus is provided, including the above-mentioned electronic component.

BRIEF DESCRIPTION OF THE DRAWINGS

By describing exemplary embodiments in detail with reference to the accompanying drawings, the above and other features and advantages of the present disclosure will become more apparent.

Figure 1:
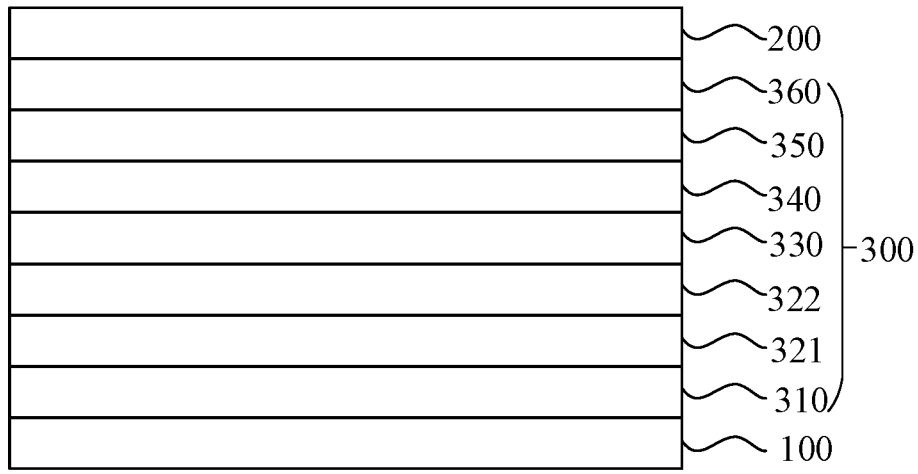
FIG. 1 is a schematic structural diagram of an organic electroluminescent device according to an embodiment of the present disclosure.

Reference numerals of the main components in the figures are explained as follows:

100—anode; 200—cathode; 310—hole injection layer; 321—hole transport layer; 322—electron blocking layer; 330—organic luminescent layer; 340—hole blocking layer; 350—electron transport layer; 360—electron injection layer; 370—photoelectric conversion layer; 400—electronic apparatus; 500—second type of electronic apparatus.

DETAILED DESCRIPTION OF EMBODIMENTS

Exemplary embodiments will now be described more fully with reference to the accompanying drawings. However, the exemplary embodiments can be implemented in multiple forms, and should not be construed as being limited to the examples set forth here. Instead, the provision of these embodiments makes the present disclosure more comprehensive and complete, and fully conveys the concept of the exemplary embodiments to those skilled in the art. The described features, structures or characteristics can be combined in one or more embodiments in any suitable way. In the following description, many specific details are provided to give a sufficient understanding of the embodiments of the present disclosure.

In the figures, the thicknesses of regions and layers may be exaggerated for clarity. The same reference numerals in the figures represent the same or similar structures, and thus their detailed descriptions will be omitted.

The structural formula of an organic compound according to an embodiment of the present disclosure is as shown in chemical formula 1:

chemical formula 1

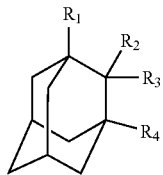

Wherein, any one of $R_1$, $R_2$, $R_3$, and $R_4$ is

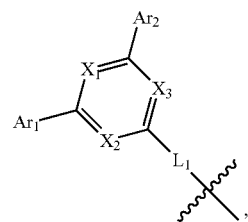

any other of $R_1$, $R_2$, $R_3$, and $R_4$ is

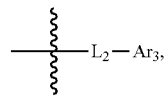

the other two of $R_1$, $R_2$, $R_3$, and $R_4$ are the same or different, each of them is independently selected from hydrogen, deuterium, fluorine, chlorine, alkyl with 1 to 12 carbon atoms, haloalkyl with 1 to 12 carbon atoms, alkoxy with 1 to 12 carbon atoms, cycloalkyl with 3 to 10 carbon atoms, aryl with 6 to 20 carbon atoms, and heteroaryl with 3 to 20 carbon atoms, and ⵎ represents a chemical bond;

$X_1$, $X_2$, and $X_3$ are the same or different, $X_1$ is $C(R^{X1})$ or N, $X_2$ is $C(R^{X2})$ or N, $X_3$ is $C(R^{X3})$ or N, and at least one of $X_1$, $X_2$, and $X_3$ is N;

$R^{X1}$, $R^{X2}$, and $R^{X3}$ are the same or different, and are each independently selected from hydrogen, deuterium, halogen, cyano, alkyl with 1 to 12 carbon atoms, haloalkyl with 1 to 12 carbon atoms, alkoxy with 1 to 12 carbon atoms, cycloalkyl with 3 to 10 carbon atoms, aryl with 6 to 20 carbon atoms, and heteroaryl with 3 to 20 carbon atoms;

$L_1$ and $L_2$ are the same or different, and are each independently selected from single bond, substituted or unsubstituted arylene with 6 to 30 carbon atoms, substituted or unsubstituted heteroarylene with 3 to 30 carbon atoms, and substituted or unsubstituted cycloalkylene with 3 to 10 carbon atoms;

$Ar_1$, $Ar_2$ and $Ar_3$ are the same or different, and are each independently selected from substituted or unsubstituted alkyl with 1 to 20 carbon atoms, substituted or unsubstituted aryl with 6 to 30 carbon atoms, substituted or unsubstituted heteroaryl with 3 to 30 carbon atoms, substituted or unsubstituted cycloalkyl with 3 to 20 carbon atoms, substituted or unsubstituted aralkyl with 7 to 30 carbon atoms, and substituted or unsubstituted heteroaralkyl with 2 to 30 carbon atoms;

substituents in $L_1$, $L_2$, $Ar_1$, $Ar_2$ and $Ar_3$ are the same or different from each other, and are each independently selected from the group consisting of deuterium, halogen, cyano, alkyl with 1 to 10 carbon atoms, haloalkyl with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms, and at least one substituent is cyano.

The compound in the present disclosure takes adamantyl as the core structure, and is a compound formed by connecting electron-deficient nitrogen-containing heteroaryl and cyano to adamantyl. The compound composed of the adamantyl and the cyano has a strong dipole moment, so that the polarity of the compound is improved. In particular, the highly polar and electrically attracting cyano can deepen the LUMO energy level, thereby the electron mobility can be further improved. Therefore, the cyano is combined with the electron-deficient nitrogen-containing heteroaryl, thereby the electron-withdrawing ability of this part of the group is significantly improved, an organic material with high electron mobility can be obtained, and the electron transport efficiency can be improved. When used as an electron transport layer of an organic electroluminescent device, the material can improve the luminous efficiency and life of the device and reduce the working voltage. In addition, the large size and rigidity of the adamantyl also improve the film-forming ability and thermal stability of the material, which makes it easier for implementation in mass production.

In this specification, the term "substituted" in "substituted or unsubstituted" indicates that the substituent of the group is selected from the group consisting of deuterium, cyano, halogen, nitro, alkoxy with 1 to 12 carbon atoms, haloalkyl with 1 to 12 carbon atoms, alkyl with 1 to 12 carbon atoms, cycloalkyl with 3 to 12 carbon atoms, heterocyclic with 3 to 12 carbon atoms, aryl with 6 to 20 carbon atoms, heteroaryl with 3 to 20 carbon atoms, alkoxy with 1 to 12 carbon atoms, alkylsilyl with 3 to 12 carbon atoms, and arylsilyl with 6 to 18 carbon atoms.

In the present disclosure, the number of carbon atoms of $L_1$, $L_2$, $Ar_1$, $Ar_2$, $Ar_3$, $R^{X1}$, $R^{X2}$, and $R^{X3}$ refers to a total number of carbon atoms on the group. For example, if $L_1$ is selected from substituted arylene with 10 carbon atoms, the number of all carbon atoms of the arylene and substituents thereon is 10. If $Ar_1$ is a 4-tert-butyl-1-phenyl, the $Ar_1$ is substituted aryl with 10 carbon atoms.

In this specification, "substituted or unsubstituted aryl with 6 to 30 carbon atoms" and "aryl with 6 to 30 carbon atoms that is substituted or unsubstituted" have the same meaning, and both indicate that the total number of carbon atoms of the aryl and substituents thereon is 6 to 30.

The descriptions "each of . . . is independently", ". . . are each independently", and " . . . are independently selected from" used in this specification are interchangeable, and should be understood in a broad sense. They indicate that the specific options expressed by the same symbols do not affect each other in different groups or in the same group. For example: in the description

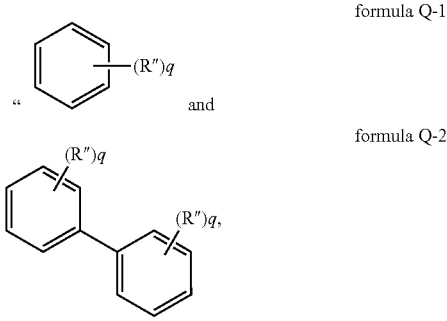

formula Q-1 and formula Q-2 wherein each q is independently 0, 1, 2 or 3, and each R" is independently selected from hydrogen, fluorine, and chlorine", formula Q-1 indicates q substituents R" on the benzene ring, each R" may be the same or different, and the option of each R" does not affect each other; formula Q-2 indicates q substituents R" on each benzene ring of the biphenyl, the numbers q of R" substituents on the two benzene rings may be the same or different, each R" may be the same or different, and the option of each R" does not affect each other.

In the present disclosure, when no specific definition is provided otherwise, the "hetero" indicates that a functional group includes at least one heteroatom selected from B, N, O, S, Se, Si and P and the remaining atoms are carbon and hydrogen. The unsubstituted alkyl is a "saturated alkyl" without any double or triple bonds.

In the present disclosure, the "alkyl" may include linear or branched alkyl. The alkyl may have 1 to 20 carbon atoms. In the present disclosure, a numerical range such as "1 to 20" refers to each integer in the given range; for example, "1 to 20 carbon atoms" indicates that the alkyl may include 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The alkyl may also be medium-sized alkyl having 1 to 10 carbon atoms. The alkyl may also be low alkyl with 1 to 6 carbon atoms. In still other embodiments, the alkyl includes 1 to 4 carbon atoms; in still other embodiments, the alkyl includes 1 to 3 carbon atoms. The alkyl is optionally substituted by one or more substituents described in the present disclosure. Examples of the alkyl include, but are not limited to, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH (CH$_3$)$_2$), sec-butyl (s-Bu, —CH(CH$_3$)CH$_2$CH$_3$), tert-butyl (t-Bu, —C(CH$_3$)$_3$), etc. In addition, the alkyl is substituted or unsubstituted.

In this specification, the "haloalkyl" or "haloalkoxy" indicates that alkyl or alkoxy is substituted by one or more halogen atoms, wherein the alkyl and the alkoxy have the meanings as described in the present disclosure, and such examples include, but are not limited to, trifluoromethyl, trifluoromethoxy, etc. In one embodiment, the C$_1$-C$_6$ haloalkyl includes fluorine-substituted C$_1$-C$_6$ alkyl; in another embodiment, the C$_1$-C$_4$ haloalkyl includes fluorine-substituted C1-C4 alkyl; in still another embodiment, the C$_1$-C$_2$ haloalkyl includes fluorine-substituted C$_1$-C$_2$ alkyl.

In the present disclosure, the cycloalkyl refers to a cyclic saturated hydrocarbon, including structures of monocyclic and polycyclic. The cycloalkyl may have 3 to 20 carbon atoms, and a numerical range such as "3 to 20" refers to each integer in the given range; for example, "3 to 20 carbon atoms" indicates that the cycloalkyl may include 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The cycloalkyl is a small ring, an ordinary ring, or a large ring with 3 to 20 carbon atoms. The cycloalkyl may also be classified as monocyclic-only one ring, bicyclic-two rings or polycyclic-three or more rings. The cycloalkyl may also be classified as two rings sharing one carbon atom-spiro ring, two rings sharing two carbon atoms-fused ring, and two rings sharing more than two carbon atoms-bridged ring. In addition, the cycloalkyl is substituted or unsubstituted. In some embodiments, the cycloalkyl is a 5- to 10-membered cycloalkyl. In other embodiments, the cycloalkyl is a 5- to 8-membered cycloalkyl. For example, examples of the cycloalkyl may be, but are not limited to: five-membered cycloalkyl (i.e. cyclopentyl), 6-membered cycloalkyl (i.e. cyclohexyl), 10-membered polycyclic alkyl such as an adamantyl, etc.

In this specification, "silyl" and "alkylsilyl" have the same meaning, and both refer to

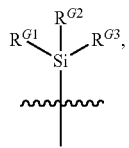

wherein R$^{G1}$, R$^{G2}$, and R$^{G3}$ are each independently alkyl. Specific examples of the alkylsilyl include, but are not limited to, trimethylsilyl, triethylsilyl, tert-butyldimethylsilyl, and propyldimethylsilyl.

In the present disclosure, the aryl refers to an optional functional group or substituent derived from an aromatic hydrocarbon ring. The aryl is monocyclic aryl or polycyclic aryl, that is, the aryl is monocyclic aryl, condensed ring aryl, two or more monocyclic aryl conjugated by carbon-carbon bonds, monocyclic aryl and fused ring aryl conjugated by carbon-carbon bonds, and two or more fused ring aryl conjugated by carbon-carbon bonds. That is, two or more aromatic groups conjugated by carbon-carbon bonds may also be regarded as aryl in the present disclosure. Wherein, the aryl does not include any heteroatom such as B, N, O, S, Se, Si or P. For example, in the present disclosure, the biphenyl, the terphenyl, etc. are aryl. Examples of the aryl may include phenyl, naphthyl, fluorenyl, anthryl, phenanthryl, biphenyl, terphenyl, quaterphenyl, quinquephenyl, sexiphenyl, benzo[9,10]phenanthryl, pyrenyl, perylene, benzofluoranthenyl, chrysenyl, spirobifluorenyl, and indenyl, but are not limited thereto.

In the present disclosure, the substituted aryl indicates that one or more hydrogen atoms in the aryl are substituted by other groups. For example, at least one hydrogen atom is substituted by deuterium atom, fluorine, chlorine, iodine, carbon, hydroxyl, amino, branched alkyl, linear alkyl, cycloalkyl, alkoxy, alkylamino, alkylthio, heterocyclic, haloalkyl, aryl, heteroaryl, alkylsilyl, arylsilyl, or others. It can be understood that the number of carbon atoms of the substituted aryl refers to total number of carbon atoms of the aryl and substituents on the aryl. For example, the substituted aryl with 18 carbon atoms indicates that the total number of carbon atoms of the aryl and the substituents on the aryl is 18. For example, the 9,9-dimethylfluorenyl is substituted aryl with 15 carbon atoms.

In the present disclosure, the fluorenyl as aryl can be substituted, and two substituent can be combined with each other to form a spiro structure. Specific examples include but are not limited to the following structures:

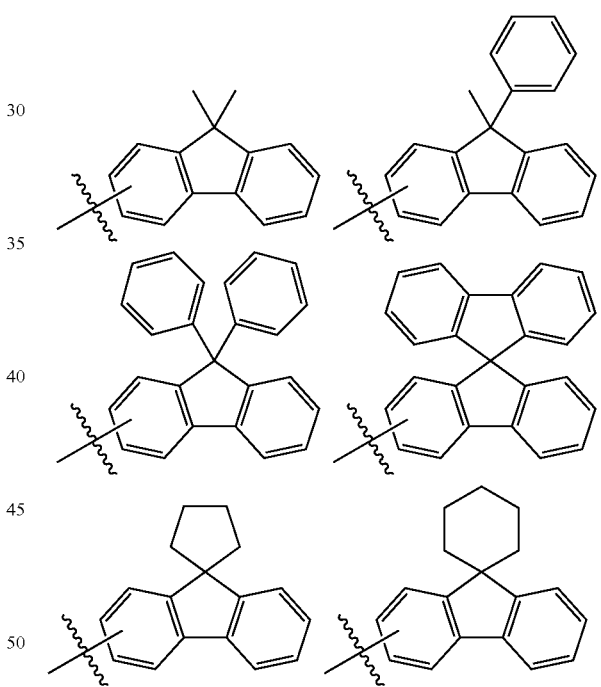

In the present disclosure, the number of carbon atoms of the aryl as a substituent is 6 to 20, such as 6, 10, 12, 14, or 18. Specific examples of the aryl as the substituent include, but are not limited to, phenyl, naphthyl, biphenyl, anthryl, phenanthryl, fluorenyl, dimethylfluorenyl, etc.

In the present disclosure, the heteroaryl is heteroaryl including at least one of B, O, N, P, Si, Se and S as heteroatom. The heteroaryl is monocyclic heteroaryl or polycyclic heteroaryl, that is, the heteroaryl is a single aromatic ring system or multiple aromatic ring systems conjugated by carbon-carbon bonds, any aromatic ring system is aromatic monocyclic ring or aromatic condensed ring, and any aromatic ring system includes the heteroatom. Exemplarily, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, dibenzosilyl, dibenzofuranyl, etc., but are not limited thereto. Among them, the thienyl, the furanyl, the phenanthrolinyl, etc. are heteroaryl of single aromatic ring system, and the N-arylcarbazolyl, the N-heteroarylcarbazolyl, the phenyl-substituted dibenzofuranyl, etc. are heteroaryl of multiple aromatic ring systems conjugated by carbon-carbon bonds.

In the present disclosure, the substituted heteroaryl indicates that one or more hydrogen atoms in the heteroaryl are substituted by other groups. For example, at least one hydrogen atom is substituted by deuterium atom, fluorine, chlorine, iodine, carbon, hydroxyl, amino, branched alkyl, linear alkyl, cycloalkyl, alkoxy, alkylamino, alkylthio, heterocyclic, haloalkyl, aryl, heteroaryl, alkylsilyl, arylsilyl, or others. It can be understood that the number of carbon atoms of the substituted heteroaryl refers to total number of carbon atoms of the heteroaryl and substituents thereon.

In the present disclosure, the explanation of the aryl can be applied to arylene, the explanation of the heteroaryl can be applied to heteroarylene, the explanation of the alkyl can be applied to alkylene, and the explanation of the cycloalkyl can be applied to cycloalkylene.

In the present disclosure, the number of carbon atoms of the heteroaryl as substituent is 3 to 20, such as 3, 4, 5, 7, 8, 9, 12, or 18. Specific examples of the heteroaryl as substituent include, but are not limited to, pyridyl, pyrimidinyl, quinolinyl, isoquinolinyl, dibenzofuranyl, dibenzothienyl, carbazolyl, N-phenyl carbazolyl, etc.

In the present disclosure, the ring system formed by n atoms is an n-membered ring. For example, the phenyl is 6-membered aryl. The 6- to 10-membered aromatic rings include benzene ring, an indene ring, naphthalene ring, etc.

The "ring" in the present disclosure includes saturated rings and unsaturated rings; the saturated rings include cycloalkyl and heterocycloalkyl, and the unsaturated rings include cycloalkenyl, heterocycloalkenyl, aryl and heteroaryl.

The term "optional" or "optionally" means that the event or environment described later may but need not occur, including occasions where the event or environment occurs or does not occur. For example, "optionally, $R^{v2}$ and $R^{v3}$ linked to the same atom are linked to each other to form a saturated or unsaturated ring", indicating that the $R^{v2}$ and $R^{v3}$ linked to the same atom can form a ring but do not have to form a ring. This solution includes the case wherein $R^{v2}$ and $R^{v3}$ are linked to form a ring, and also includes the case wherein $R^{v2}$ and $R^{v3}$ exist independently.

The non-localized bond in the present disclosure refers to single bond " ┼ " extending from a ring system, which indicates that one end of the bond can be linked to any position in the ring system through which the bond penetrates, and the other end is linked to the rest part of the compound molecule.

For example, as shown in the following formula (f), the naphthyl represented by formula (f) is linked to other positions of a molecule through two non-localized bonds that penetrate the dual rings, including any possible link shown in formulae (f-1) to (f-10).

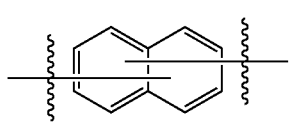

(f)

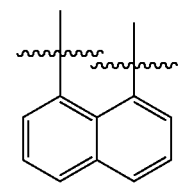

(f-1)

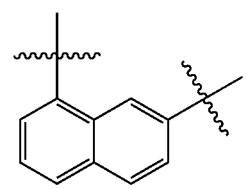

(f-2)

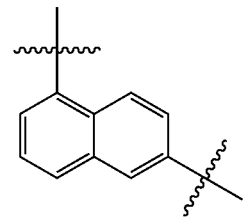

(f-3)

(f-4)

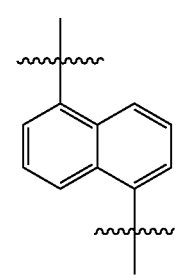

(f-5)

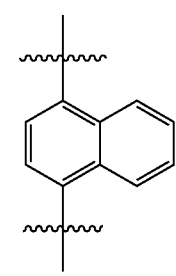

(f-6)

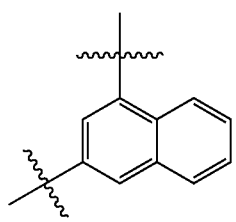

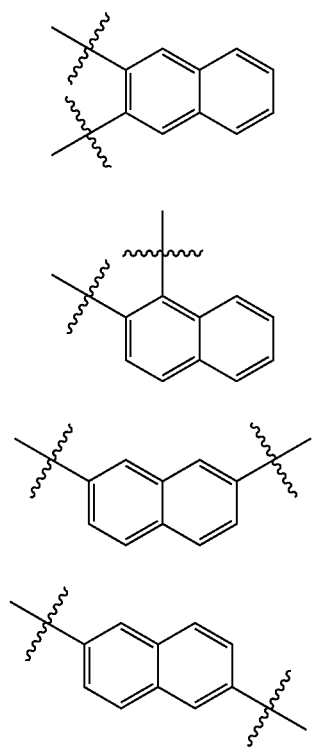

For another example, as shown in the following formula (X'), the phenanthryl represented by the formula (X') is linked to other positions of a molecule through a non-localized bond extending from the middle of a benzene ring on one side, including any possible link shown in formulae (X'-1) to (X'-4).

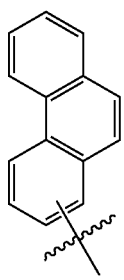

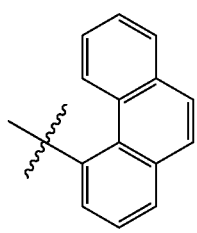

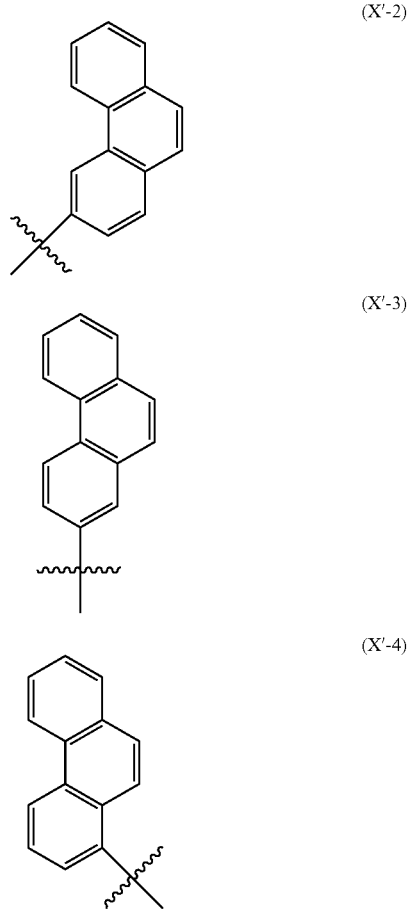

The non-localized substituent in the present disclosure refers to a substituent linked by single bond extending from the center of a ring system, which indicates that the substituent can be linked to any possible position in the ring system. For example, as shown in the following formula (Y), the substituent R represented by the formula (Y) is linked to a quinolyl ring by a non-localized bond, including any possible link shown in formulae (Y-1) to (Y-7).

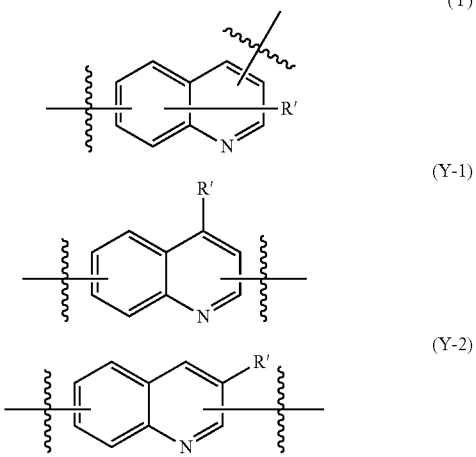

(Y-3)

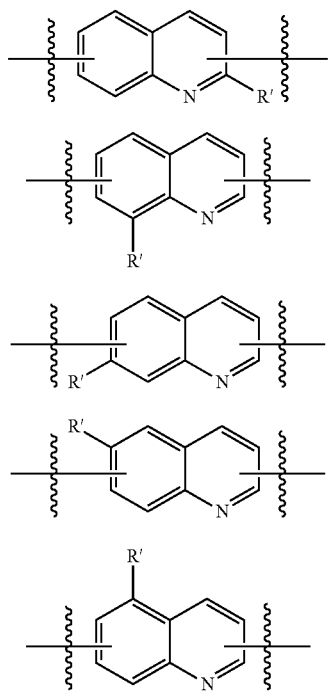

(Y-4)

(Y-5)

(Y-6)

(Y-7)

The meaning of non-localized link or non-localized substitution below is the same as here, and will not be repeated below.

Optionally, the above-mentioned compound has the following structure:

(chemical formula 2)

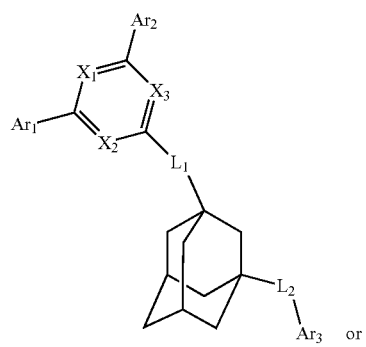 or (chemical formula 3)

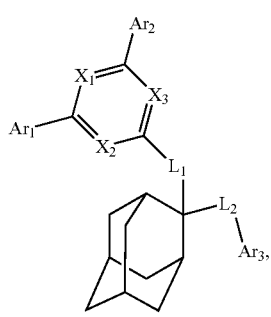

Wherein, $Ar_3$ has at least one cyano substituent.

Chemical formula 2 shows that in chemical formula 1, $R_1$ is

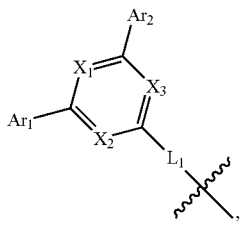

$R_4$ is

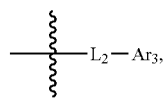

and $R_2$ and $R_3$ are hydrogen. Chemical formula 3 shows that in chemical formula 1, $R_2$ is

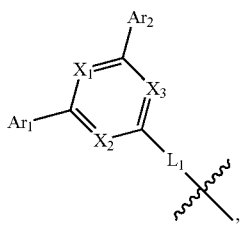

$R_3$ is

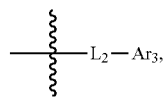

and $R_1$ and $R_4$ are hydrogen.

Optionally, in some embodiments, the compound of the present disclosure has a structure shown as follows (chemical formula 2) or (chemical formula 3):

(chemical formula 2)

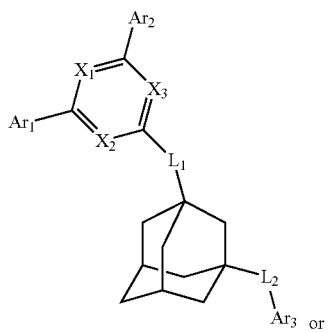 or

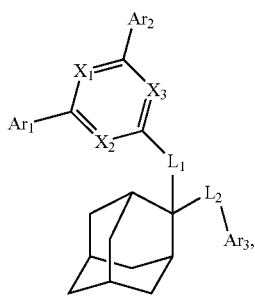
(chemical formula 3)

wherein $L_2$ and $Ar_3$ optionally include 1, 2, or 3 cyano substituents, and the substituents of $Ar_1$, $Ar_2$ and $L_1$ do not include cyano. That is, the substituents in $L_2$ and $Ar_3$ are independent of each other, and the cyano substituent is on the group of only one of them, or may exist in both $L_2$ and $Ar_3$; $Ar_1$, $Ar_2$ and $L_1$ is optionally substituted, but their substituents must not include cyano.

Optionally, in some embodiments, the compound of the present disclosure has a structure shown as follows (chemical formula 2) or (chemical formula 3):

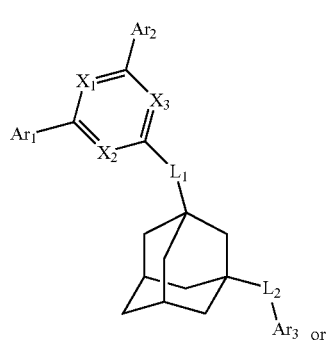
(chemical formula 2)

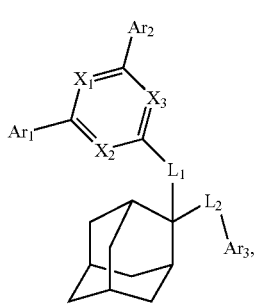
(chemical formula 3)

wherein the substituents in $L_2$ and $Ar_3$ do not include cyano, and the substituents in $Ar_1$, $Ar_2$, and $L_1$ include at least one cyano. That is, the substituents in $L_1$, $Ar_1$, and $Ar_2$ are independent of each other, and the cyano substituent is on the group of only one of them, or exist in any two of $L_1$, $Ar_1$, and $Ar_2$, or exist in all the three; $L_2$ and $Ar_3$ is optionally substituted, but their substituents must not include cyano.

Optionally, in some embodiments, the compound of the present disclosure has a structure shown as follows (chemical formula 2) or (chemical formula 3):

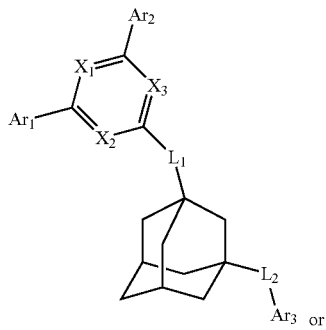
(chemical formula 2)

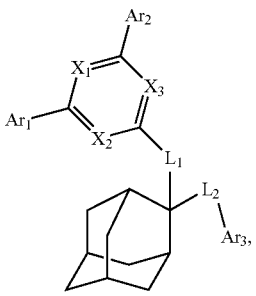
(chemical formula 3)

wherein the substituents in $L_2$ and $Ar_3$ include at least one cyano, and the substituents in $Ar_1$, $Ar_2$, and $L_1$ include at least one cyano. That is, the substituents in $L_2$ and $Ar_3$ are independent of each other, and the cyano substituent is on the group of only one of them, or may exist in both $L_2$ and $Ar_3$; the substituents in the $L_1$, $Ar_1$ and $Ar_2$ are also independent of each other, and the cyano substituent is on the group of only one of them, or exist in any two of $L_1$, $Ar_1$, and $Ar_2$, or exist in all the three.

Optionally, $R^{X1}$, $R^{X2}$, and $R^{X3}$ are all hydrogen. That is, any one of $R_1$, $R_2$, $R_3$, and $R_4$ may be

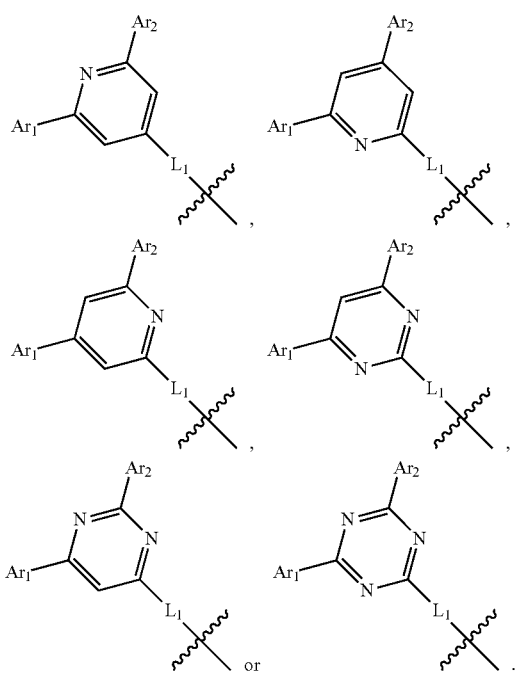

Optionally, $R^{X1}$, $R^{X2}$, and $R^{X3}$ are the same or different from each other, and are each independently selected from hydrogen, deuterium, fluorine, chlorine, and cyano.

Optionally, $L_1$ and $L_2$ are the same or different, and are selected from single bond, substituted or unsubstituted arylene with 6 to 25 ring-forming carbon atoms, and substituted or unsubstituted heteroarylene with 3 to 18 ring-forming carbon atoms.

Optionally, $L_1$ or $L_2$ is selected from single bond and the group consisting of the following groups represented by chemical formulae j-1 to j-16:

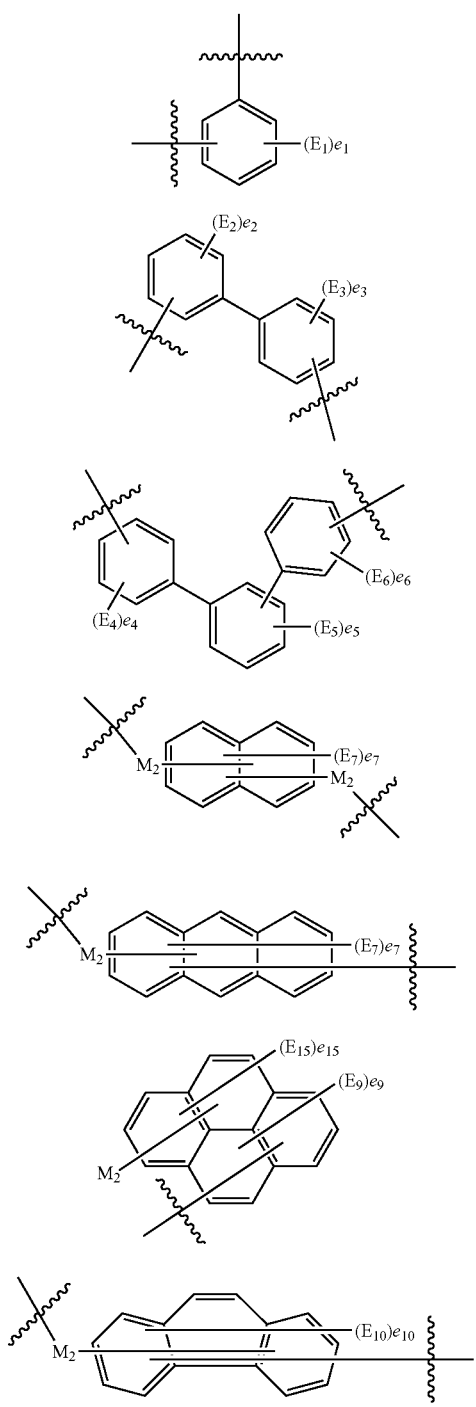
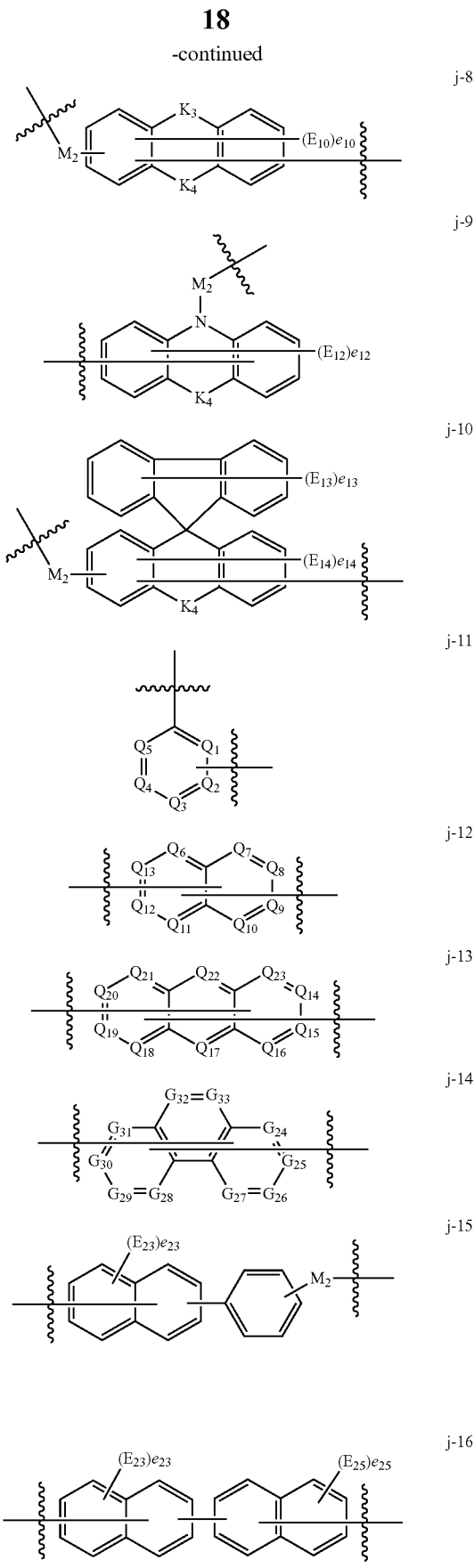

Wherein, $M_2$ is selected from single bond and

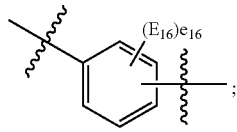

$Q_1$ to $Q_5$ are each independently selected from N and $C(F_1)$, and at least one of $Q_1$ to $Q_5$ is selected from N; when two or more of $Q_1$ to $Q_5$ are selected from $C(F_1)$, any two $F_1$ are the same or different;

$Q_6$ to $Q_{13}$ are each independently selected from N and $C(F_2)$, and at least one of $Q_6$ to $Q_{13}$ is selected from N; when two or more of $Q_6$ to $Q_{13}$ are selected from $C(F_2)$, any two $F_2$ are the same or different;

$Q_{14}$ to $Q_{23}$ are each independently selected from N and $C(F_3)$, and at least one of $Q_{14}$ to $Q_{23}$ is selected from N; when two or more of $Q_{14}$ to $Q_{23}$ are selected from $C(F_3)$, any two $F_3$ are the same or different;

$Q_{24}$ to $Q_{33}$ are each independently selected from N and $C(F_4)$, and at least one of $Q_{24}$ to $Q_{33}$ is selected from N; when two or more of $Q_{24}$ to $Q_{33}$ are selected from $C(F_4)$, any two $F_4$ are the same or different;

$E_1$ to $E_{16}$, $E_{23}$ to $E_{25}$, and $F_1$ to $F_4$ are each independently selected from: hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, alkyl with 1 to 10 carbon atoms, haloalkyl with 1 to 10 carbon atoms, cycloalkyl with 3 to 10 carbon atoms, alkylamino with 1 to 10 carbon atoms, aryloxy with 6 to 18 carbon atoms, and arylthio with 6 to 18 carbon atoms;

$e_r$ is the number of substituents $E_r$, and r is any integer from 1 to 16; when r is selected from 1, 2, 3, 4, 5, 6, 9, 15, 16, and 23 to 25, $e_r$ is selected from 1, 2, 3 and 4; when r is selected from 7, 11 or 14, $e_r$ is selected from 1, 2, 3, 4, 5 and 6; when r is 12, $e_r$ is selected from 1, 2, 3, 4, 5, 6 and 7; when r is selected from 8, 10 and 13, $e_r$ is selected from 1, 2, 3, 4, 5, 6, 7 and 8; when $e_r$ is greater than 1, any two $E_r$ are the same or different;

$K_3$ is selected from O, S, Se, $N(E_{17})$, $C(E_{18}E_{19})$, and $Si(E_{18}E_{19})$; wherein, $E_{17}$, $E_{18}$, and $E_{19}$ are each independently selected from: aryl with 6 to 18 carbon atoms, heteroaryl with 3 to 18 carbon atoms, alkyl with 1 to 10 carbon atoms, and cycloalkyl with 3 to 10 carbon atoms, or $E_{18}$ and $E_{19}$ are linked to each other to form a saturated or unsaturated 5- to 13-membered ring together with atoms linked to the both. For example, in chemical formula j-8, when $K_4$ is single bond, $M_2$ is single bond, and $K_3$ is $C(E_{18}E_{19})$, $E_{18}$ and $E_{19}$ may be linked to each other to form a saturated or unsaturated ring together with atoms linked to the both, and they may exist independently of each other. When $E_{18}$ and $E_{19}$ form a ring, the ring formed by $E_{18}$ and $E_{19}$ is spiro-linked with other parts of a molecule. It should be noted that when $E_{18}$ and $E_{19}$ are linked to each other to form a saturated or unsaturated ring together with the atoms to which they are both linked, the ring with such carbon atoms may be a 5-membered ring

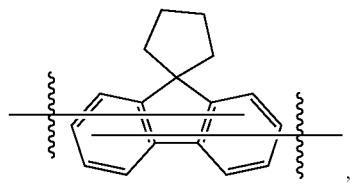

a 6-membered ring

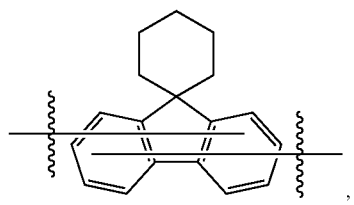

or a 13-membered ring

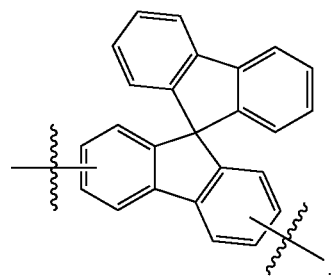

Of course, the number of carbon atoms on the ring formed by the link between $E_{18}$ and $E_{19}$ may also be other values, which will not be listed here.

$K_4$ is selected from single bond, O, S, Se, $N(E_{20})$, $C(E_{21}E_{22})$, and $Si(E_{21}E_{22})$; wherein, $E_{20}$, $E_{21}$, and $E_{22}$ are each independently selected from: aryl with 6 to 18 carbon atoms, heteroaryl with 3 to 18 carbon atoms, alkyl with 1 to 10 carbon atoms, and cycloalkyl with 3 to 10 carbon atoms, or $E_{21}$ and $E_{22}$ are linked to each other to form a saturated or unsaturated 5- to 13-membered ring together with the atoms to which they are both linked. Here, the understanding of optional ring formation of $E_{21}$ and $E_{22}$ is consistent with the understanding in other technical solutions (when $E_{18}$ and $E_{19}$ are linked to each other to form a ring) of the present disclosure.

Optionally, the $L_1$ and $L_2$ is the same or different, and is independently selected from single bond, substituted or unsubstituted group $W_1$, and the group $W_1$ is selected from the group consisting of the following groups:

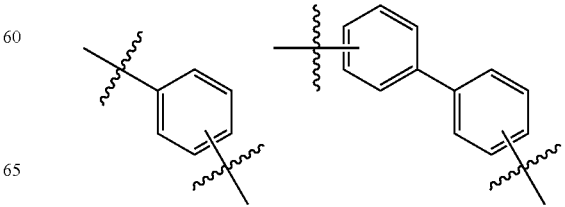

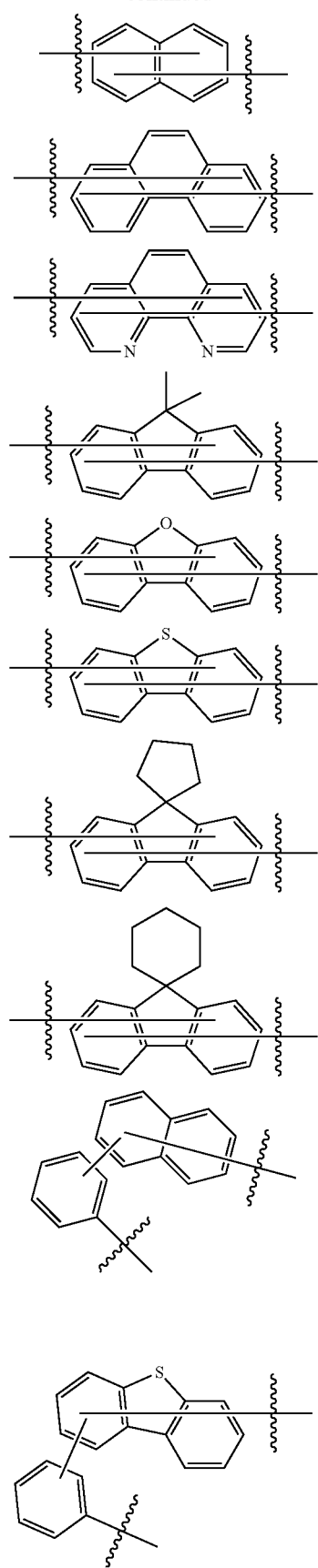
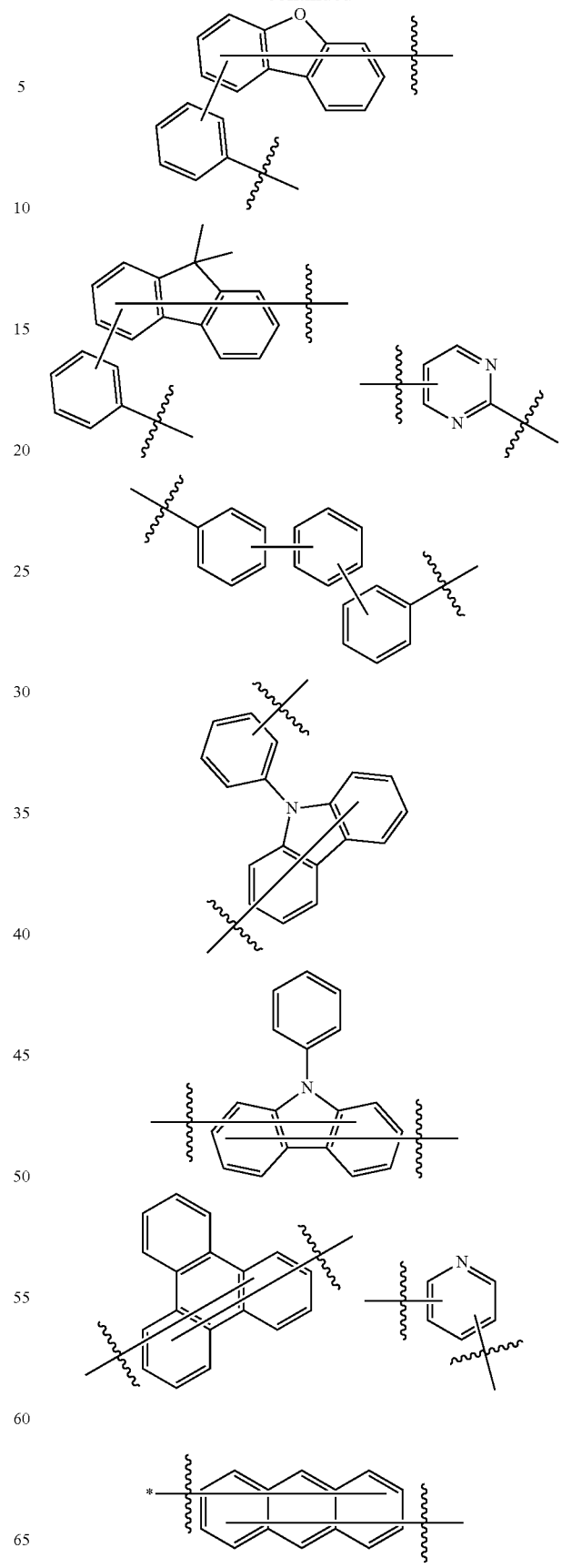

-continued

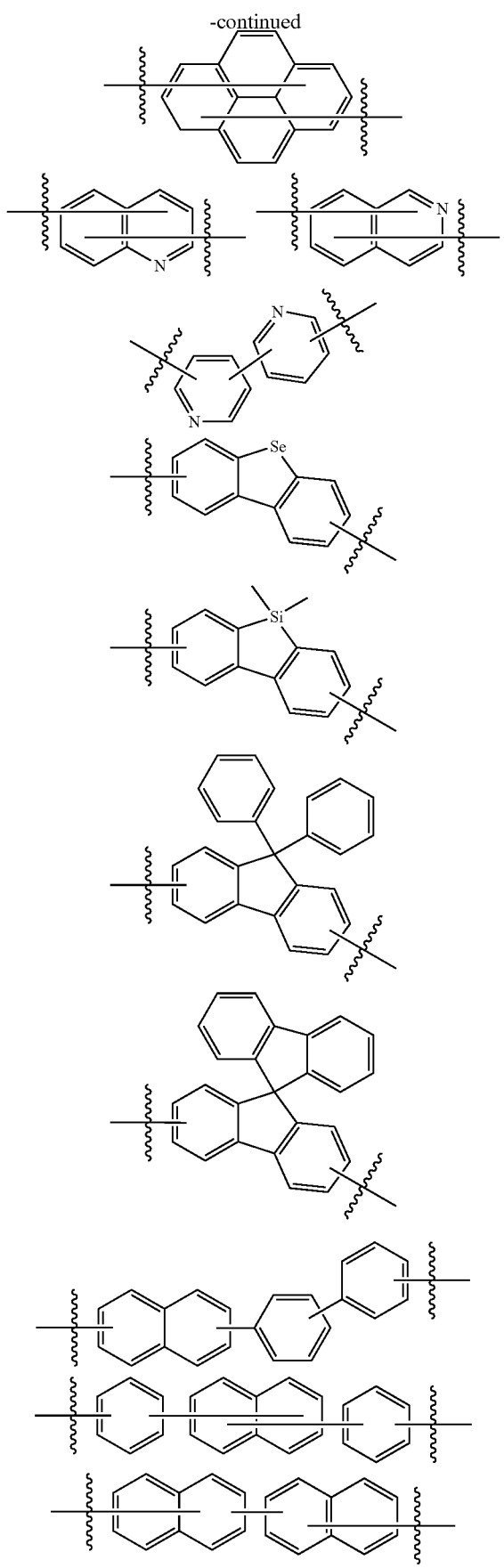

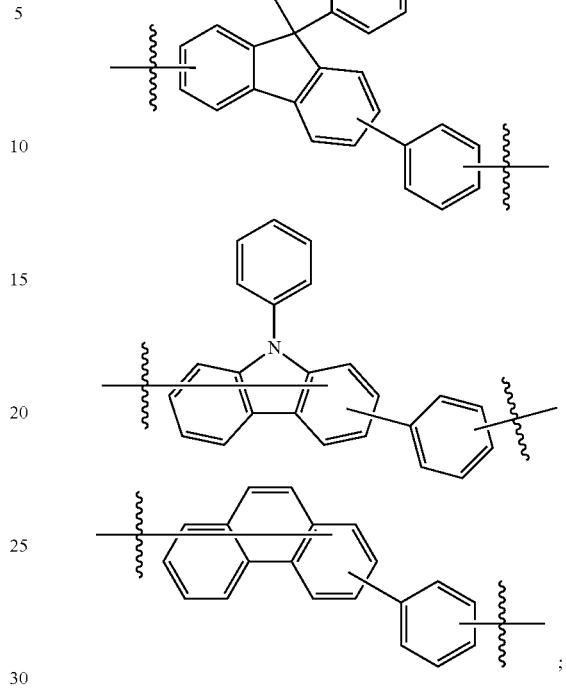

When the $W_1$ group is substituted, the substituent of $W_1$ is selected from deuterium, fluorine, chlorine, cyano, alkyl with 1 to 6 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms, and heteroaryl with 3 to 12 carbon atoms; when the $W_1$ has a plurality of substituents, the substituents are the same or different. In addition, the number of substituents of $W_1$ is plural, such as 1, 2, 3, 4, 5 or more, which is not specifically limited in the present disclosure.

Alternatively, in other embodiments, the $L_1$ and $L_2$ is the same or different, and is independently selected from single bond, substituted or unsubstituted group $W_2$, and the group $W_2$ is selected from the group consisting of the following groups:

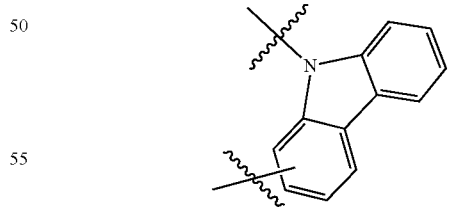

When the $W_2$ group is substituted, the substituent of $W_2$ is selected from deuterium, fluorine, chlorine, cyano, alkyl with 1 to 6 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms, and heteroaryl with 3 to 12 carbon atoms; when the $W_2$ has a plurality of substituents, the substituents are the same or different.

Further, the substituents of $W_1$ and $W_2$ are each independently selected from deuterium, fluorine, cyano, methyl, ethyl, isopropyl, tert-butyl, trifluoromethyl, phenyl, naphthyl, carbazolyl, and trimethylsilyl.

In some more specific embodiments of the present disclosure, each of $L_1$ and $L_2$ is independently selected from: single bond, substituted or unsubstituted phenylene, substituted or unsubstituted biphenylene, substituted or unsubstituted terphenylene, substituted or unsubstituted naphthylene, substituted or unsubstituted dibenzofuranylene, substituted or unsubstituted dibenzothiophenylene, substituted or unsubstituted quinolylene, substituted or unsubstituted carbazolylene, substituted or unsubstituted naphthylene, substituted or unsubstituted fluorenylene, substituted or unsubstituted anthrylene, substituted or unsubstituted phenanthrylene, substituted or unsubstituted N-phenylcarbazolylene, substituted or unsubstituted pyridylene, substituted or unsubstituted spirobifluorenylene, substituted or unsubstituted quinolinylene, substituted or unsubstituted isoquinolinylene, substituted or unsubstituted quinazolinylene, and a subunit group formed by linking two or three of them through single bond; the substitution of each of $L_1$ and $L_2$ refers to independently substituted by 1, 2, 3 or 4 substituents selected from deuterium, fluorine, chlorine, cyano, methyl, ethyl, isopropyl, tert-butyl, trifluoromethyl, phenyl, carbazolyl, naphthyl, and trimethylsilyl.

Optionally, the $L_1$ and $L_2$ is the same or different, and is independently selected from single bond, or the group consisting of the following groups:

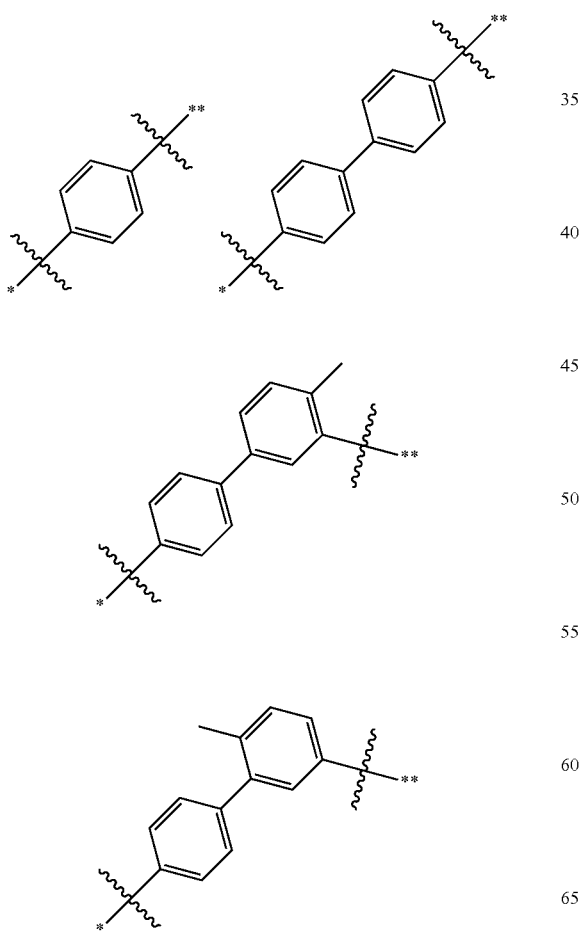

-continued

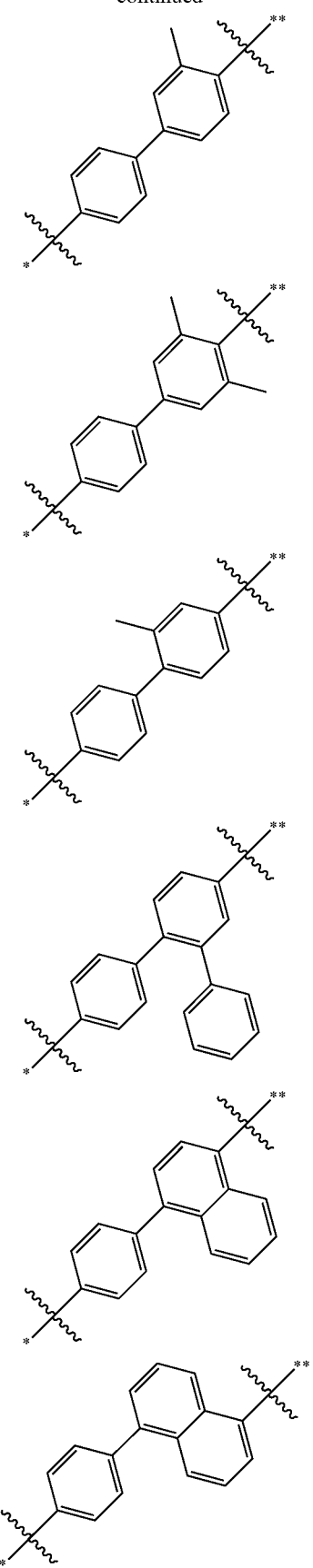

-continued
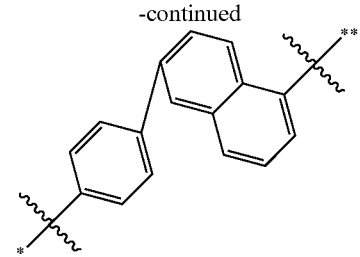
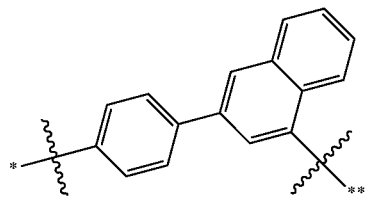
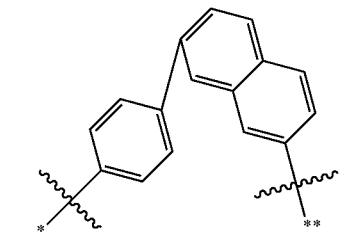
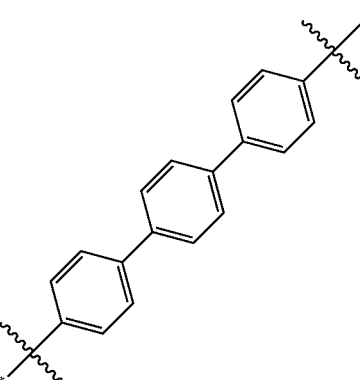
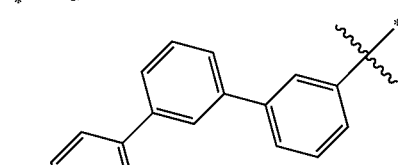
-continued
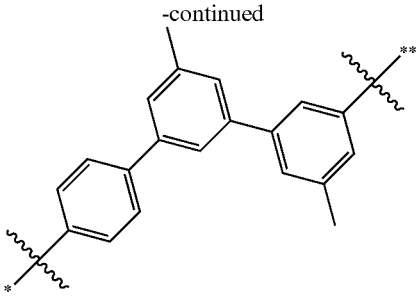
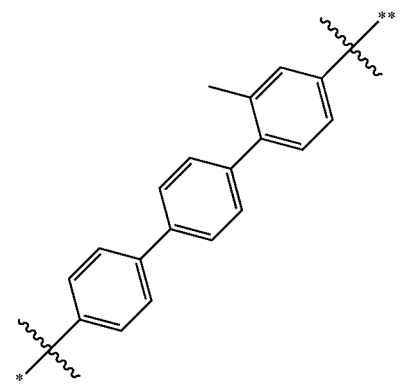
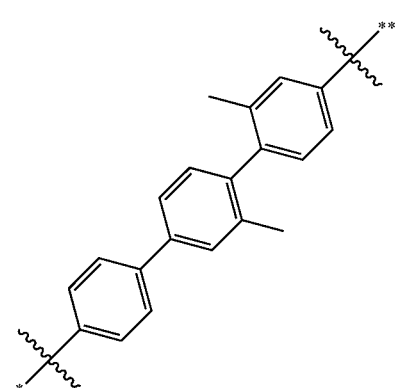
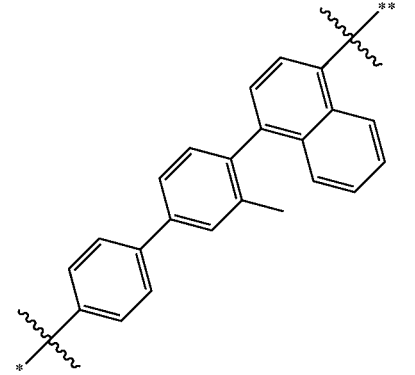

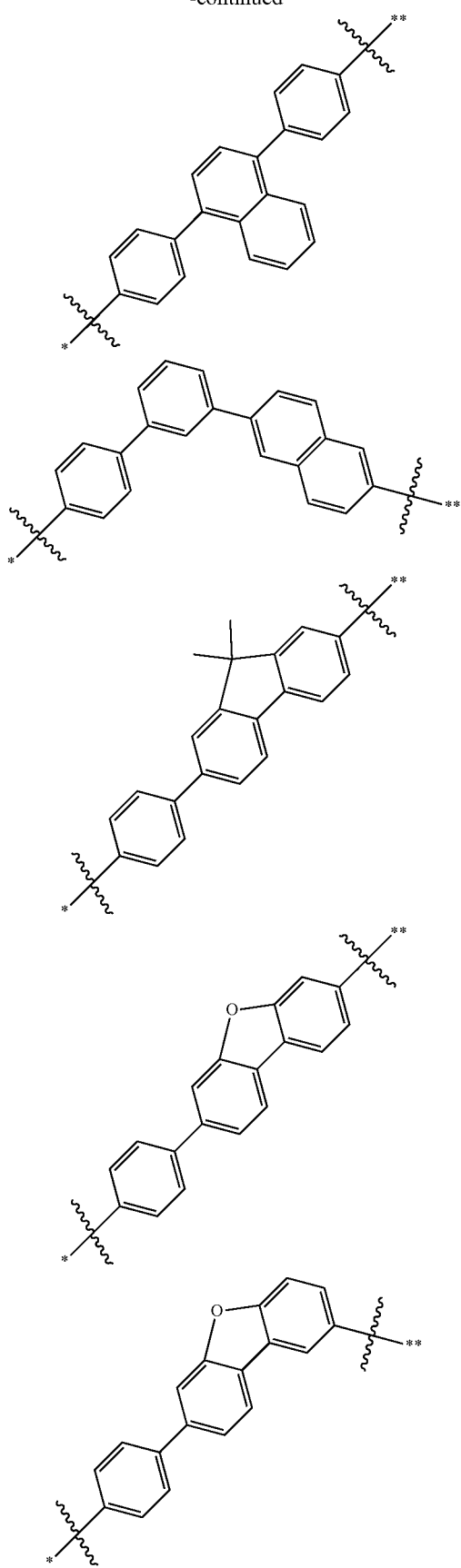

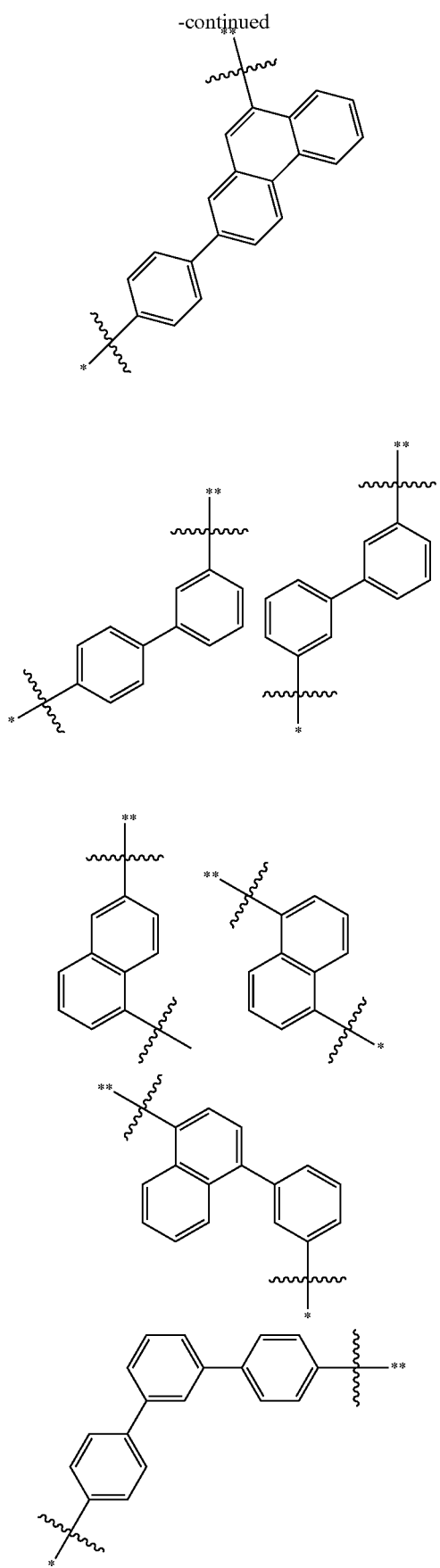
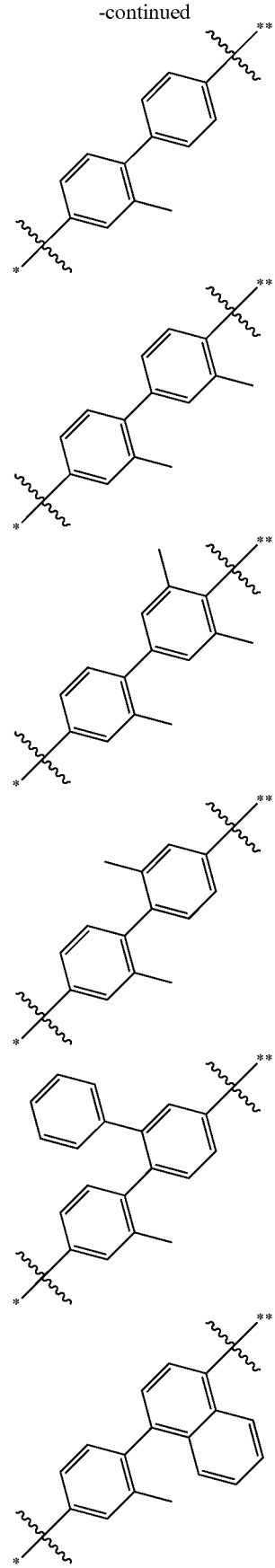

33
-continued
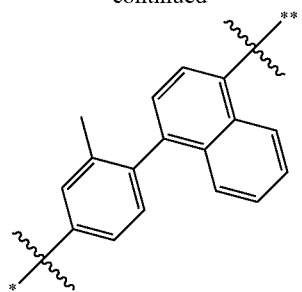
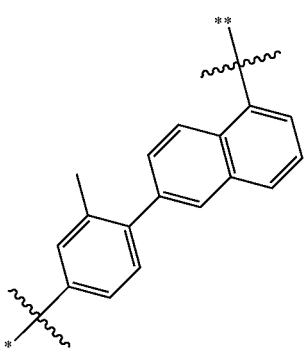
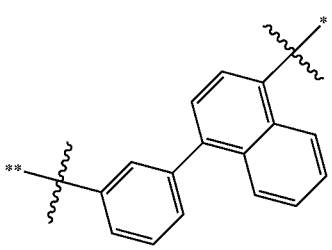
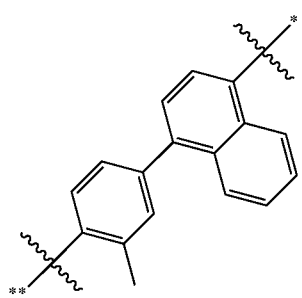
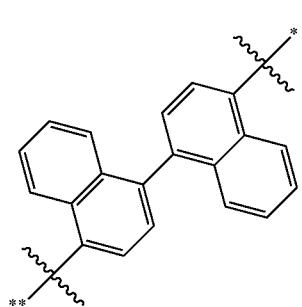
34
-continued
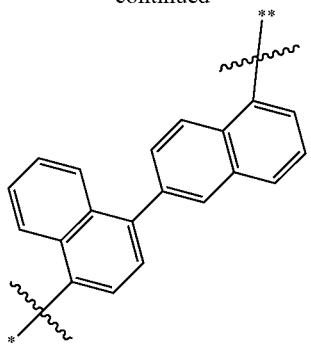
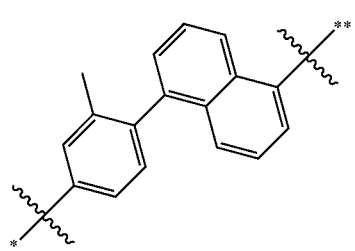
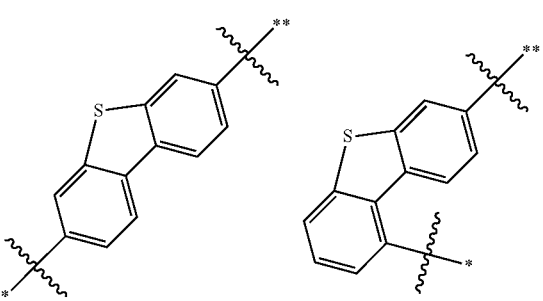
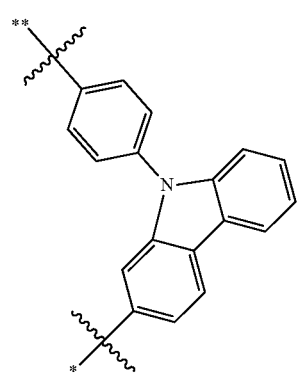
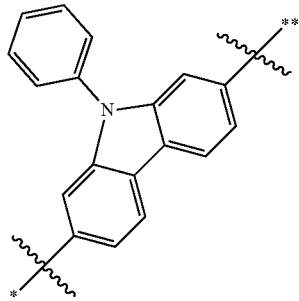

35
-continued
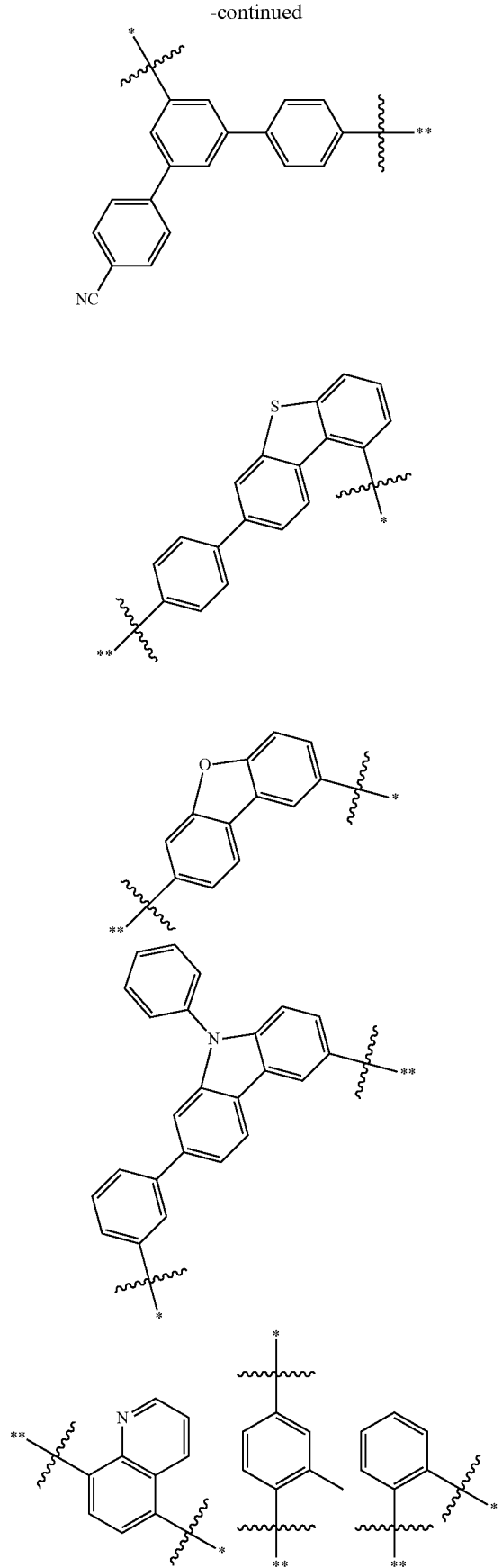
36
-continued
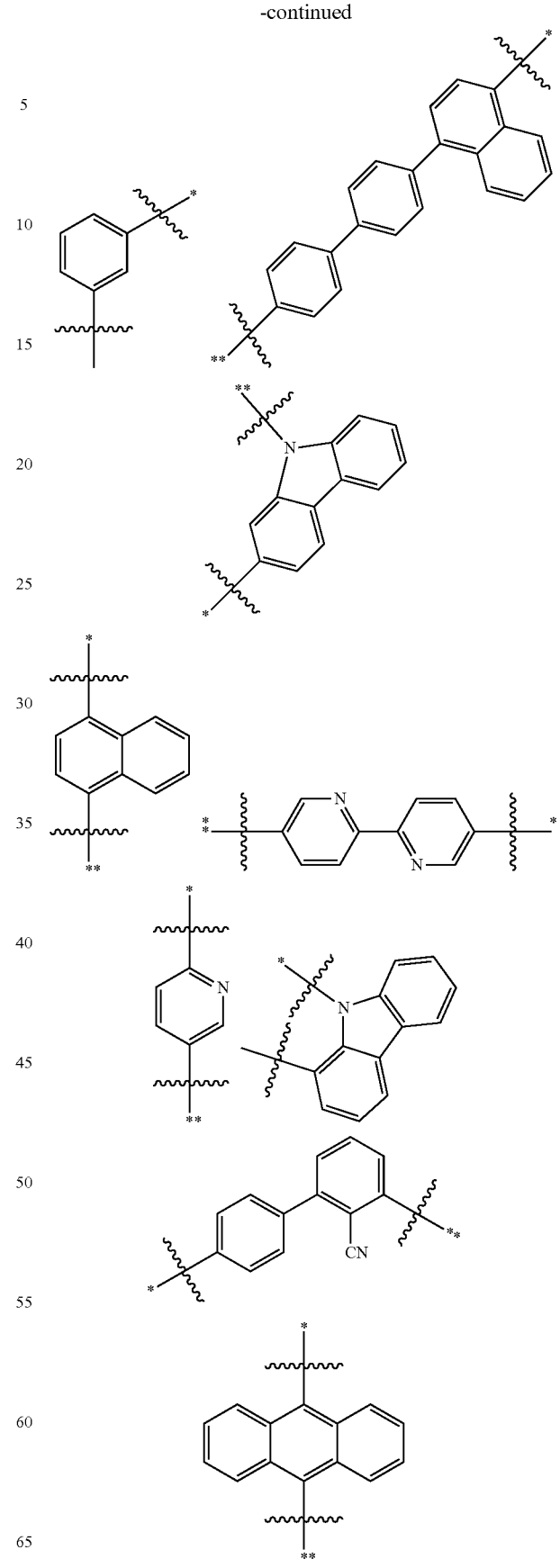

-continued
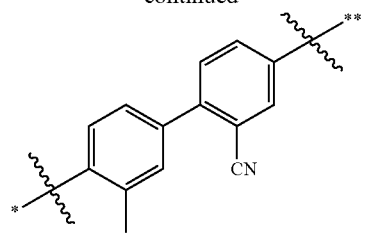
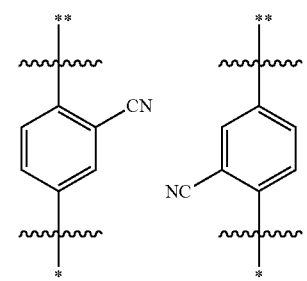
or selected from the group consisting of the following groups.
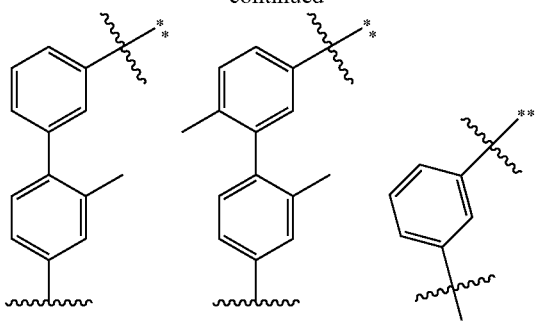
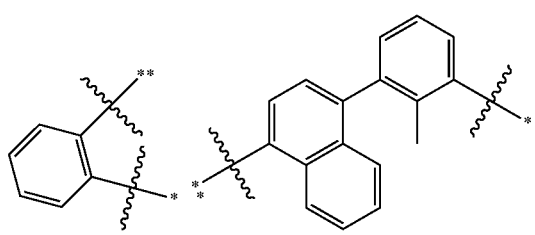
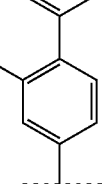
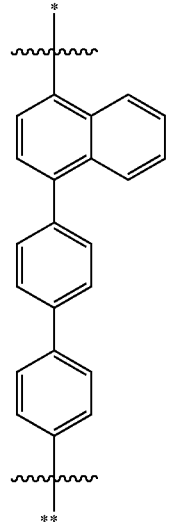
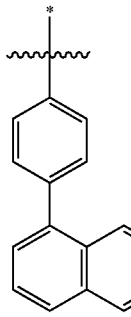
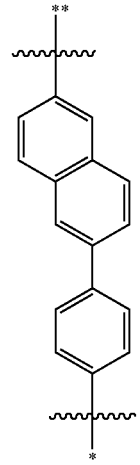
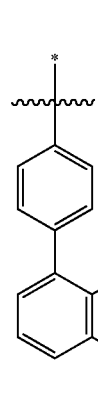
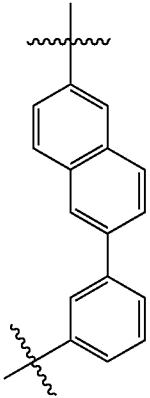

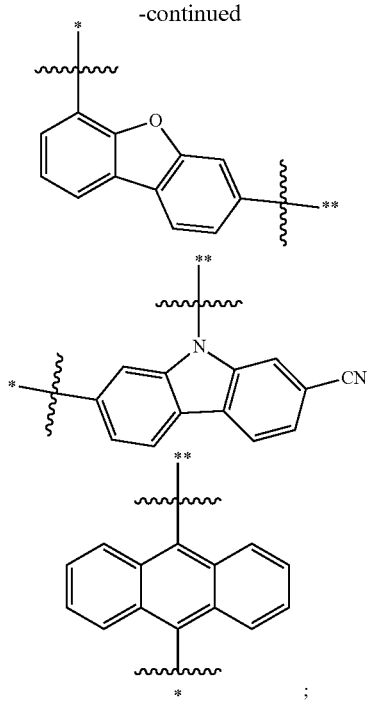

Wherein, * represents linking with adamantyl, and ** represents linking with

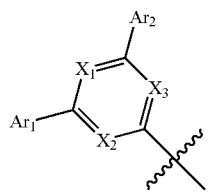

or Ar₃. The choices of $L_1$ and $L_2$ in the compound of the present disclosure are not limited to the above groups.

Optionally, $Ar_1$, $Ar_2$ and $Ar_3$ are the same or different, and are each independently selected from substituted or unsubstituted aryl with 6 to 25 ring-forming carbon atoms, and substituted or unsubstituted heteroaryl with 3 to 18 ring-forming carbon atoms. For example, $Ar_1$, $Ar_2$ and $Ar_3$ are each independently selected from substituted or unsubstituted aryl with 6, 10, 12, 13, 14, 15, 16, 17, 18, 19, 20, 21, 24, and 25 ring-forming carbon atoms, or substituted or unsubstituted heteroaryl with 5, 8, 9, 12, 16, or 18 ring-forming carbon atoms.

Optionally, the substituents in the $Ar_1$, $Ar_2$ and $Ar_3$ are the same or different from each other, and are each independently selected from the group consisting of deuterium, halogen, cyano, alkyl with 1 to 10 carbon atoms, haloalkyl with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms, and the $Ar_3$ is substituted by at least one cyano.

Optionally, the substituents in the $Ar_1$, $Ar_2$ and $Ar_3$ are the same or different from each other, and are each independently selected from the group consisting of deuterium, fluorine, chlorine, cyano, alkyl with 1 to 4 carbon atoms, haloalkyl with 1 to 4 carbon atoms, cycloalkyl with 5 to 10 carbon atoms, aryl with 6 to 12 carbon atoms, and heteroaryl with 3 to 12 carbon atoms.

Optionally, the $Ar_1$, $Ar_2$ and $Ar_3$ are the same or different, and are each independently selected from the group consisting of the following groups:

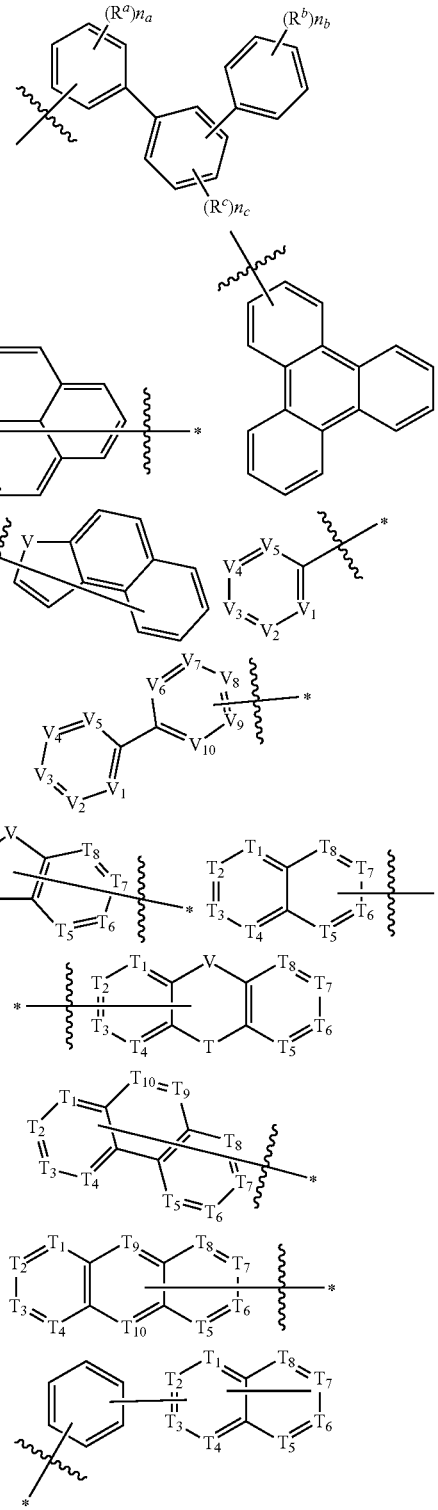

-continued

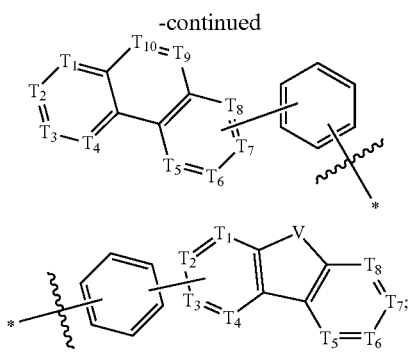

In the above groups, $n_a$ and $n_d$ are each independently 1, 2, 3 or 4; $n_b$ is 1, 2, 3, 4 or 5 $V_1$ to $V_{10}$ are each independently selected from C(R$^v$) and N, and when a group includes two or more R$^v$, any two R$^v$ are the same or different;

each V is selected from the group consisting of O, S, Se, N(R$^{v1}$), C(R$^{v2}$R$^{v3}$) and Si(R$^{v2}$R$^{v3}$);

T is selected from O, S or N (R$^{v1}$);

$T_1$ to $T_{10}$ are each independently selected from C(R$^t$) and N, and when a group includes two or more R$^t$, any two R$^t$ are the same or different;

R$^a$, R$^b$, R$^c$, R$^t$, R$^v$, R$^{v2}$, and R$^{v3}$ are each independently hydrogen, deuterium, fluorine, chlorine, bromine, cyano, $C_1$-$C_6$ alkyl, $C_1$-$C_6$ haloalkyl, $C_3$-$C_{12}$ alkylsilyl, $C_6$-$C_{12}$ aryl, $C_3$-$C_{12}$ heteroaryl and $C_3$-$C_{10}$ cycloalkyl;

optionally, R$^{v2}$ and R$^{v3}$ linked to the same atom are linked to each other to form a saturated or unsaturated 5- to 13-membered ring. For example, in

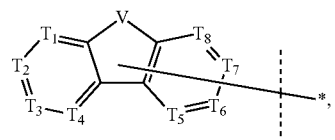

when $T_1$ to $T_8$ are all CH and V is C(R$^{v2}$R$^{v3}$), R$^{v2}$ and R$^{v3}$ is linked to each other to form a ring or exist independently of each other; when they form a ring, the ring with such carbon atoms may be a 5-membered ring

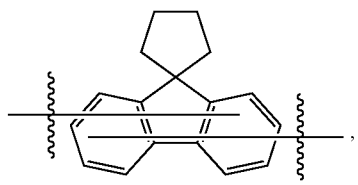

a 6-membered ring

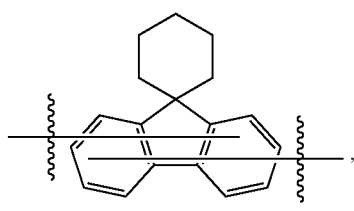

or a 13-membered ring

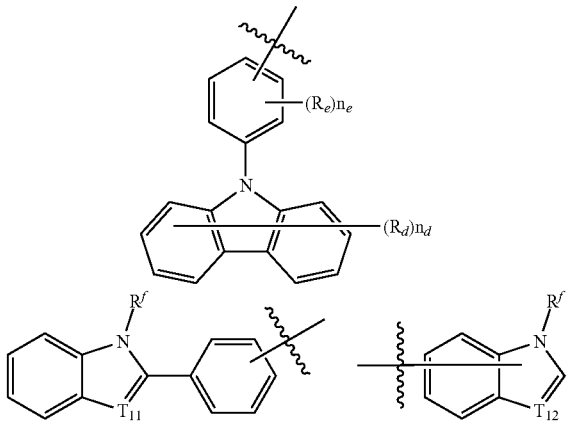

Of course, the number of carbon atoms on the ring formed by the link between R$^{v2}$ and R$^{v3}$ may also be other values, which will not be listed here.

Each R$^{v1}$ is selected from the group consisting of hydrogen, deuterium, alkyl with 1 to 6 carbon atoms, haloalkyl with 1 to 6 carbon atoms, aryl with 6 to 12 carbon atoms, heteroaryl with 3 to 12 carbon atoms and cycloalkyl with 3 to 10 carbon atoms, and when the same group has two R$^{v1}$, each R$^{v1}$ is the same or different.

Alternatively, in other embodiments, the Ar$_1$, Ar$_2$ and Ar$_3$ are the same or different, and are each independently selected from the group consisting of the following groups:

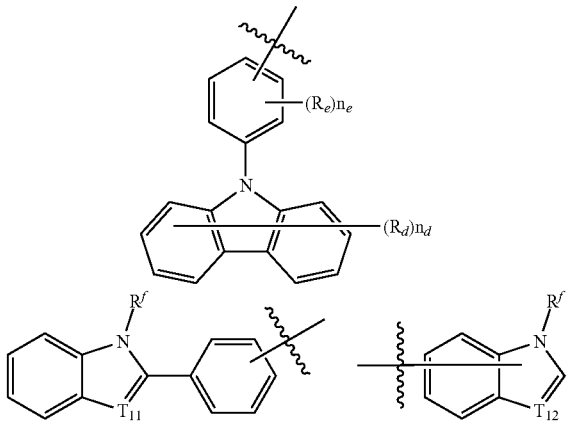

In the above groups, $n_d$ is selected from 1, 2, 3, 4, 5, 6, 7 or 8; $n_e$ is selected from 1, 2, 3 or 4;

$T_{11}$ and $T_{12}$ are each independently selected from C(R$^{ro}$) and N, and when a group includes two or more R$^{ro}$, any two R$^{ro}$ are the same or different;

R$^d$, R$^e$, R$^f$, and R$^{ro}$ are each independently hydrogen, deuterium, fluorine, chlorine, bromine, cyano, alkyl with 1 to 6 carbon atoms, haloalkyl with 1 to 6 carbon atoms, alkylsilyl with 3 to 12 carbon atoms, aryl with 6 to 12 carbon atoms, heteroaryl with 3 to 12 carbon atoms and cycloalkyl with 3 to 10 carbon atoms.

As an alternative, the Ar$_1$ and Ar$_2$ are the same or different, and are each independently selected from single bond and substituted or unsubstituted group Y$_1$, and the group Y$_1$ is selected from the following groups:

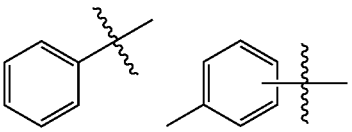

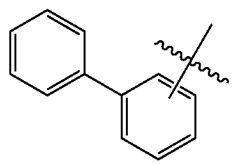
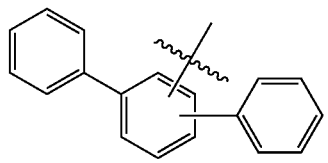
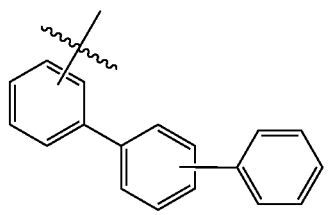
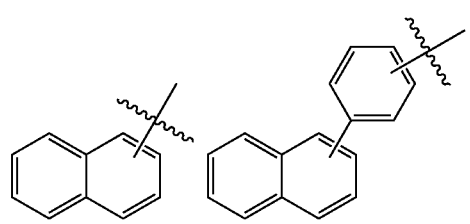
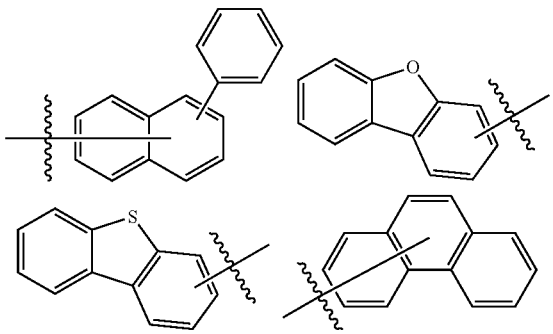
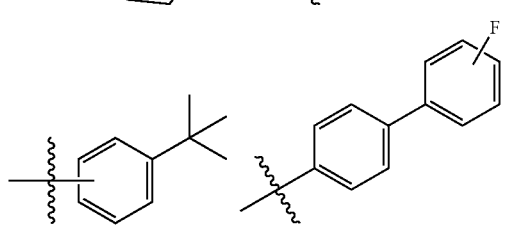
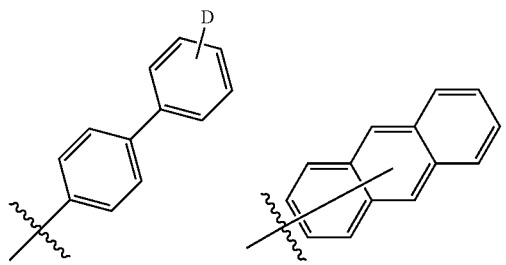
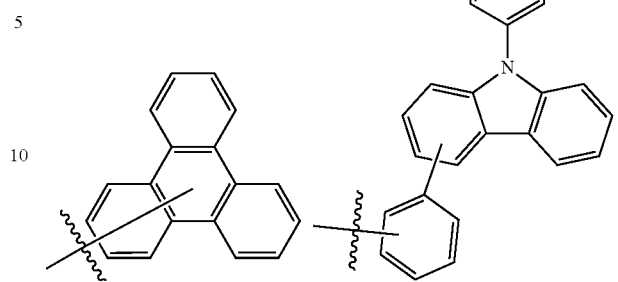
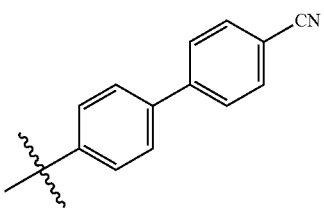
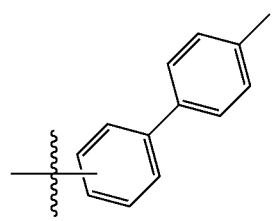
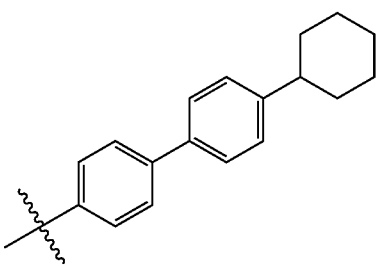
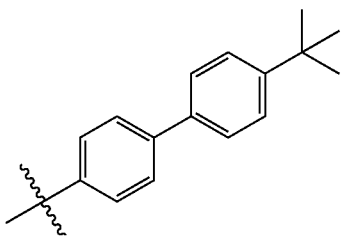
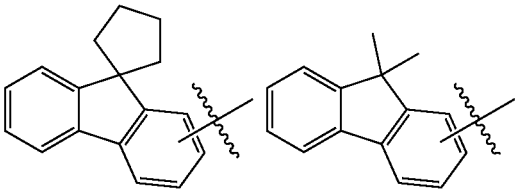

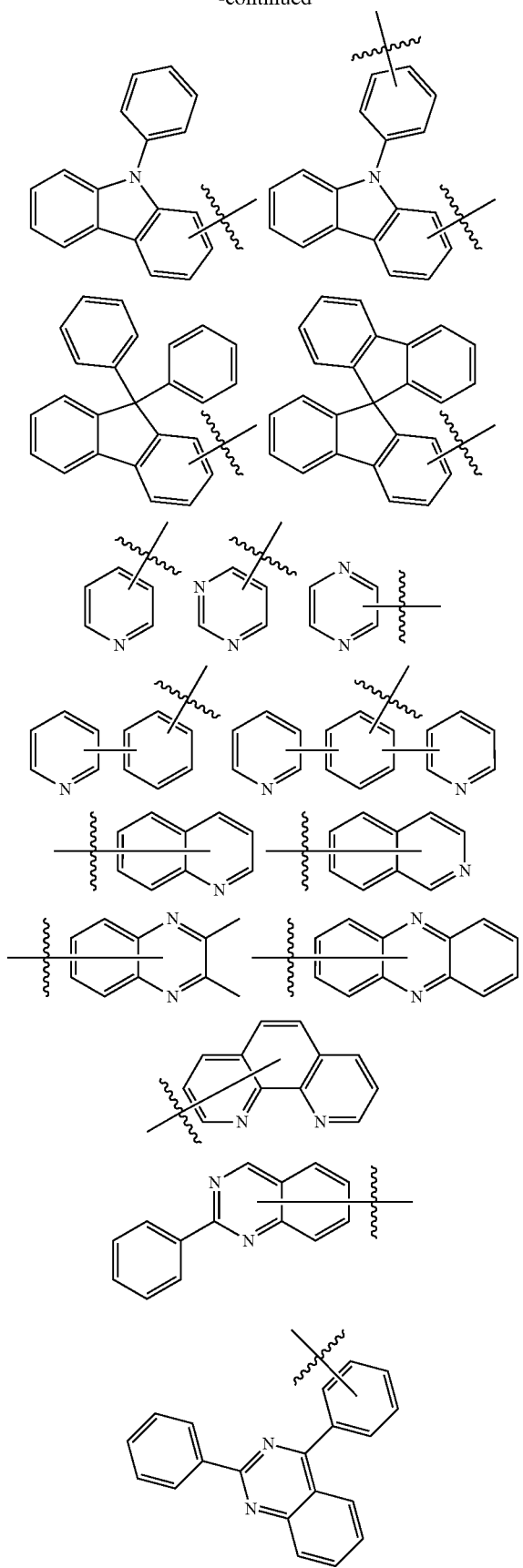
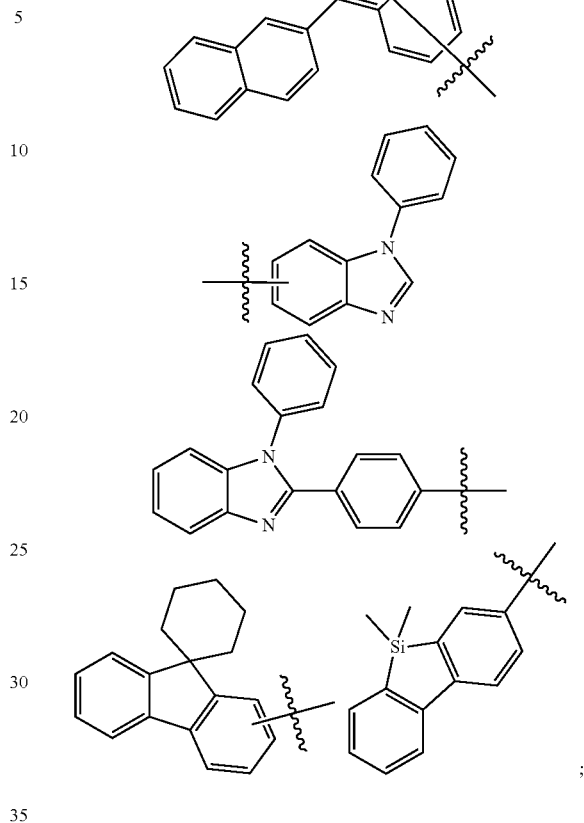

When the group $Y_1$ is substituted, the substituent of $Y_1$ is selected from deuterium, fluorine, chlorine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Y_1$ has a plurality of substituents, the substituents are the same or different. In addition, the number of substituents of $Y_1$ is plural, such as 1, 2, 3, 4, 5 or more, which is not specifically limited in the present disclosure.

As a further alternative, the $Ar_1$ and $Ar_2$ are the same or different, and are each independently selected from the following groups.

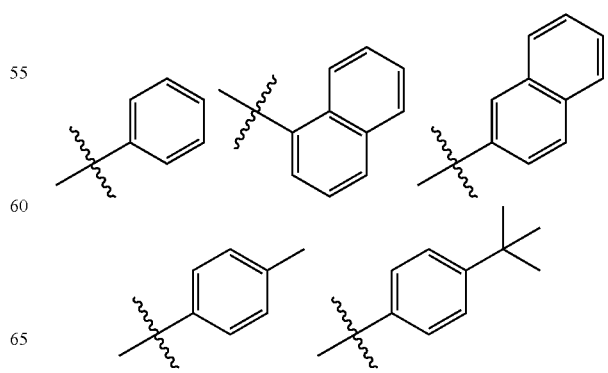

-continued
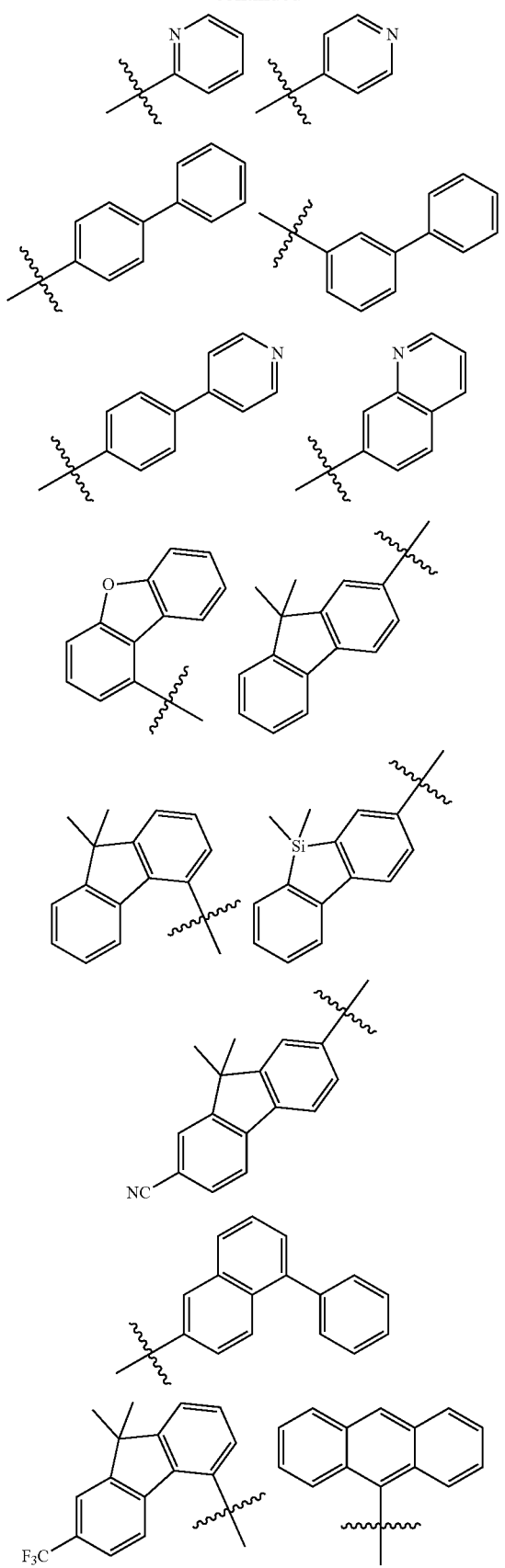
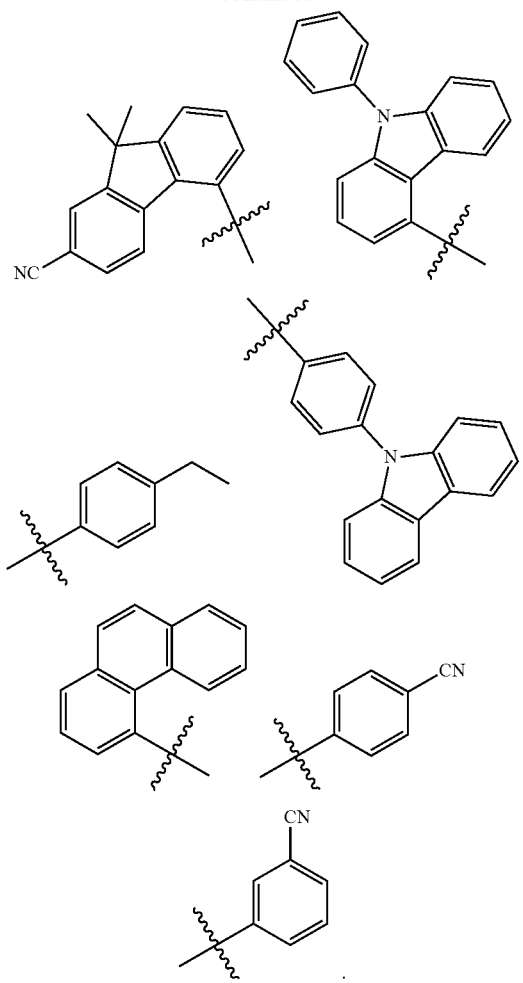
Alternatively, in other embodiments, the $Ar_1$ and $Ar_2$ are the same or different, and are each independently selected from the following groups:
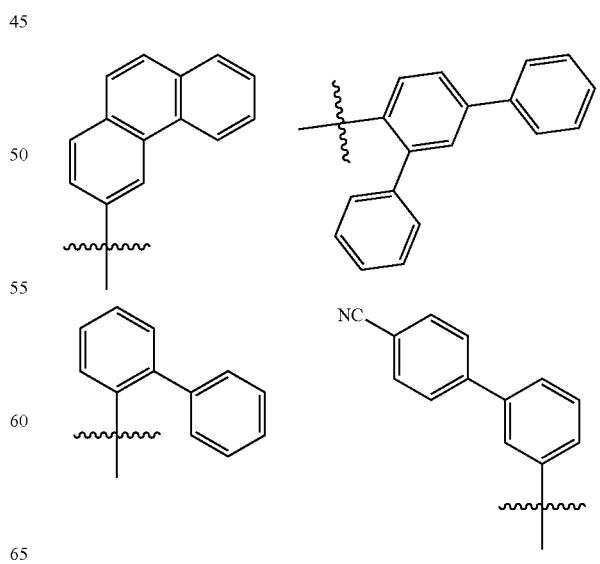

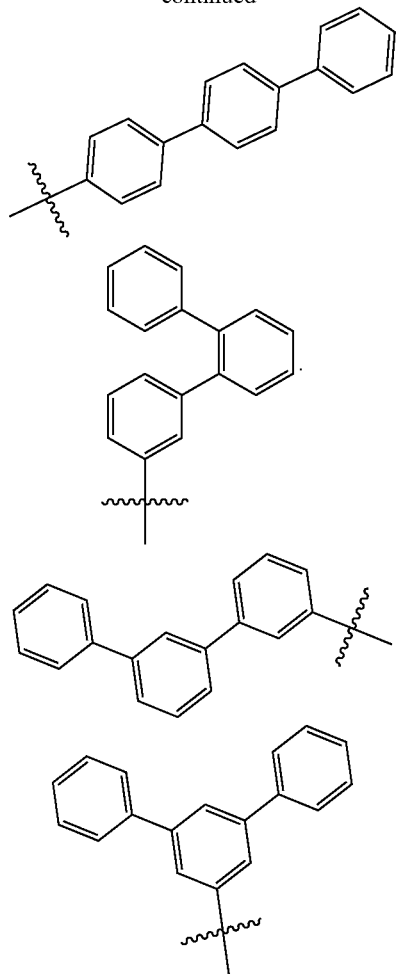
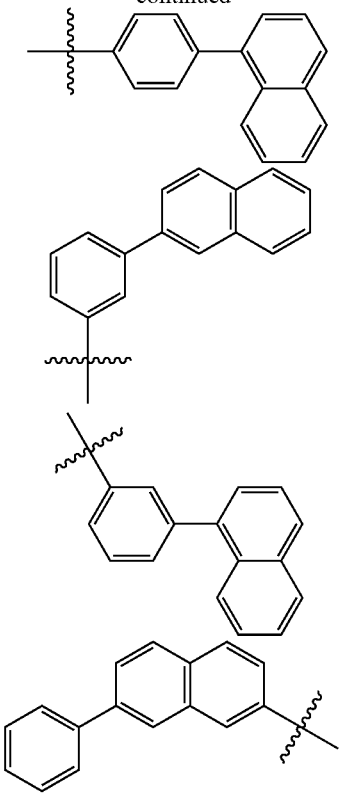
The choices of the $Ar_1$ and $Ar_2$ in the compound of the present disclosure are not limited to the above groups.
Optionally, the $Ar_3$ is selected from substituted or unsubstituted group $Z_1$, and the group $Z_1$ is selected from the following groups
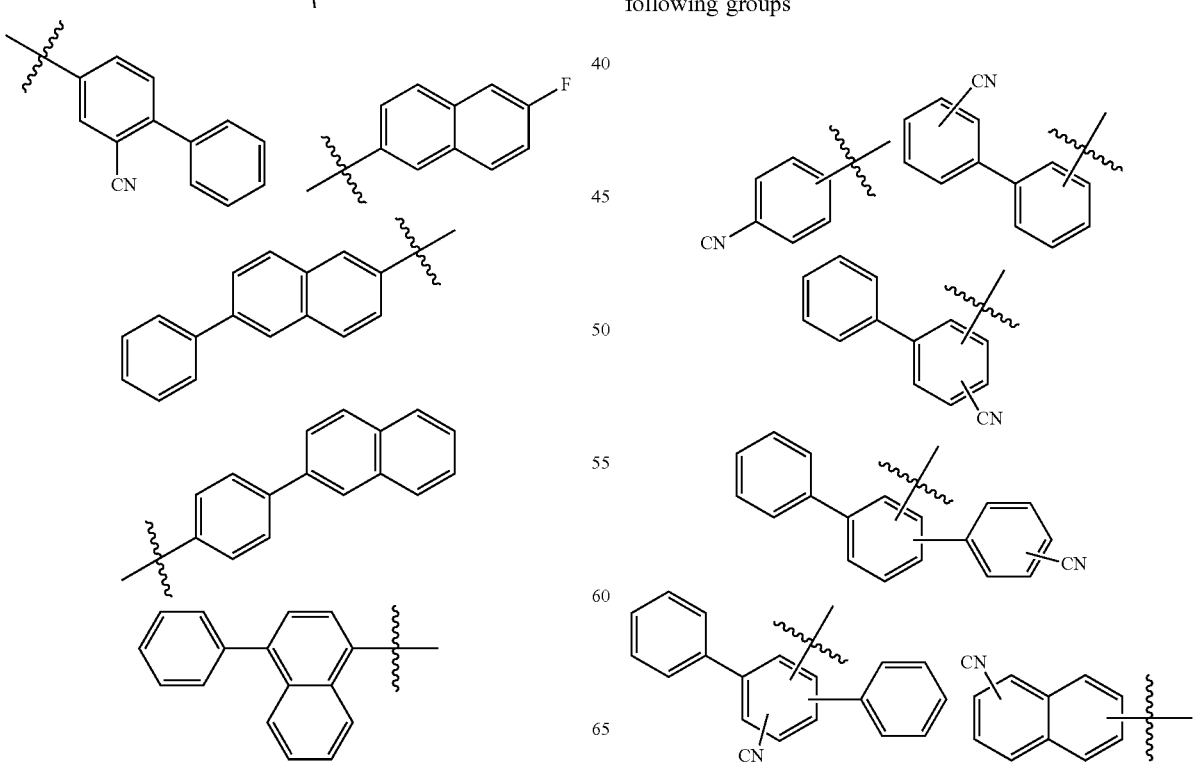

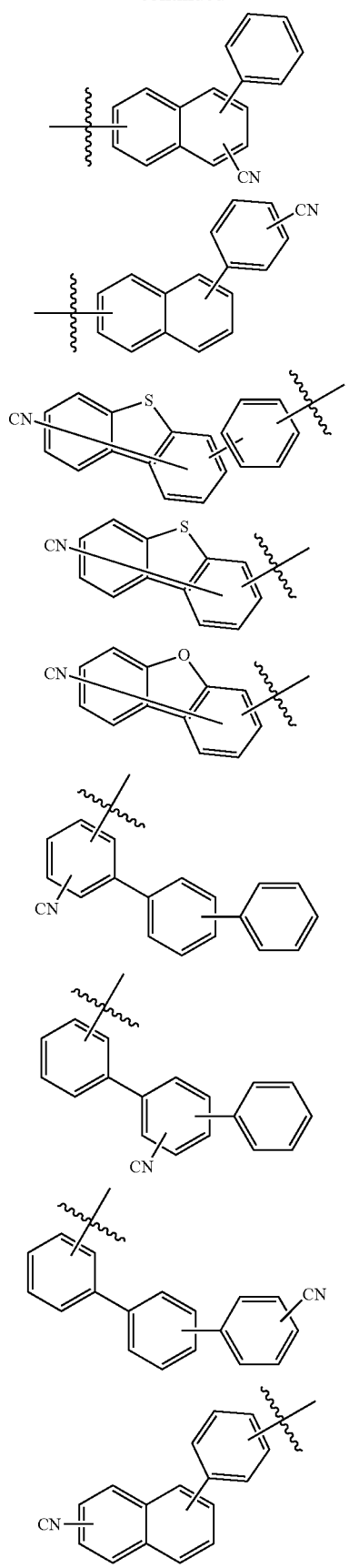
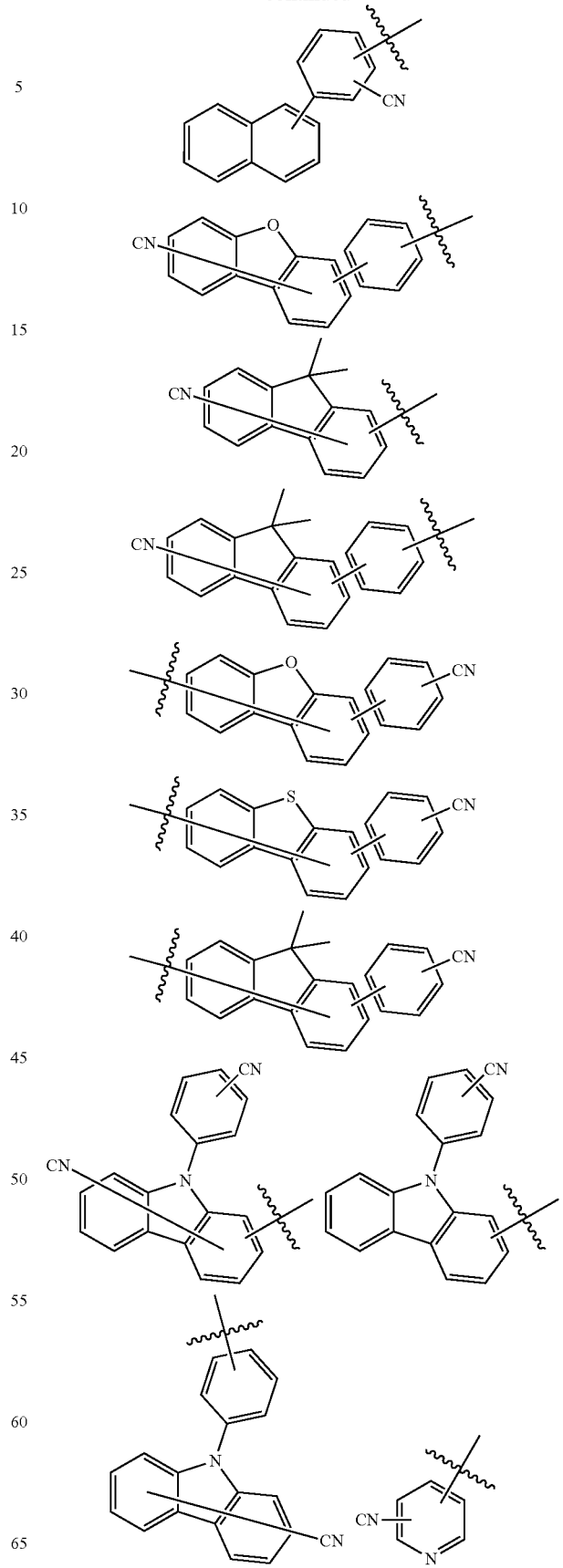

-continued
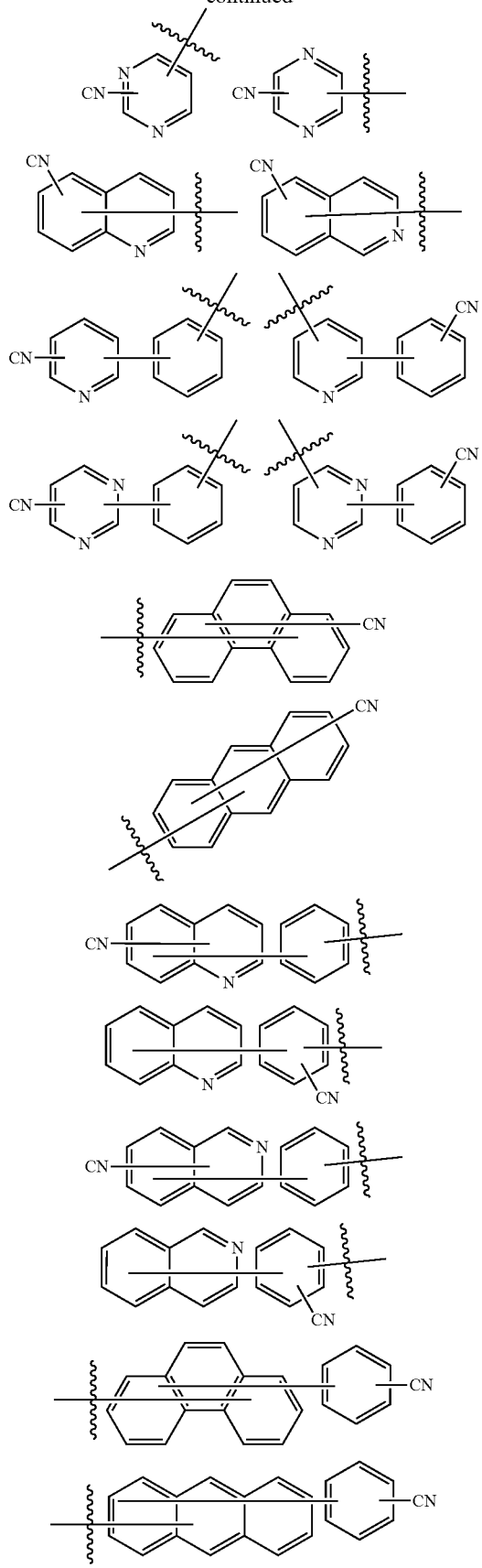
-continued
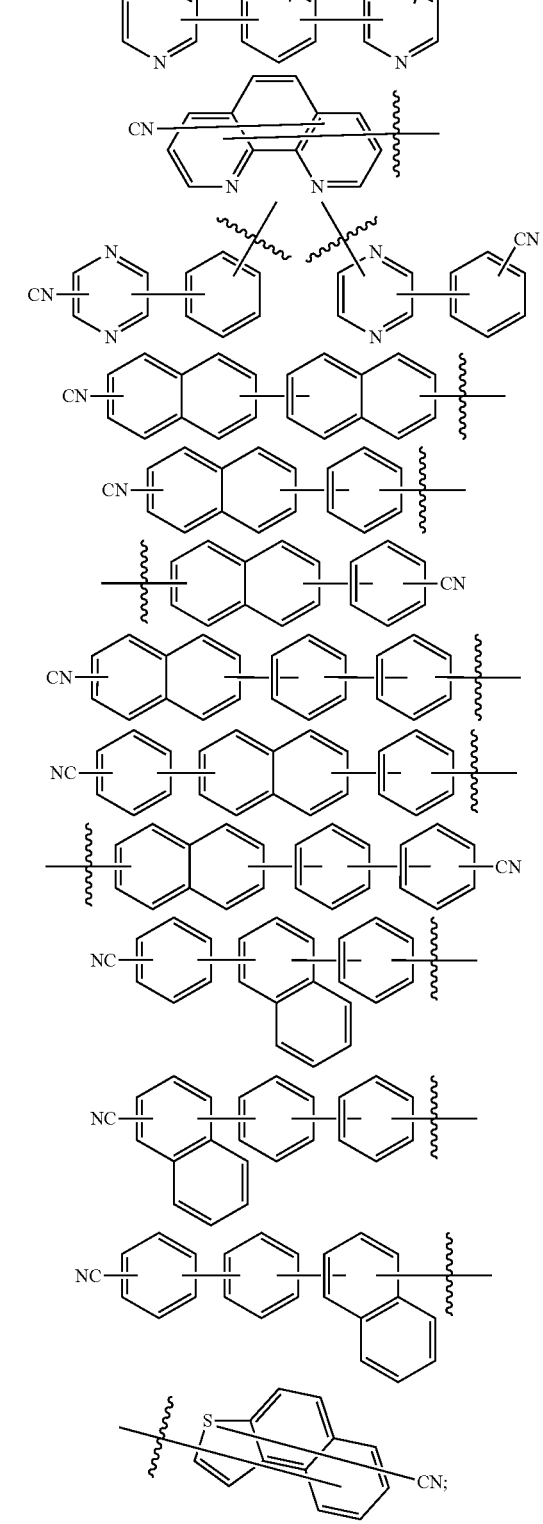
When the group $Z_1$ is substituted, the substituent of $Z_1$ is selected from deuterium, fluorine, chlorine, cyano, alkyl with 1 to 4 carbon atoms, haloalkyl with 1 to 4 carbon atoms, alkylsilyl with 3 to 9 carbon atoms, cycloalkyl with 3 to 10 carbon atoms, aryl with 6 to 12 carbon atoms, and heteroaryl with 3 to 12 carbon atoms; when the $Z_1$ has a plurality of substituents, the substituents are the same or different. In addition, the number of substituents of $Z_1$ is plural, such as 1, 2, 3, 4, 5 or more, which is not specifically limited in the present disclosure.

As a further alternative, $Ar_3$ is selected from the following groups:

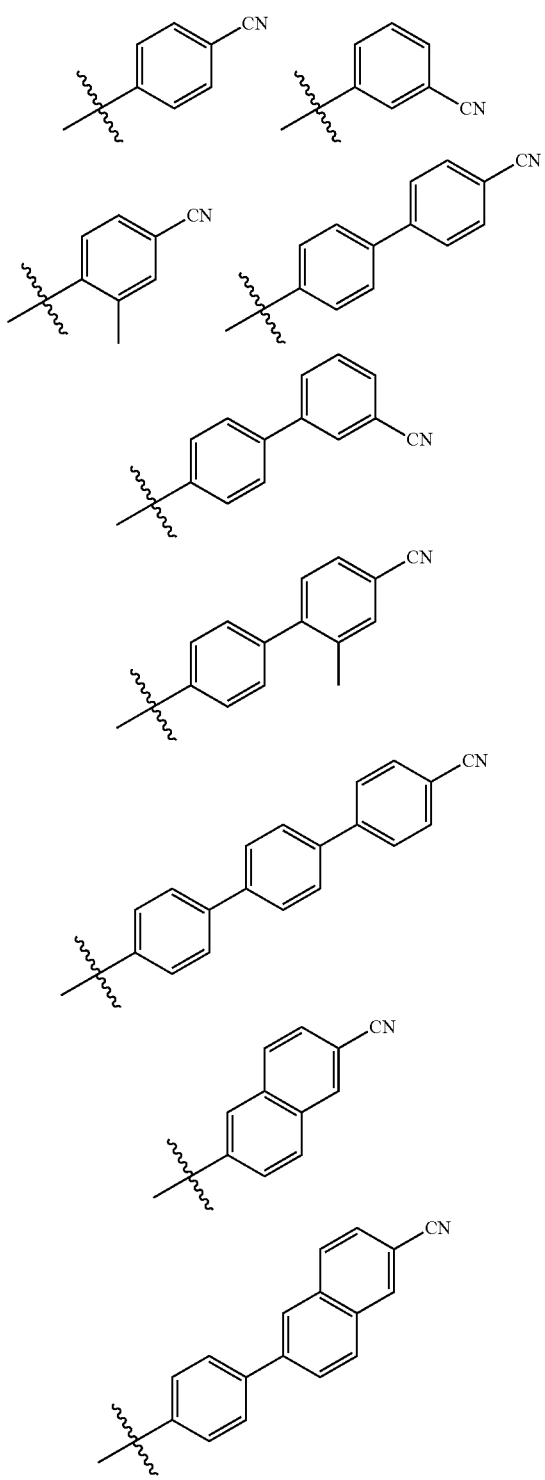

-continued

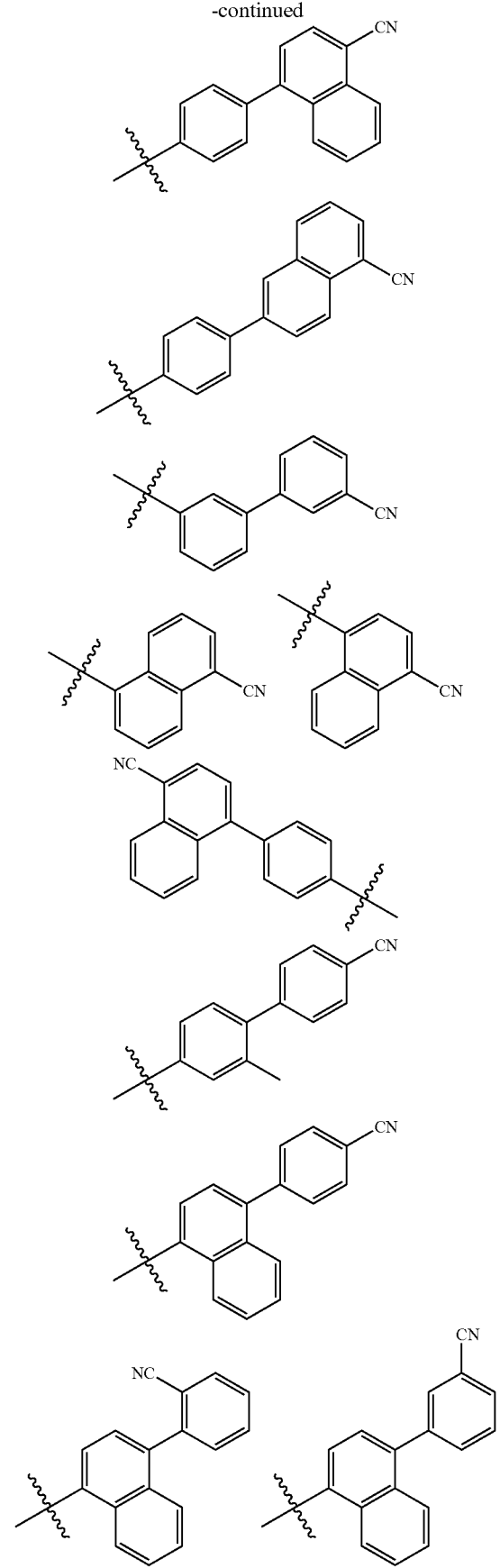

57
-continued
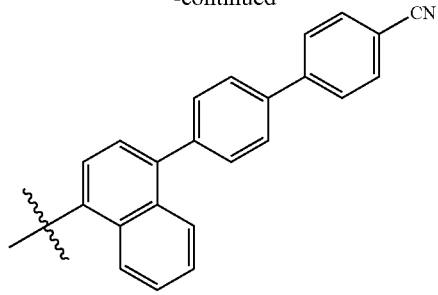
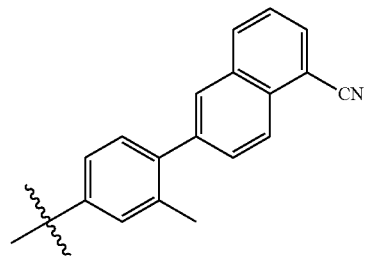
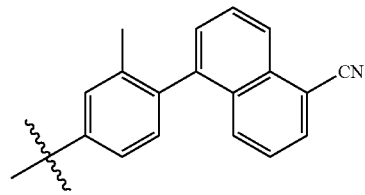
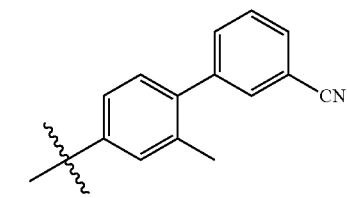
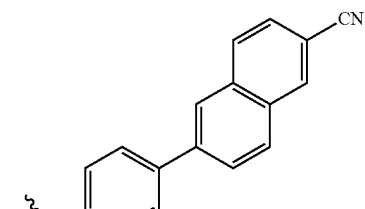
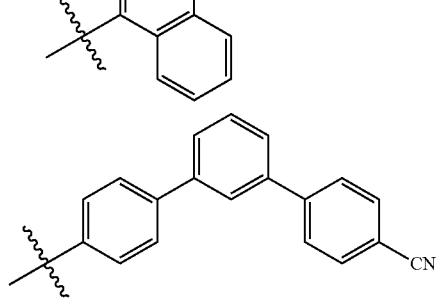
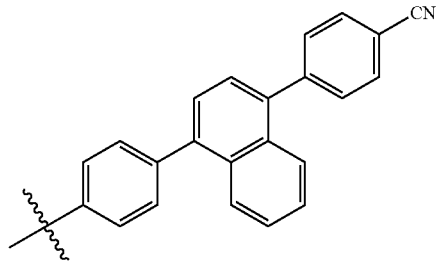
58
-continued
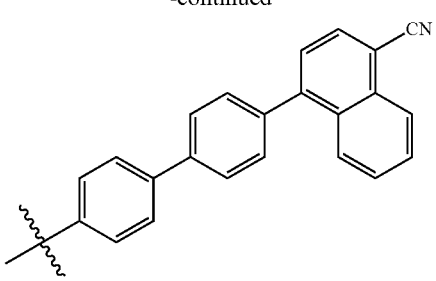
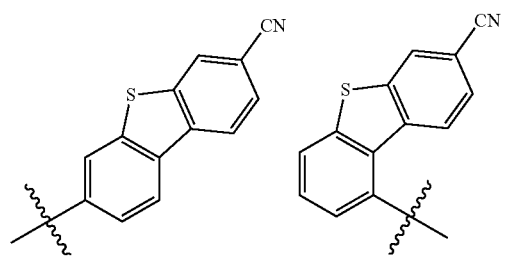
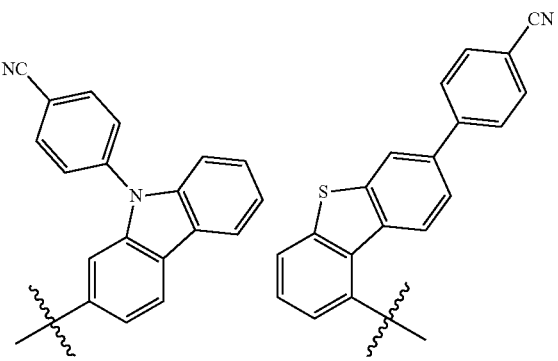
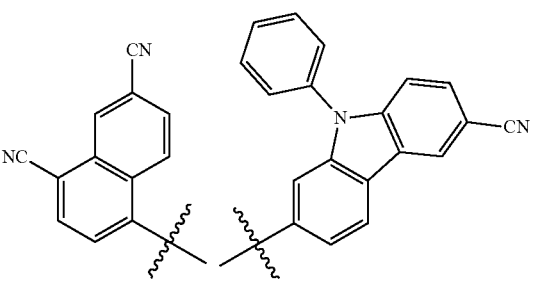
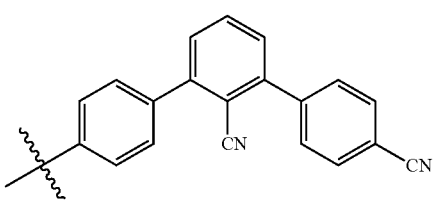
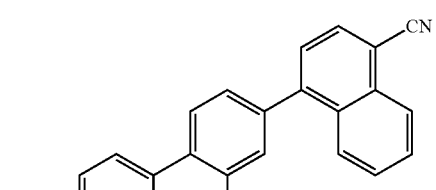
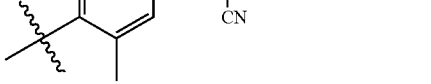

59
-continued
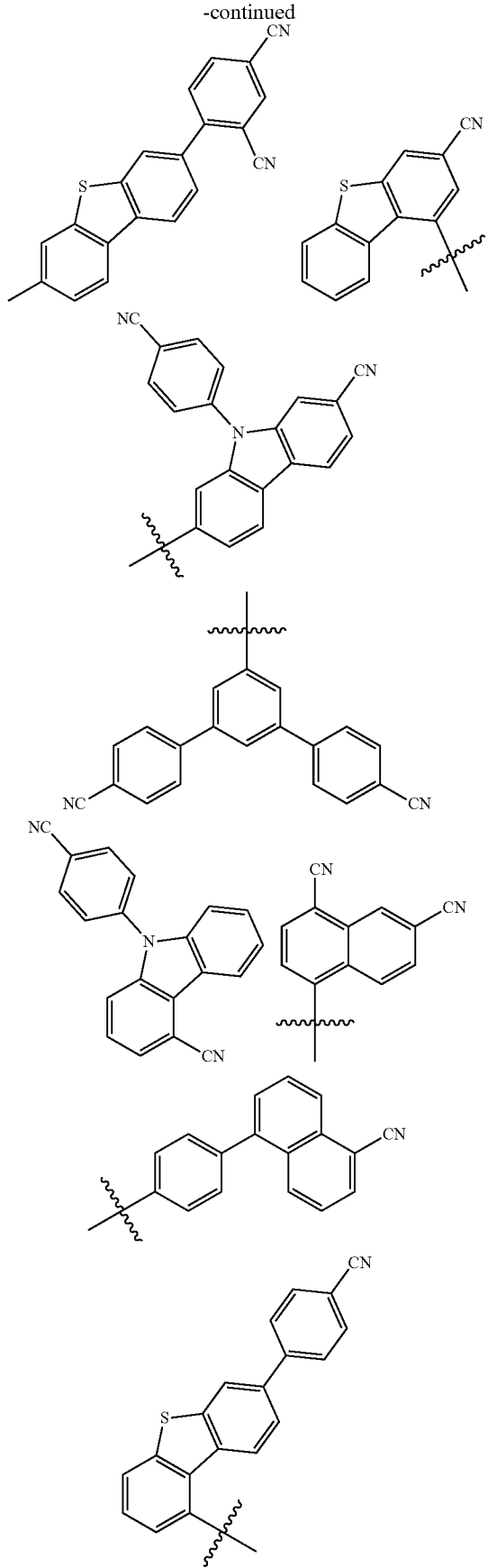
60
-continued
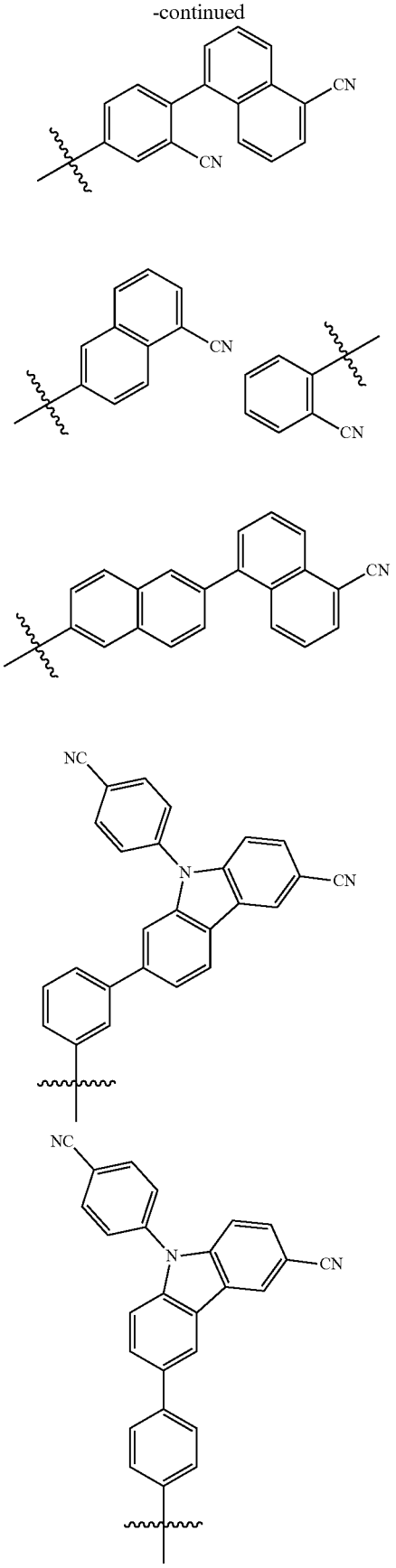

-continued
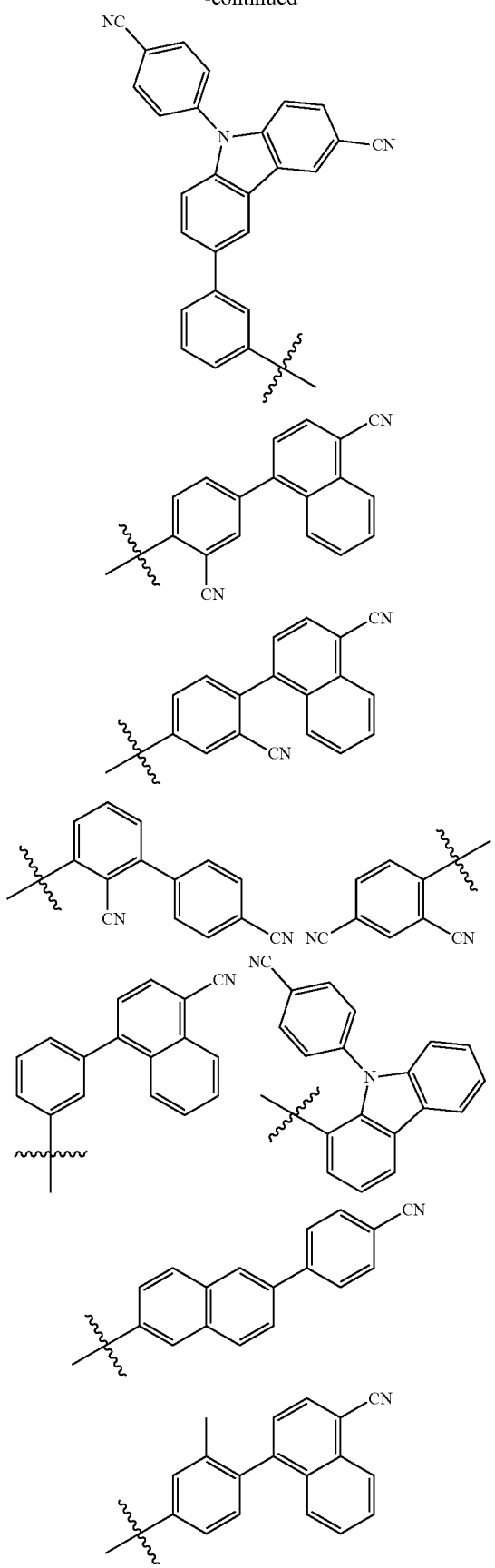
-continued
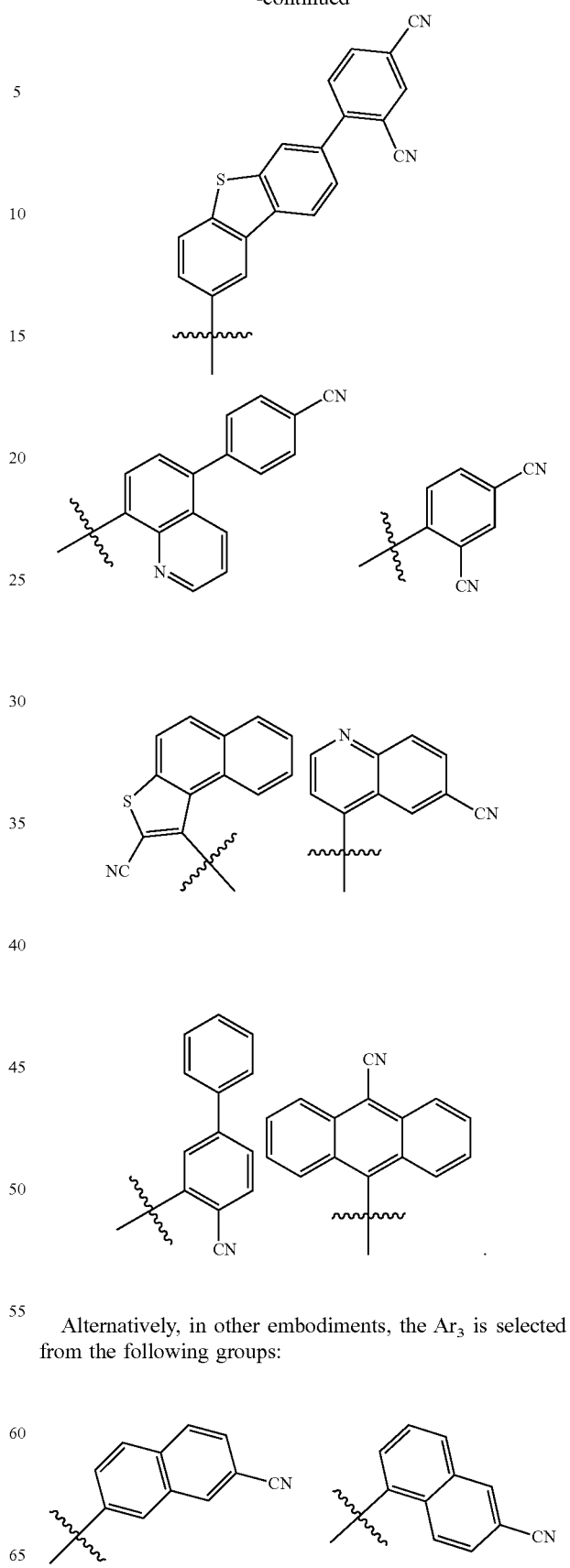
Alternatively, in other embodiments, the Ar₃ is selected from the following groups:

63
-continued
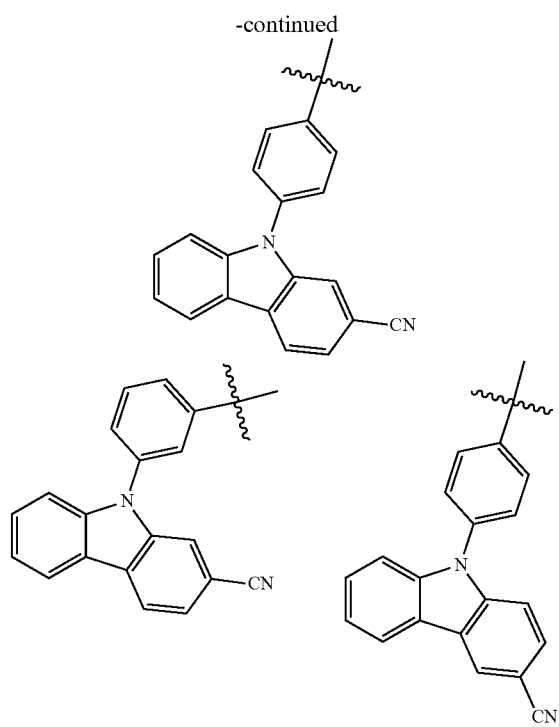
64
-continued
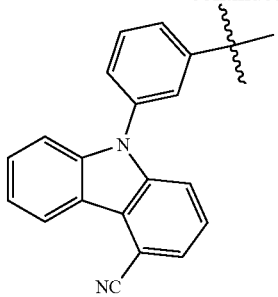
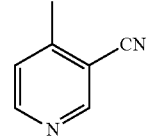
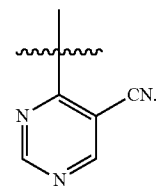
The choice of $Ar_3$ in the compound of the present disclosure is not limited to the above groups.
Optionally, the organic compound of the present disclosure is selected from the group consisting of the following compounds:
1
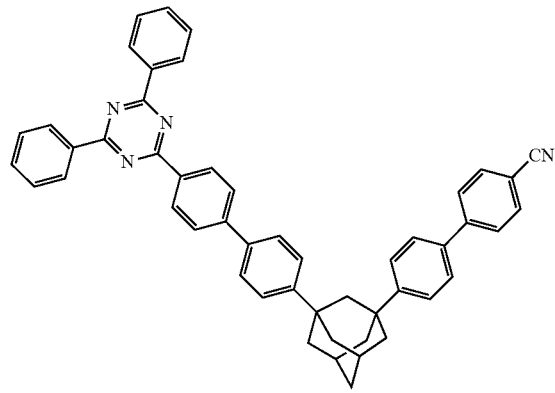
2
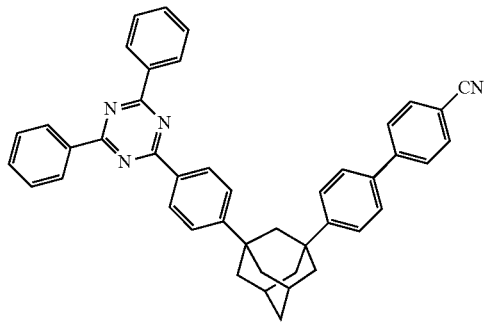
3
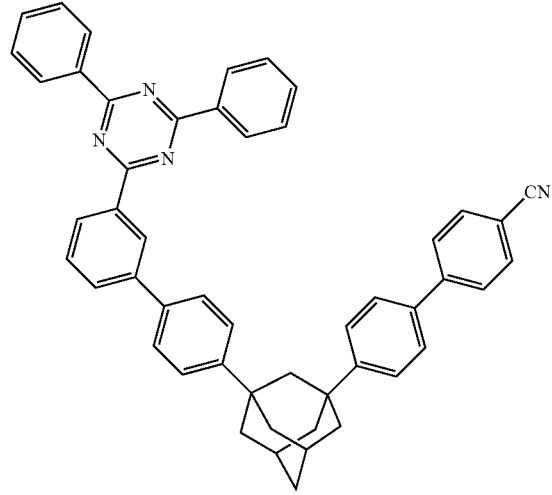
4
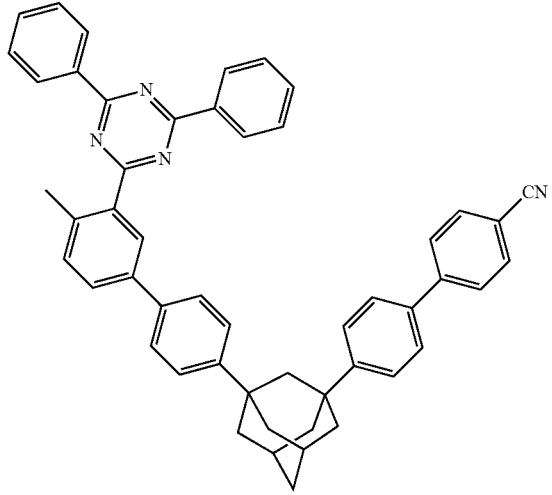

-continued
5
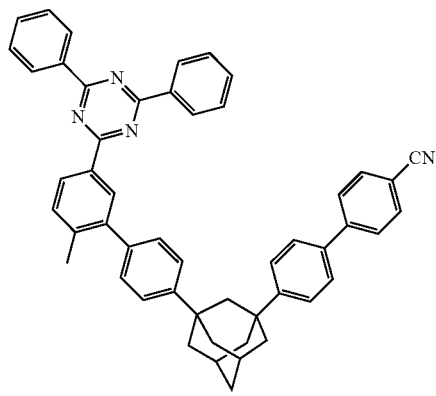
6
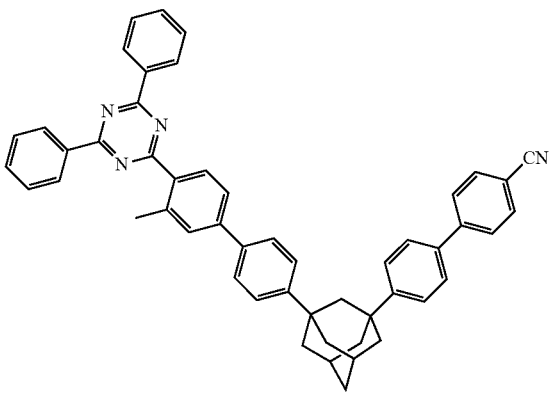
7
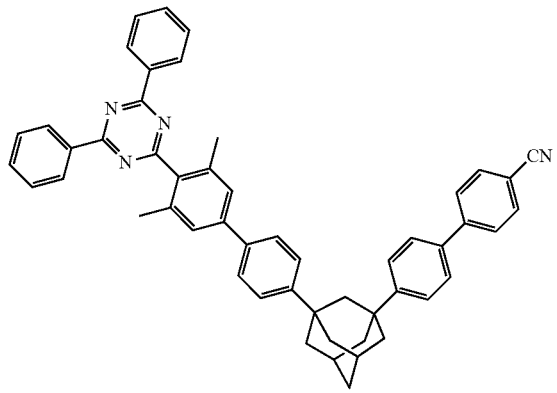
8
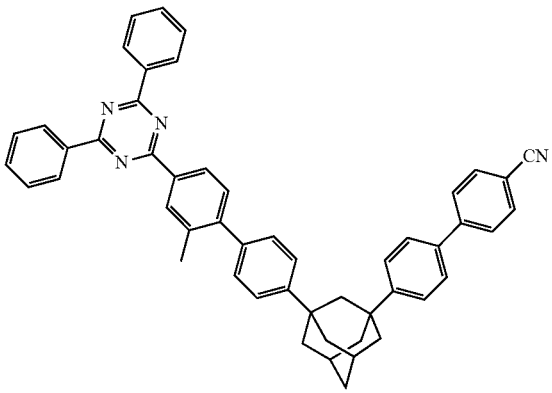
9
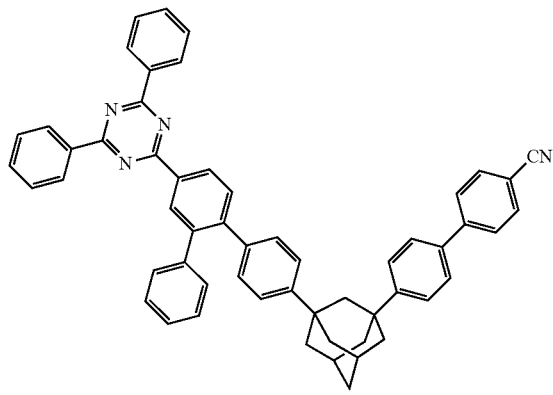
10
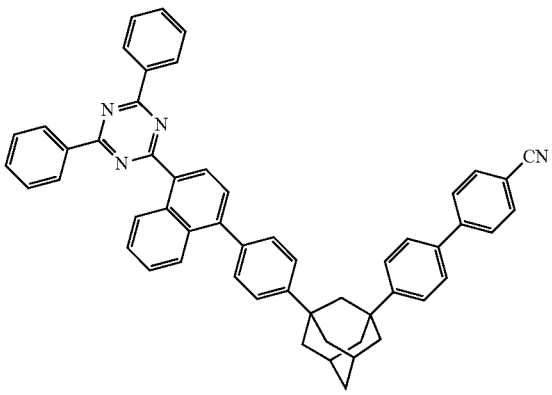
11
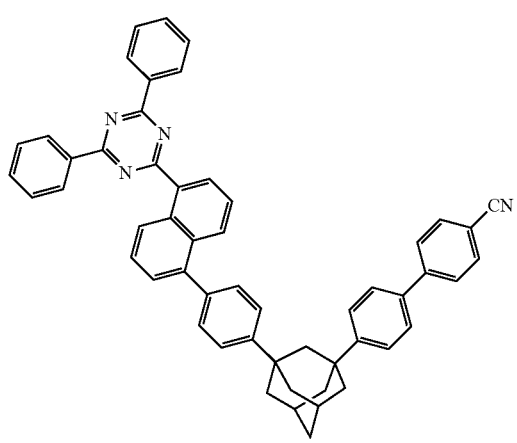
12
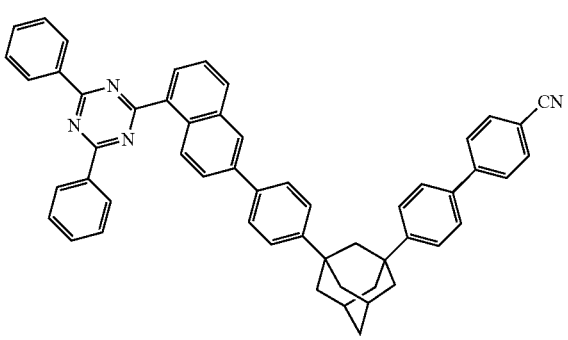

-continued
13
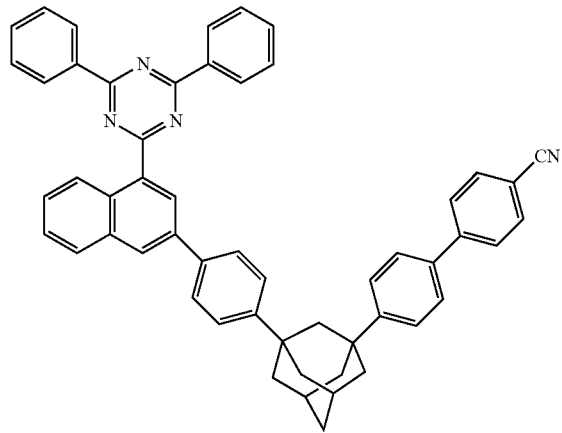
14
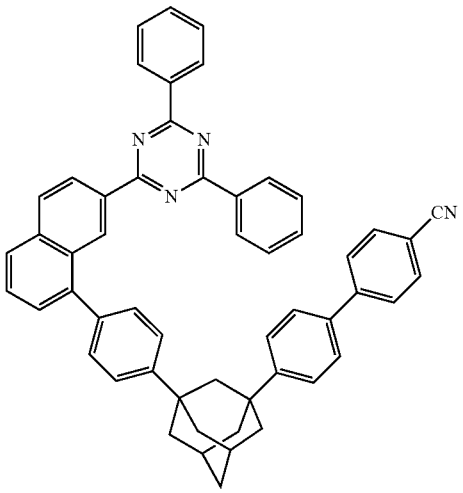
15
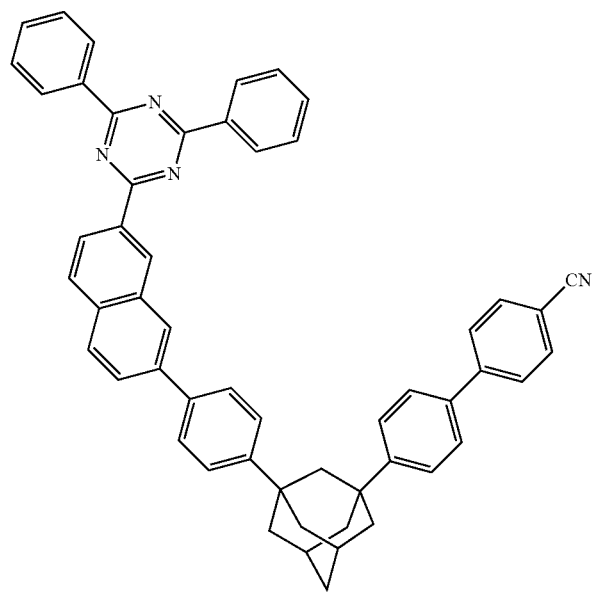
16
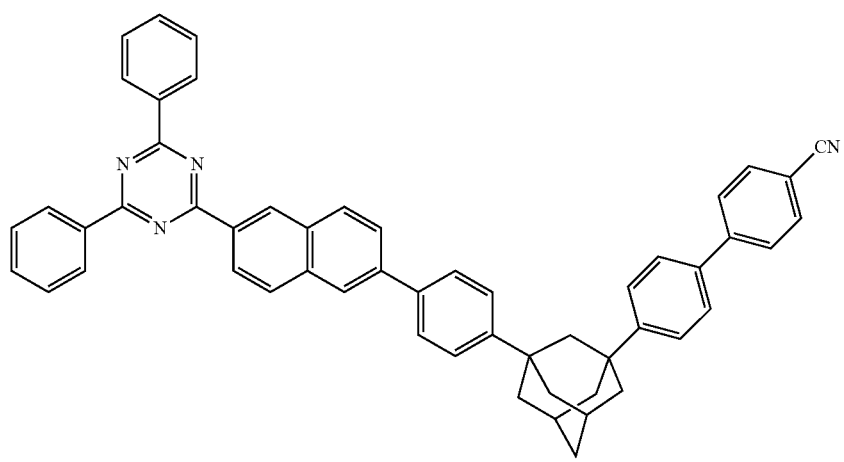

17
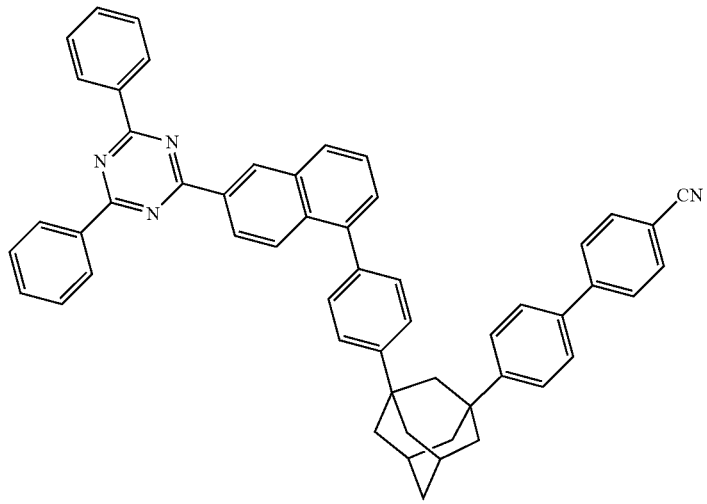
18
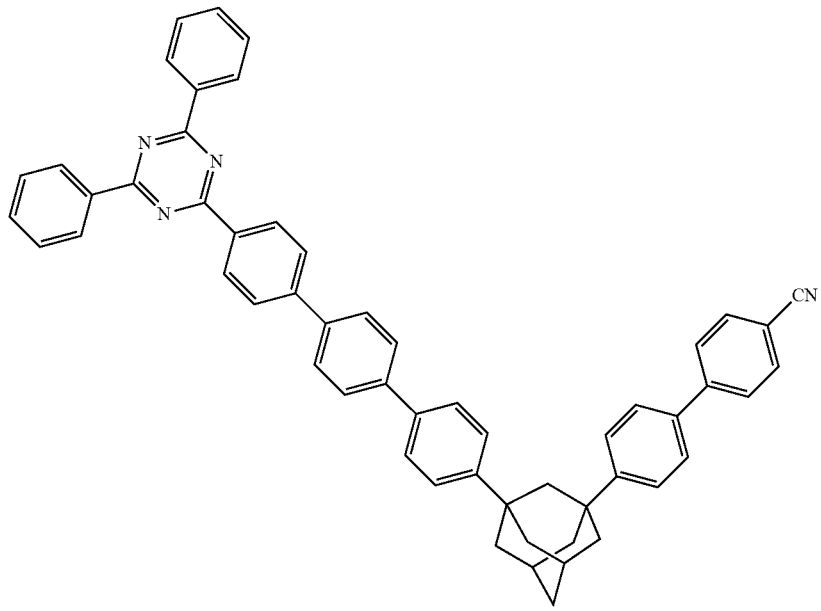
19
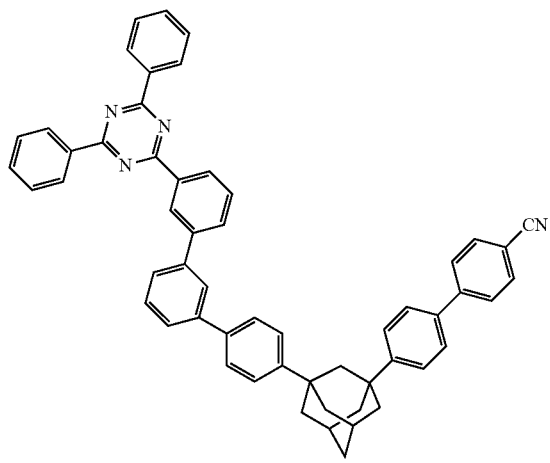
20
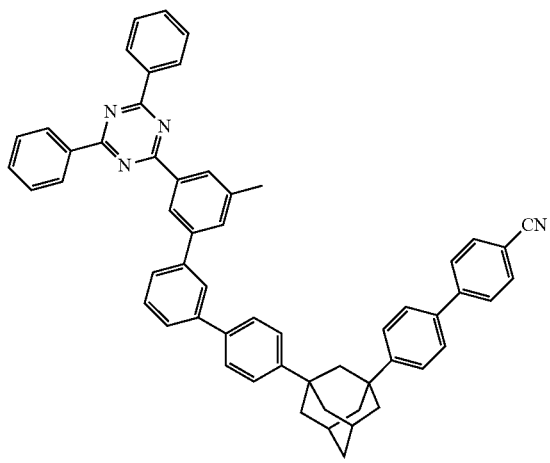

21
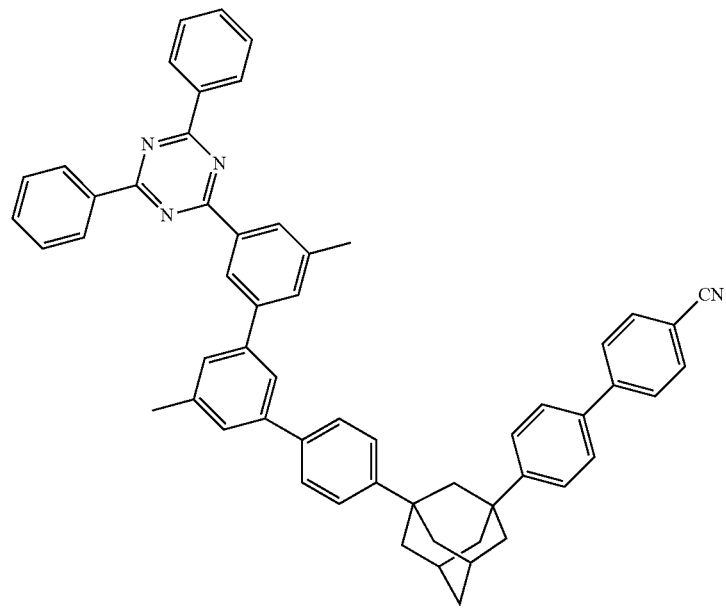
22
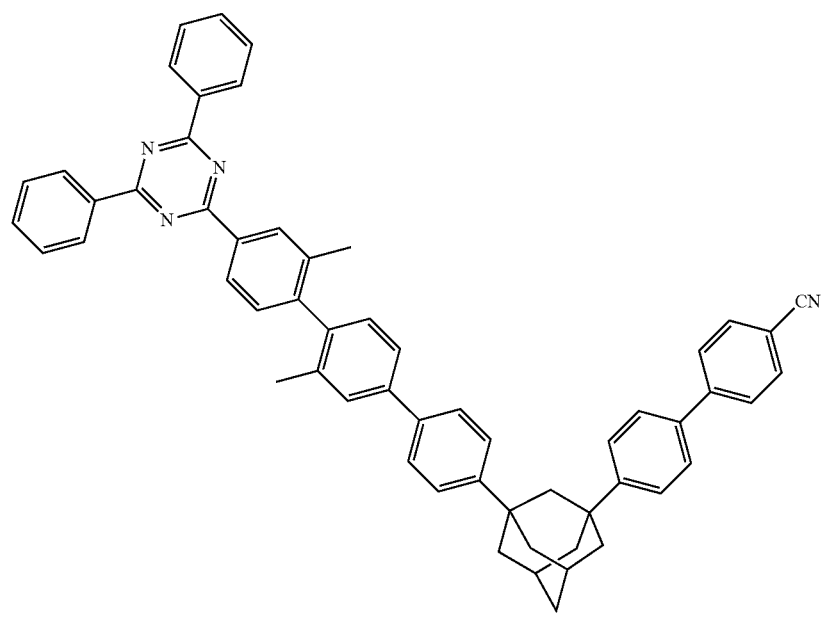

23
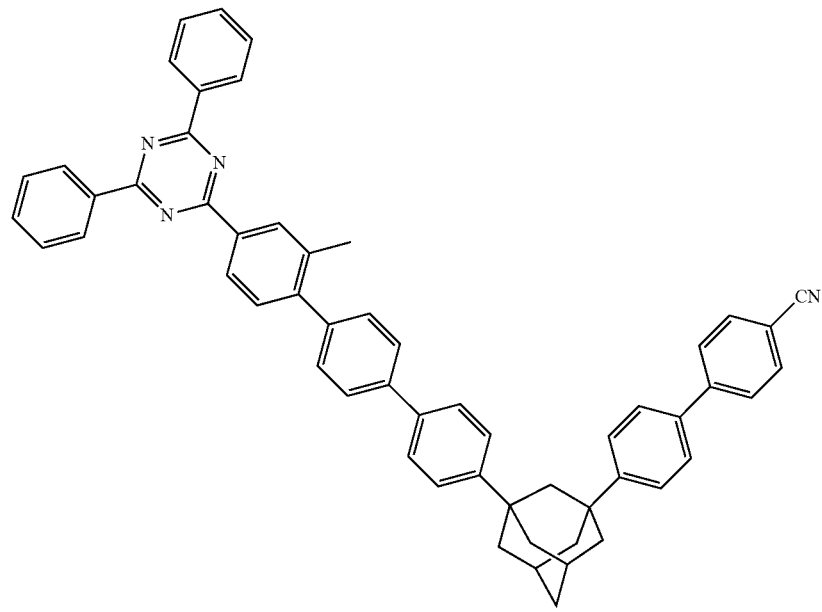
24
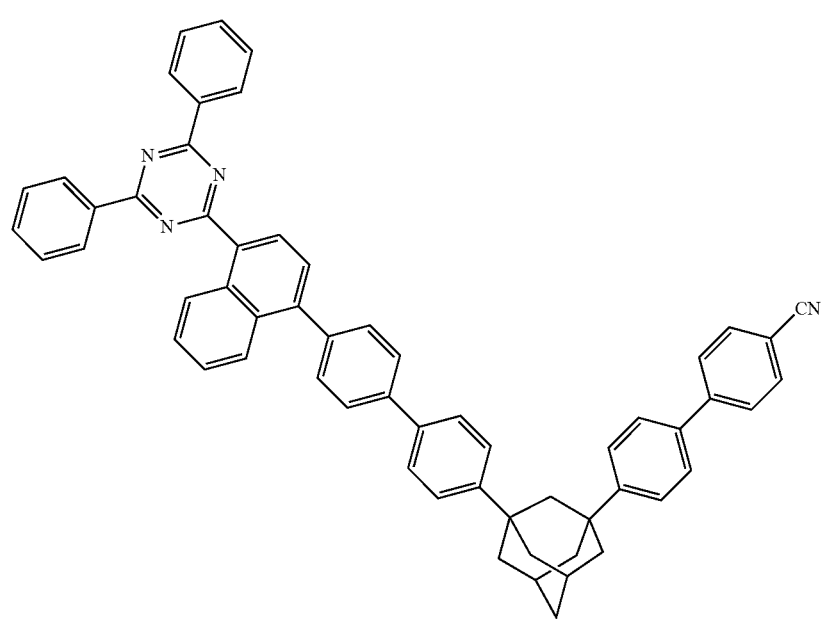

25
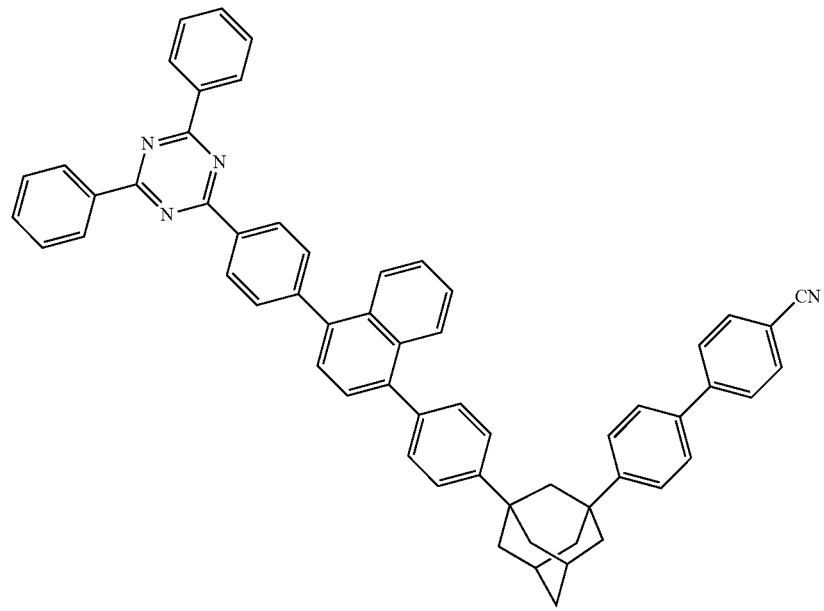
26
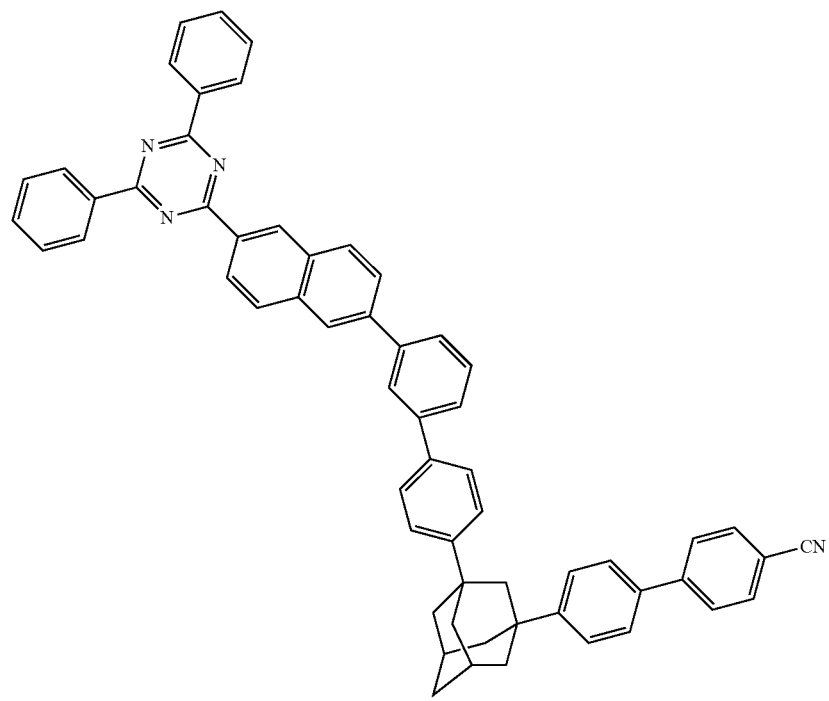

27
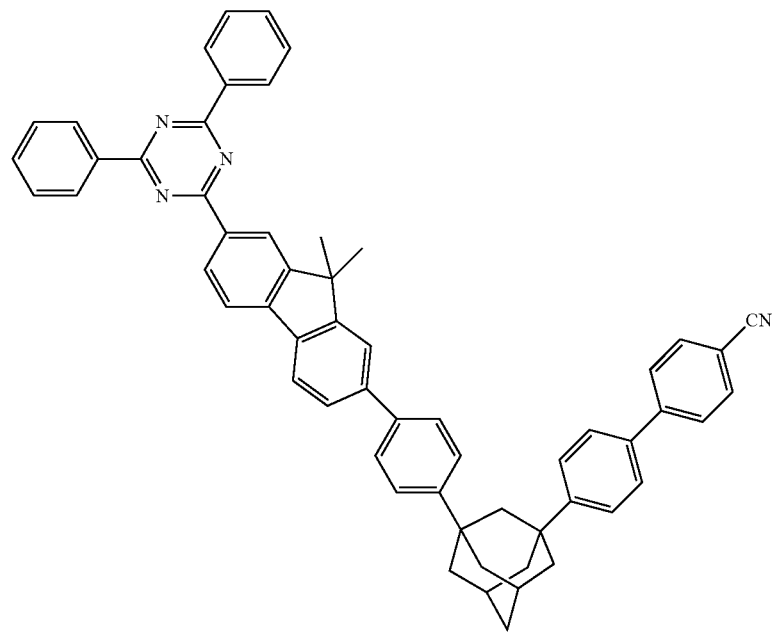
28
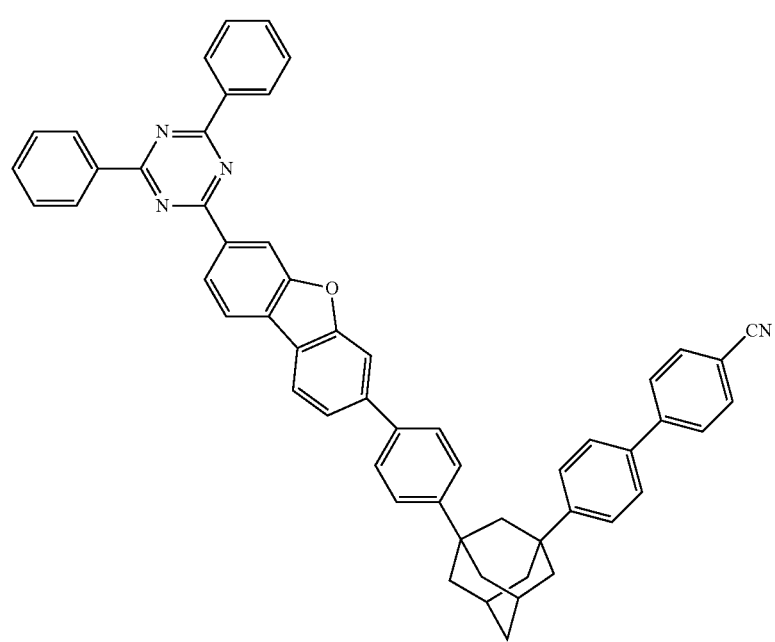

-continued
29
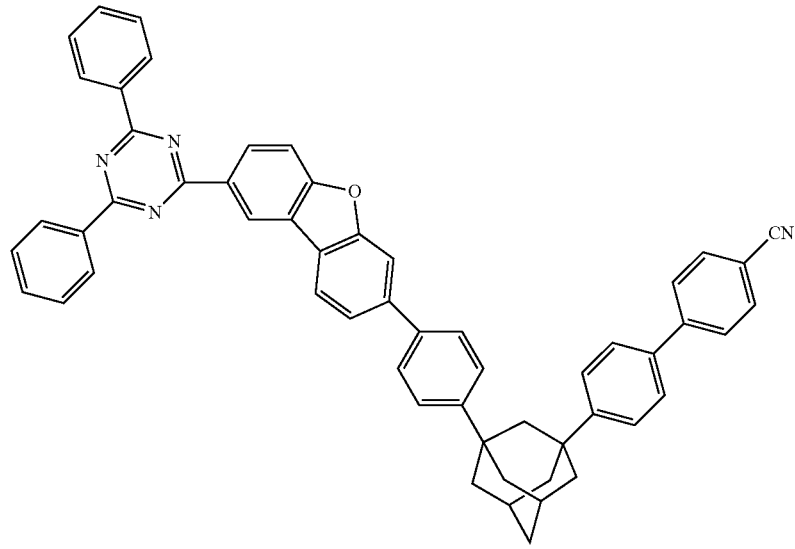
30
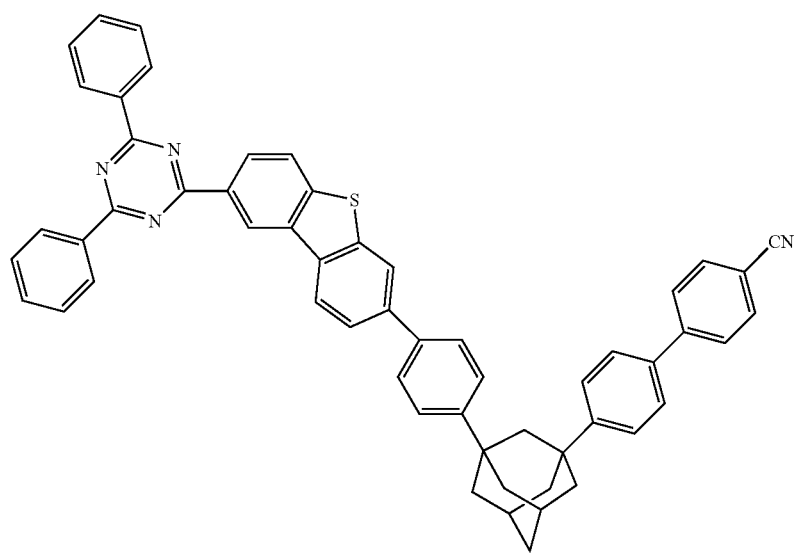

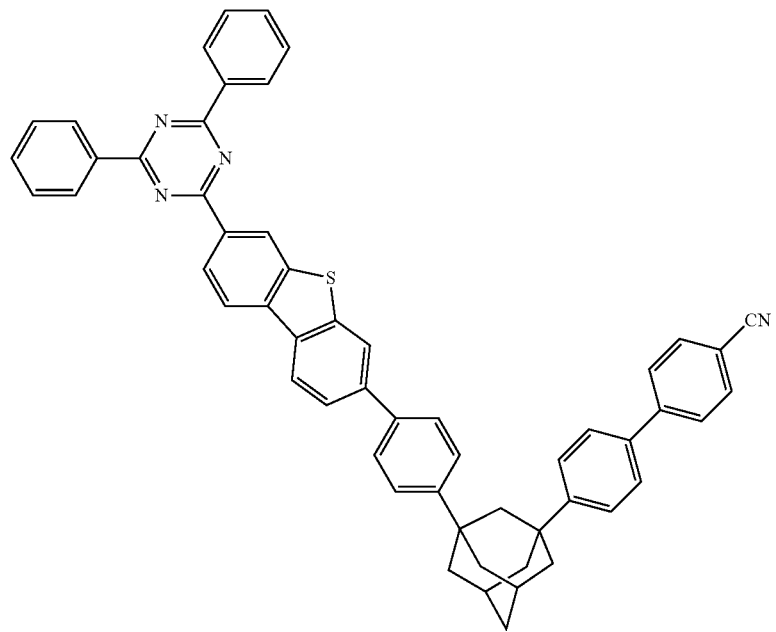
31
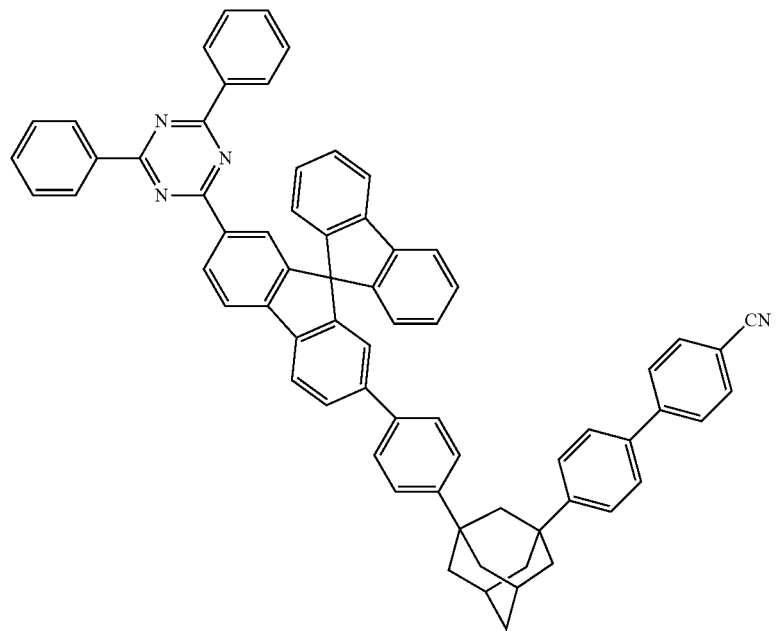
32

33
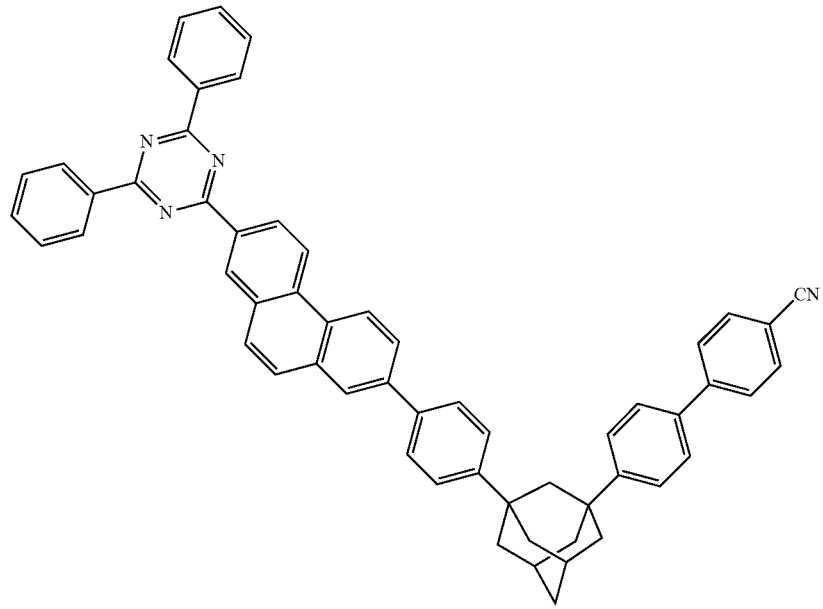
34
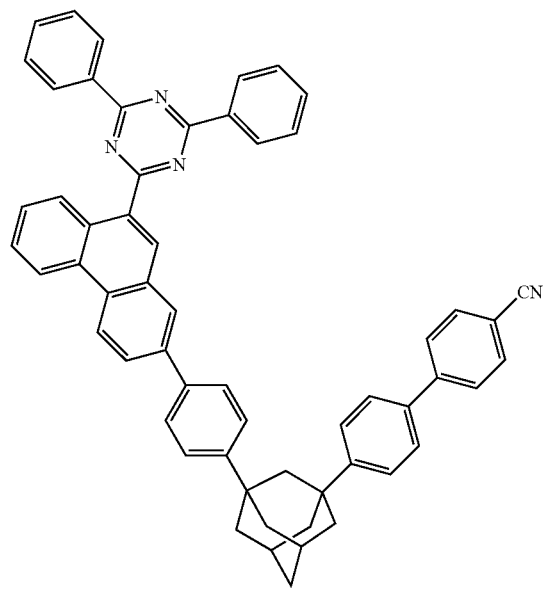
35
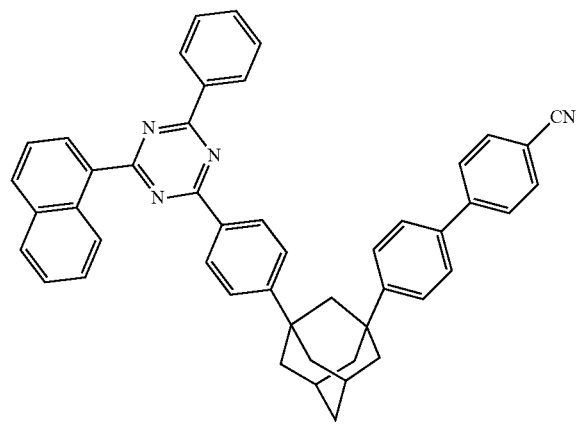
36
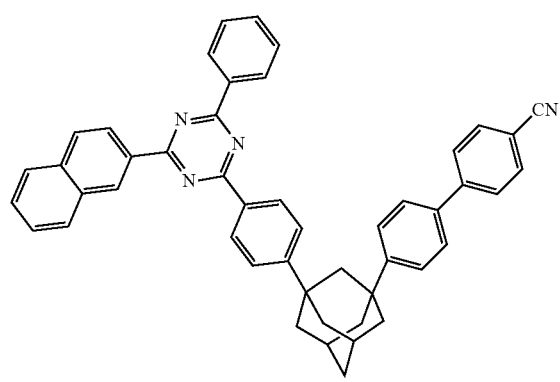
37
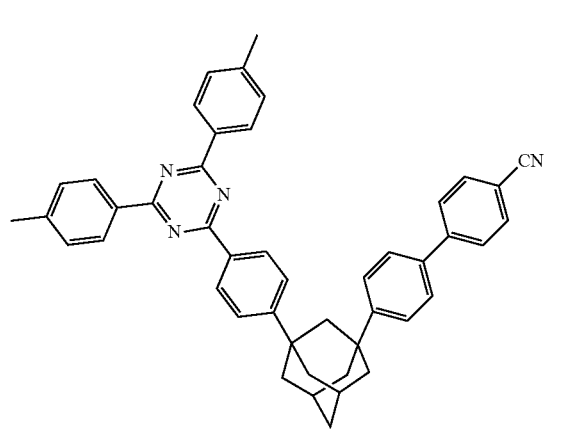

-continued
38
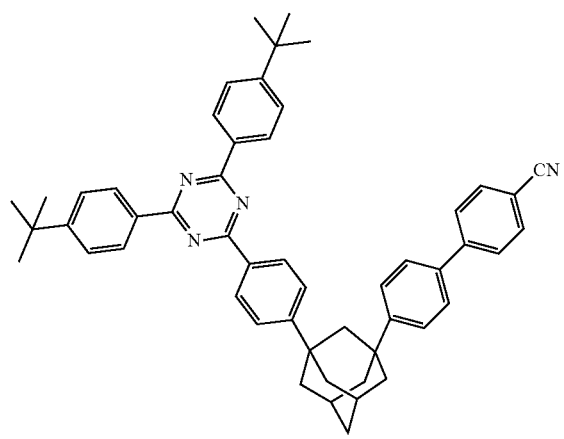
39
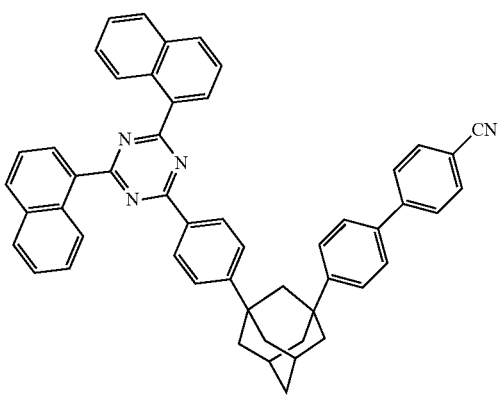
40
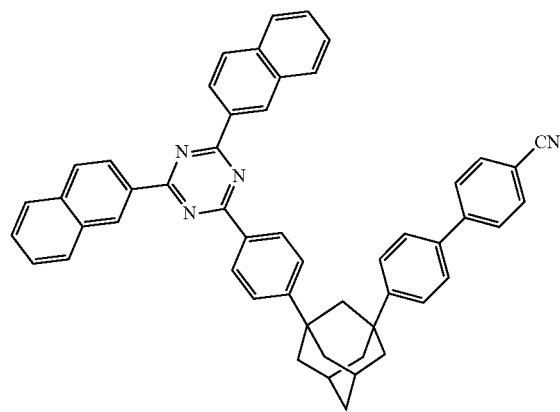
41
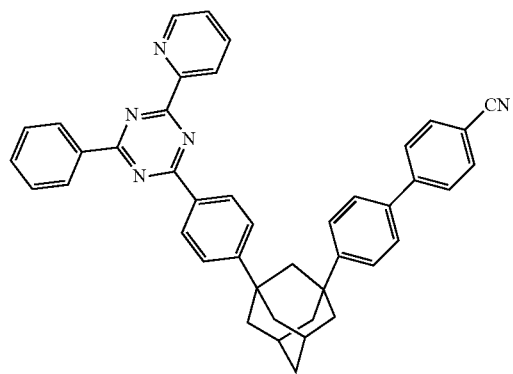
42
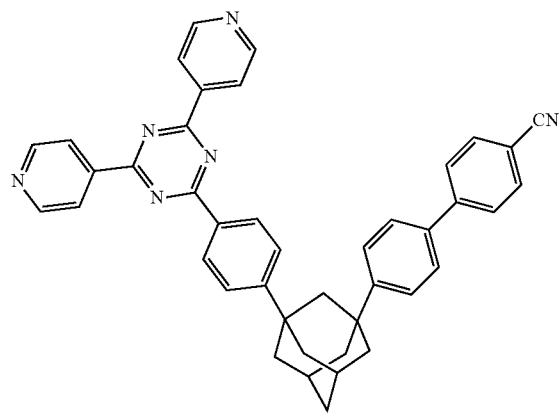
43
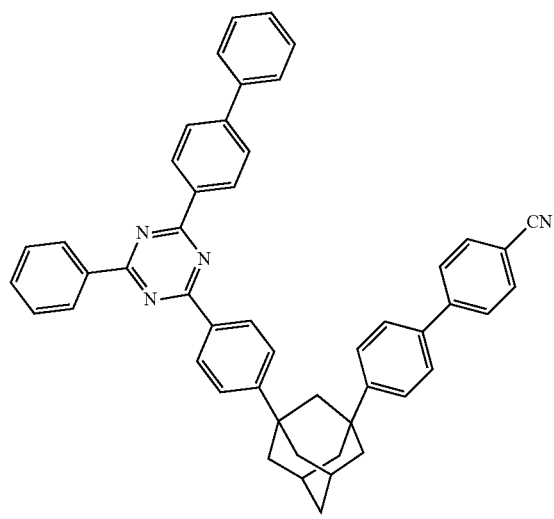

-continued
44
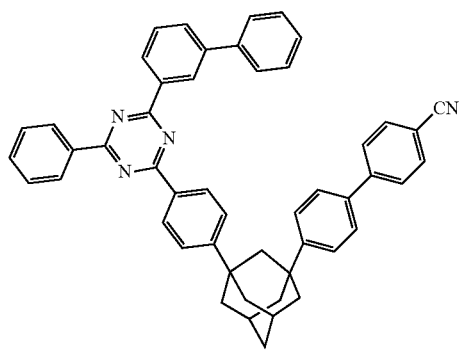
45
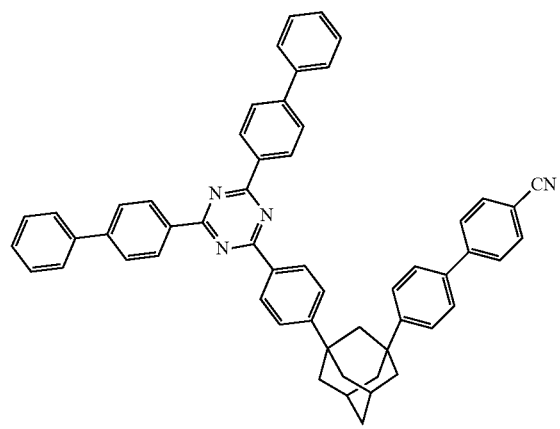
46
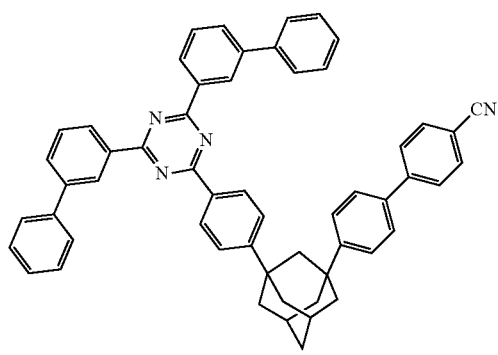
47
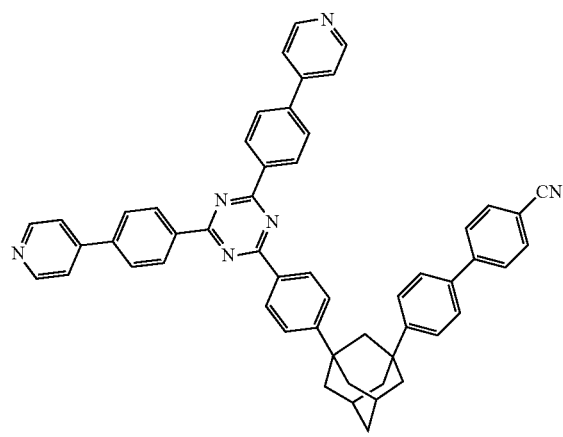
48
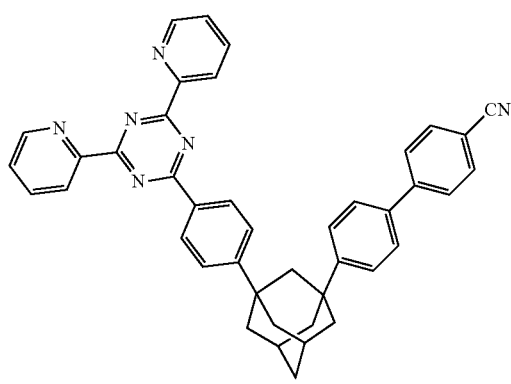
49
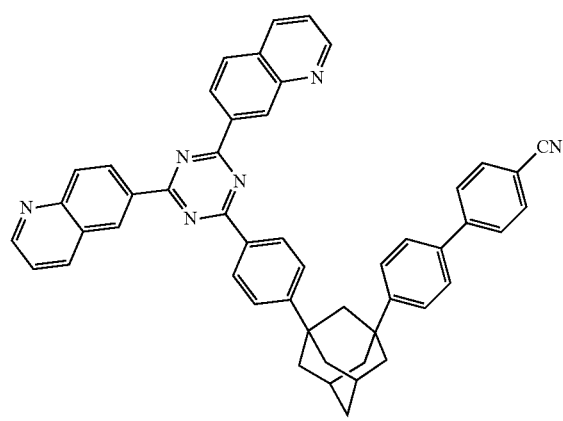

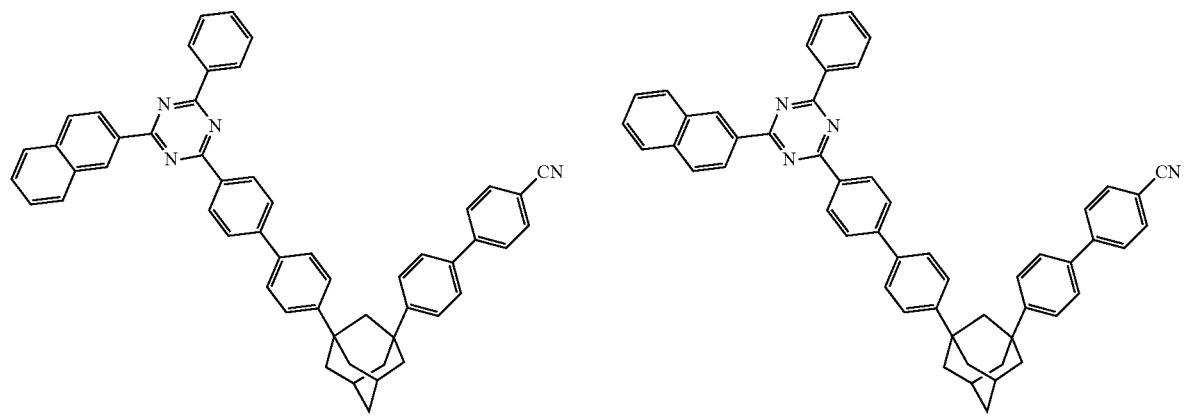
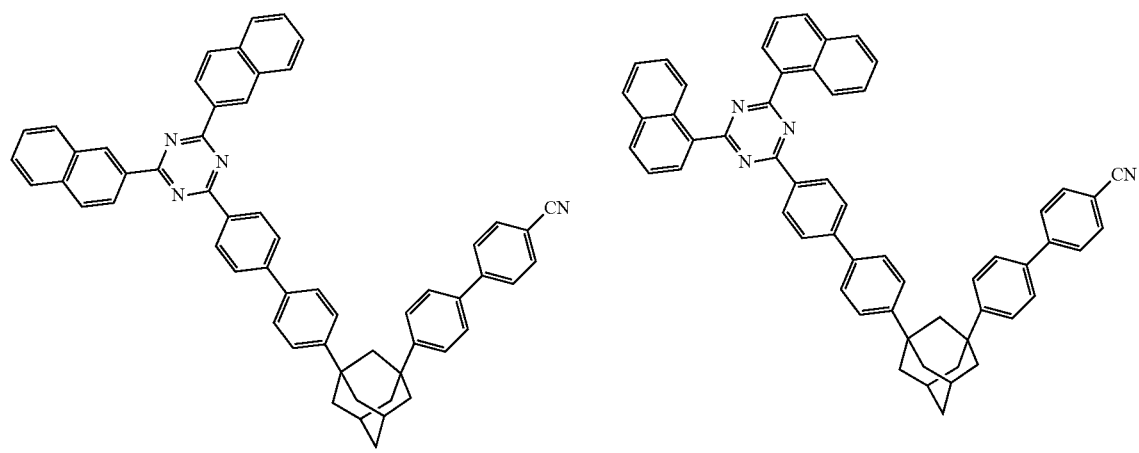
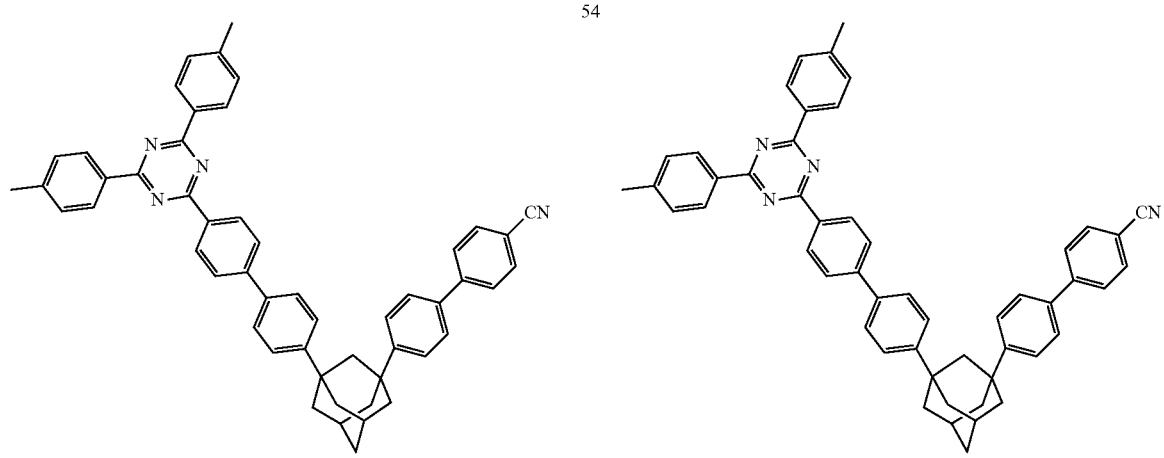

-continued
56
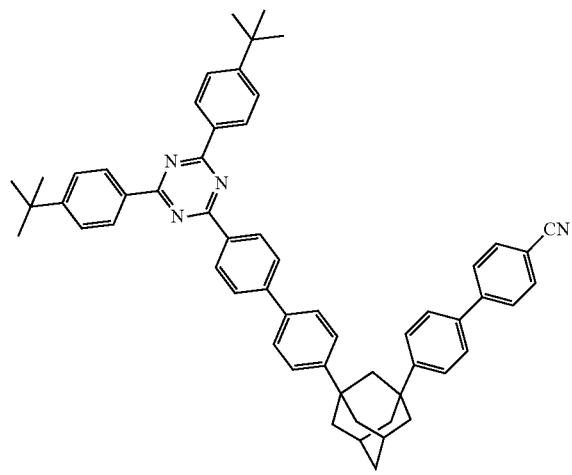
57
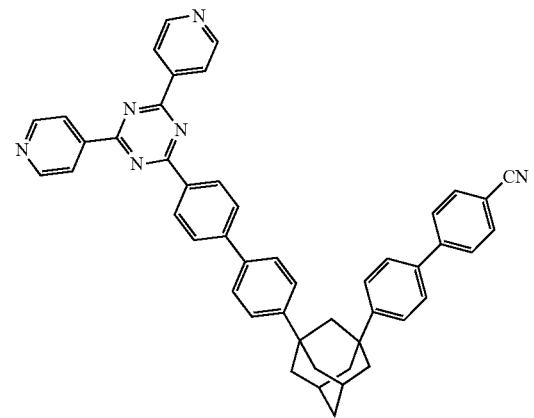
58
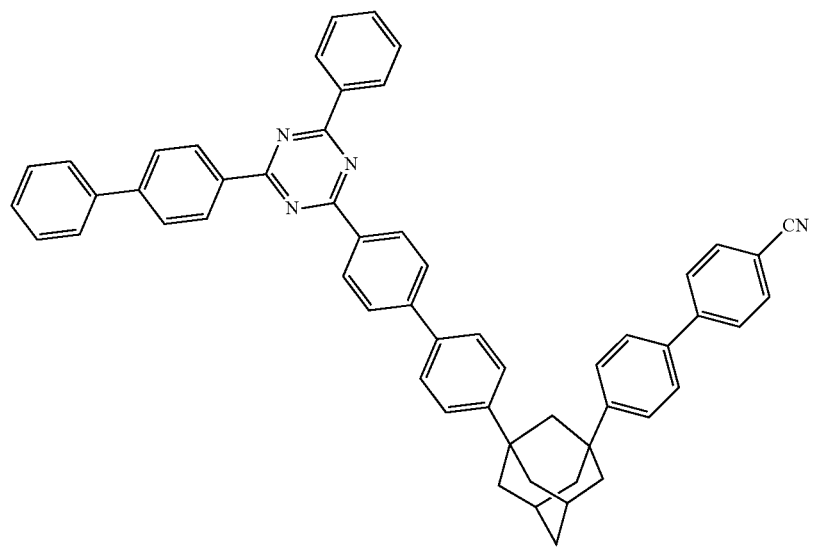
59
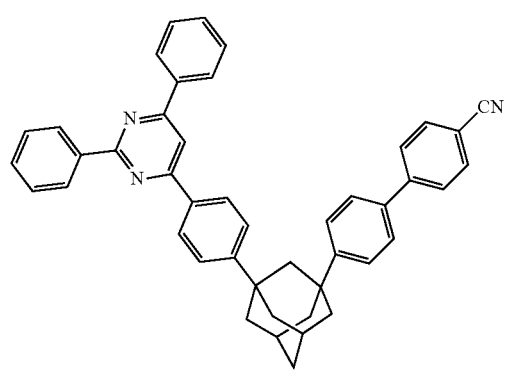
60
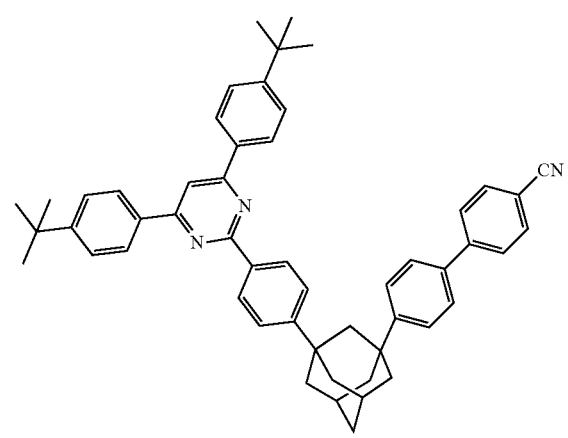

-continued
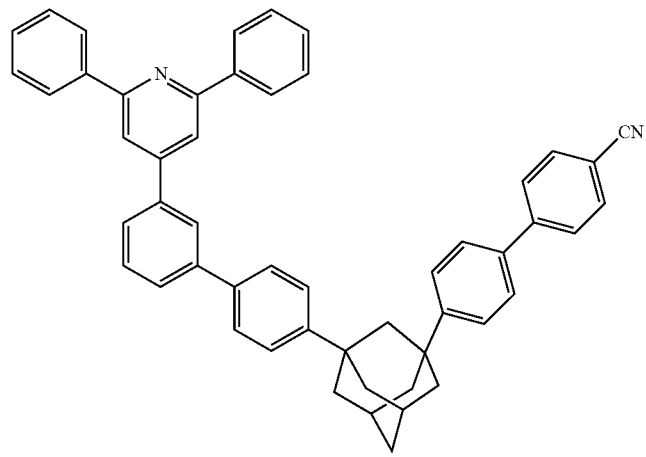
61
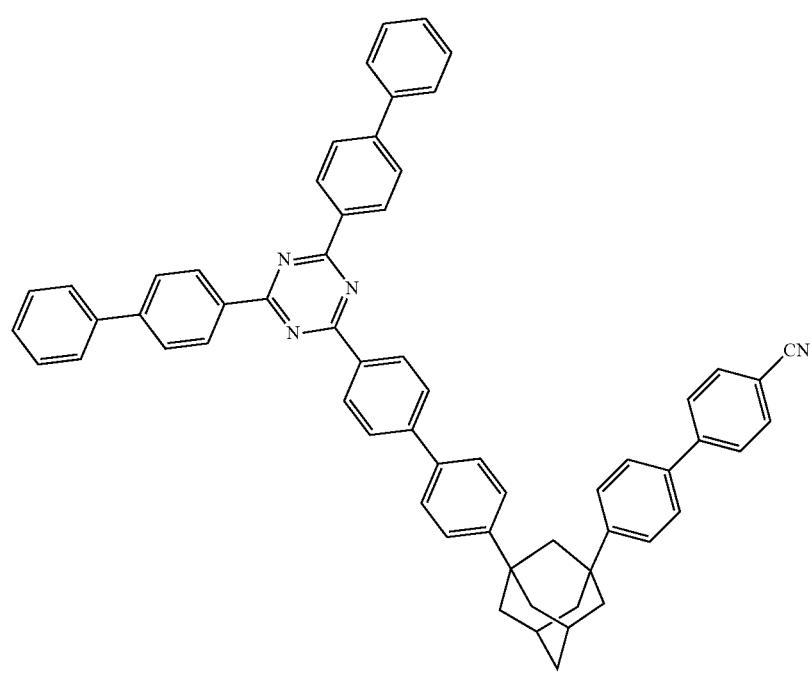
62

63
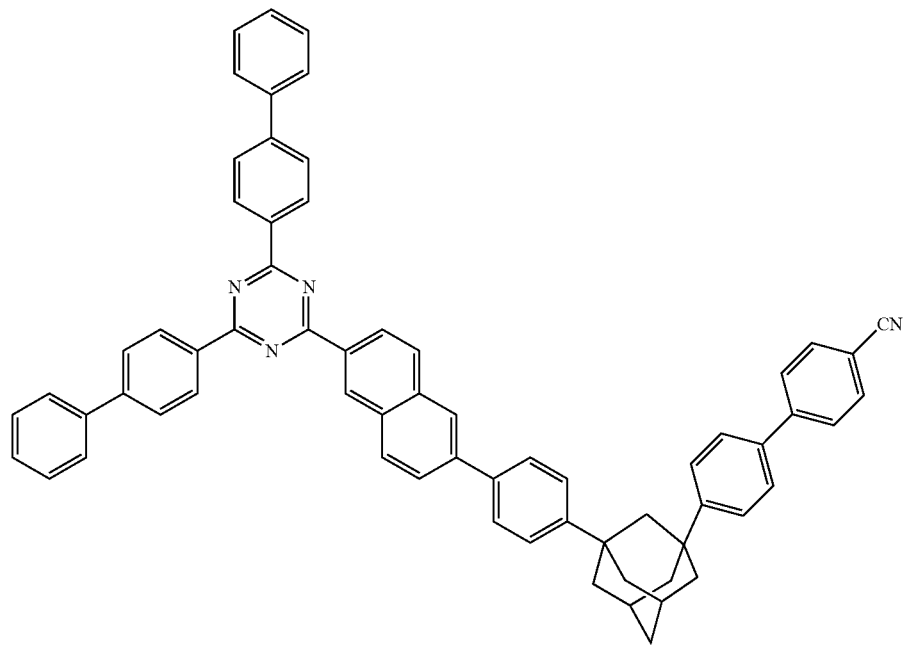
64
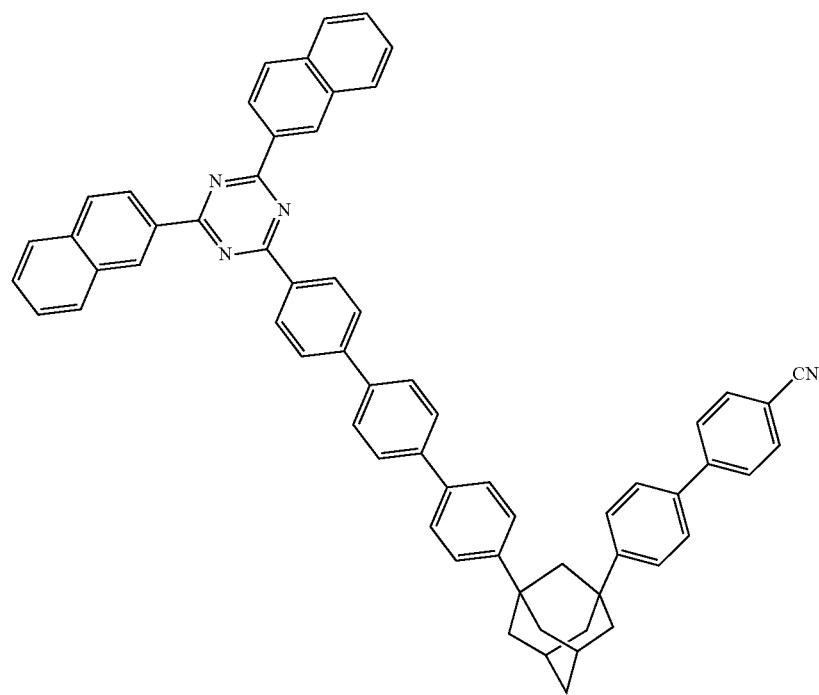

-continued
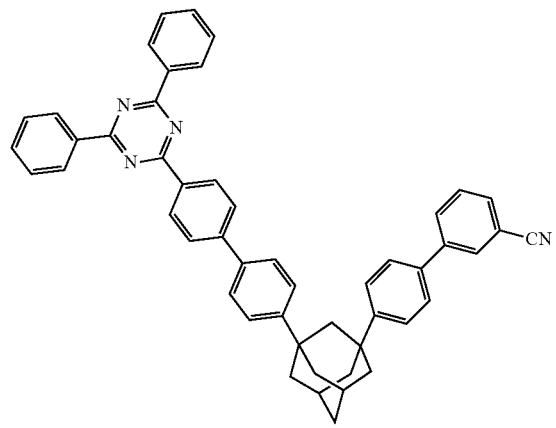
65
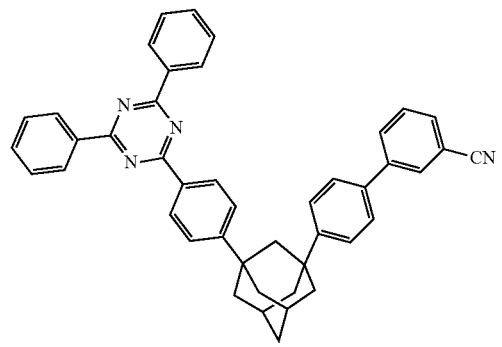
66
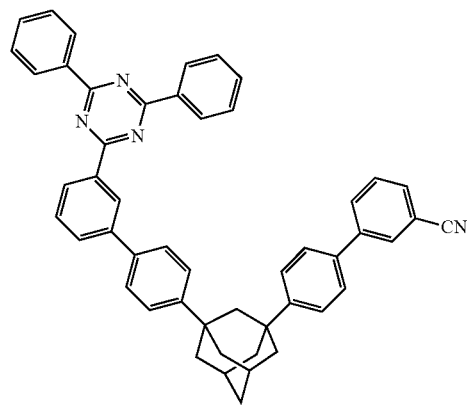
67
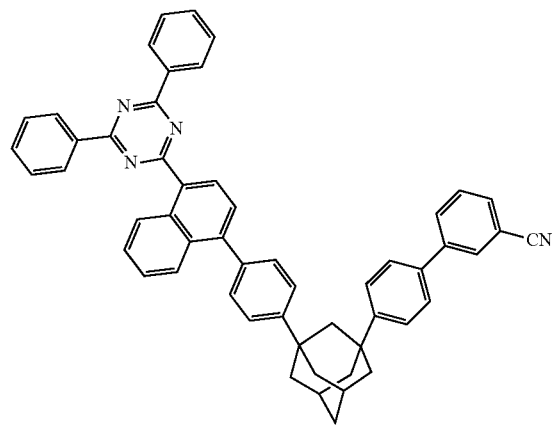
68
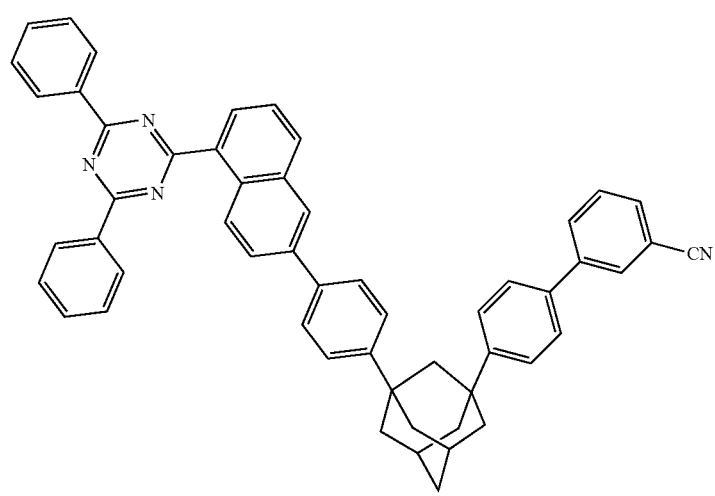
69

-continued
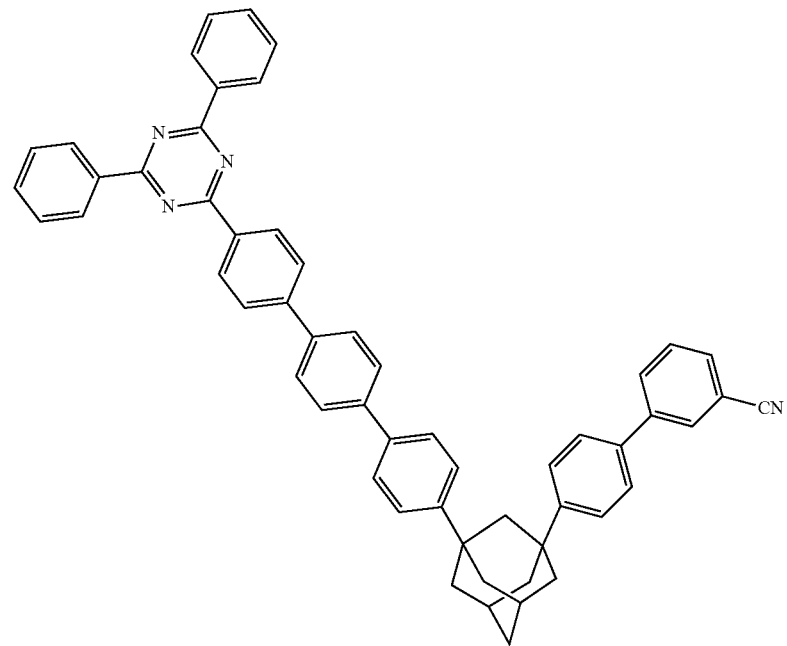
70
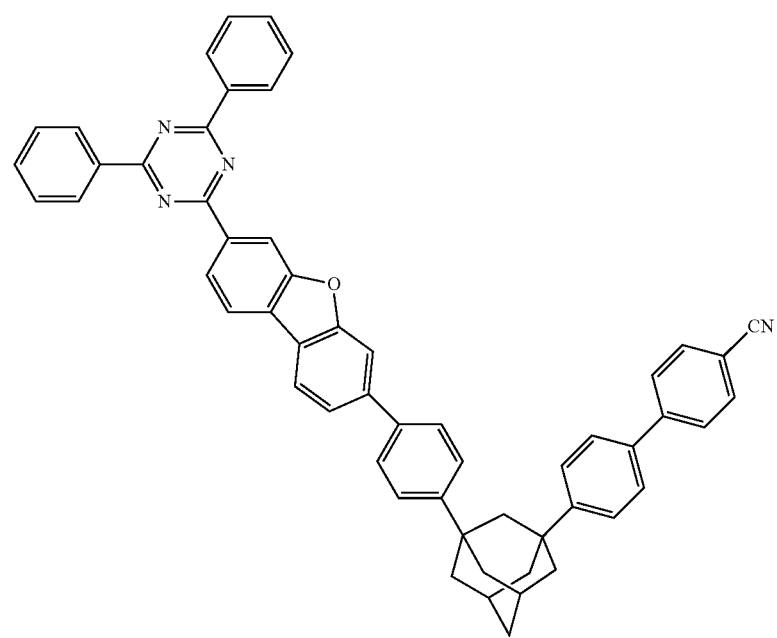
71

-continued
72
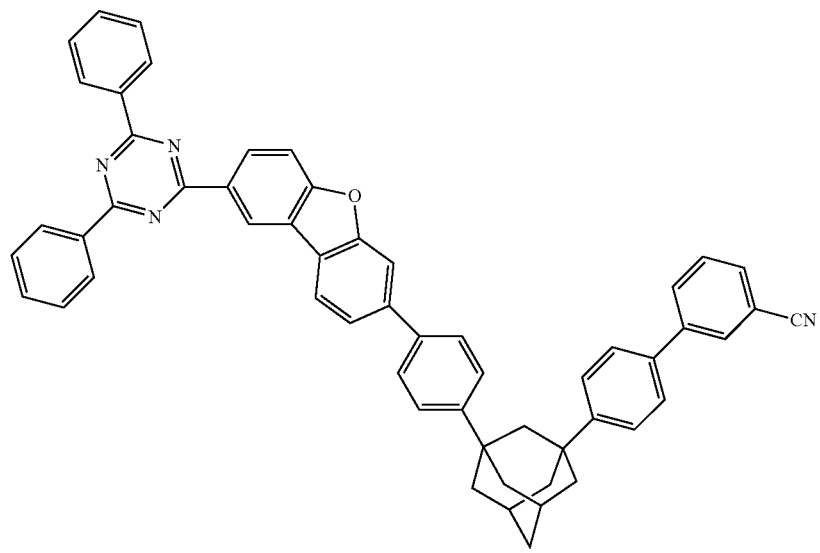
73
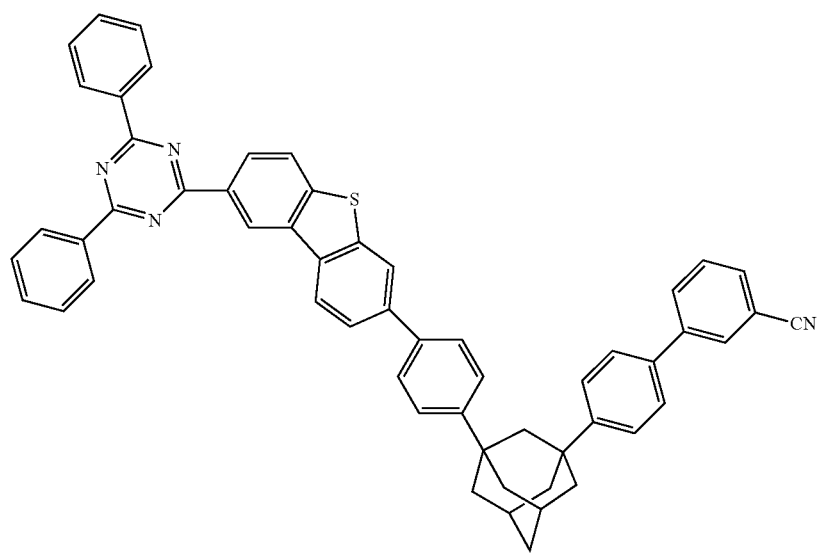

74
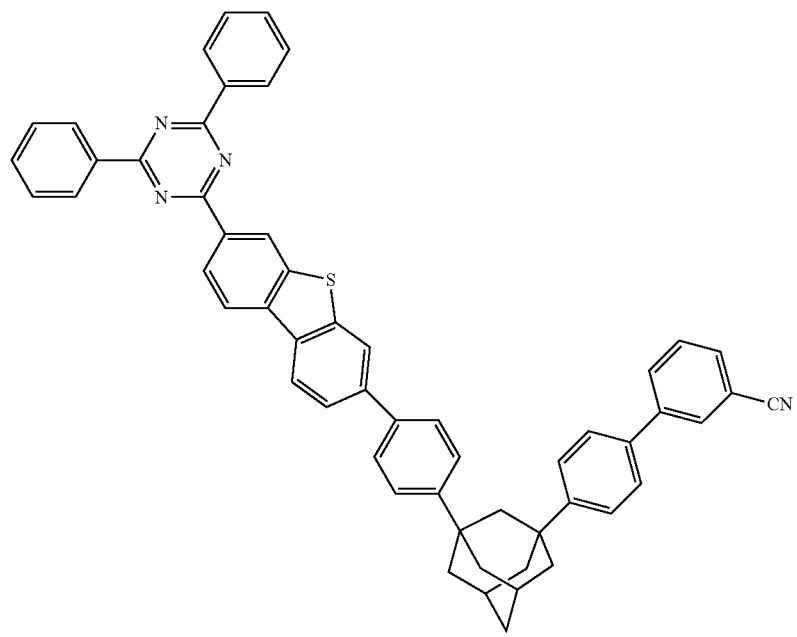
75
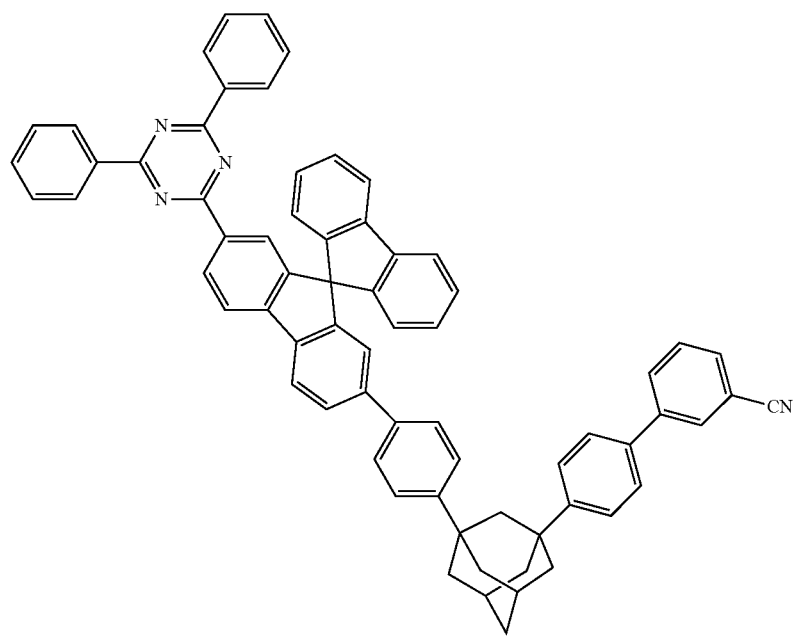

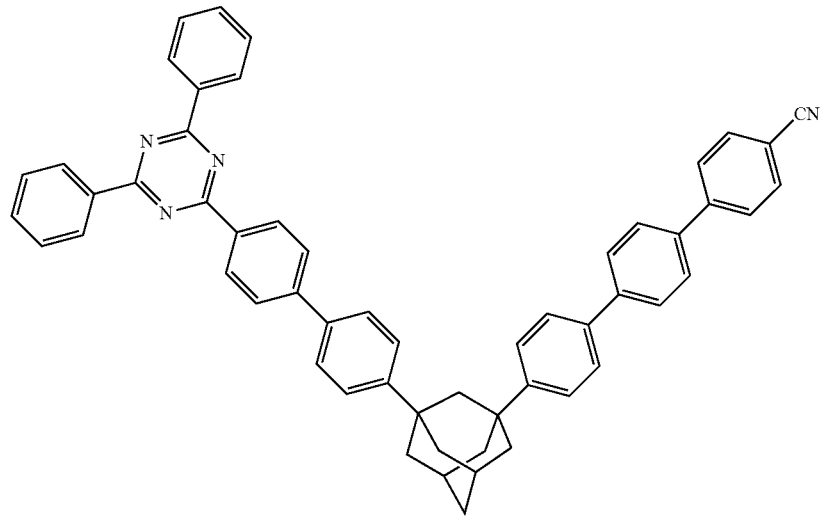
76
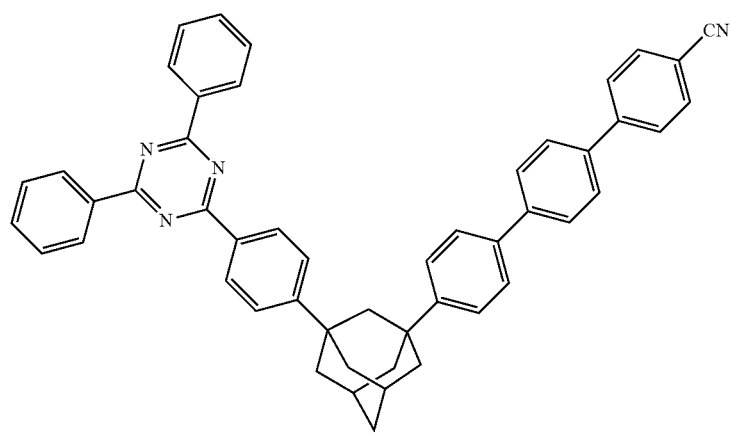
77
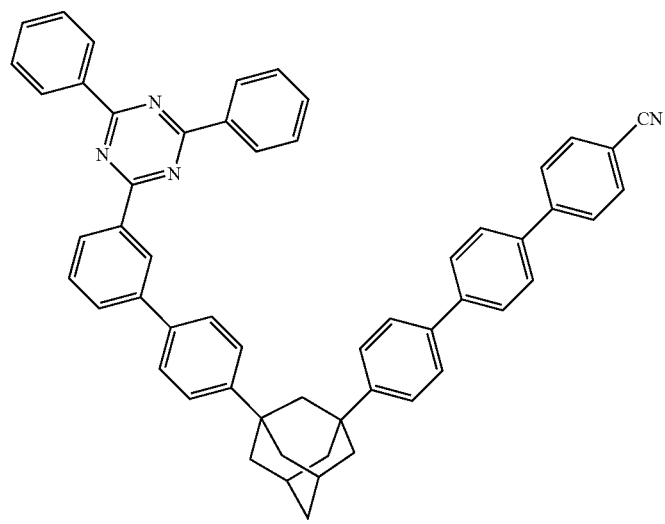
78

79
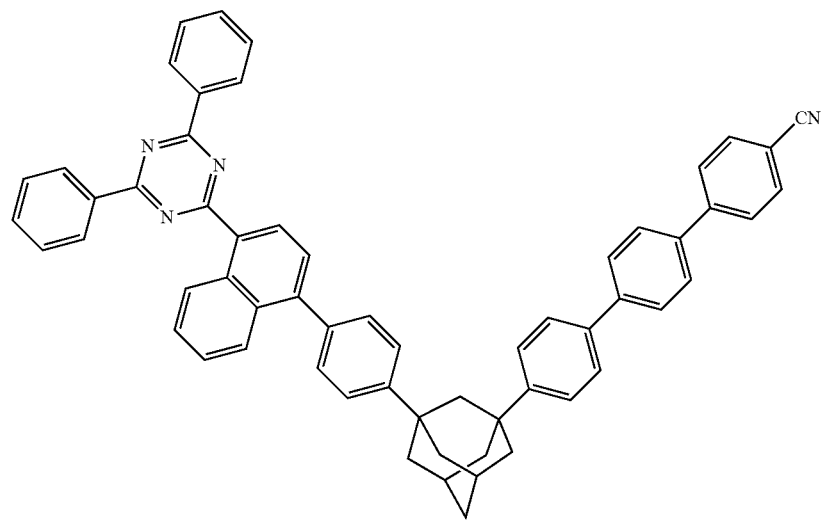
80
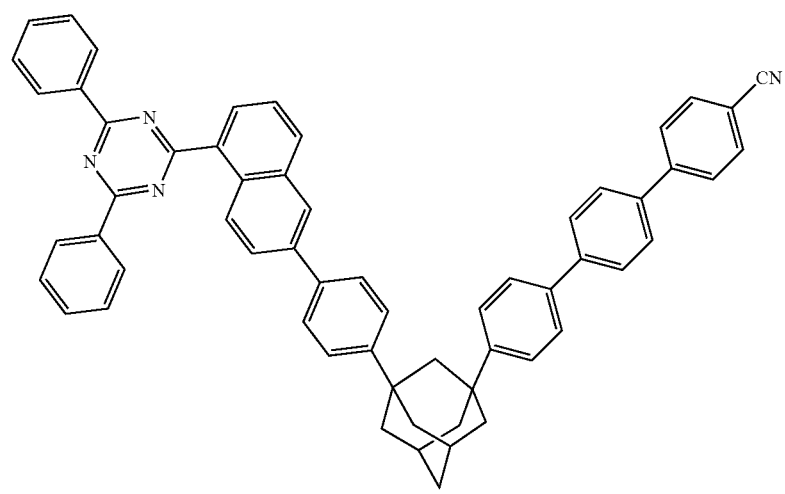
81
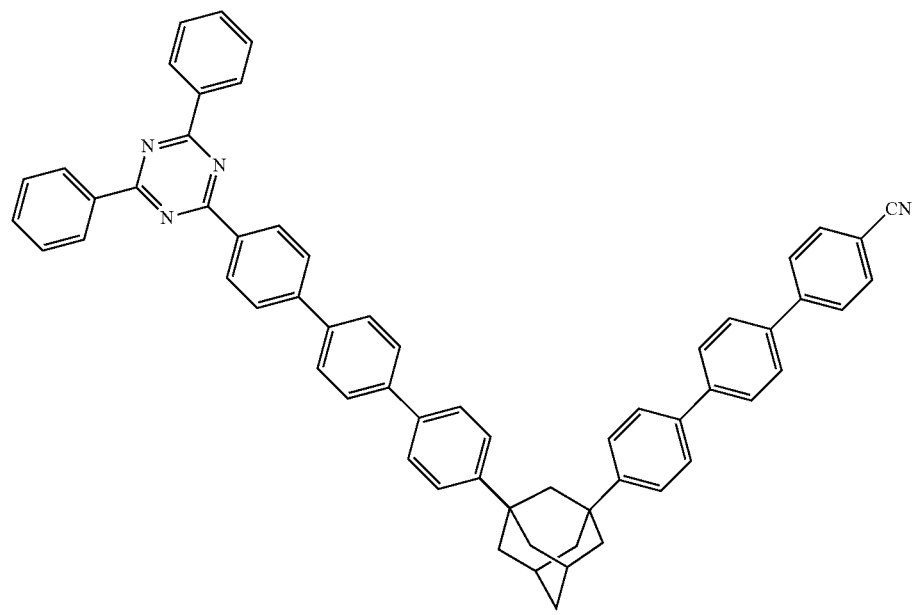

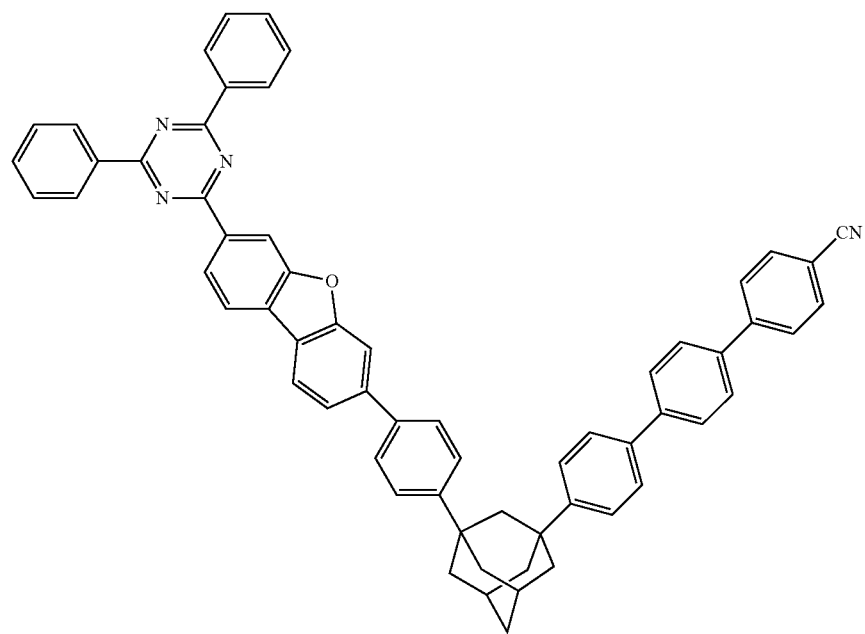
82
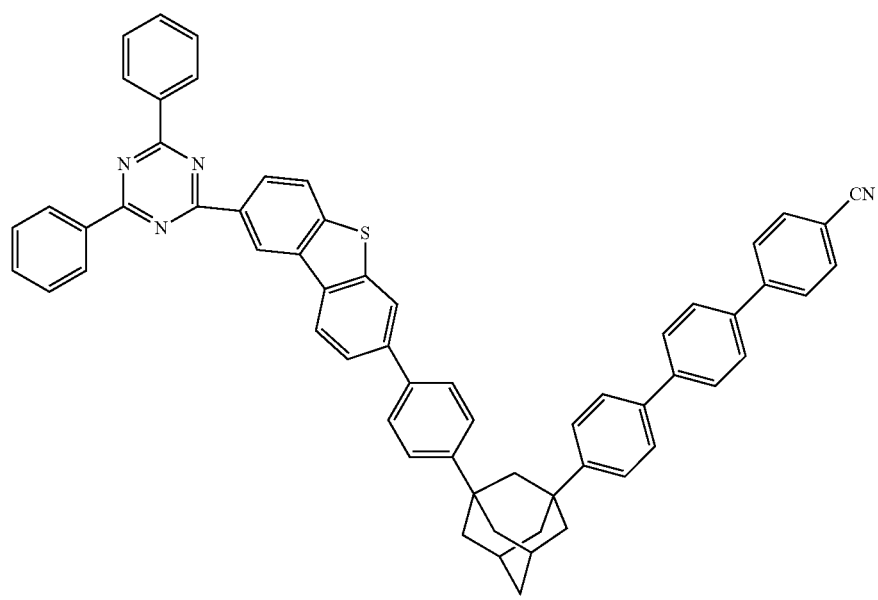
83

84
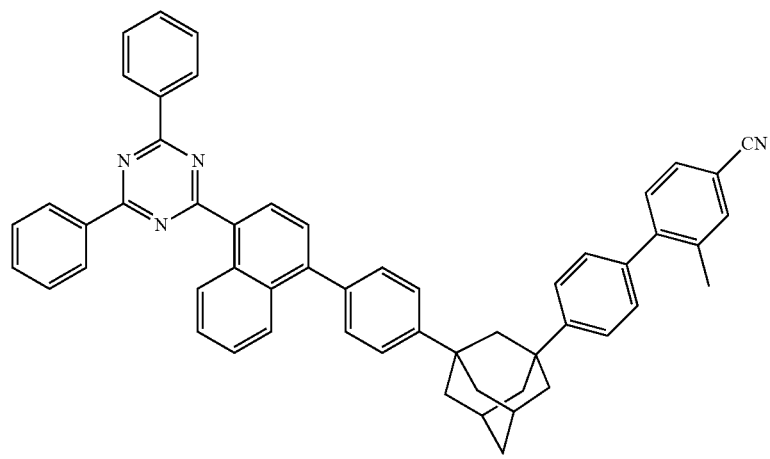
85
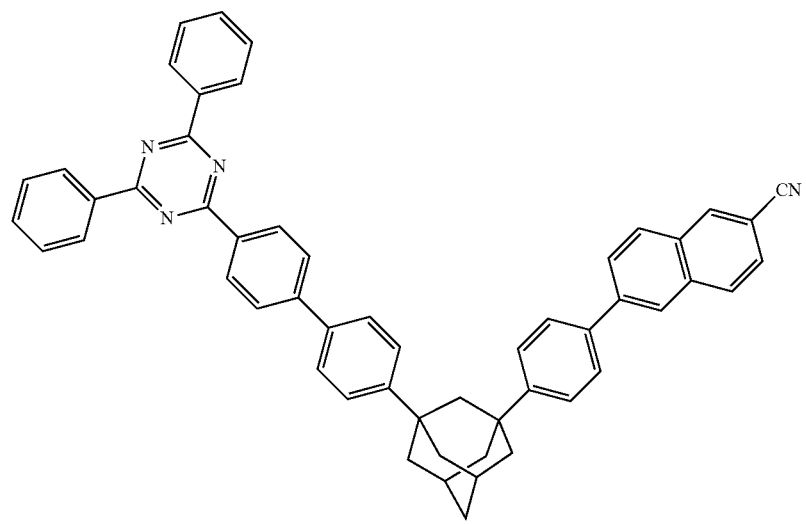
86 87
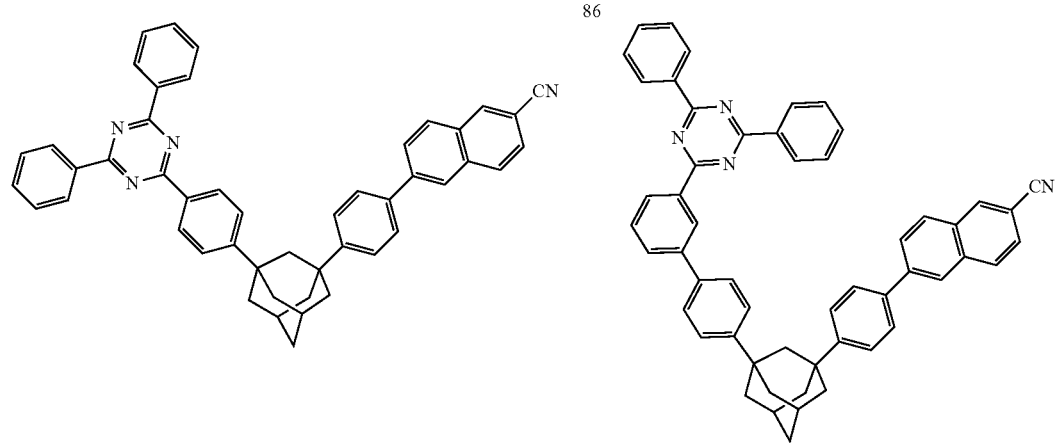

88
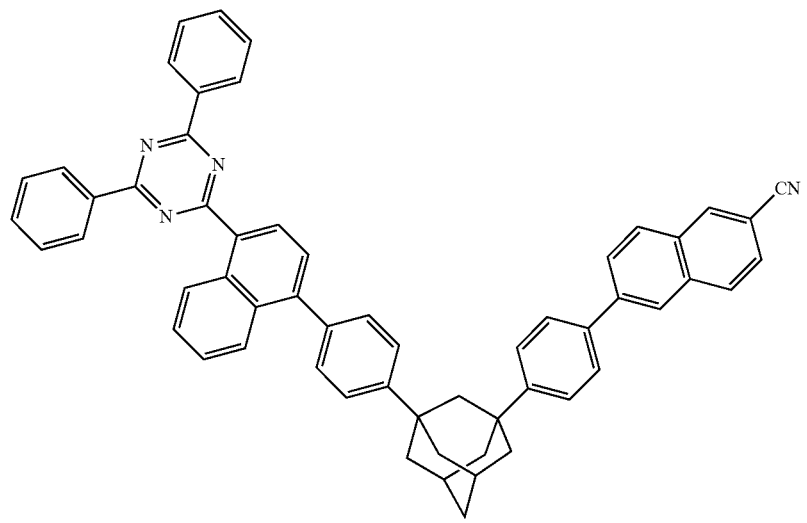
89
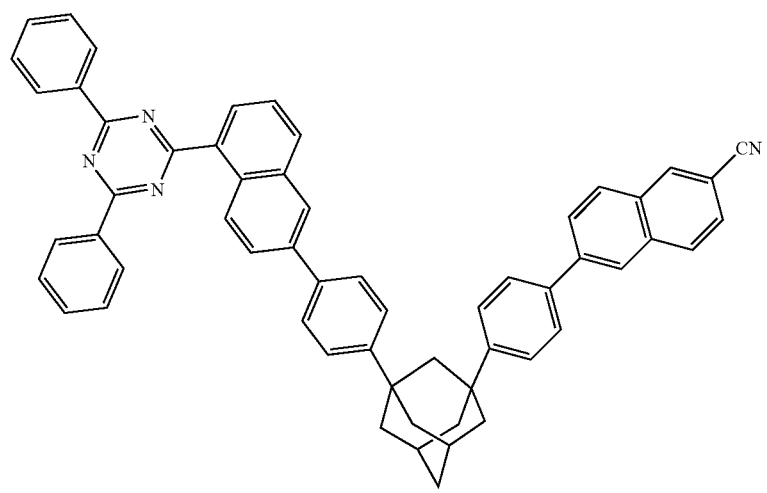
90
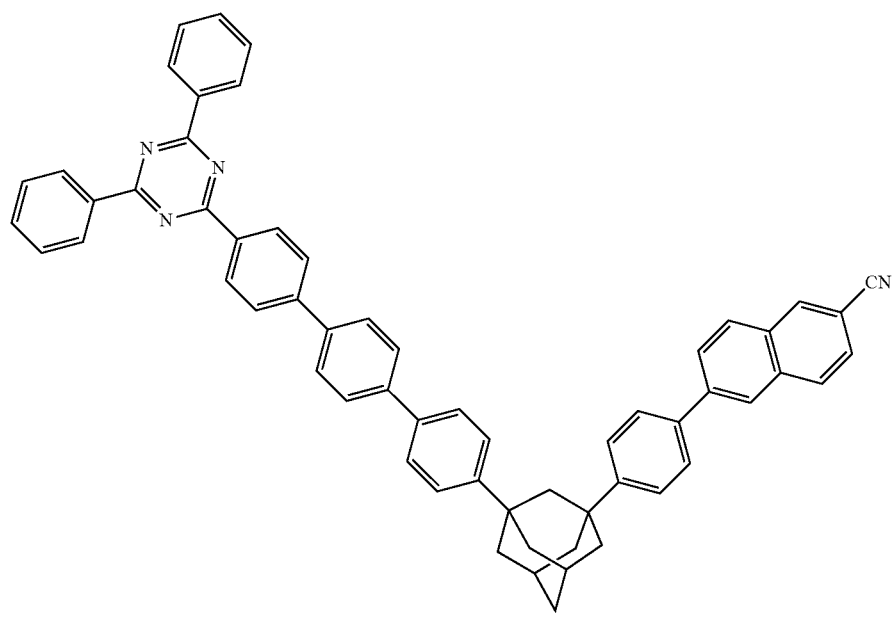

91
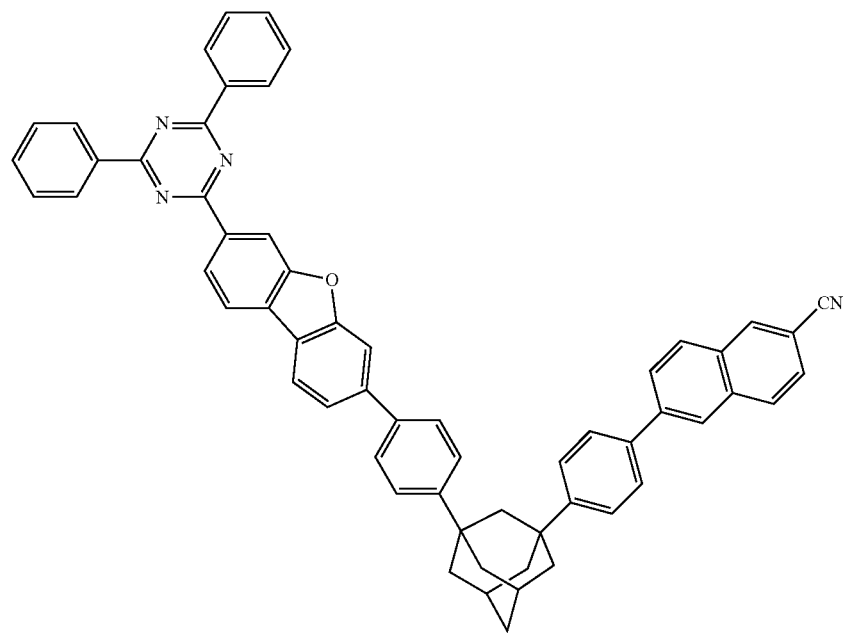
92
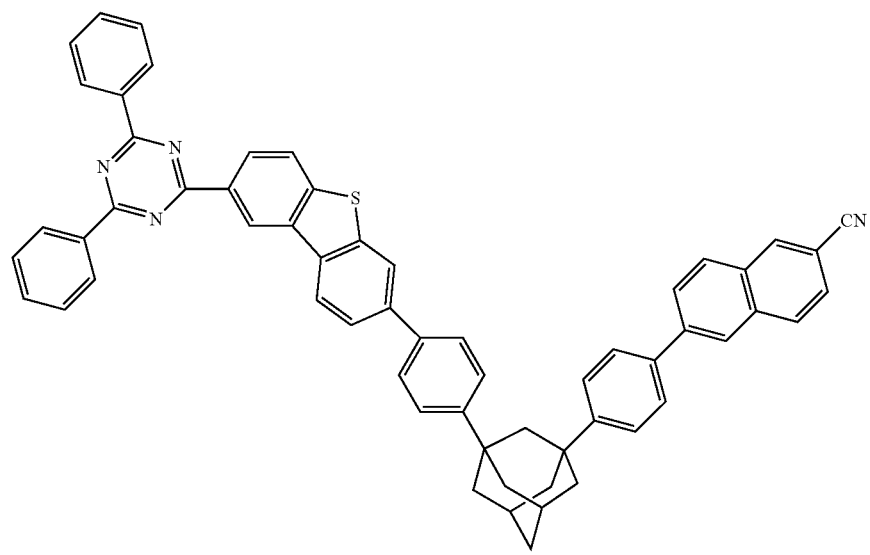
93
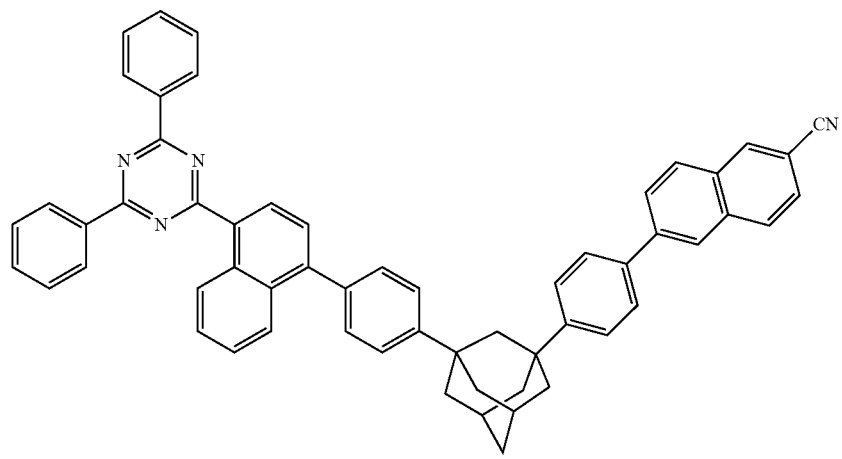

94
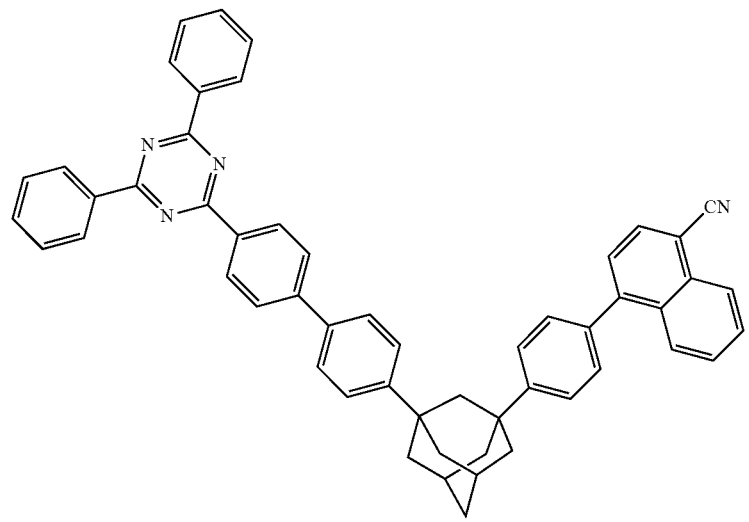
95
96
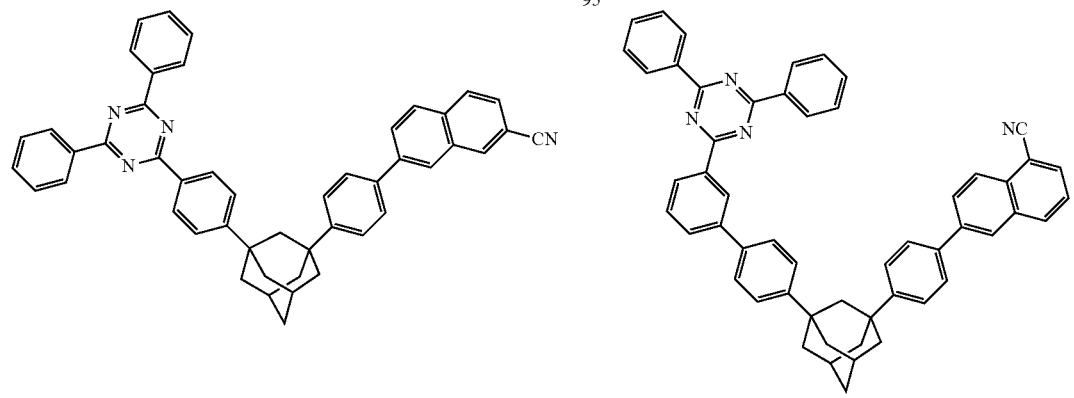
97
98
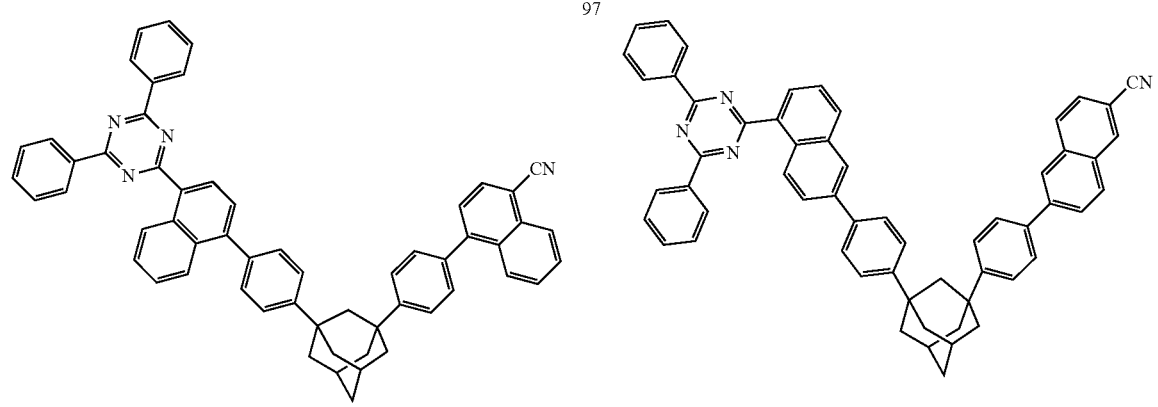

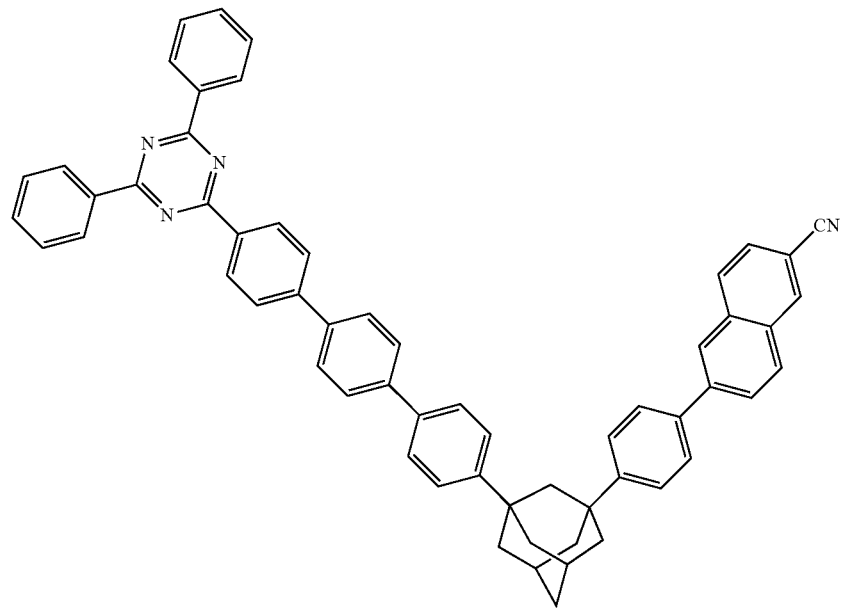
99
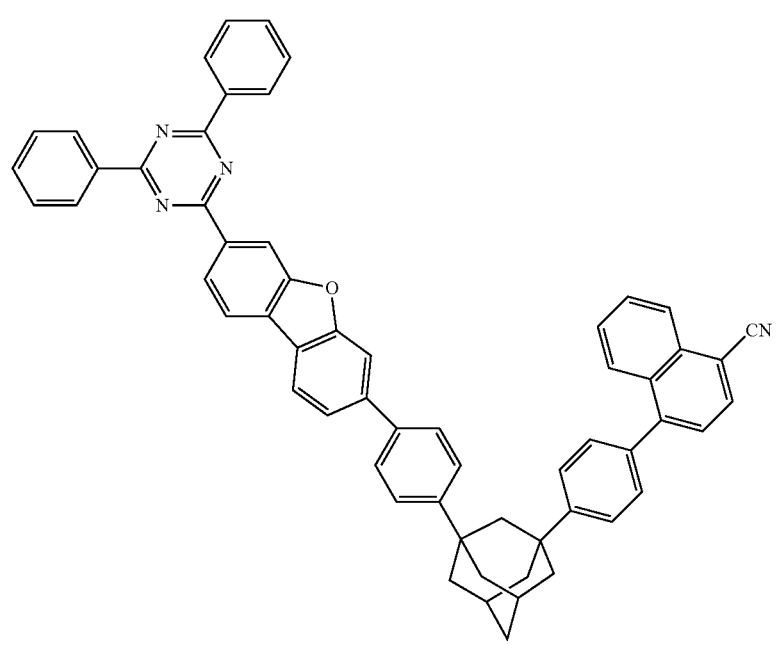
100

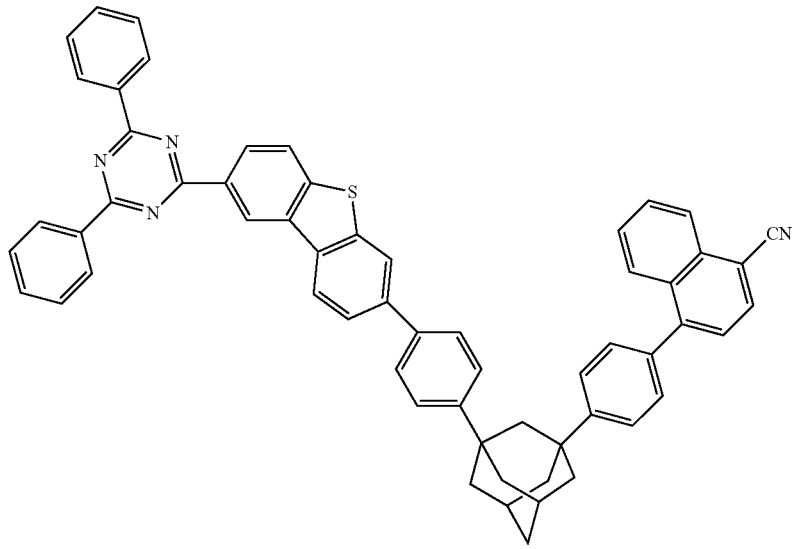
101
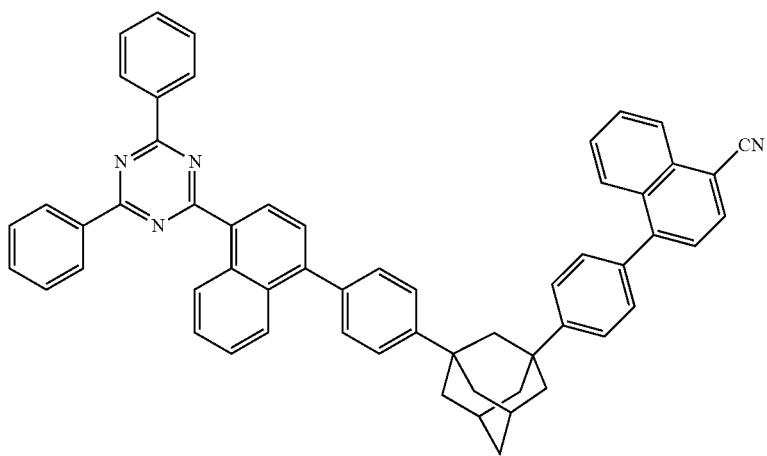
102
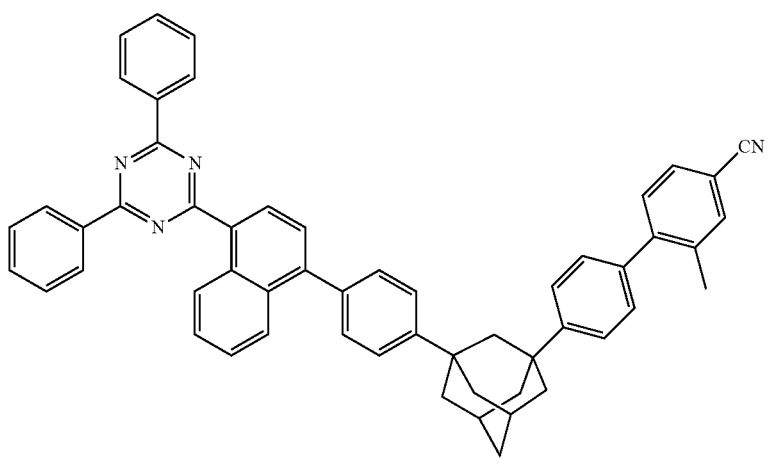
103

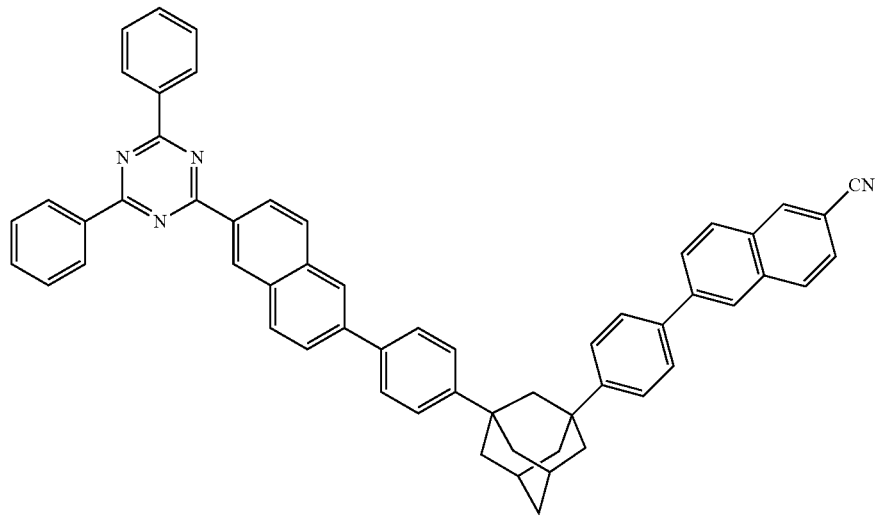
104
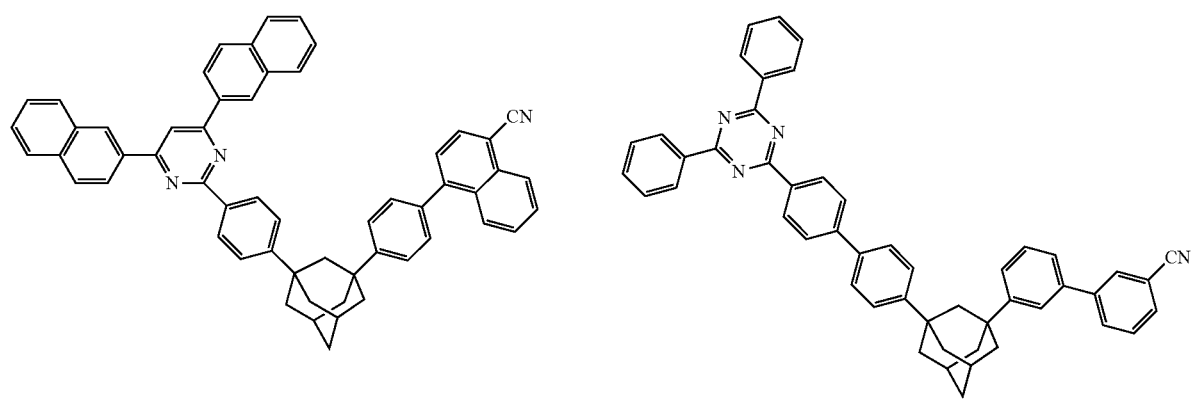
105 106
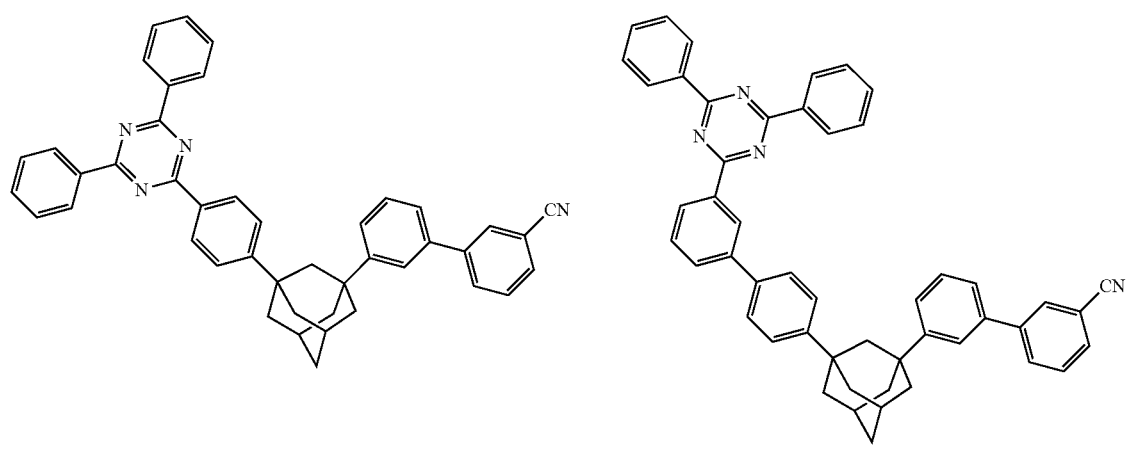
107 108

-continued
109
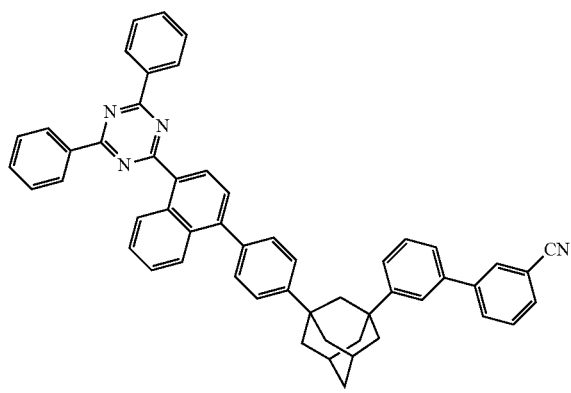
110
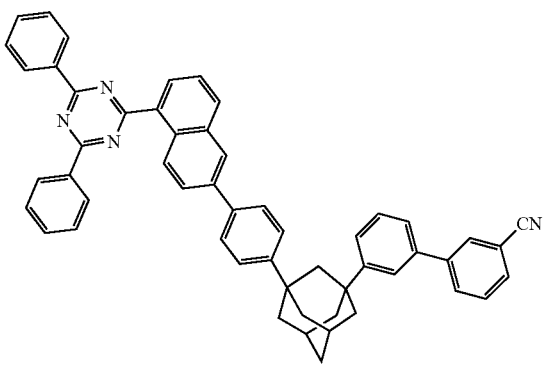
111
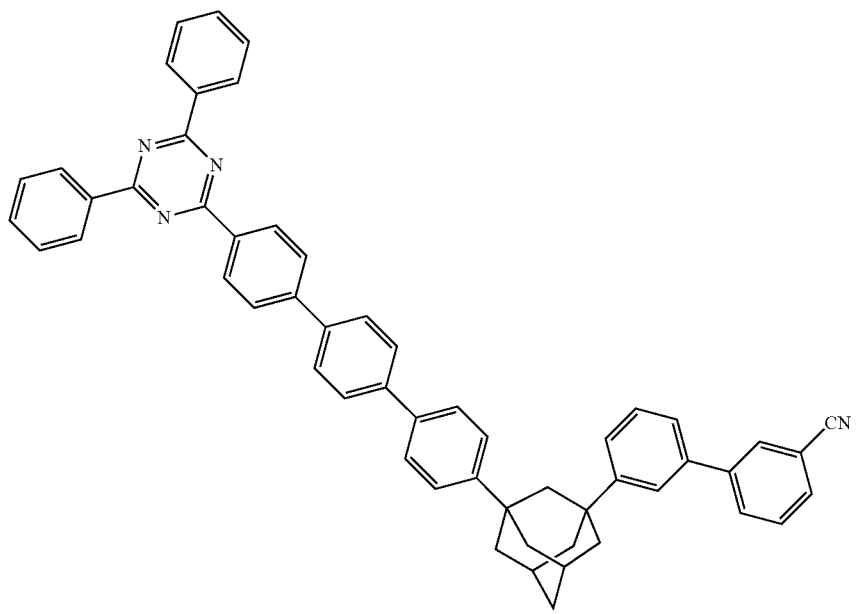
112
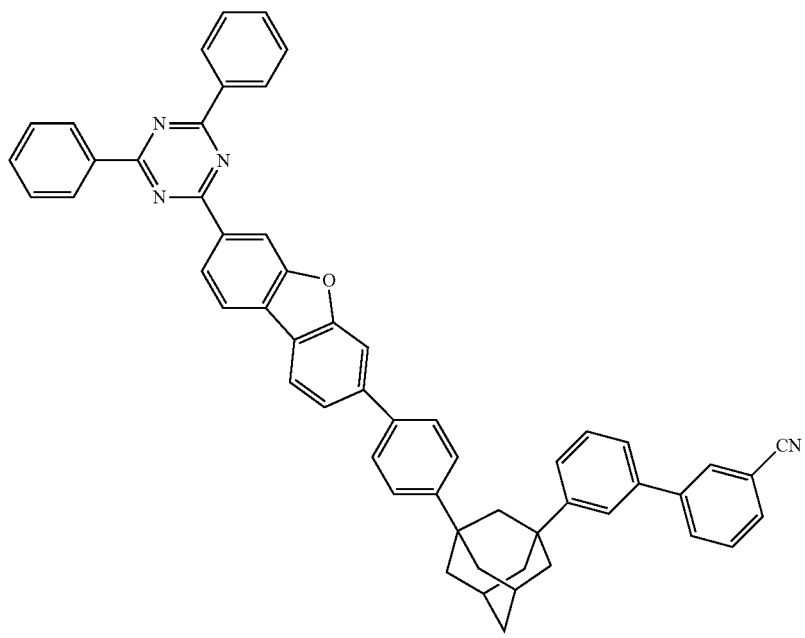

-continued
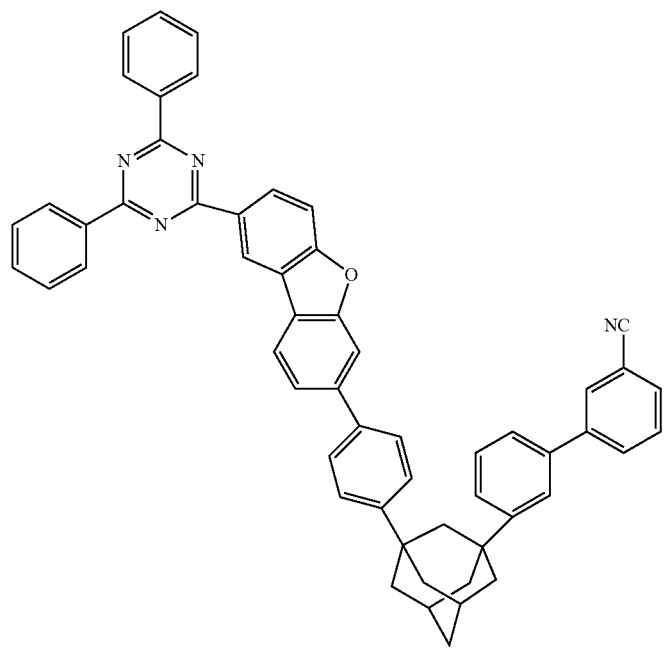
113
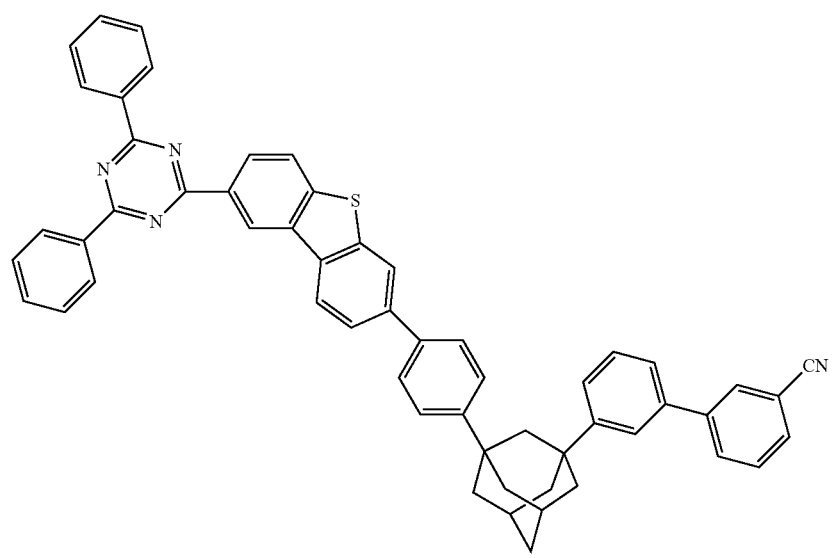
114

-continued
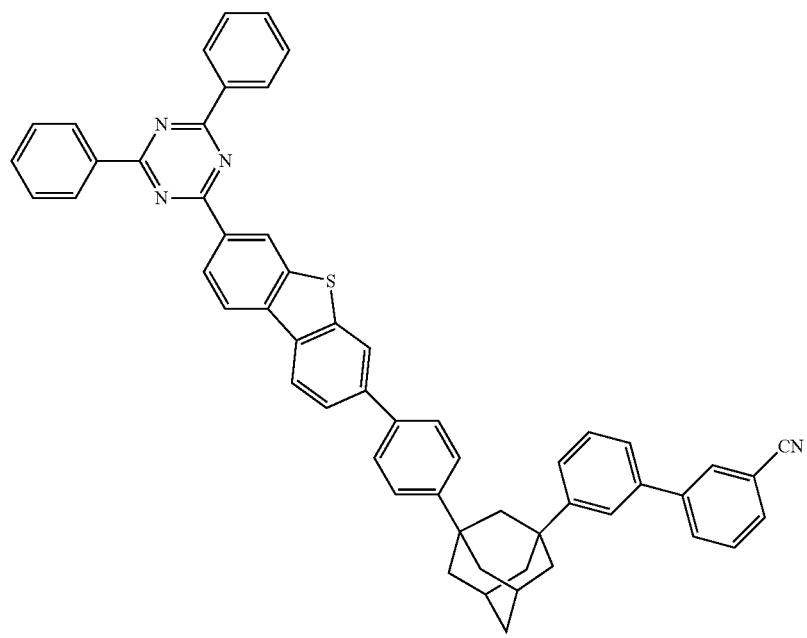
115
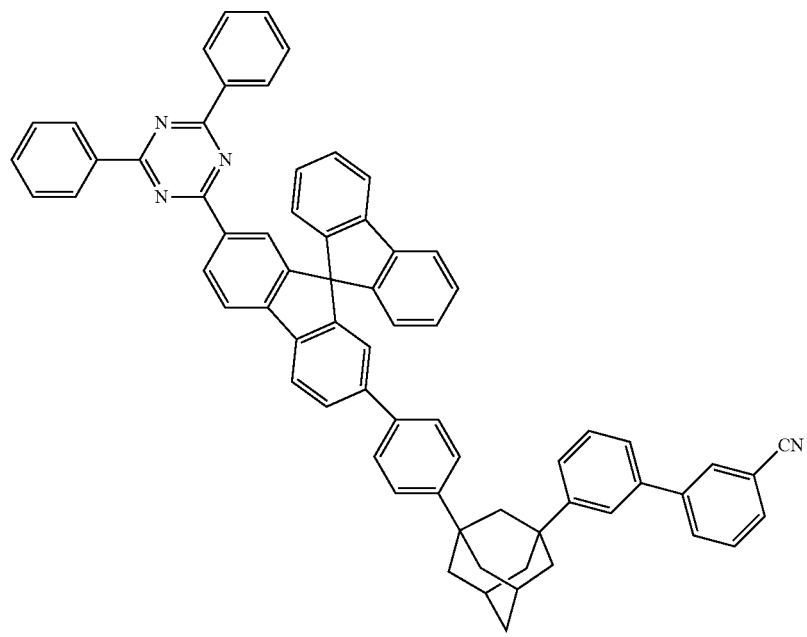
116
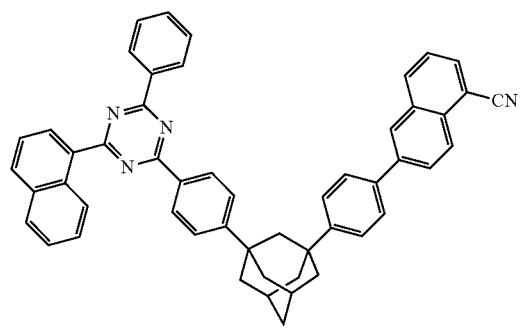
117
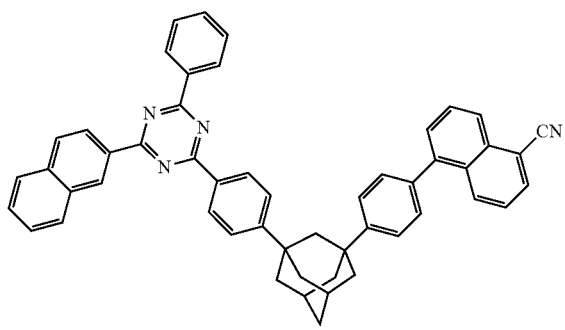
118

-continued
119
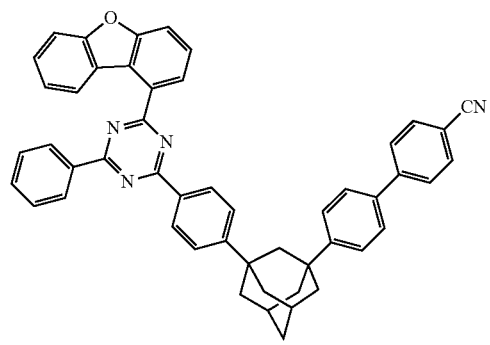
120
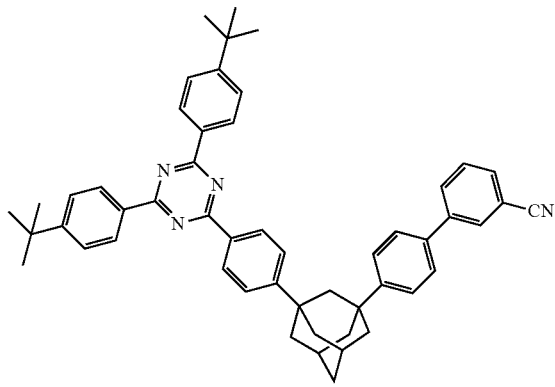
121
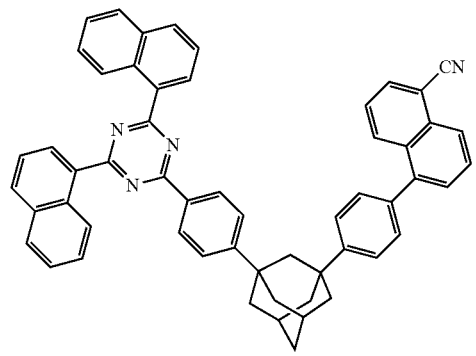
122
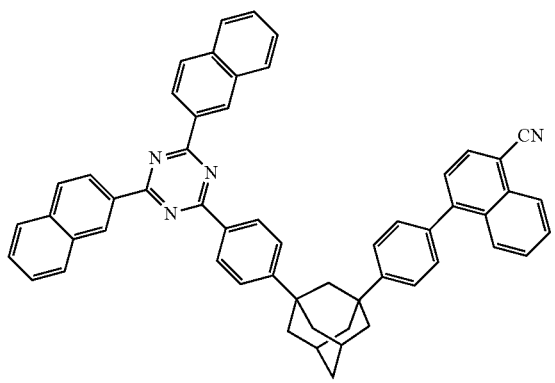
123
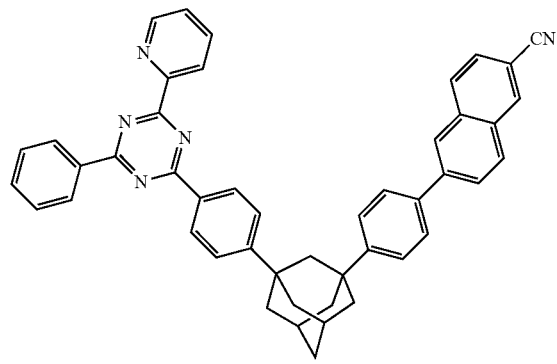
124
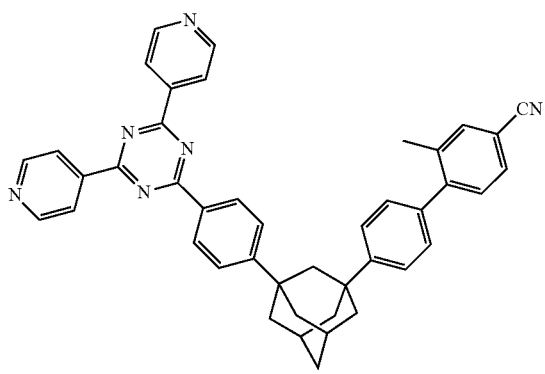

125
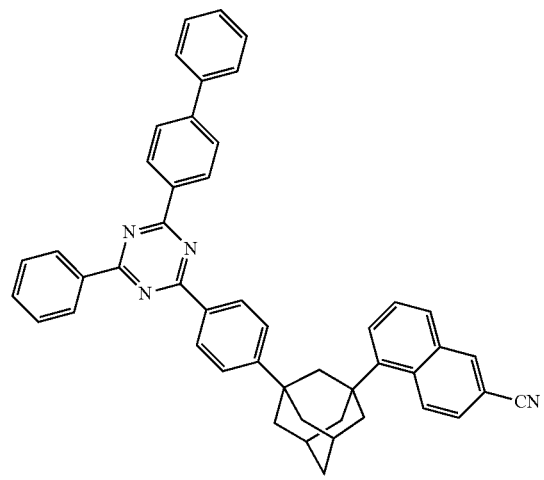
126
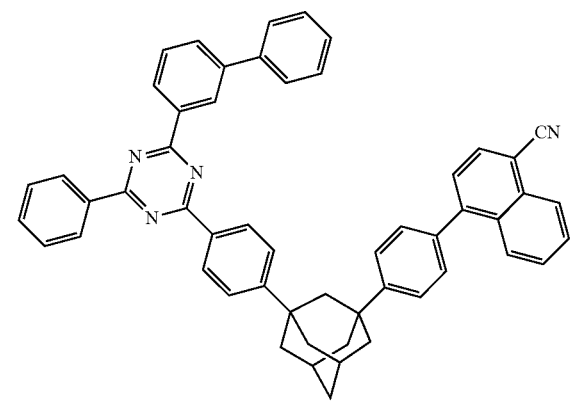
127
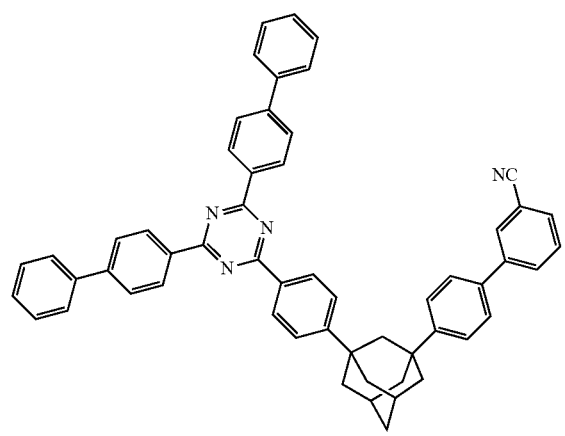
128
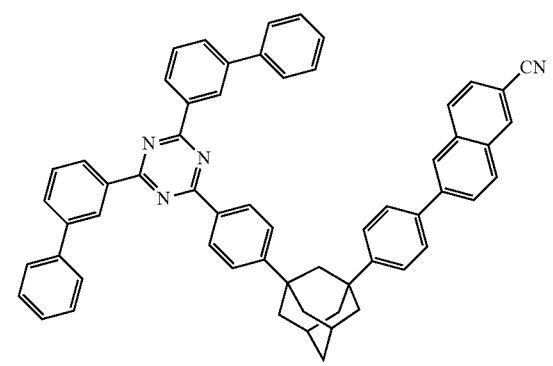
129
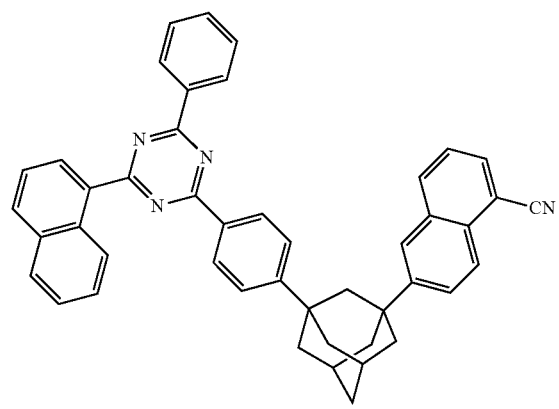
130
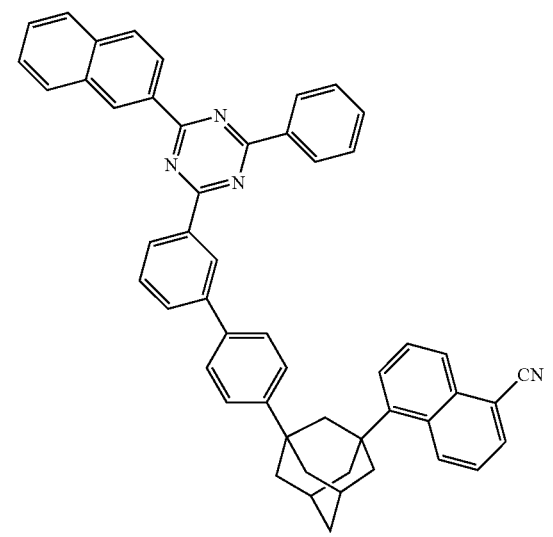

-continued
131
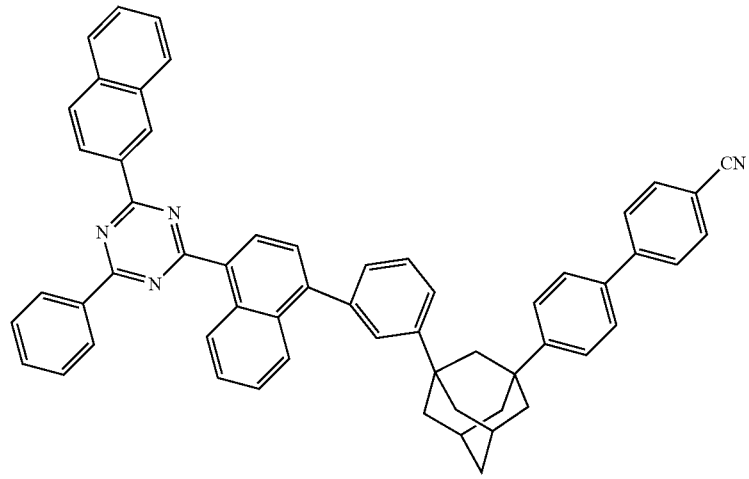
132
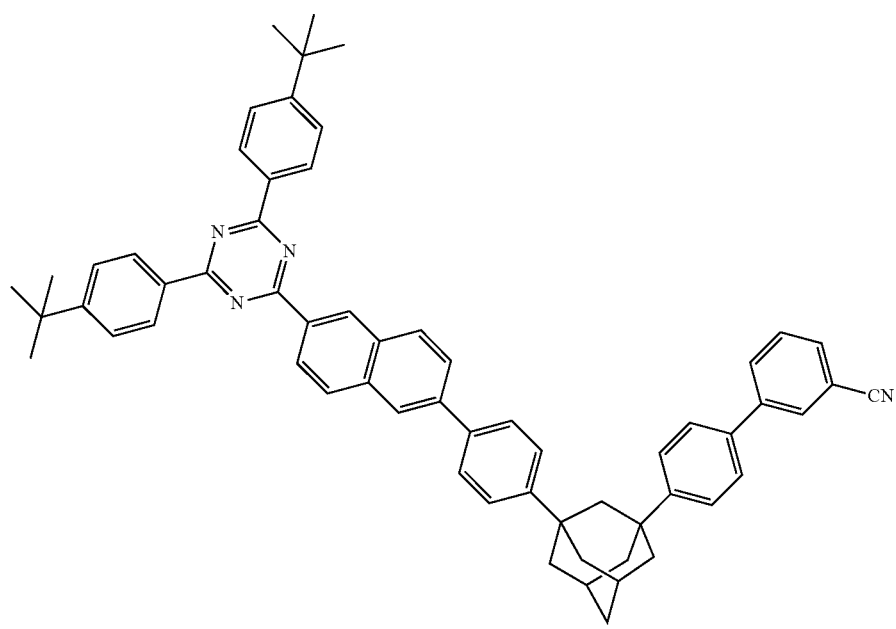
133
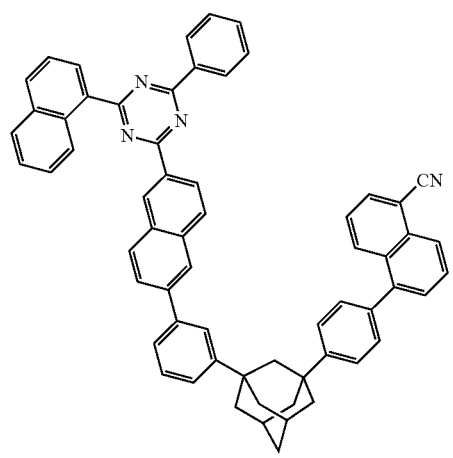
134
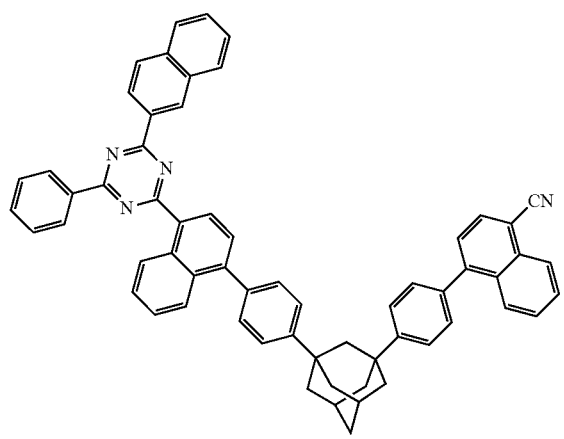

135
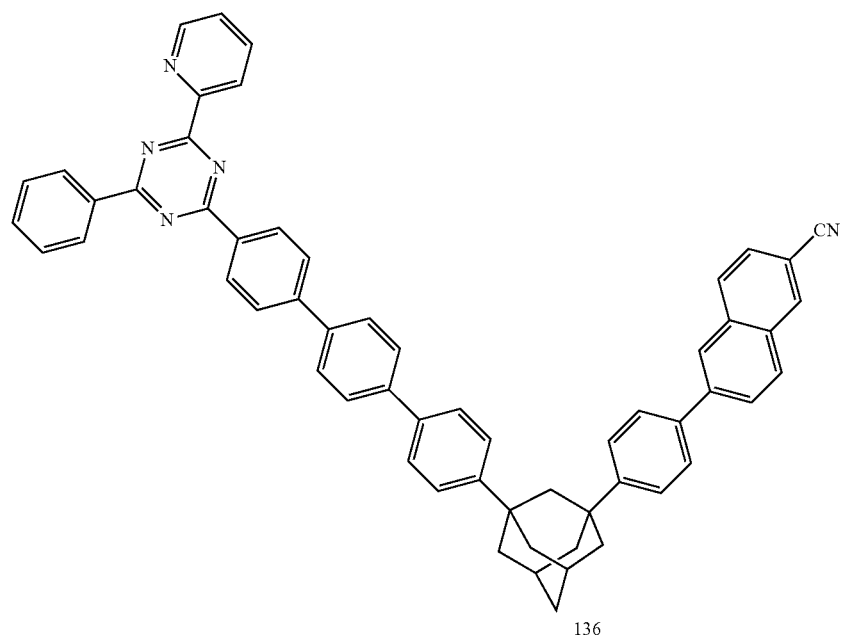
136
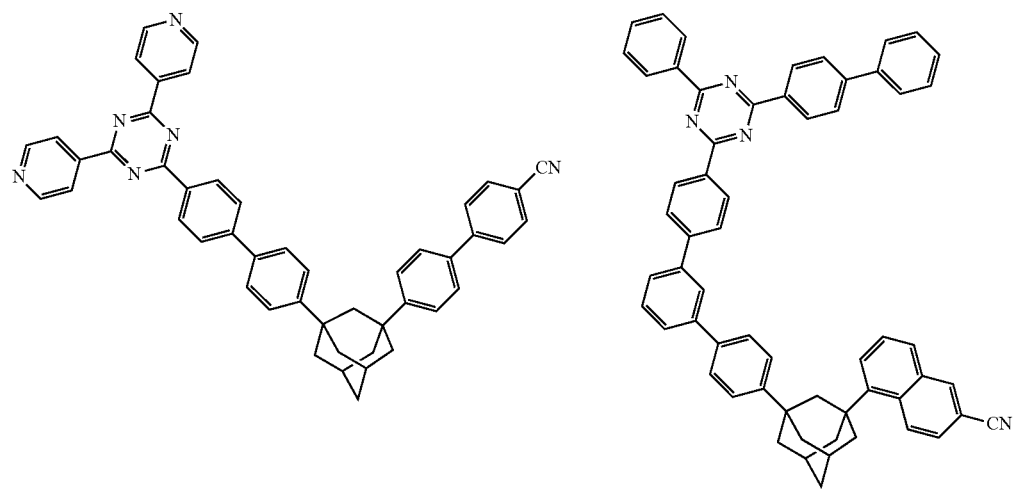
137
138
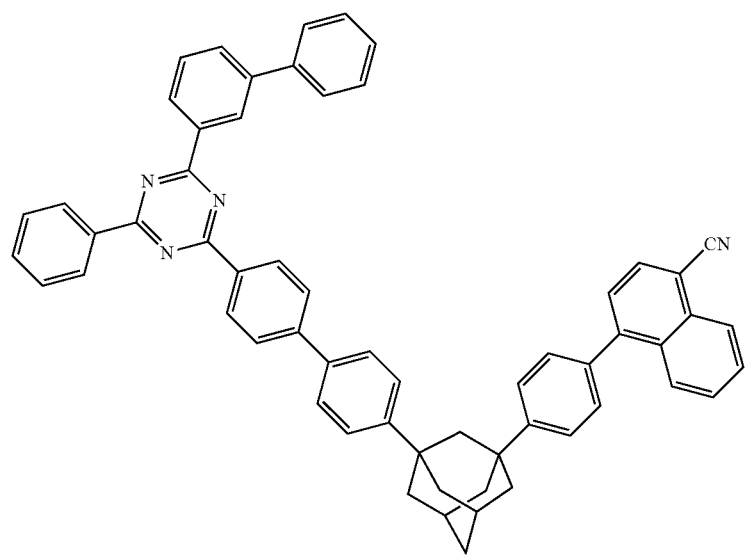

139
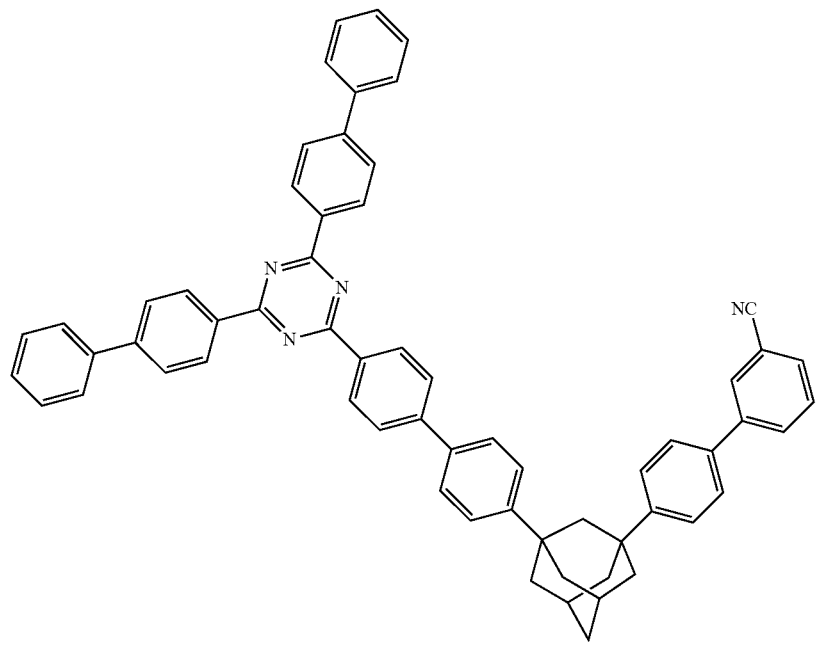
140
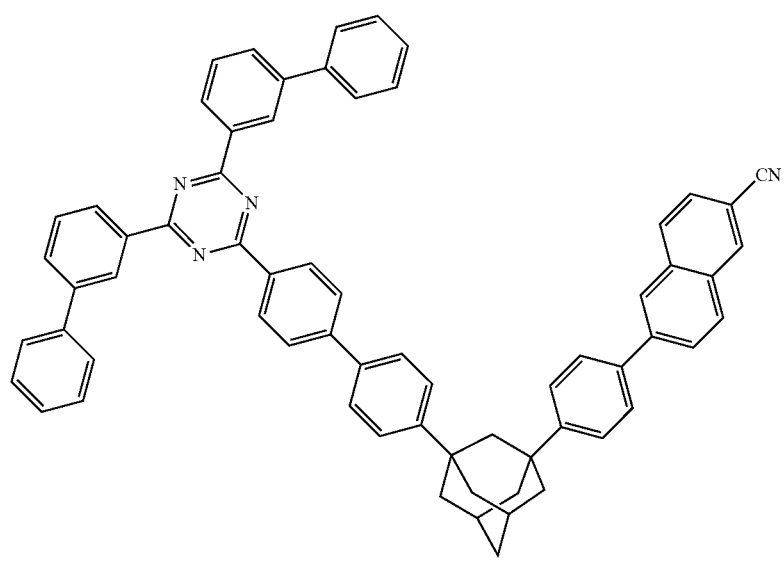
141
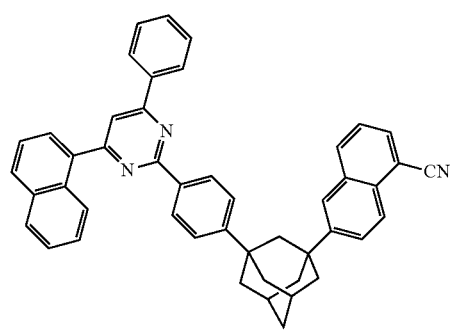
142
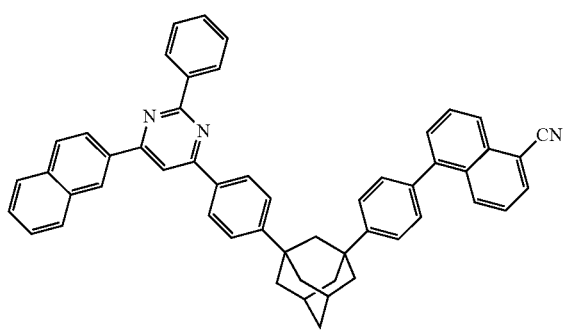

143
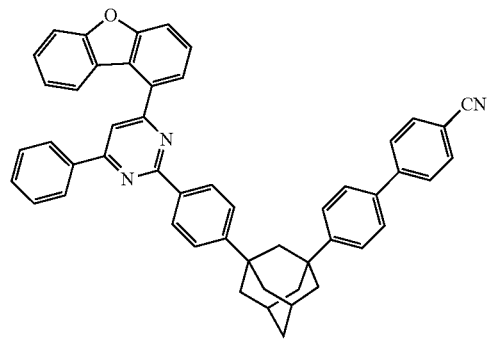
144
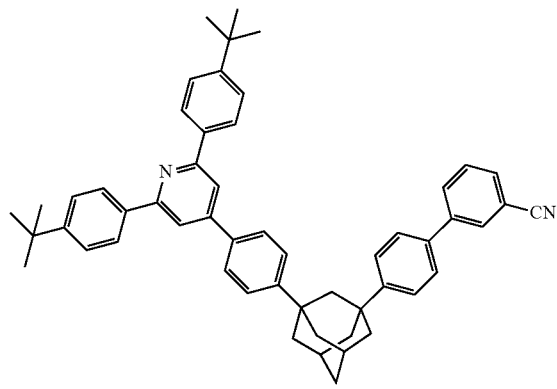
145
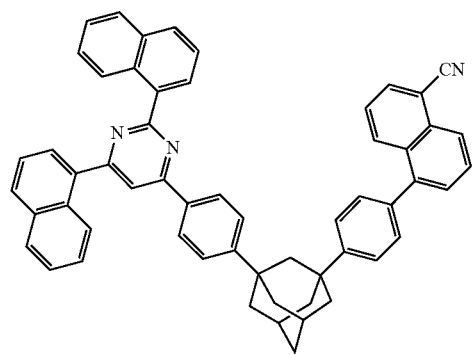
146
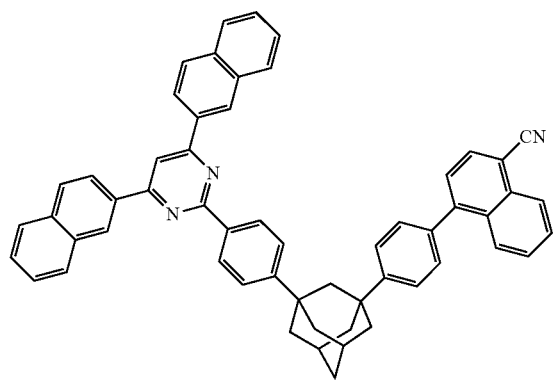
147
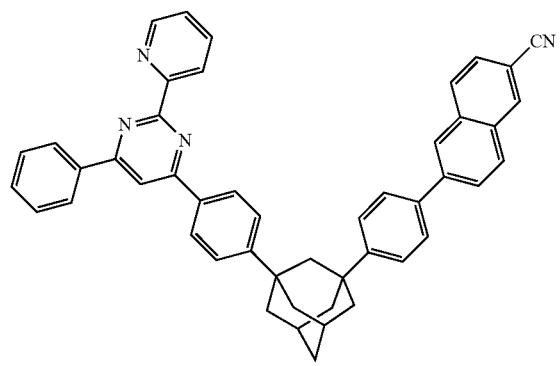
148
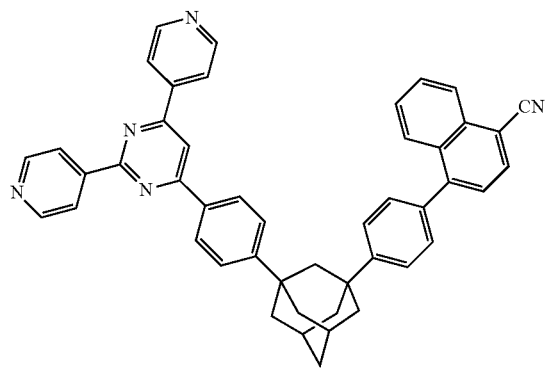
149
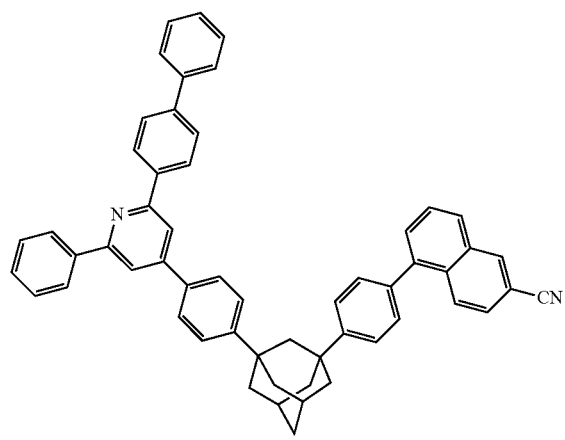
150
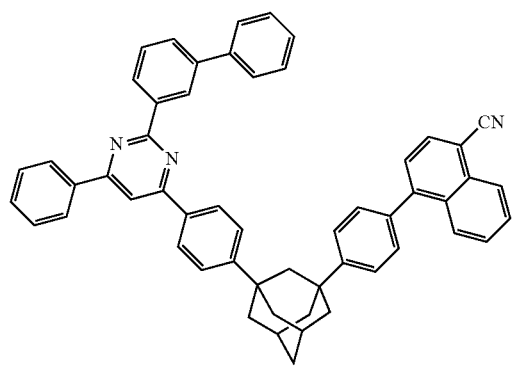

-continued
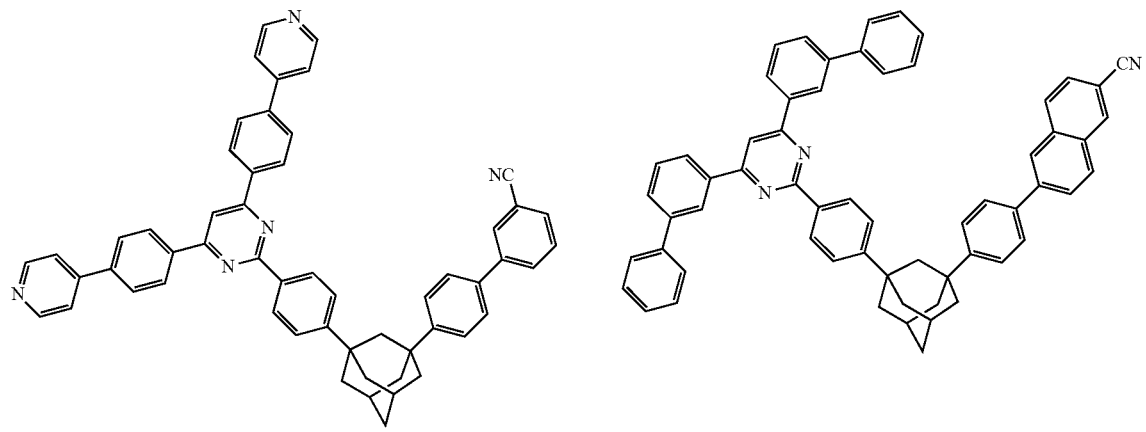
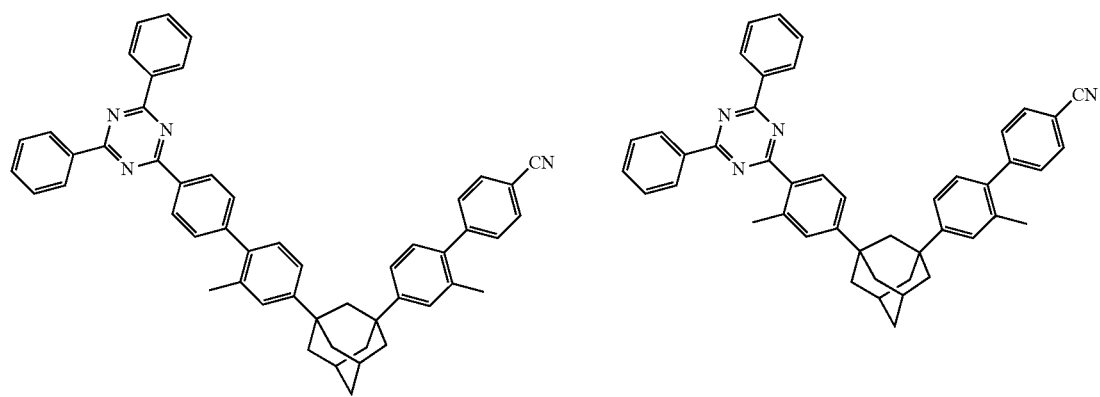
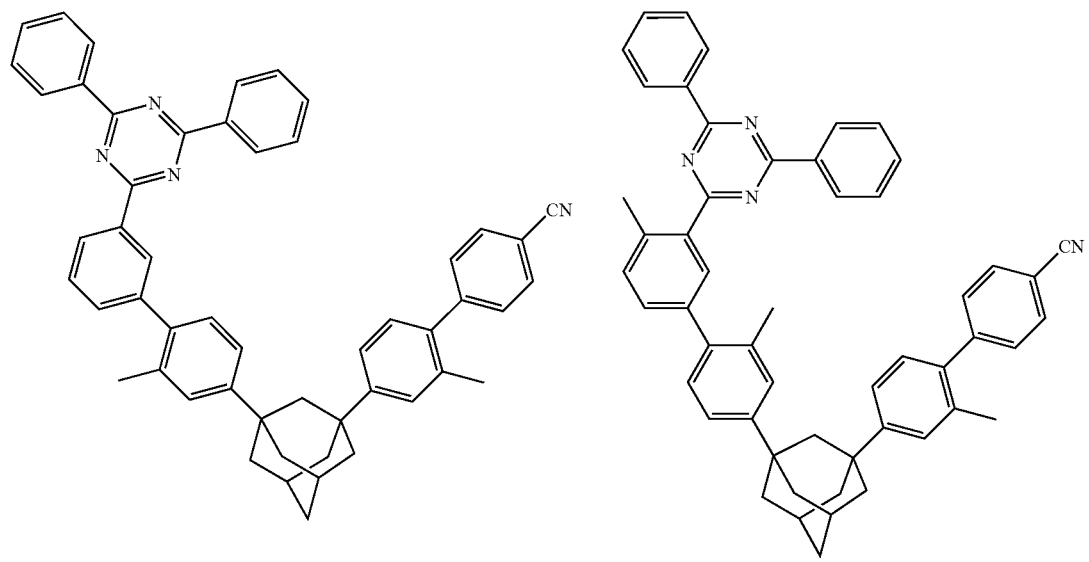

-continued
157
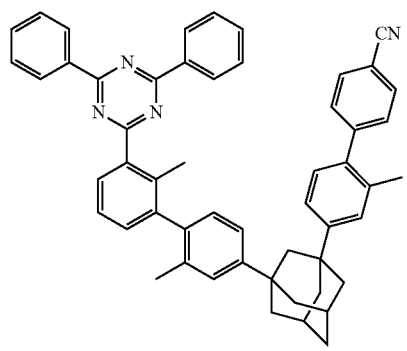
158
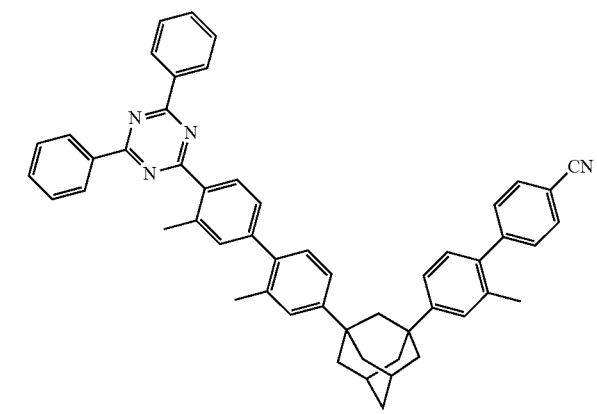
159
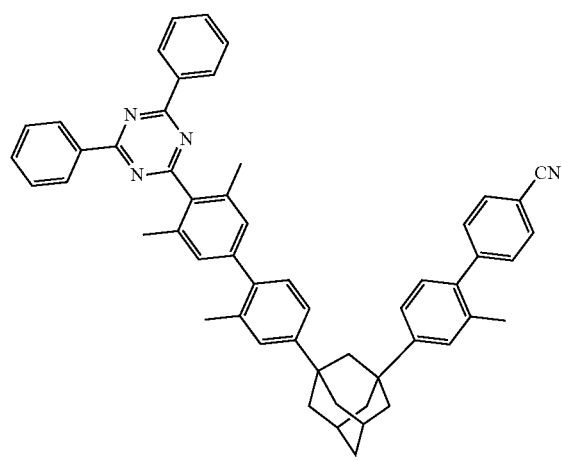
160
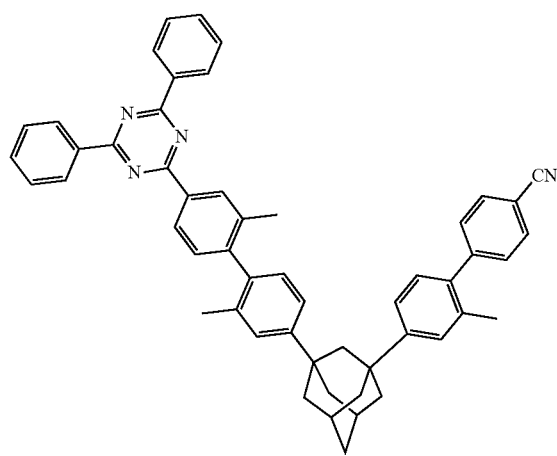
161
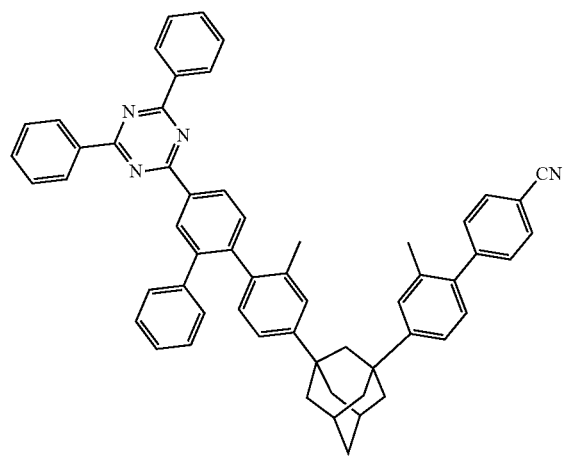
162
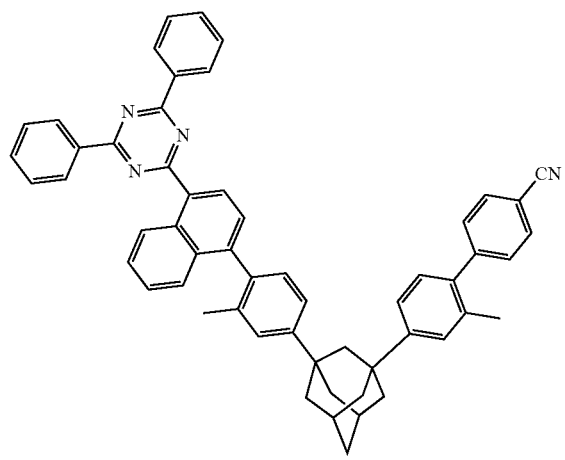

-continued
163
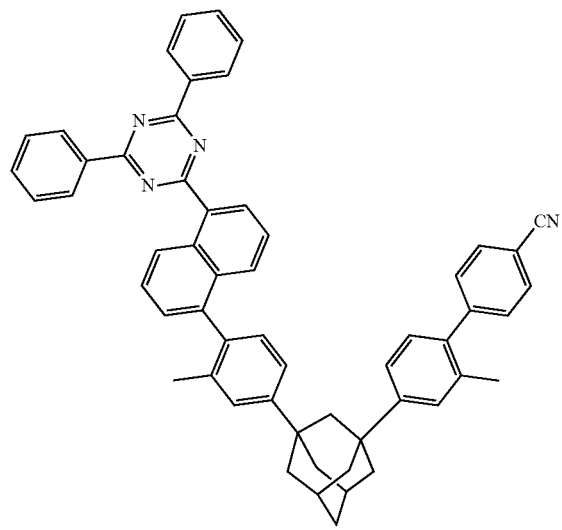
164
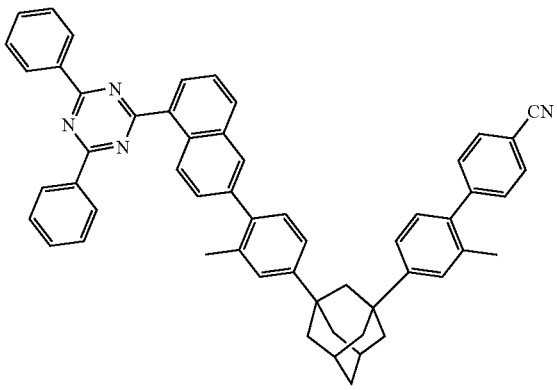
165
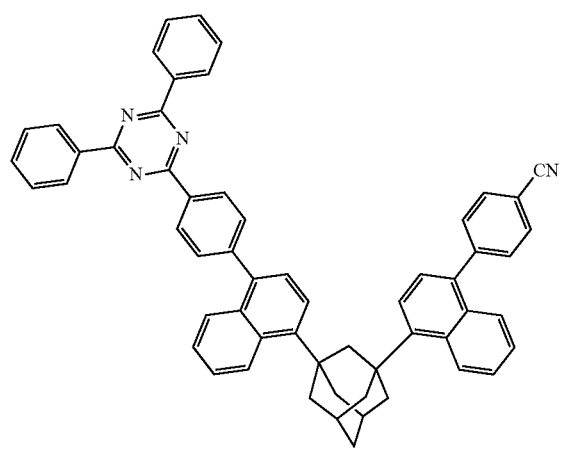
166
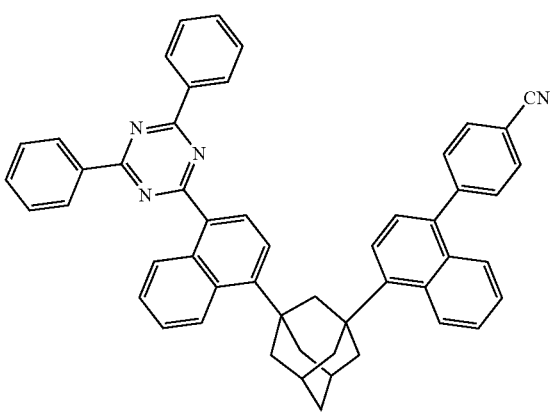
167
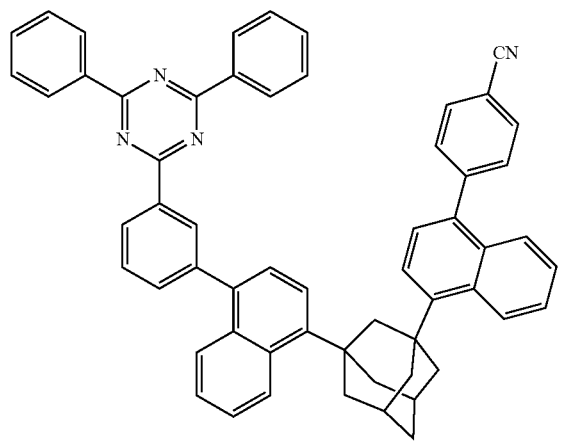
168
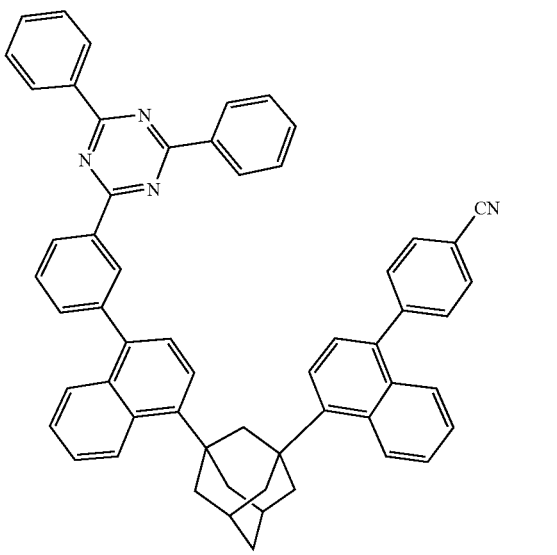

-continued
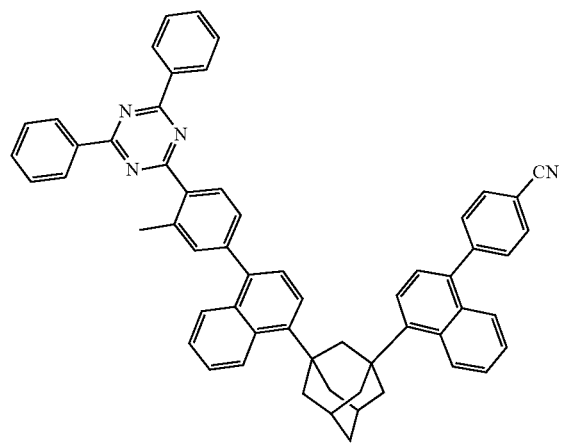

-continued
175
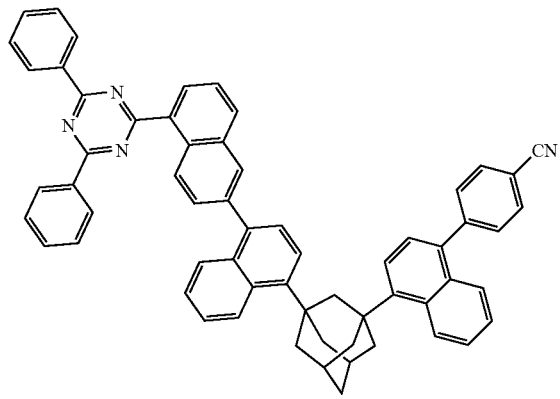
176
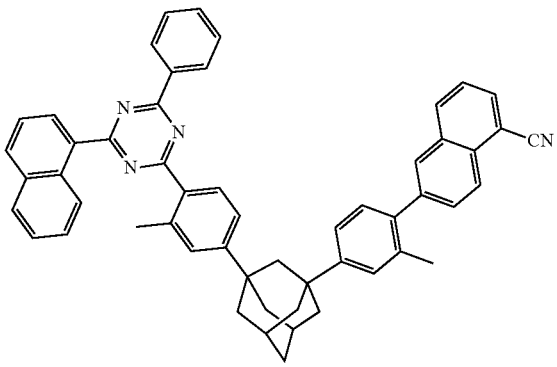
177
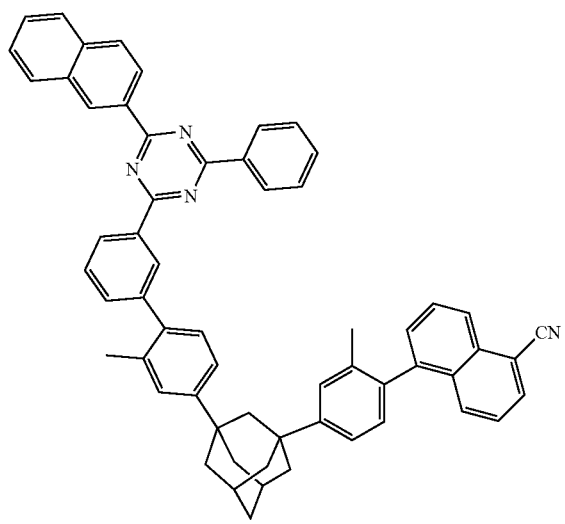
178
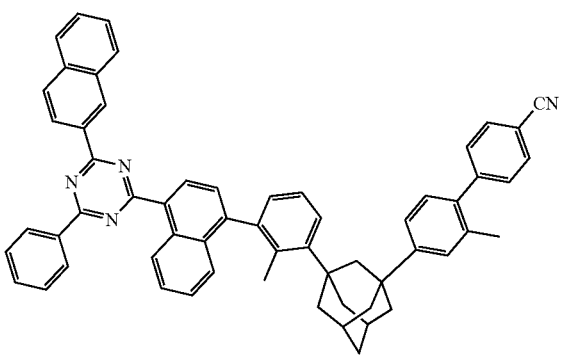
179
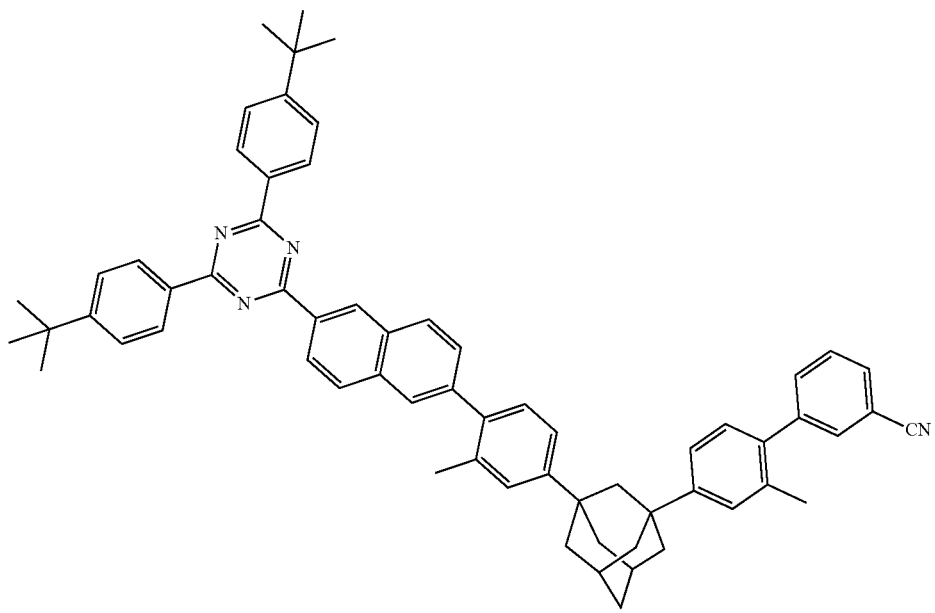

-continued
180
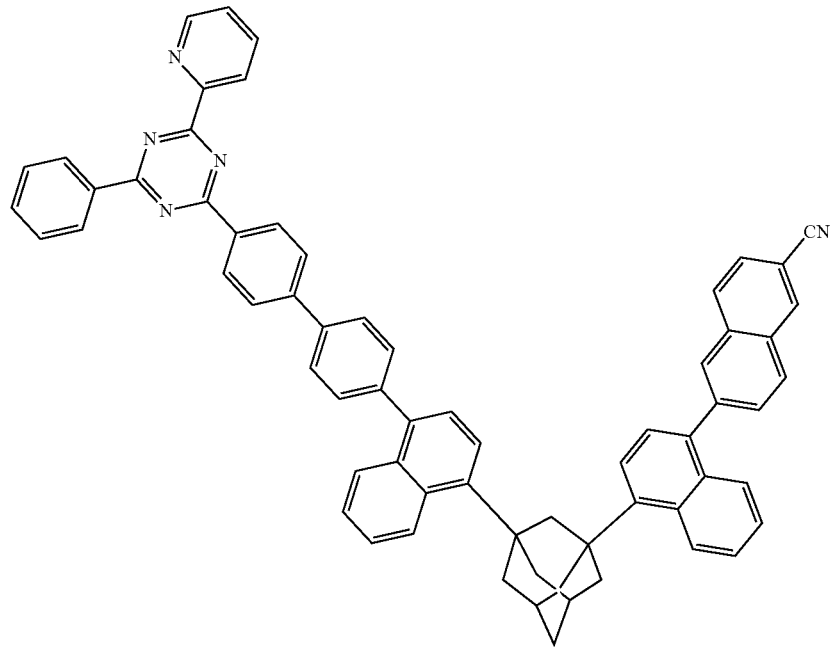
181 182
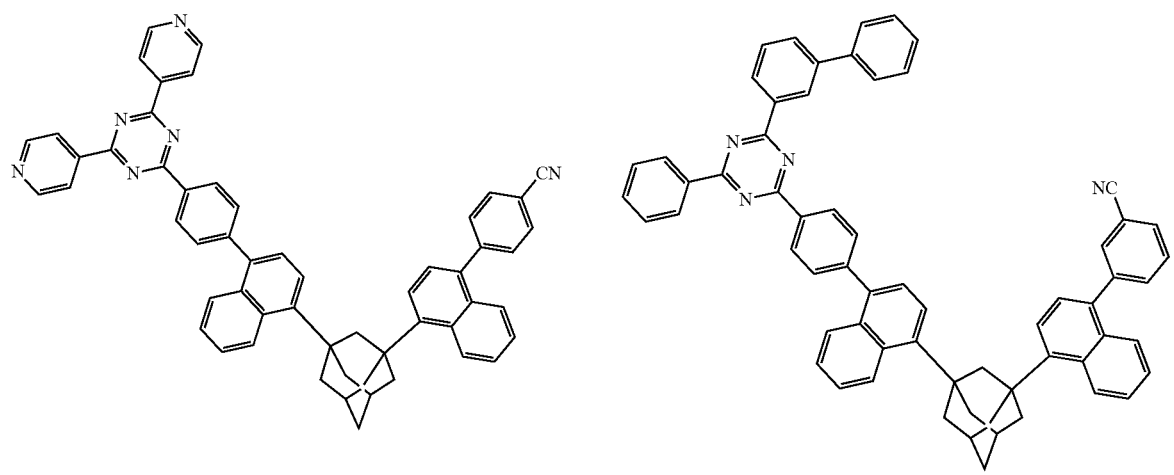
183 184
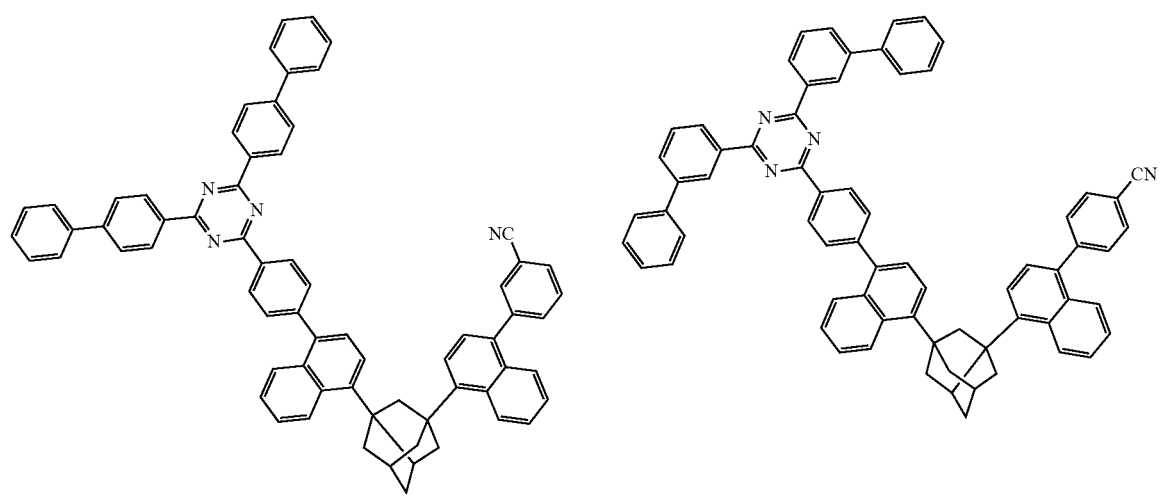

185
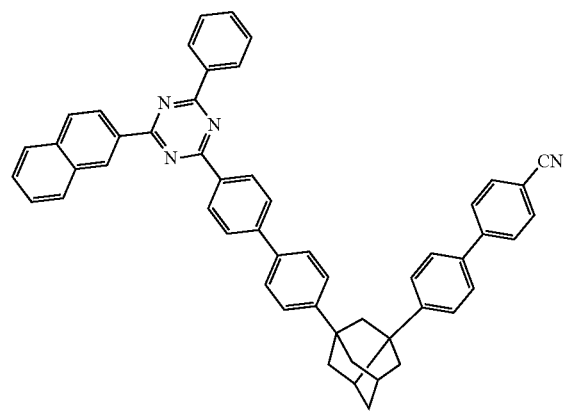
186
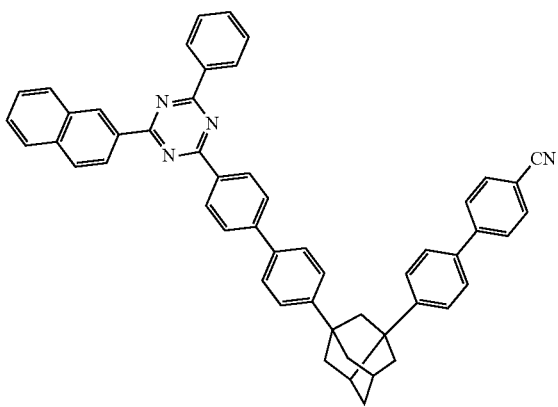
187
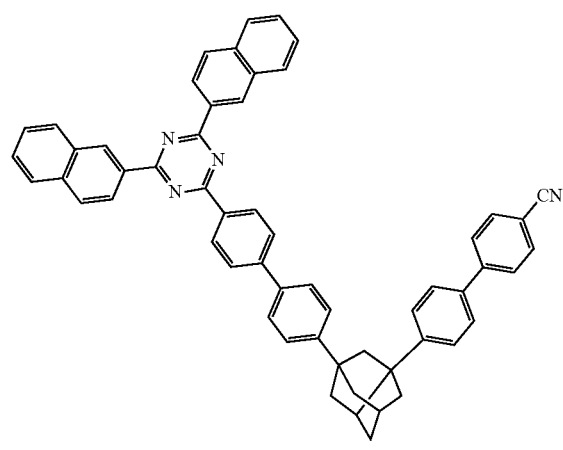
188
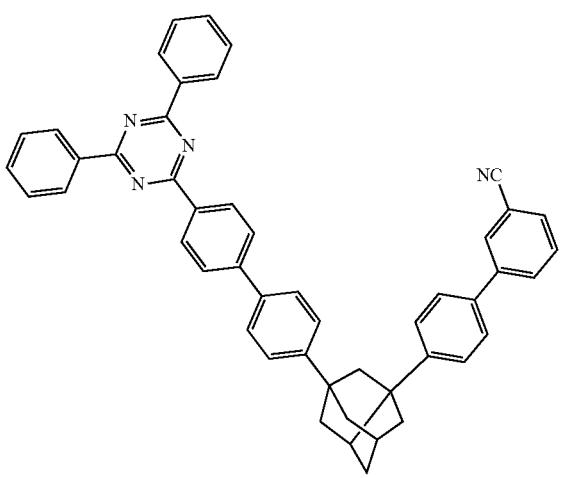
189
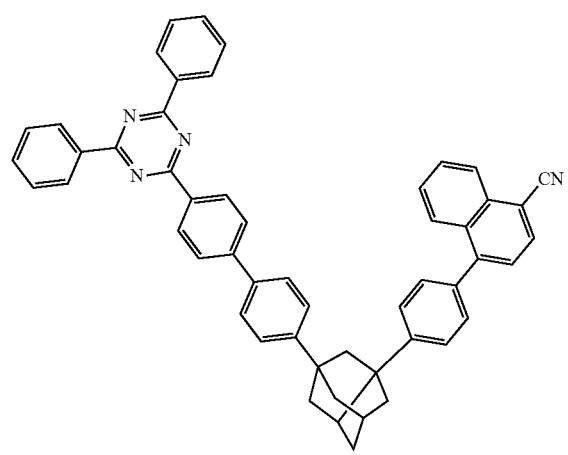
190
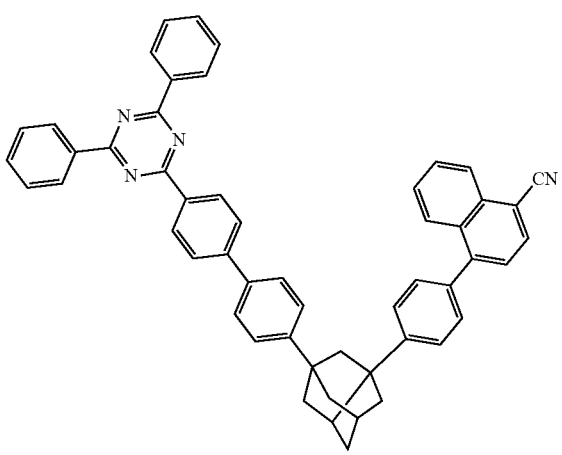

-continued
191
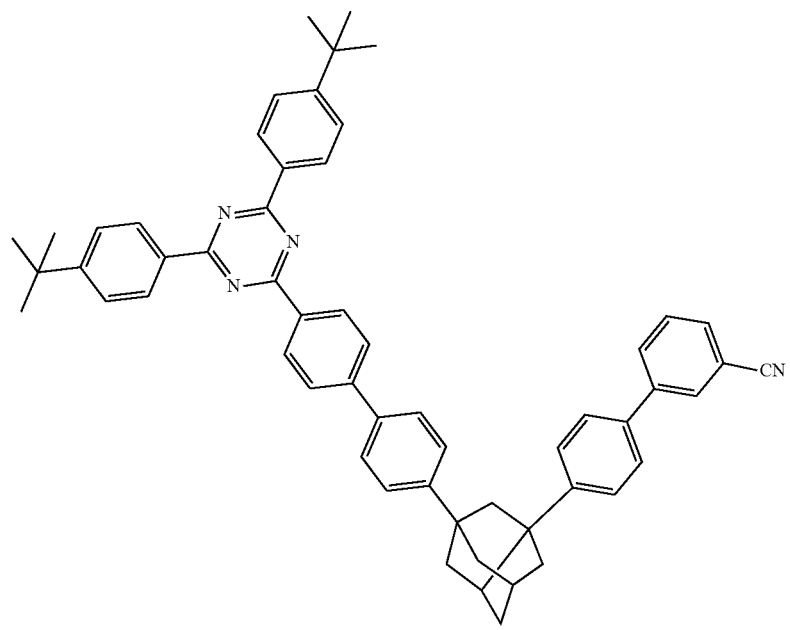
192
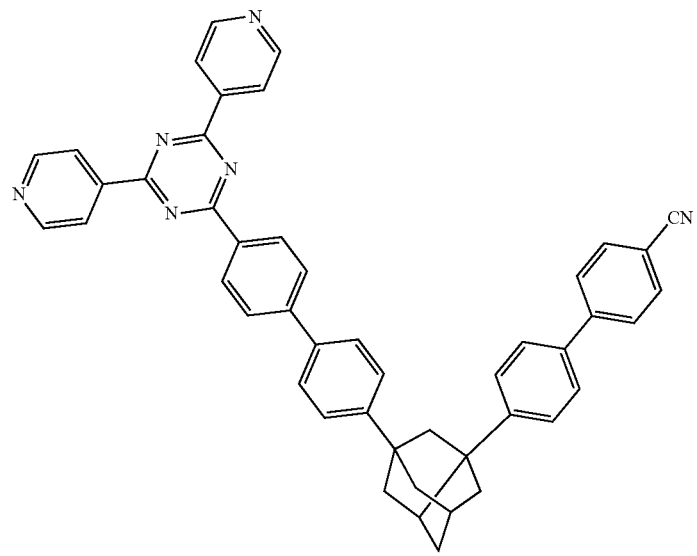

193
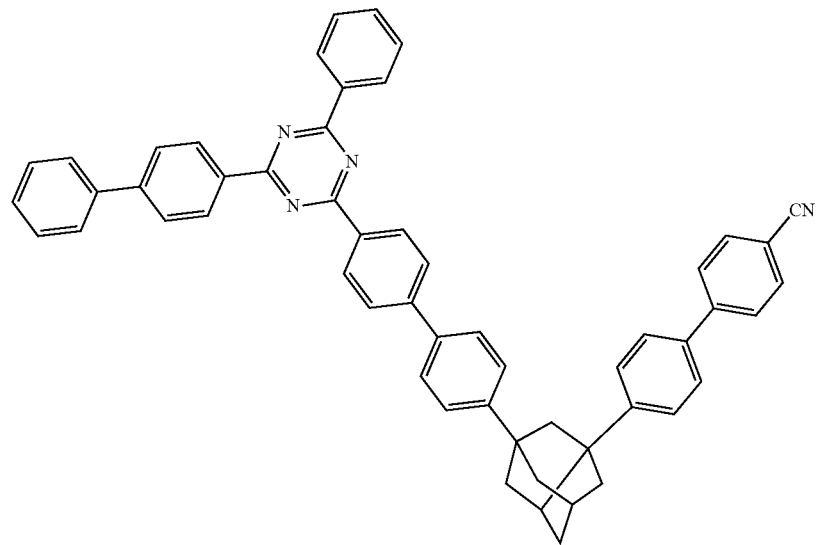
194 195
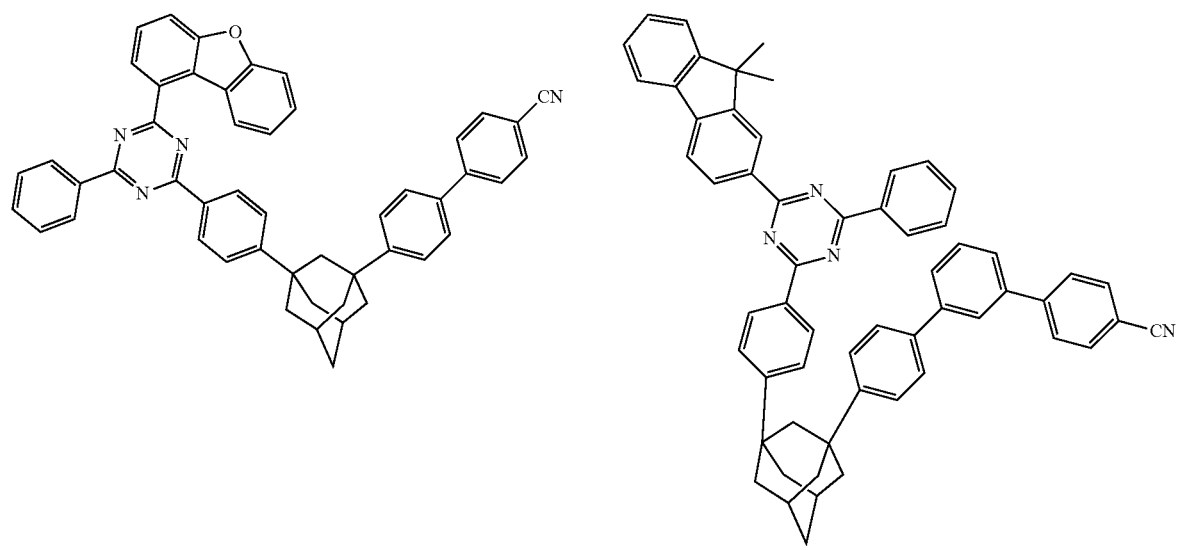

196
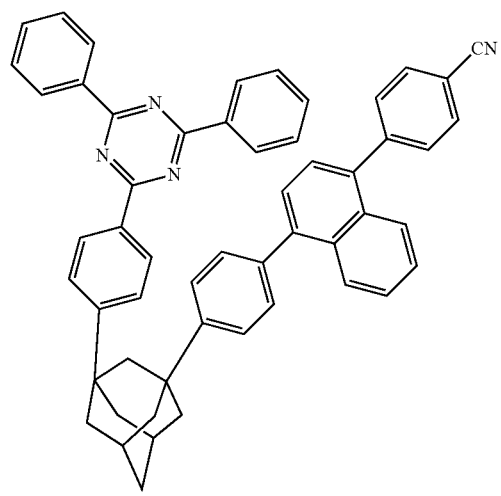
197
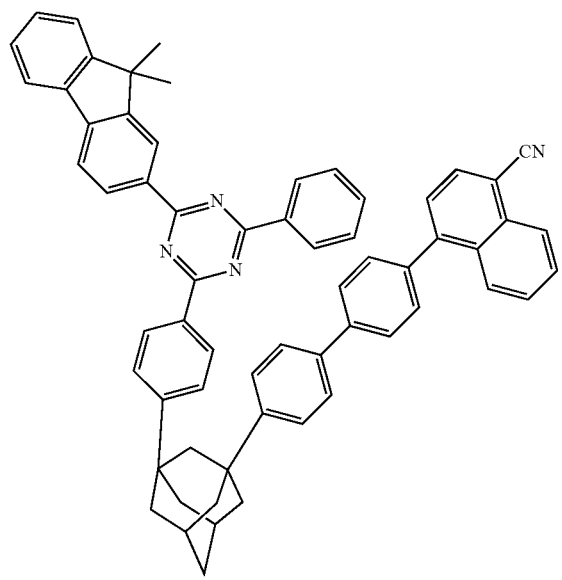
198
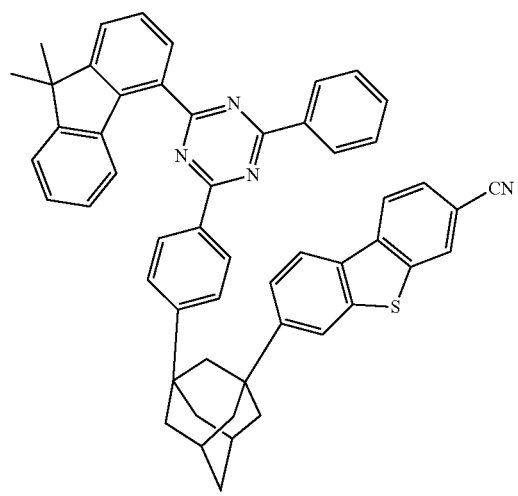
199
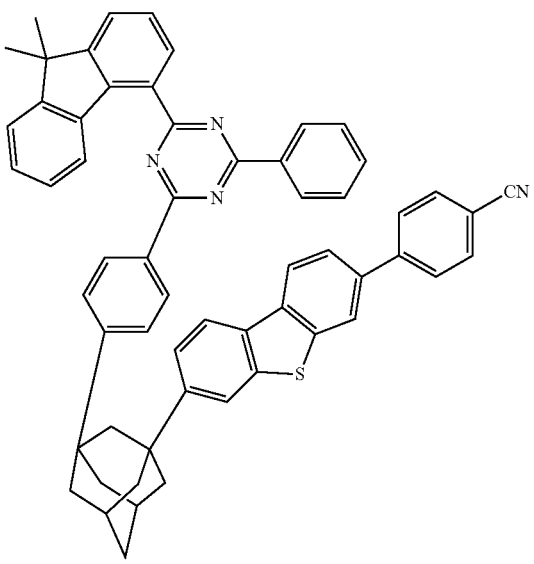

-continued
163
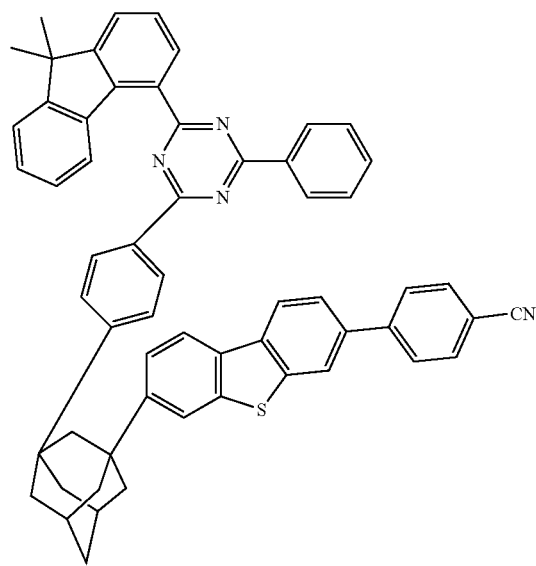
200
164
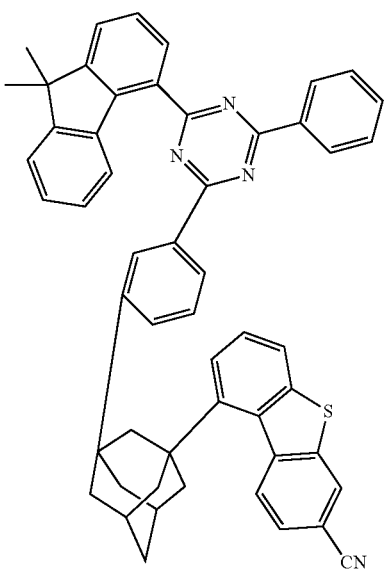
201
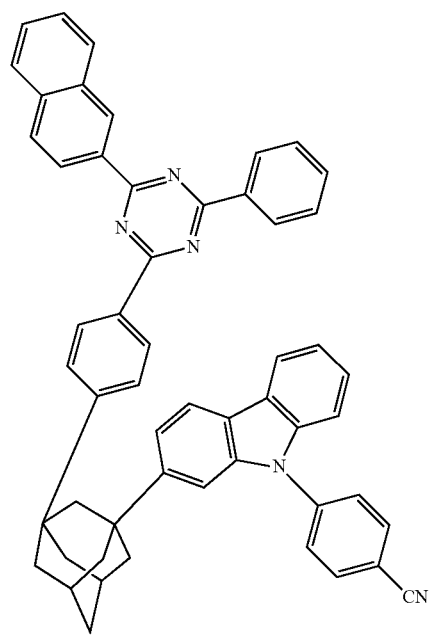
202
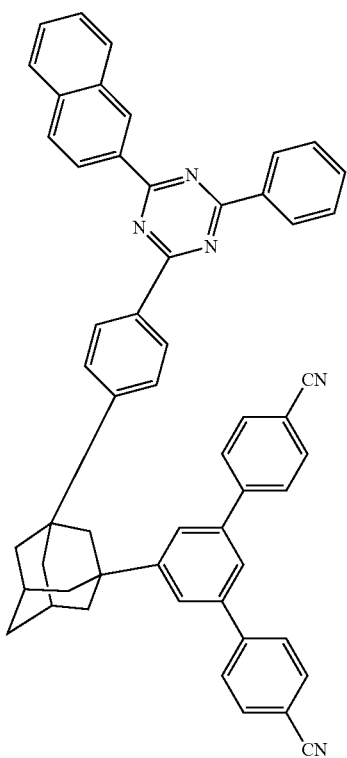
203

165 166
-continued
204 205
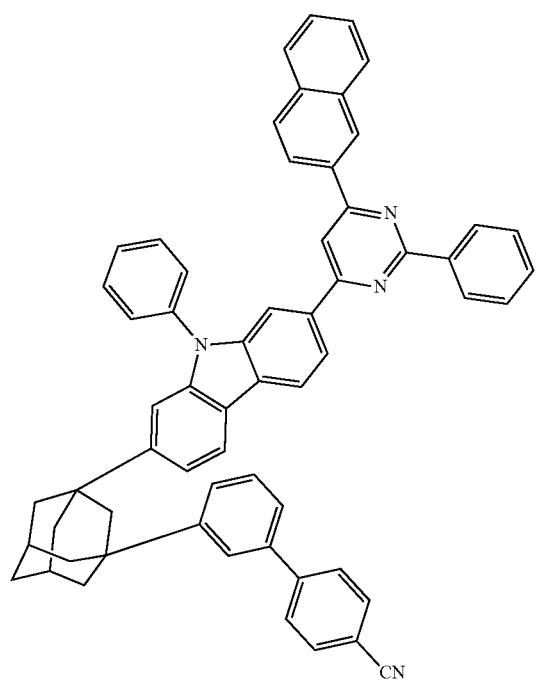
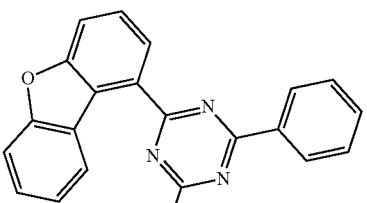
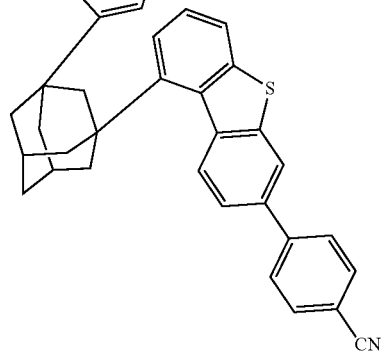
206 207
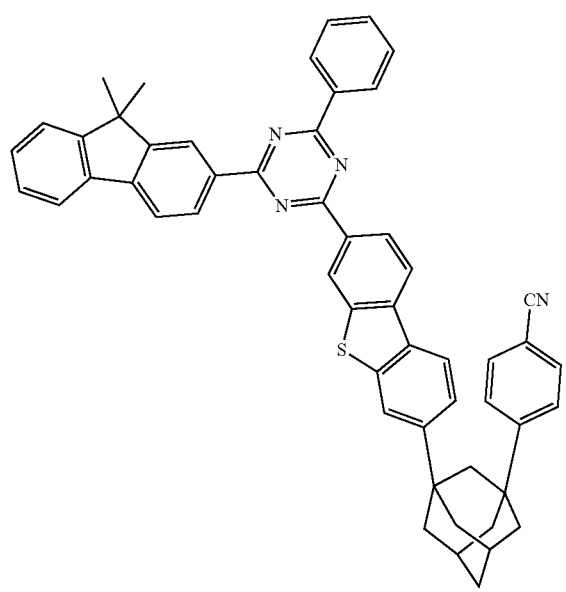
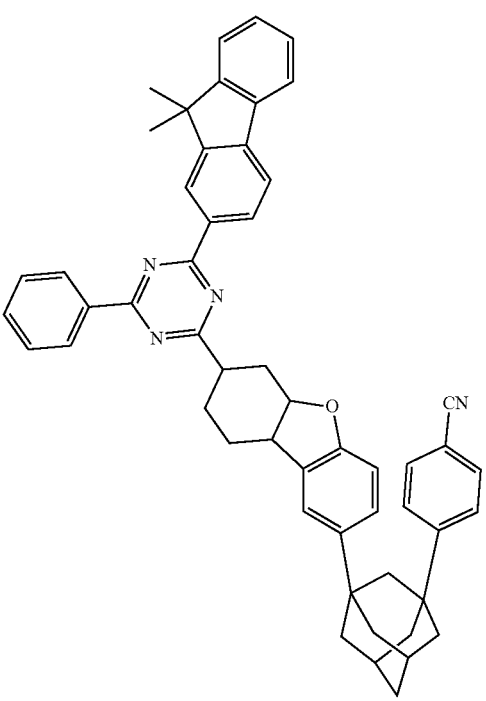

-continued
167 208 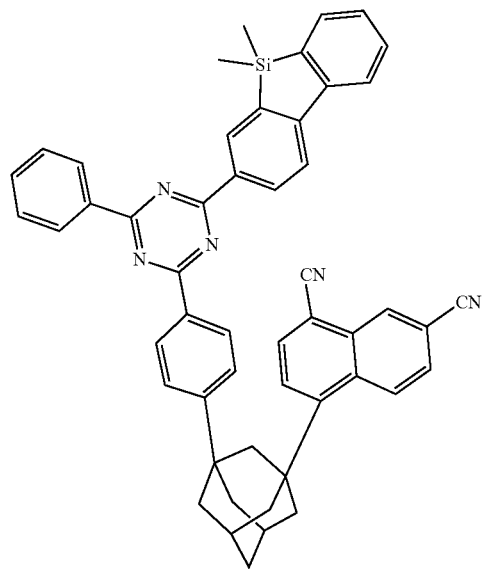
168 209 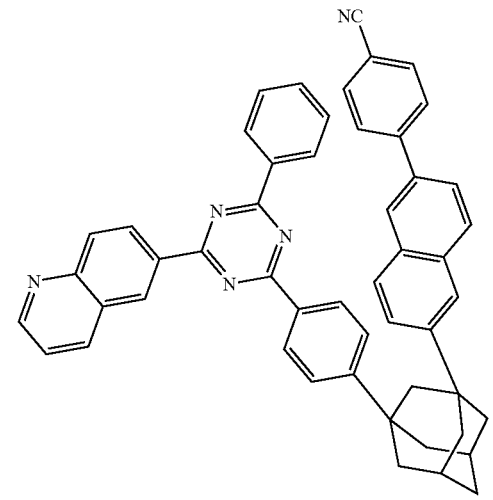
210 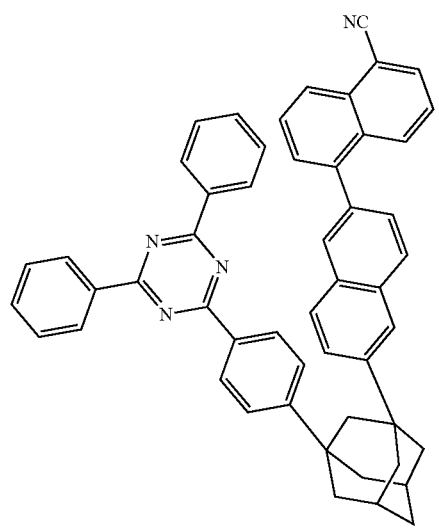
211 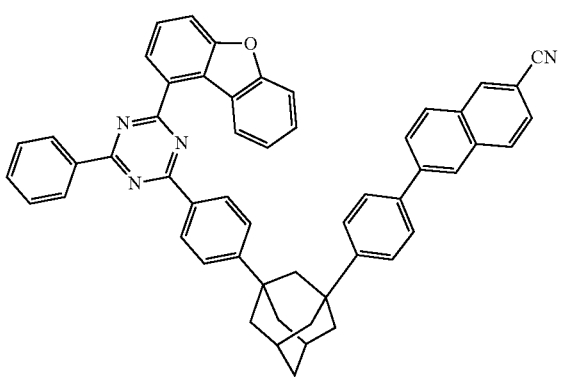

-continued
212
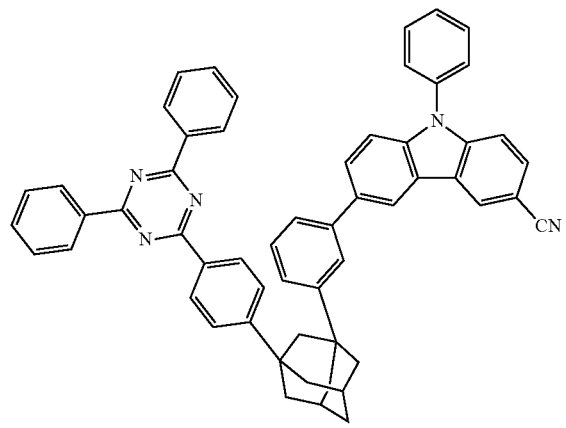
213
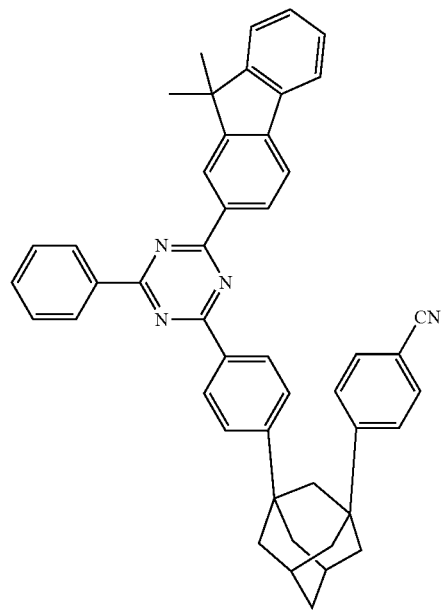
214
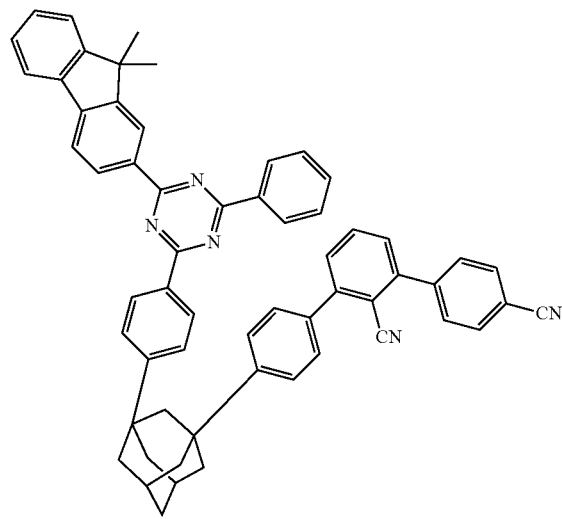
215
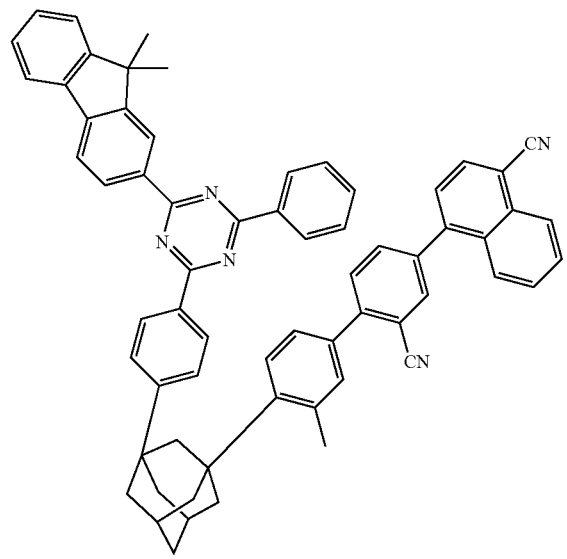

-continued
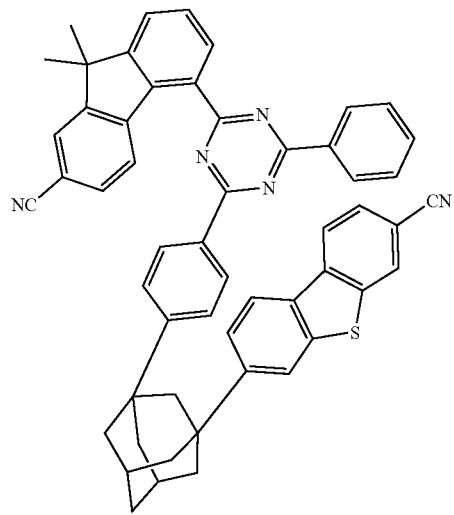
216
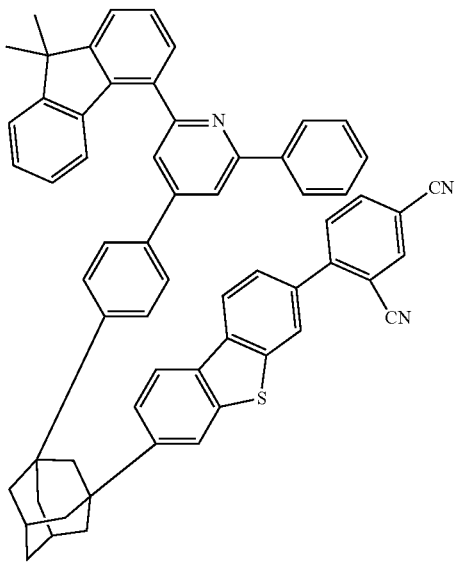
217
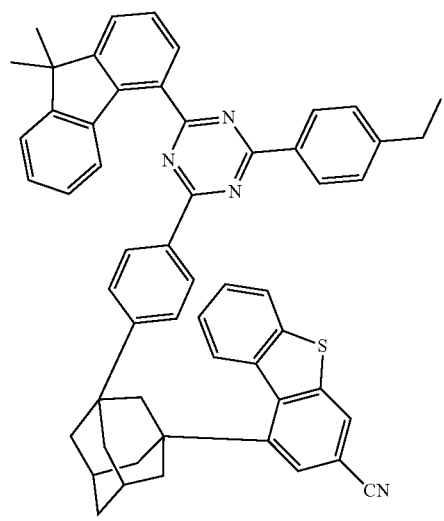
218
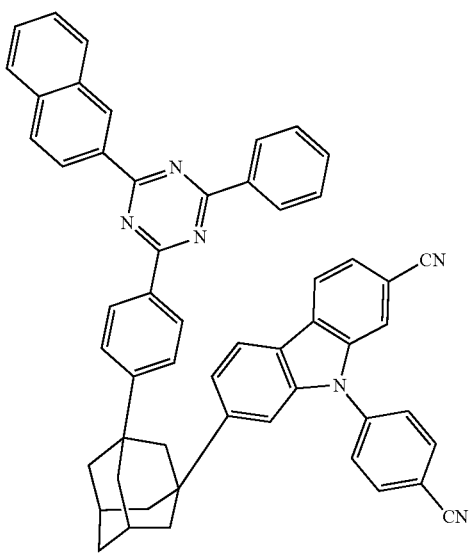
219

-continued
173 220
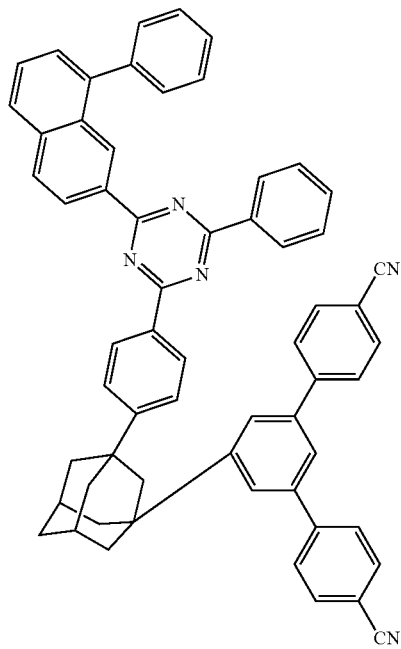
174 221
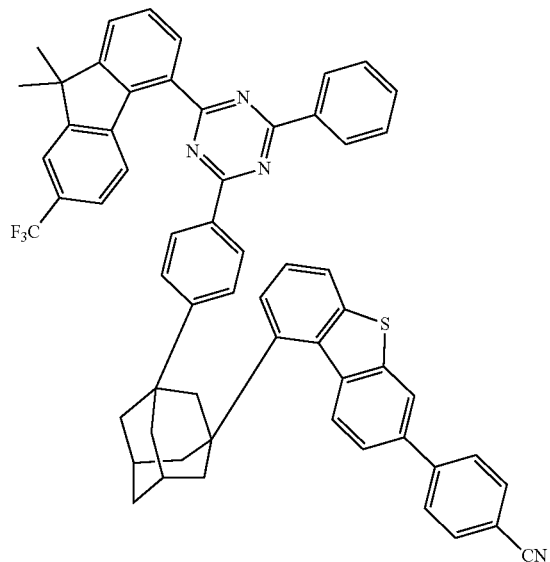
222
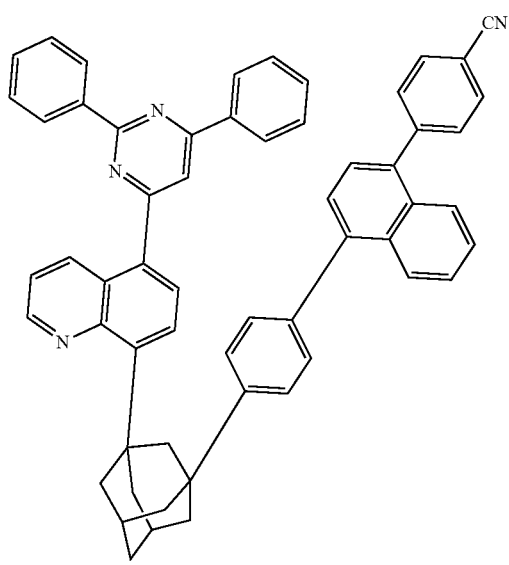
223
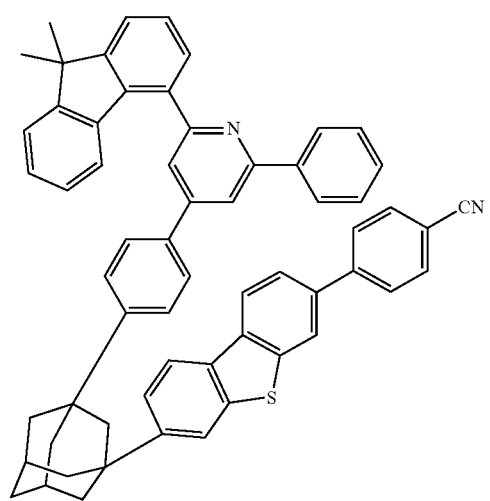

224
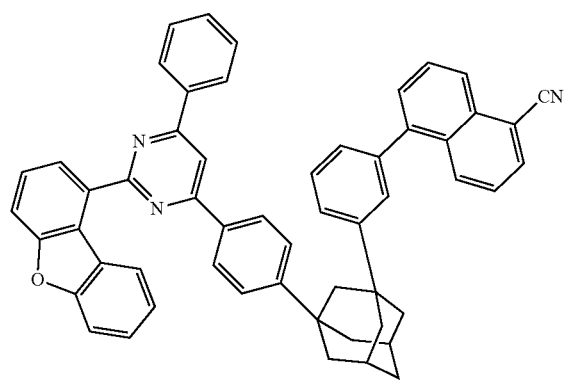
225
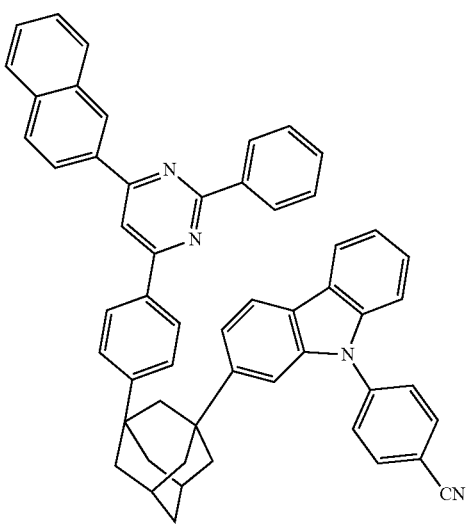
226
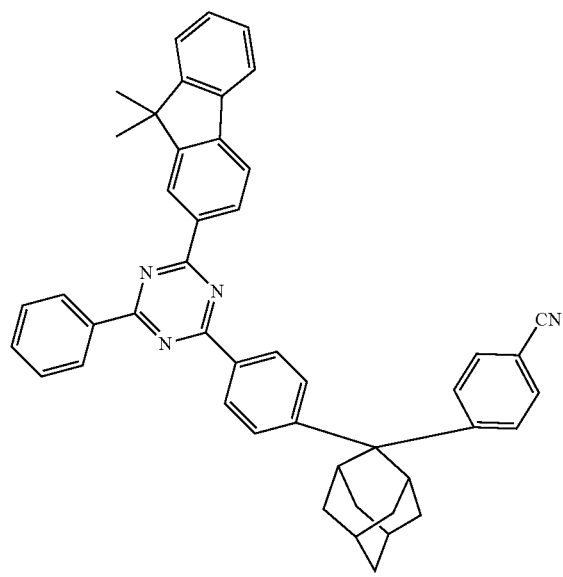
227
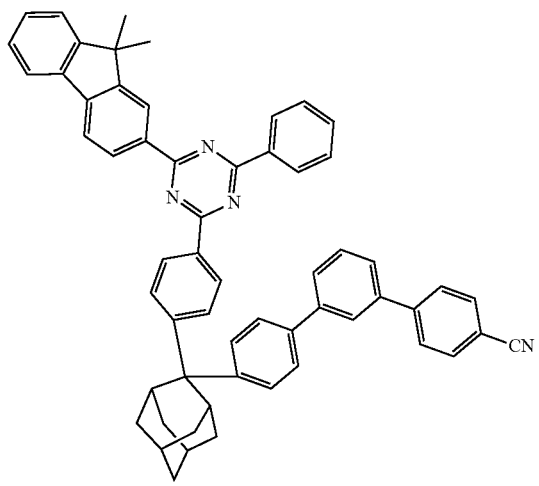

-continued
228
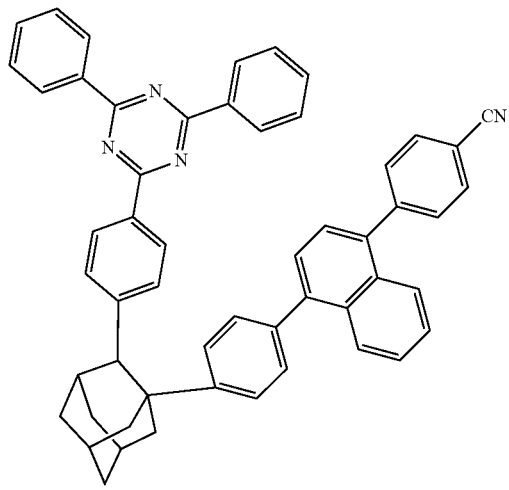
229
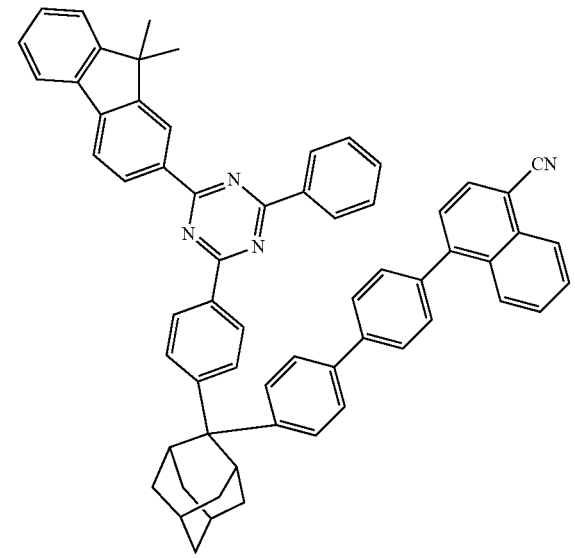
230
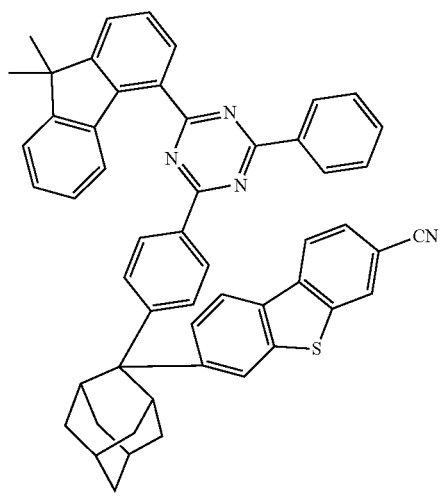
231
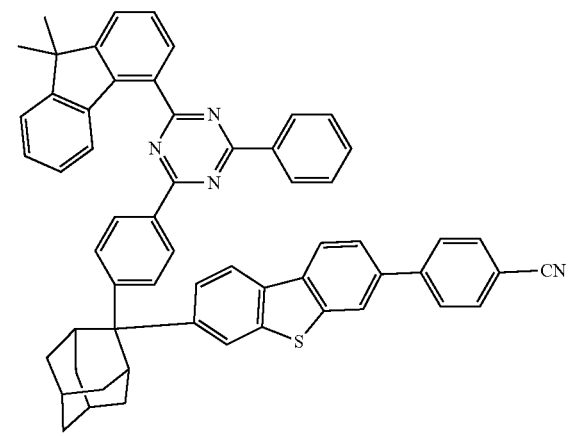
232
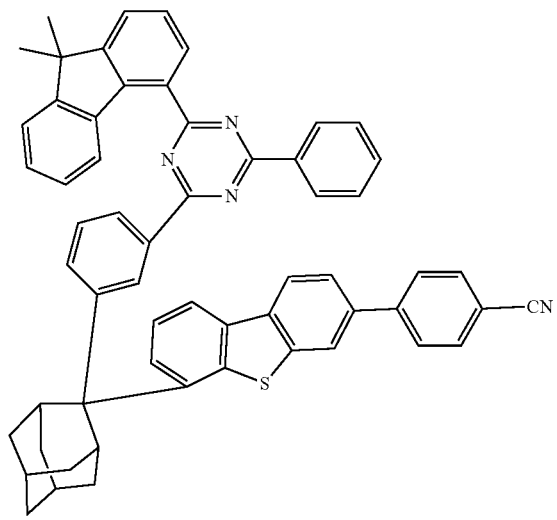
233
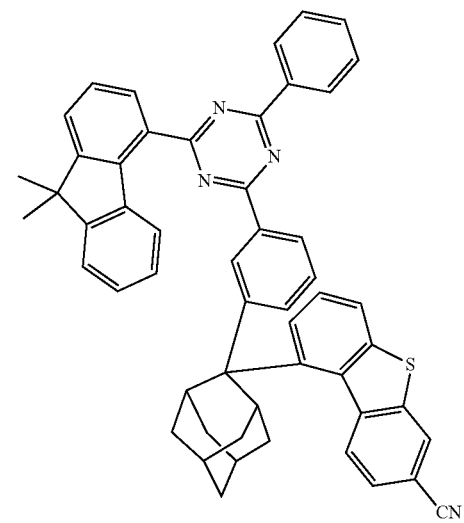

-continued
179 234
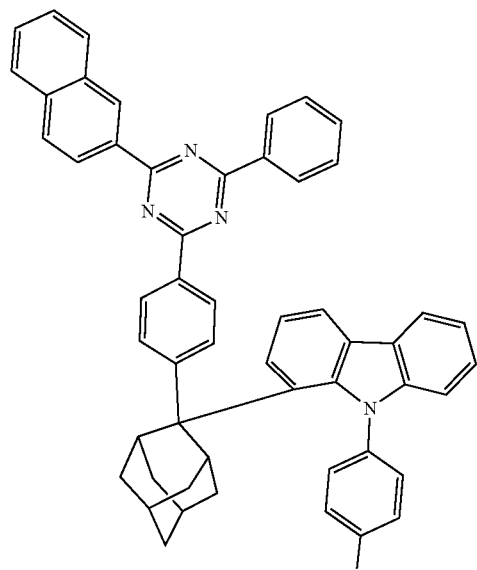
180 235
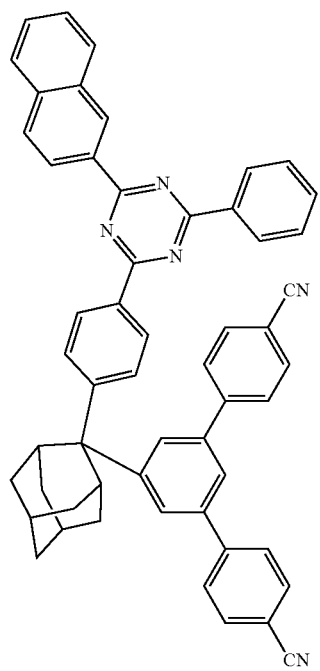
236
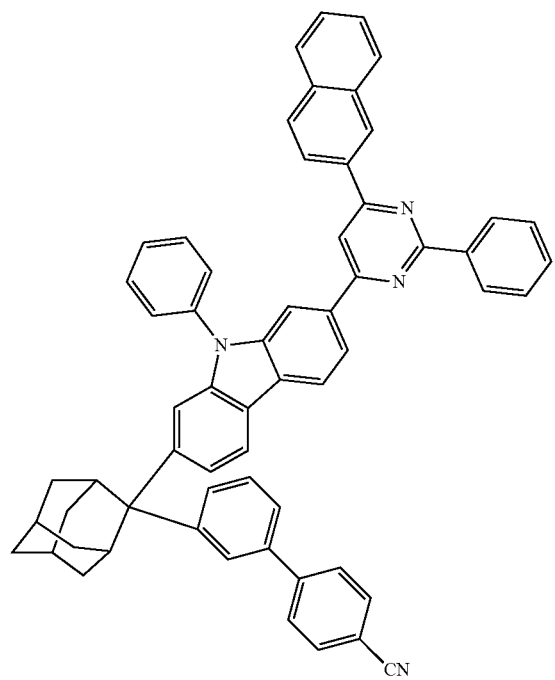
237
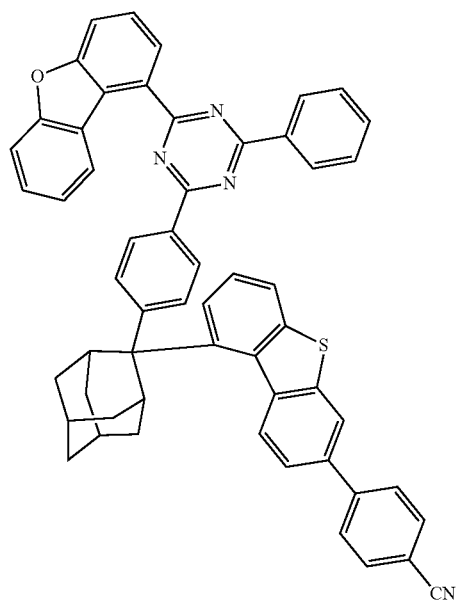

181 182
-continued
238
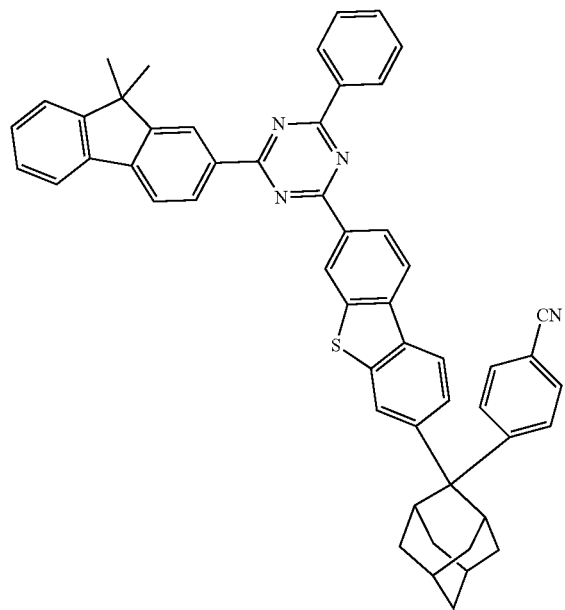
239
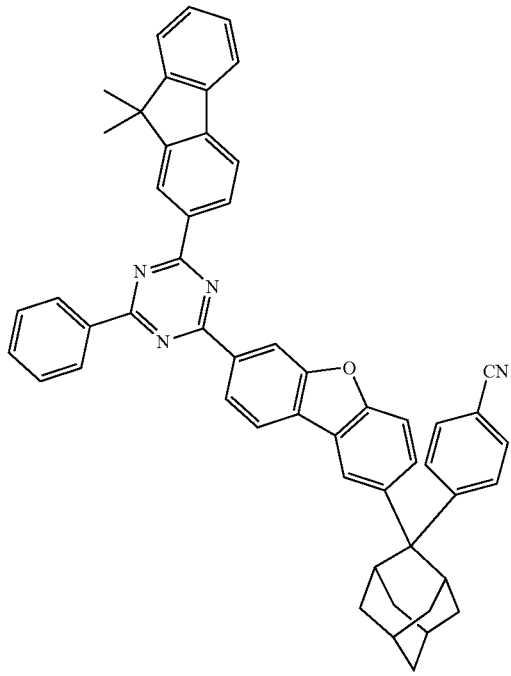
240
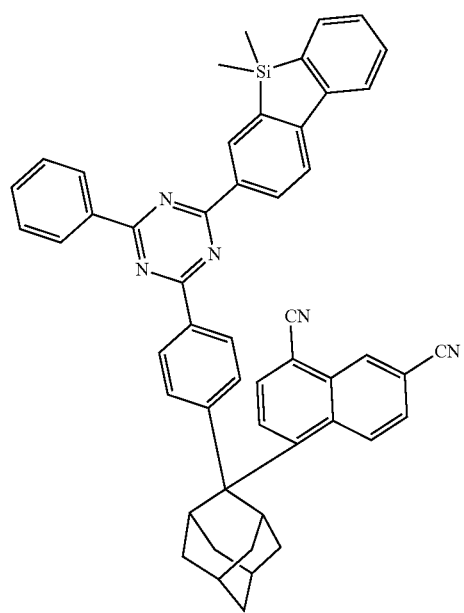
241
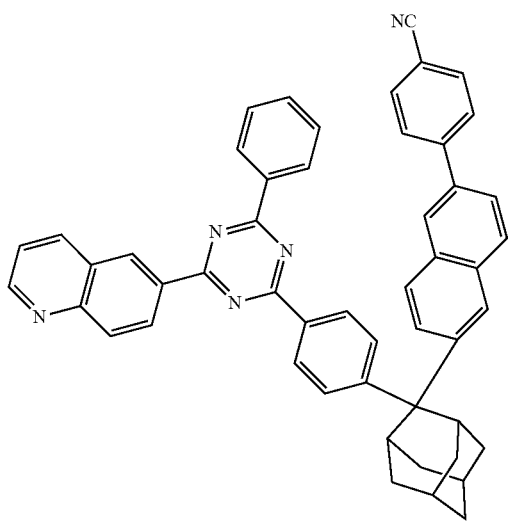

-continued
242
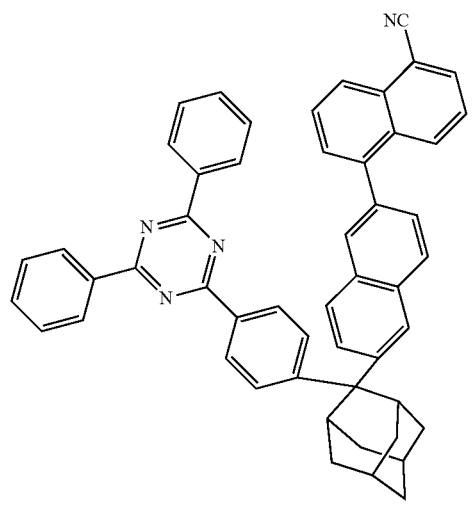
243
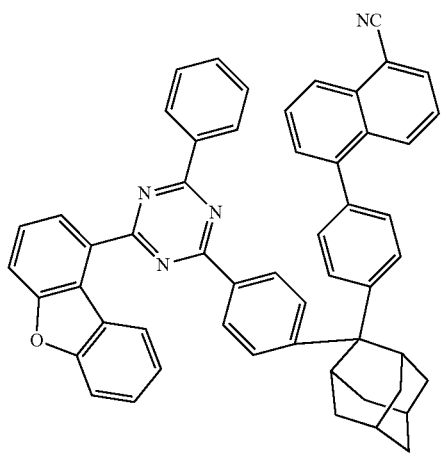
244
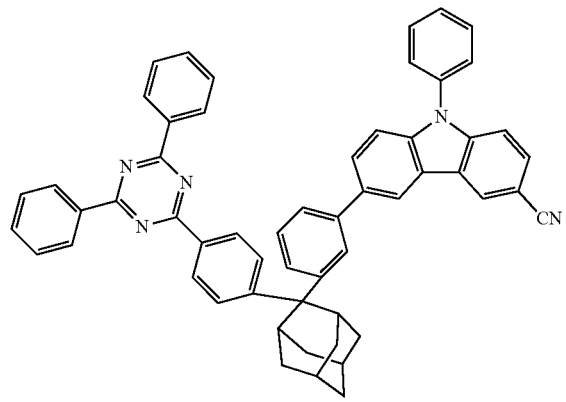
245
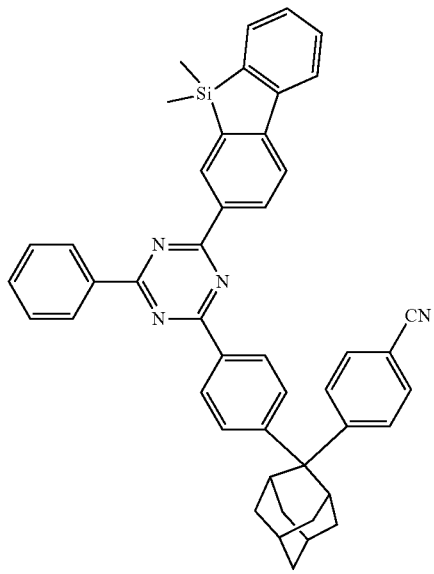
246
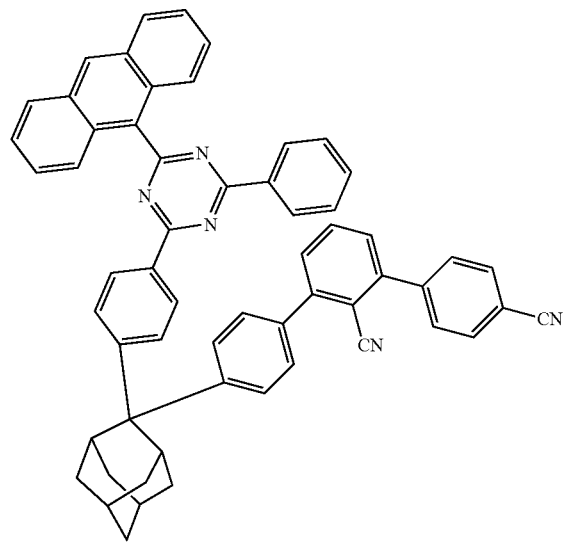
247
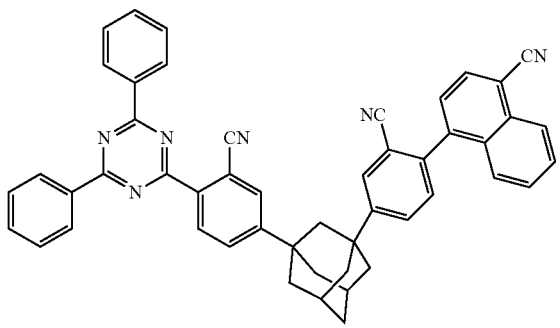

-continued
185
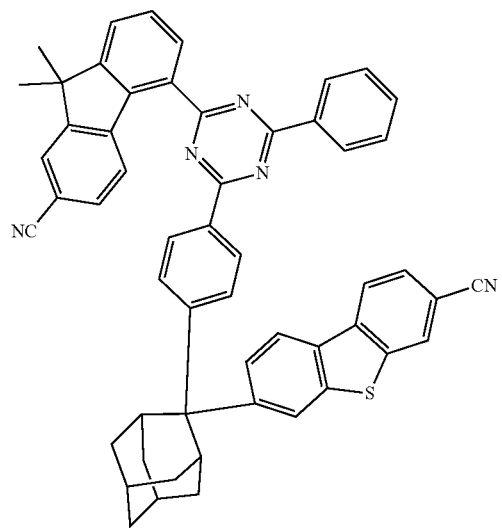
186
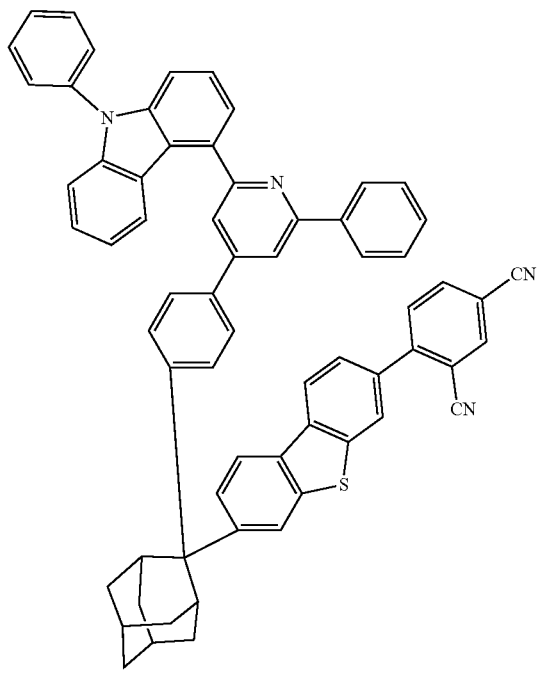
248
249
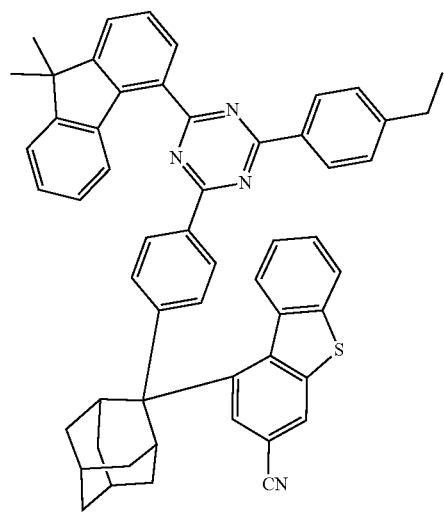
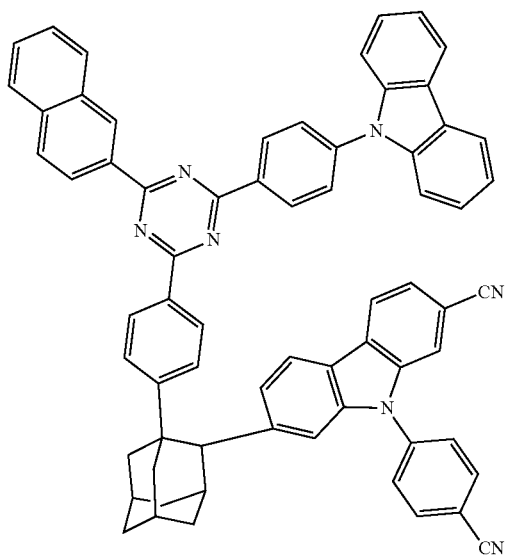
250
251

-continued
187
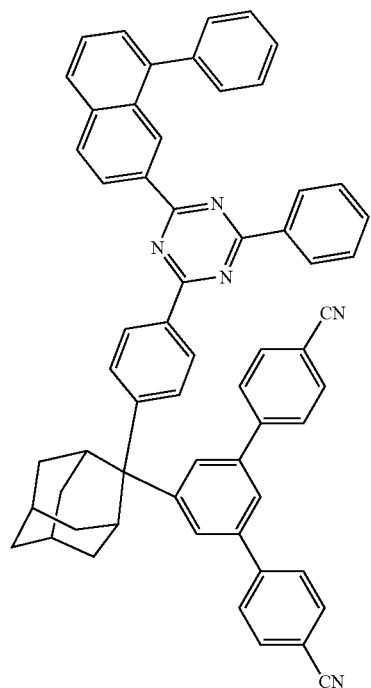
188
252
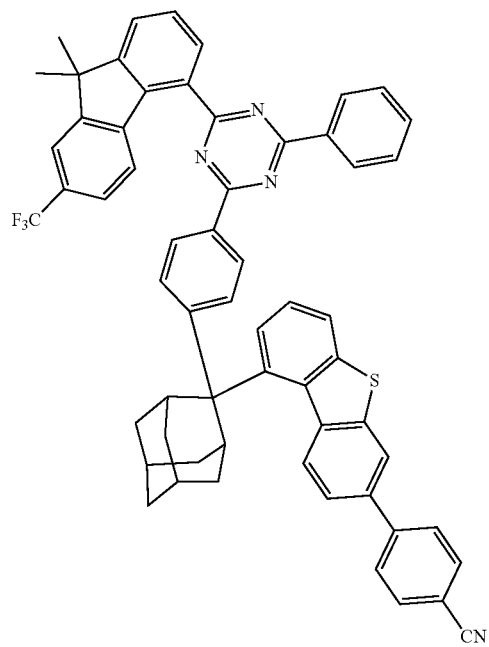
253
254
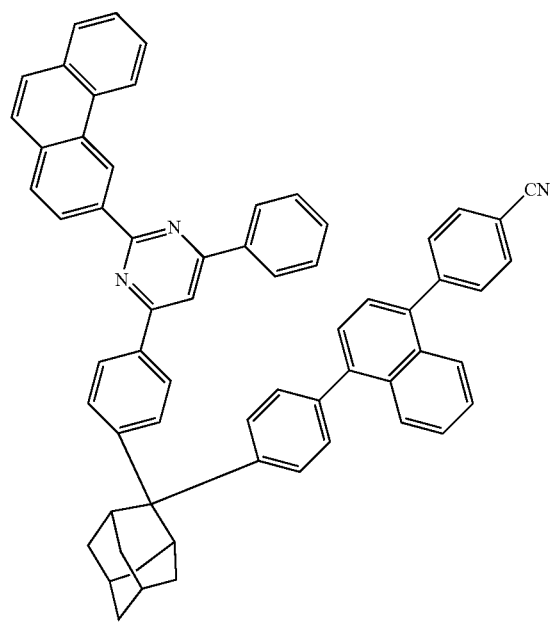
255
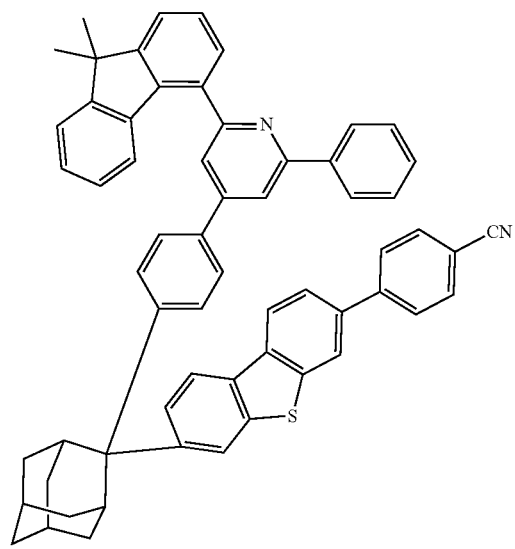

-continued
256
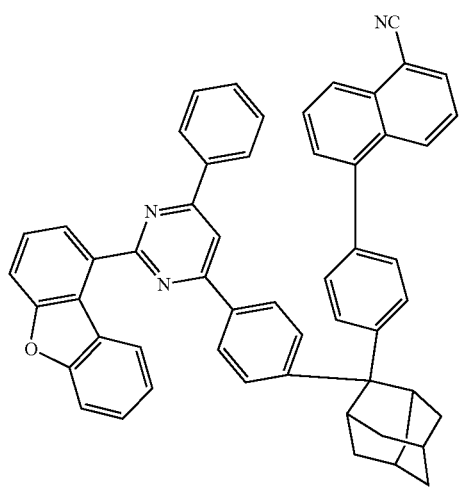
257
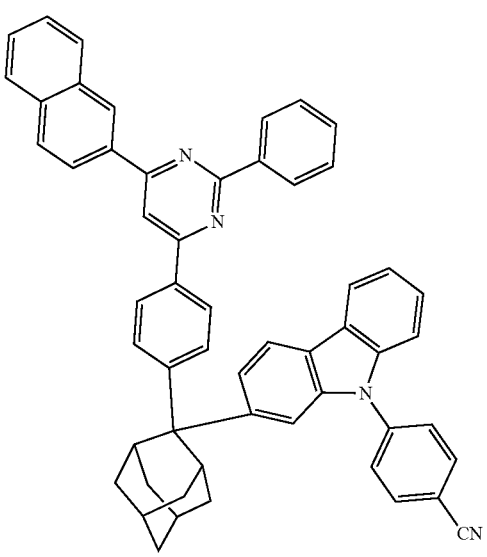
258
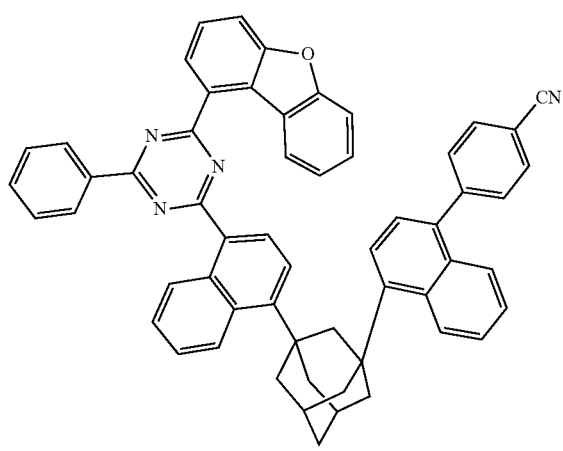
259
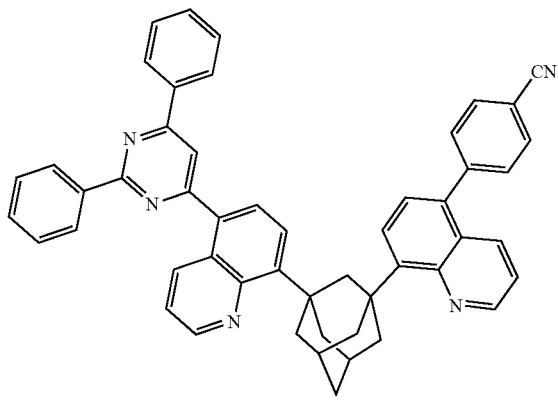
260
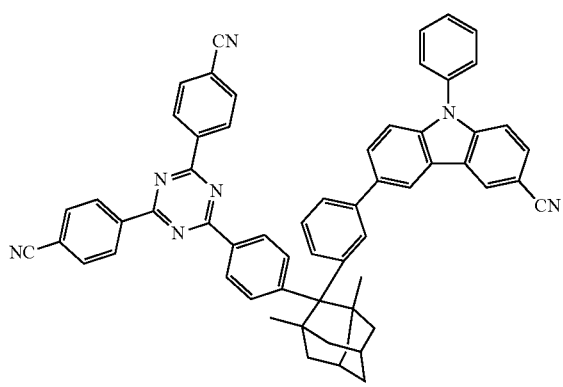
261
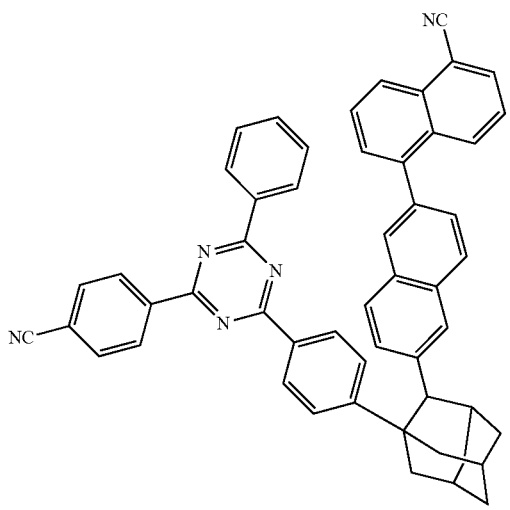

-continued
262
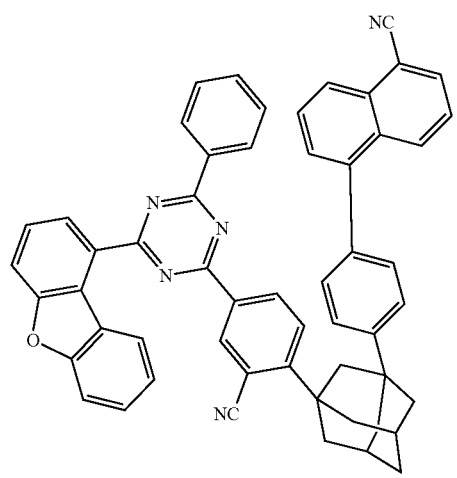
263
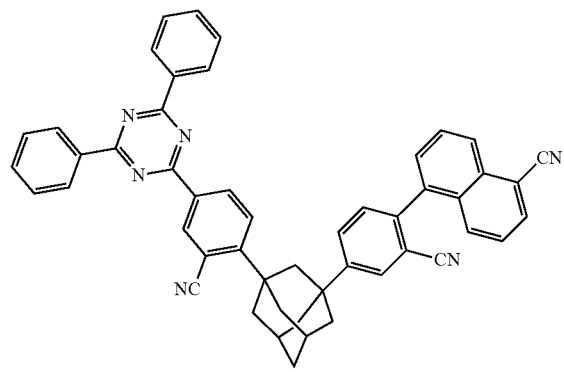
264
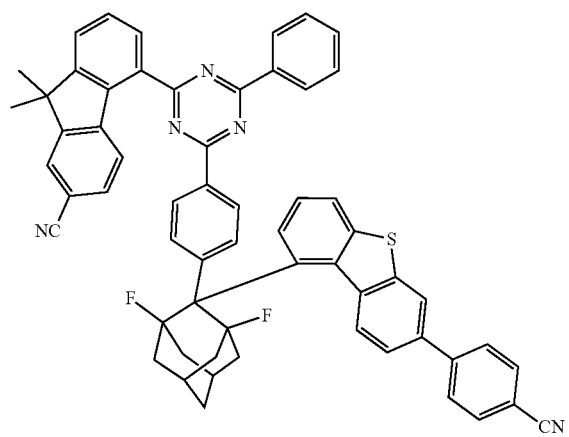
265
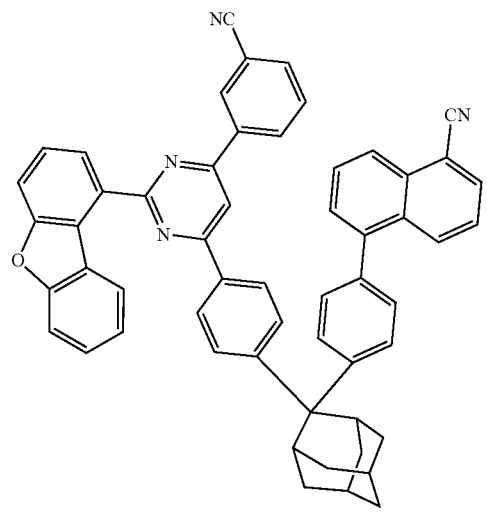
266
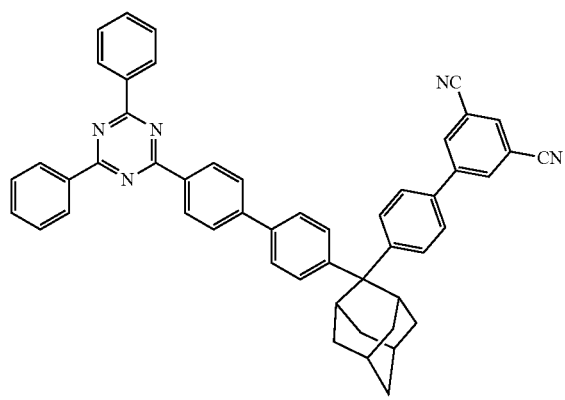
267
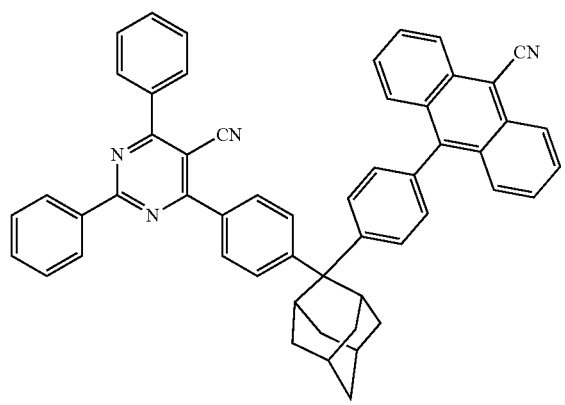

-continued
268
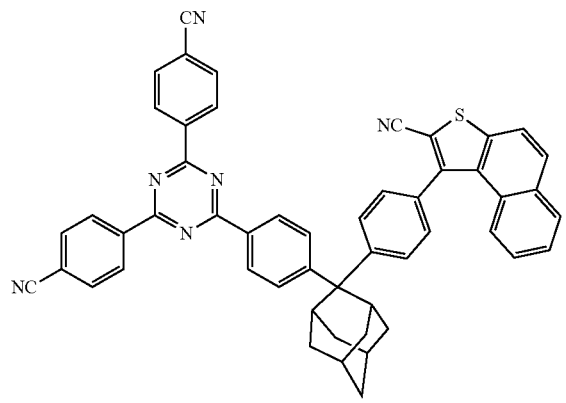
269
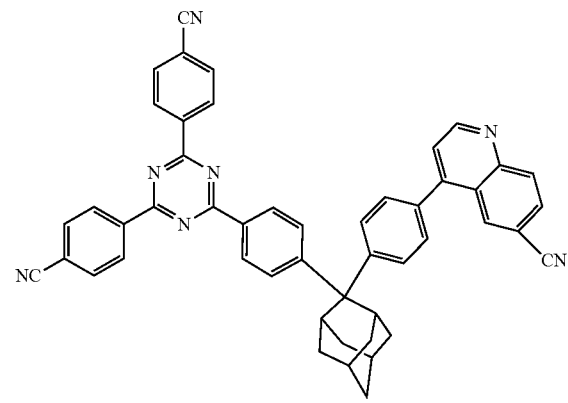
270
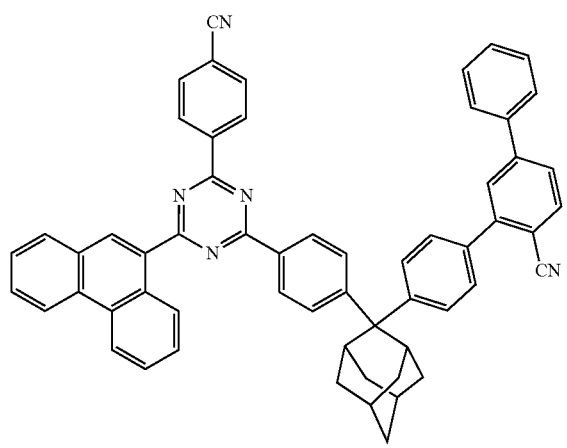
271
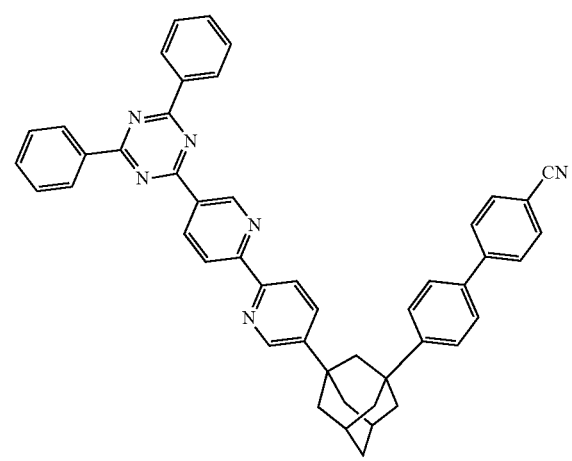
272
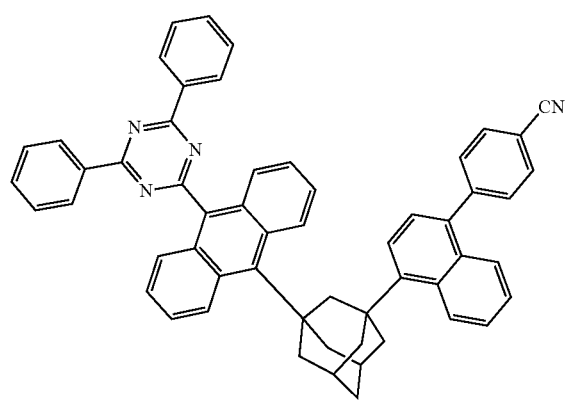
273
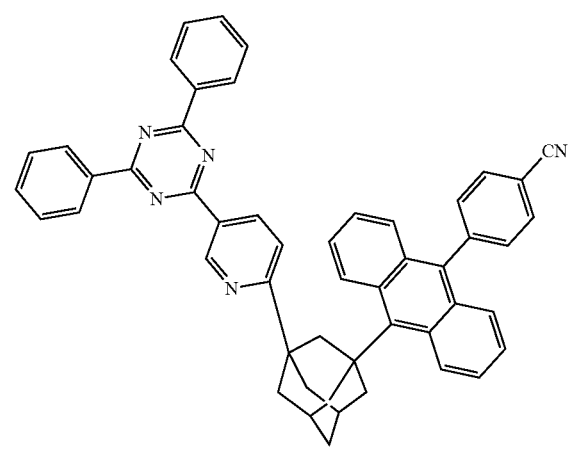

-continued
274
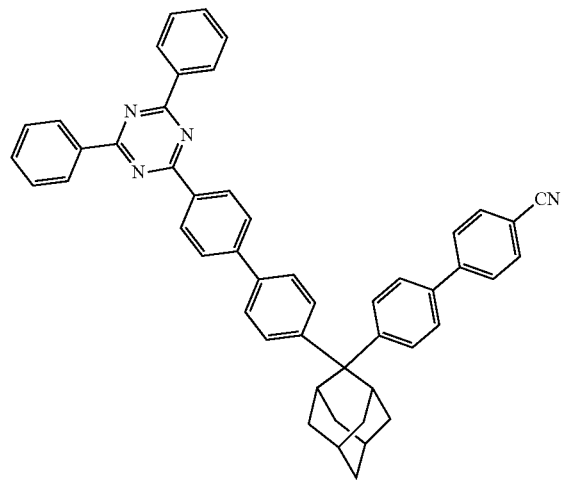
275
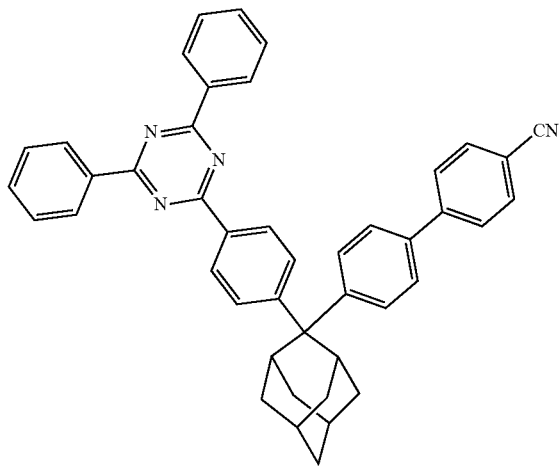
276
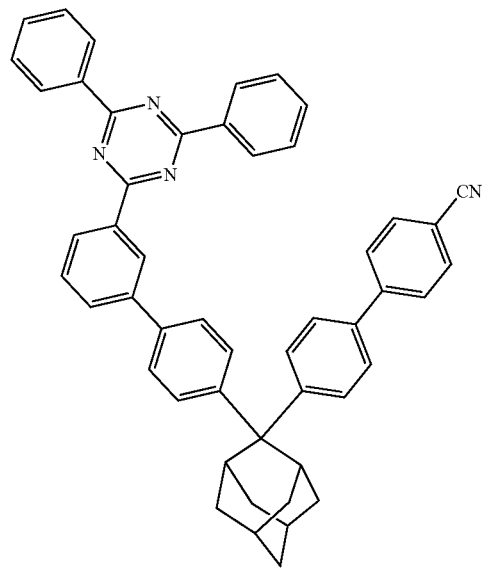
277
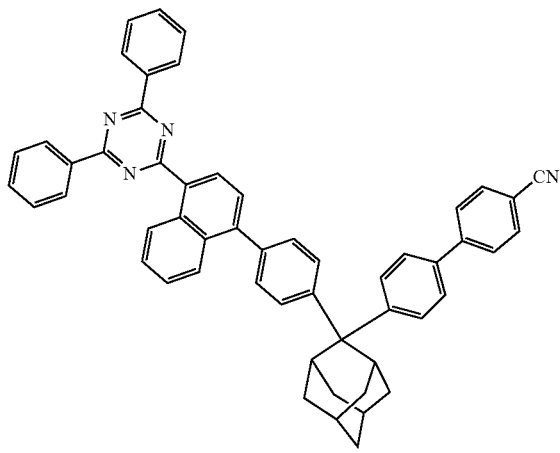
278
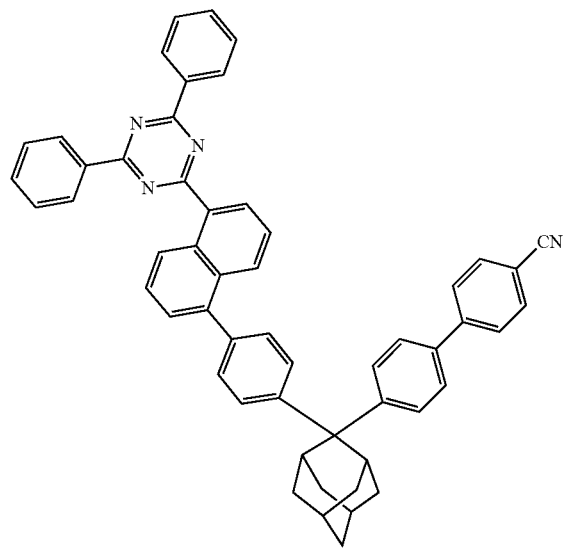
279
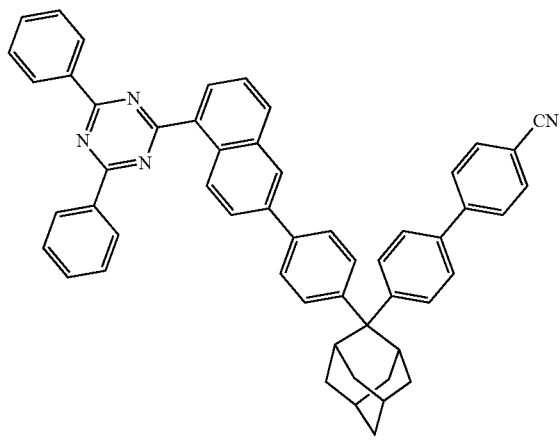

-continued

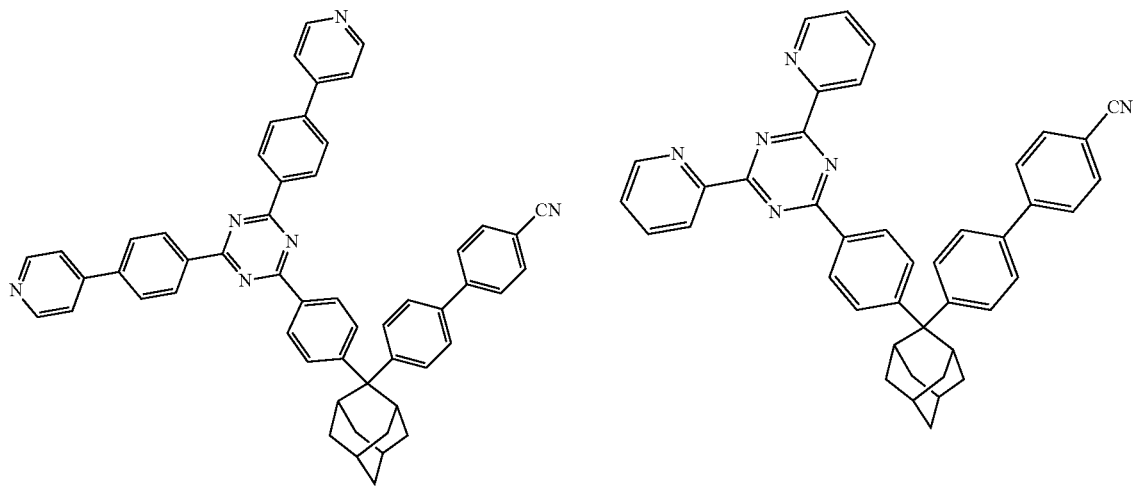

280

281

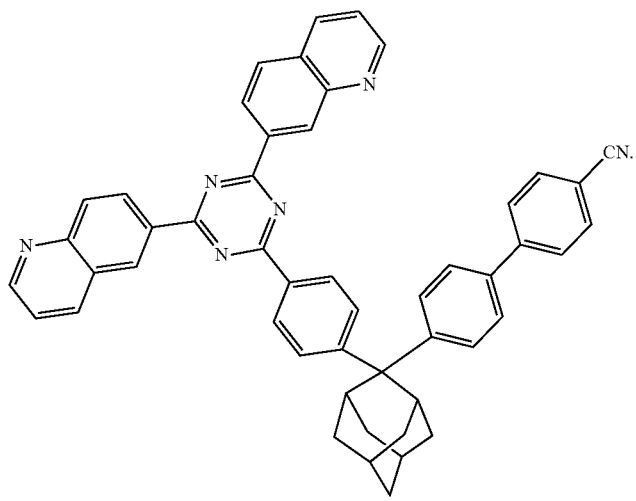

282

The following synthesis examples and embodiments are used to further illustrate and explain the content of the present disclosure.

Generally, the organic compound of the present disclosure can be prepared by the method described in the present disclosure, and those skilled in the art will recognize that the chemical reactions described in the present disclosure can be used to appropriately prepare many other compounds in the present disclosure, and other methods used to prepare the organic compound of the present disclosure are all considered to fall within the scope of the present disclosure. For example, those skilled in the art can synthesize other organic compounds in the present disclosure by referring to or appropriately modifying the preparation method provided in the present disclosure, for example, by using appropriate protecting groups, using other known reagents in addition to those described in the present disclosure, modifying reaction conditions, etc.

In the synthesis examples described below, the temperature is in degrees Celsius unless otherwise stated.

Some reagents were purchased from commercial suppliers such as Aldrich Chemical Company, Arco Chemical Company and Alfa Chemical Company, etc. Unless otherwise stated, these reagents were used without further purification. Some conventional reagents were purchased from Shantou Xilong Chemical Factory, Guangdong Guanghua Chemical Reagent Factory, Guangzhou Chemical Reagent Factory, Tianjin Haoyuyu Chemical Co., Ltd., Tianjin Fuchen Chemical Reagent Factory, Wuhan Xinhuayuan Technology Development Co., Ltd., Qingdao Tenglong Chemical Reagent Co., Ltd. and Qingdao Ocean Chemical Plant.

Among them, anhydrous tetrahydrofuran, dioxane, toluene and ether were obtained by refluxing and drying of sodium metal. Anhydrous dichloromethane and chloroform were obtained by refluxing and drying of calcium hydride. Ethyl acetate, petroleum ether, n-hexane, N,N-dimethylacetamide and N,N-dimethylformamide were dried with anhydrous sodium sulfate before use.

Unless otherwise stated, the following reactions were generally carried out under a positive pressure of nitrogen or argon, or a drying tube was set on an anhydrous solvent; reaction flasks were all stoppered with suitable rubber stoppers, and substrates were injected into the reaction flasks through syringes. Glassware was dried.

Silica gel columns were used as chromatographic columns. Silica gel (100-200 meshes) was purchased from Qingdao Ocean Chemical Plant.

Measurement conditions of low-resolution mass spectrometry (MS) data were: Agilent 6120 quadrupole HPLC-M (column model: Zorbax SB-C18, 2.1×30 mm, 3.5 microns, 6 min, flow rate 0.6 mL/min. Mobile phase: the ratio of 5%-95% (acetonitrile containing 0.1% formic acid) in ($H_2O$ containing 0.1% formic acid), electrospray ionization (ESI), and UV detection at 210 nm/254 nm.

$^1$H NMR spectra were recorded using the Bruker 400 MHz or 600 MHz nuclear magnetic resonance spectrometer. The $^1$H NMR spectra took $CDCl_3$, $CD_2Cl_2$, $D_2O$, DMSO-$d_6$, $CD_3OD$ or acetone-$d_6$ as a solvent (in ppm) and TMS (0 ppm) or chloroform (7.26 ppm) as the reference standard. When multiple peaks appeared, the following abbreviations were used: s (singlet), d (doublet), t (triplet), m (multiplet), br (broadened), and dd (doublet of doublets).

For pure compounds, Agilent 1260 pre-HPLC or Calesep pump 250 pre-HPLC (column model: NOVASEP 50/80 mm DAC) was used, and UV detection was performed at 210 nm/254 nm.

General Synthesis Scheme:

A part of the compound (Final Product) of the present disclosure, as represented by the following chemical formula 1', was prepared by the reaction of intermediates sub 1 and sub 2, but was not limited thereto. Other part of the compound (Final Product) of the present disclosure, as represented by the following chemical formula 2', was prepared by the reaction of intermediates sub 1' and sub 2', but was not limited thereto.

<Reaction Process 1>

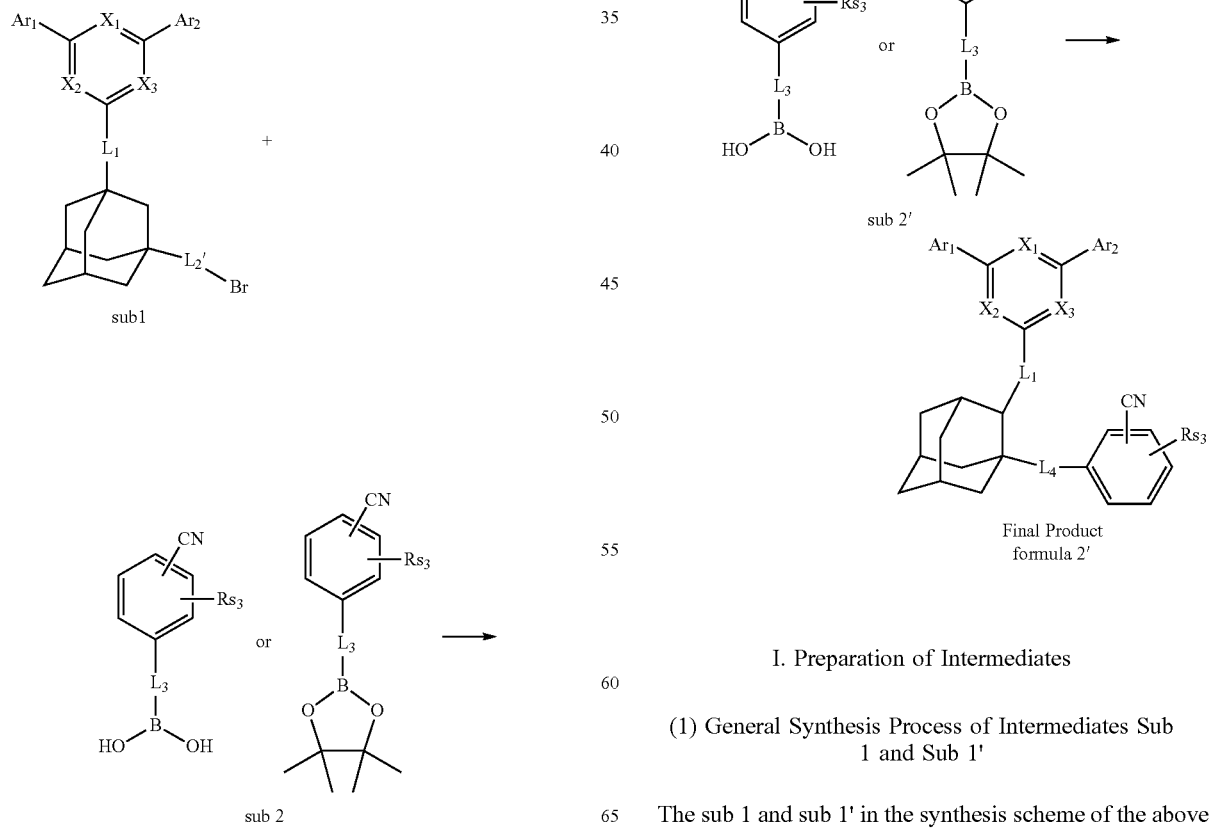

<Reaction Process 2>

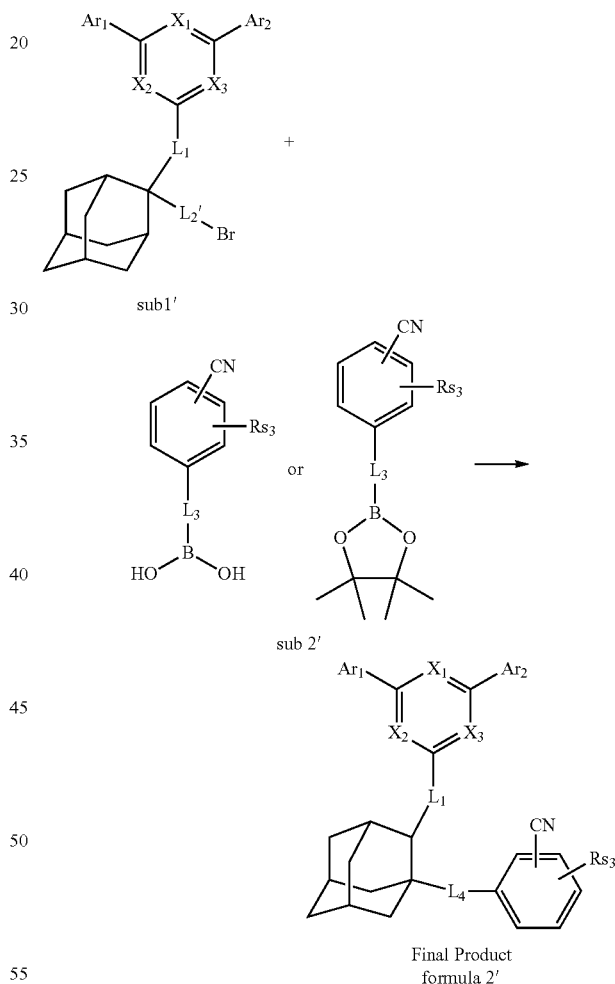

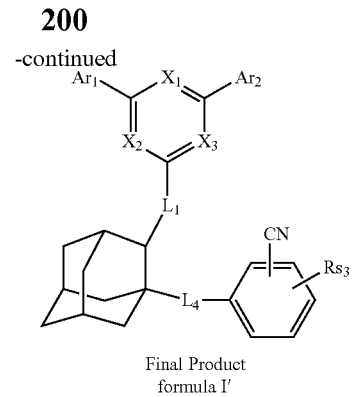

I. Preparation of Intermediates (1) General Synthesis Process of Intermediates Sub 1 and Sub 1'

The sub 1 and sub 1' in the synthesis scheme of the above compound 1' and compound 2' can be synthesized by the following <reaction process 3>, but was not limited thereto.

<Reaction Process 3>

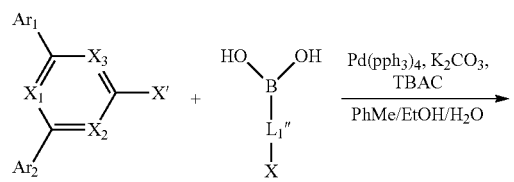

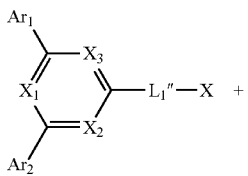

sub 1-I

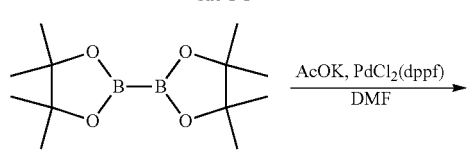

sub 1-II

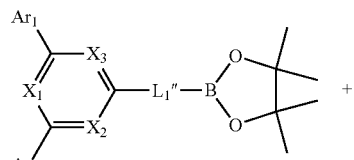

sub 1-III

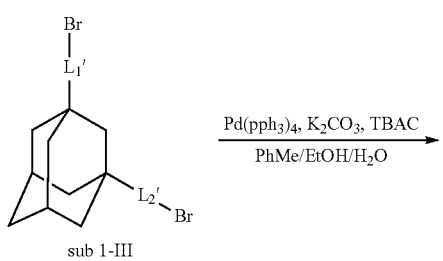

sub 1

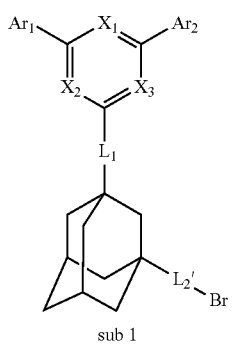

sub 1

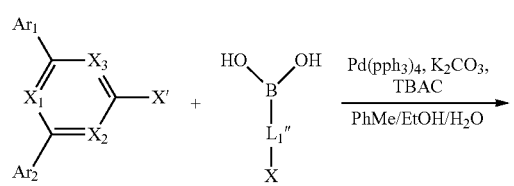

-continued

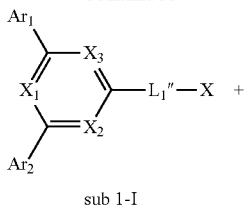

sub 1-I

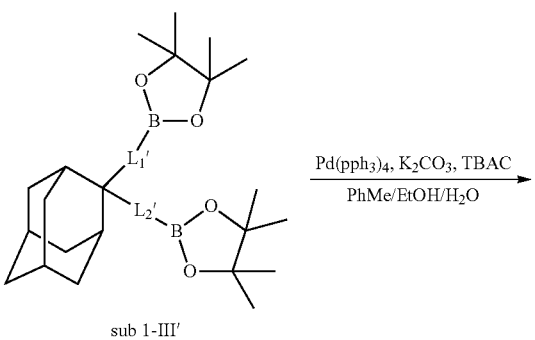

sub 1-III'

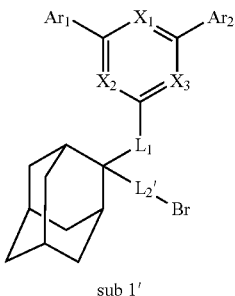

sub 1'

In the above <reaction process 1> to <reaction process 3>, $Ar_1$, $Ar_2$, $X_1$, $X_2$, $X_3$ and $L_1$ had the same meanings as in other parts of the specification, and Rs3 was selected from the group consisting of deuterium, halogen, cyano, alkyl with 1 to 10 carbon atoms, haloalkyl with 1 to 10 carbon atoms, aryl with 1 to 10 carbon atoms, haloalkyl with 1 to 10 carbon atoms, aryl with 6 to 20 carbon atoms, heteroaryl with 3 to 20 carbon atoms, aryloxy with 6 to 20 carbon atoms, arylthio with 6 to 20 carbon atoms, alkylsilyl with 3 to 12 carbon atoms, alkylamino with 1 to 10 carbon atoms and cycloalkyl with 3 to 10 carbon atoms; $L_2'$, $L_3'$, $L_4$, and $L_1''$ were substituted or unsubstituted arylenes with 6 to 30 carbon atoms, or substituted or unsubstituted heteroarylenes with 3 to 30 carbon atoms; X and X' were halogen.

(2) Preparation Example 1: Specific Synthesis Examples of Intermediate Compounds Sub 1 and Sub 1' are as Follows
Synthesis Routes of Sub 1-B1 and Sub 1-C1
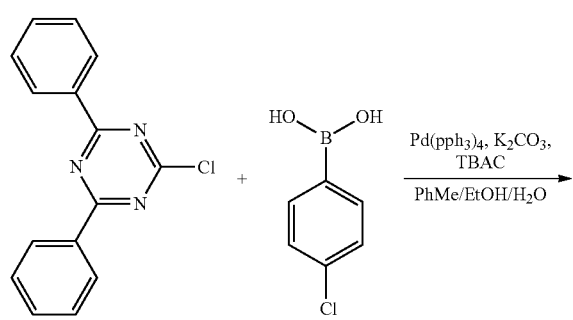
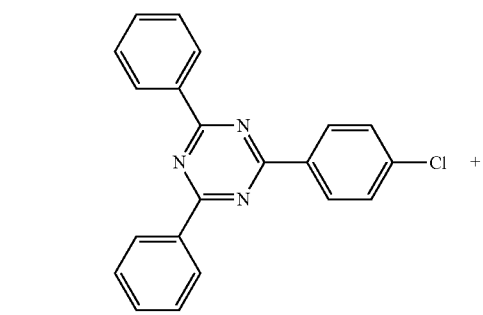
sub 1-I-B1
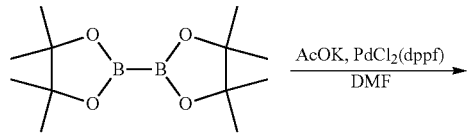
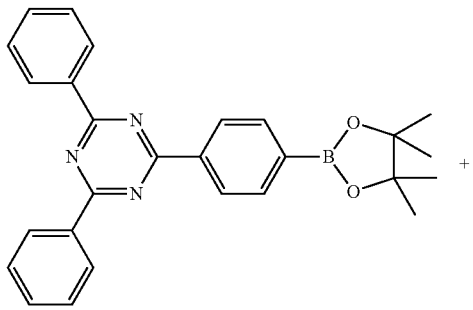
sub 1-I-B2
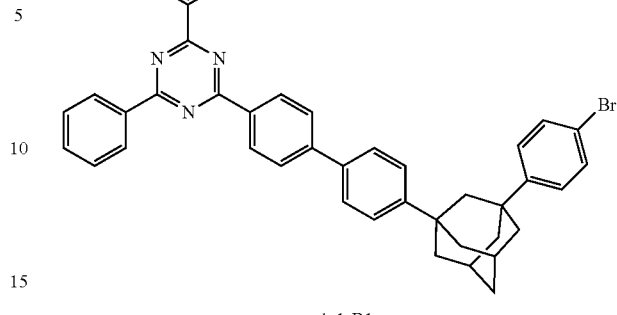
sub 1-II-B2
-continued
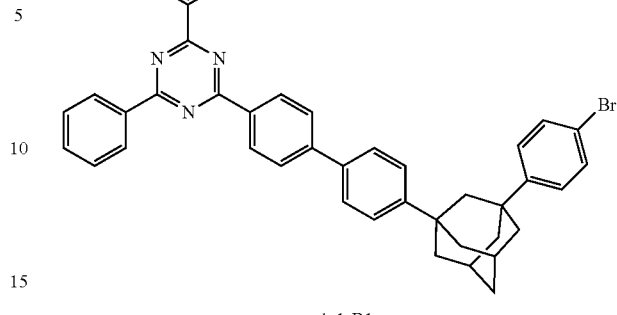
sub 1-B1
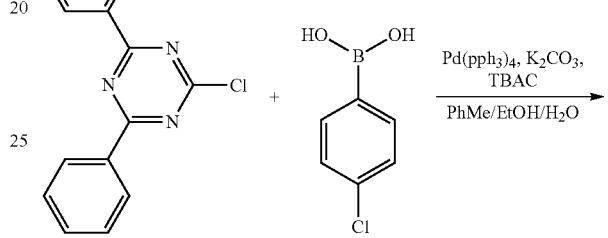
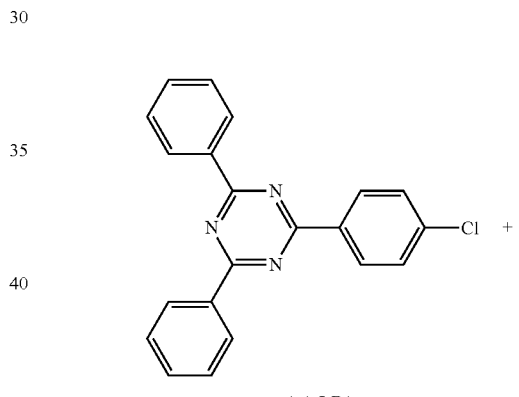
sub 1-I-B1
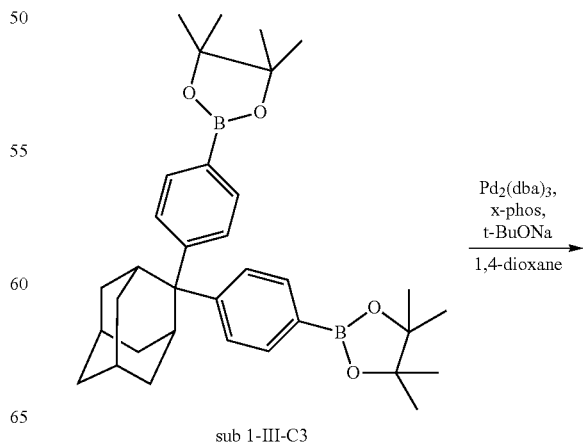
sub 1-III-C3

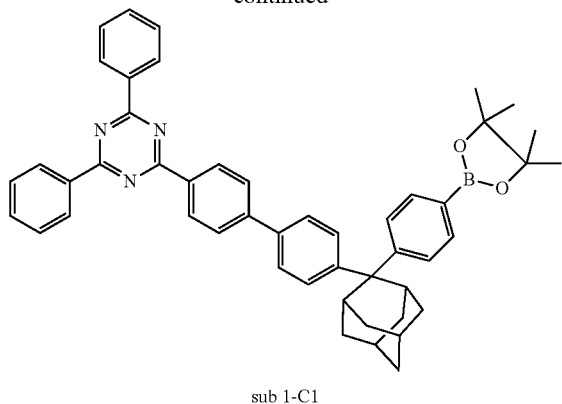

sub 1-C1

1) Synthesis of Sub 1-I-B1

2-chloro-4,6-diphenyl-1,3,5-triazine (20.00 g, 74.70 mmol), p-chlorophenylboronic acid (14.01 g, 89.64 mmol), tetrakis(triphenylphosphine)palladium (1.72 g, 1.49 mmol), potassium carbonate (22.71 g, 164.35 mmol), tetrabutylammonium chloride (4.15 g, 14.94 mmol), toluene (160 mL), ethanol (80 mL) and deionized water (40 mL) were added to a three-necked flask, the mixture was heated to 78° C. under nitrogen atmosphere for reflux and stirred for 8 h. After the reaction completed, the solution was cooled to room temperature, extracted with toluene (200 mL). The combined organic phases were dried over anhydrous MgSO$_4$ and filtered. The filtrate was concentrated in vacuo to obtain a crude product. The crude product was purified by silica gel column chromatography to obtain intermediate sub 1-I-B1 as a solid (20.59 g, yield 80%).

2) Synthesis of Sub 1-II-B2

The sub 1-I-B1 (20.00 g, 58.17 mmol), bis(pinacol) diboron (16.24 g, 63.98 mmol), Pd(dppf)Cl$_2$ (0.42 g, 0.58 mmol), and KOAc (14.37 g, 145.43 mmol) were added to 1,4-dioxane (200 mL), the mixture was heated to reflux at 100° C. and stirred for 12 h. After the reaction completed, the solution was cooled to room temperature, extracted with CH$_2$Cl$_2$ and water. The combined organic phases were dried over anhydrous MgSO$_4$ and filtered. The filtrate was concentrated in vacuo to obtain a crude product. The obtained crude product was stirred with n-heptane for 1 h and filtered to obtain a product sub 1-II-B2 (16.45 g, yield: 65%).

3) Synthesis of Sub 1-III-B3

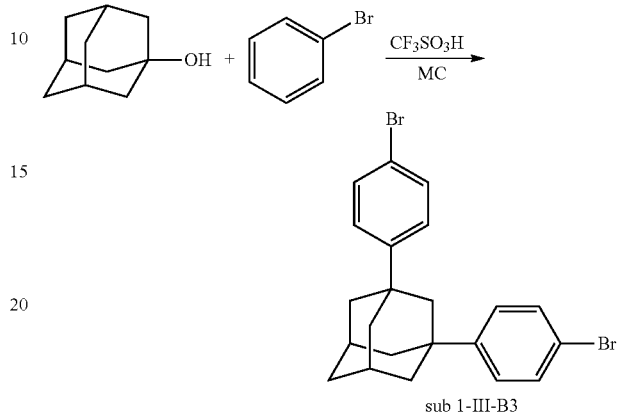

sub 1-III-B3

1-adamantanol (50.00 g, 328.45 mmol), bromobenzene (113.45 g, 722.59 mmol), and dichloromethane (500 mL) were added into a round bottom flask, the mixture was cooled to −5° C. under nitrogen atmosphere, and then added with trifluoromethanesulfonic acid (123.23 g, 821.12 mmol) dropwise. After dropwise addition, the solution was thermally insulated and stirred for 3 h, then deionized water (300 mL) was added to the reaction solution. The resulted mixture was washed with water to pH=7 and added with dichloromethane (100 mL) for extraction. The combined organic phases were dried over anhydrous MgSO$_4$ and filtered. The filtrate was concentrated in vacuo to obtain a crude product. The obtained crude product was purified by silica gel column chromatography and eluted with n-heptane to obtain intermediate sub 1-III-B3 as a white solid (58.62 g, yield 40.00%).

4) Synthesis of Sub 1-III-C3

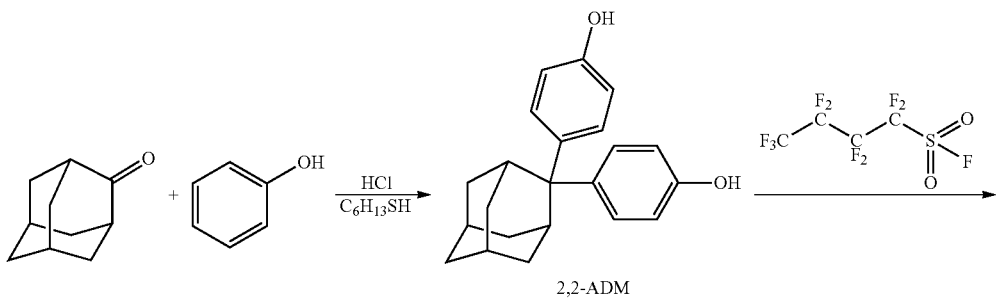

2,2-ADM

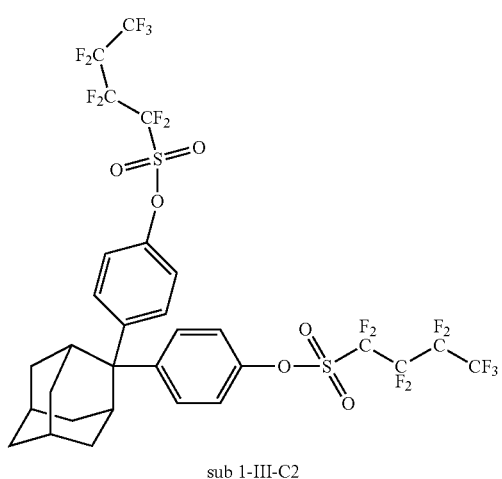
sub 1-III-C2

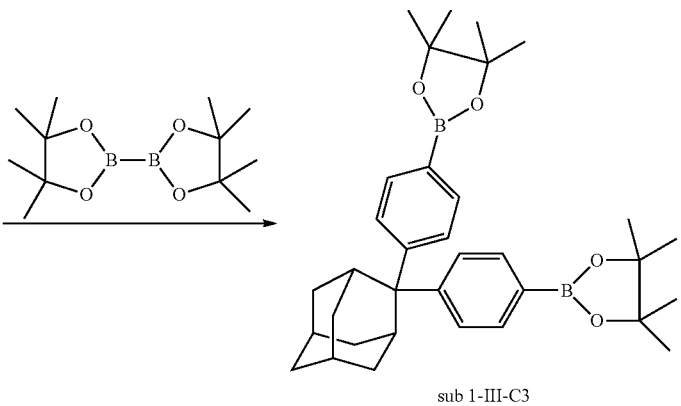
sub 1-III-C3

Synthesis of 2,2-ADM:

2-adamantanone (25.0 g, 166.4 mmol), phenol (125.2 g, 1331.5 mmol), and 1-hexyl mercaptan (1.2 g, 10.65 mmol) were dissolved in a three-necked flask. After completely dissolved, a hydrochloric acid solution (6.1 mL, 166.4 mol) was added dropwise to the solution, the mixture was allowed to stirred under nitrogen atmosphere for 24 h, and the temperature was preserved at 70° C. After the reaction was completed, the reaction mixture was cooled to 50° C., poured into 150 mL of water, and extracted three times with 200 mL of dichloromethane. The separated organic phase was wasted with water three times and dried over anhydrous magnesium sulfate, and then concentrated in vacuo to obtain a crude product. Then, the crude product was purified by recrystallization using ethanol to obtain intermediate 2,2-(4-hydroxyphenyl)adamantane (2,2-ADM), as a white solid yield: 69%, m=36.6 g, melting point 318° C.

Synthesis of Sub1-III-C2:

In a nitrogen atmosphere, the intermediate 2,2-ADM (36.6 g, 114.2 mmol) was dissolved in 400 mL of acetonitrile, then a solution of potassium carbonate (47.4 g, 342.6 mmol) dissolved in 100 mL of water was added thereto, and 1,1,2,2,3,3,4,4,4-nonafluorobutane-1-sulfonyl fluoride (FX-4, 86.30 g, 285.6 mmol) was added dropwise slowly. The resulted mixture was stirred for 4 h to complete the reaction, then stand for layering, and the separated organic phase was wasted with water and dried over anhydrous magnesium sulfate, and then concentrated in vacuo to obtain intermediate sub 1-III-C2 (87.6 g, yield 90%).

Synthesis of Sub1-III-C3:

In a nitrogen atmosphere, the intermediate sub 1-III-C2 (87.0 g, 102.4 mmol), bis(pinacol)diboron (62.2 g, 244.9 mmol) and potassium acetate (101.9 g, 1.084 mmol) were mixed and added to 600 mL of dioxane, and the mixture was heated to 100° C. and stirred. Bis(dibenzylideneacetone) palladium (3.5 g, 6.1 mmol) and tricyclohexyl phosphine (3.4 g, 12.24 mmol) were added thereto while heating to reflux and stirring for another 10 hours, the reaction was completed. The reaction mixture was cooled to room temperature and then filtered. The filtrate was poured into water and extracted with dichloromethane, the separated organic layer was dried with anhydrous magnesium sulfate and concentrated in vacuo to obtain the crude product, and the crude product was recrystallized with ethanol to prepare an intermediate sub 1-III-C3 (34.1 g, yield: 62%).

Intermediates sub 1-III-B3-2 and sub 1-III-B3-3 were prepared in the same way as the sub 1-III-B3, except that raw material 2 was used instead of the raw material bromobenzene in the synthesis example of preparing sub 1-III-B3, to react with raw material 1 (1-adamantanol) respectively.

| Preparation example | Raw material 1 | Raw material 2 | Sub 1-III-B3 | Output (g) | Yield/% |
|---|---|---|---|---|---|
| Sub 1-III-B3-2 | (1-adamantanol-OH) | (2-bromobenzonitrile) | (structure) | 37.60 | 52 |

-continued

| Preparation example | Raw material 1 | Raw material 2 | Sub 1-III-B3 | Output (g) | Yield/% |
|---|---|---|---|---|---|
| Sub 1-III-B3-3 | 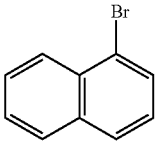 | 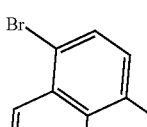 | 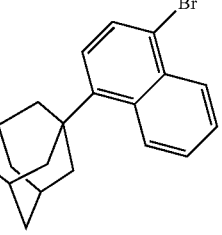 | 38.90 | 54 |
| Sub 1-III-B3-4 | 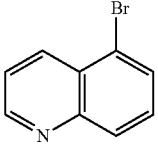 [SMILES: Brc1cccc2ncccc12] | 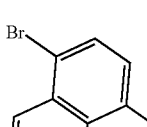 | 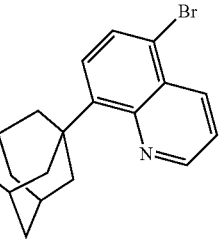 | 42.50 | 51 |

5) Synthesis of Sub 1-B1 and Sub 1-C1

Synthesis of Sub 1-B1:

The sub 1-II-B2 (10.00 g, 22.97 mmol), the sub 1-III-B3 (10.45 g, 22.97 mmol), tetrakis(triphenylphosphine)palladium (0.53 g, 0.46 mmol), potassium carbonate (6.98 g, 50.53 mmol), tetrabutylammonium chloride (1.27 g, 4.59 mmol), toluene (80 mL), ethanol (40 mL) and deionized water (20 mL) were added to a three-necked flask, and the mixture was heated to reflux at 78° C. under nitrogen atmosphere, and stirring for 8 h.

After the reaction completed, the solution was cooled to room temperature, toluene (100 mL) was added to extract the reaction solution. The combined organic phases were dried over anhydrous $MgSO_4$ and filtered. The filtrate was concentrated in vacuo to obtain a crude product. The crude product was purified by silica gel column chromatography and eluted with a mixture of dichloromethane and n-heptane to obtain intermediate sub 1-B1 as a solid (9.33 g, yield 67%).

Synthesis of Sub 1-C1:

The sub 1-I-B1 (5.00 g, 14.54 mmol), the sub 1-III-B3' (8.25 g, 15.27 mmol), tris(dibenzylideneacetone)dipalladium (0.13 g, 0.15 mmol), 2-(dicyclohexylphosphino)-2,4,6-triisopropylbiphenyl (0.14 g, 0.29 mmol), sodium tert-butoxide (2.09 g, 21.81 mmol), and 1,4-dioxane (50 mL) were added into a three-necked flask, the mixture was heated to reflux at 100° C. under nitrogen atmosphere and stirred for 4 h. After the reaction completed, the solution was cooled to room temperature, toluene (200 mL) was added to extract the reaction solution. The combined organic phases were dried over anhydrous $MgSO_4$ and filtered. The filtrate was concentrated in vacuo to obtain a crude product. The obtained crude product was recrystallized with ethanol to obtain intermediate sub 1-C1 as a solid (7.34 g, yield 70%).

The intermediates sub 1-B2 to sub 1-B10 were prepared by the same process as in sub 1-B1, except that raw material 4 was used instead of the p-chlorophenylboronic acid in the synthesis example of sub 1-I-B1 in Preparation Example 1, to react with 2-chloro-4,6-diphenyl-1,3,5-triazine (raw material 3) respectively, then react with Sub1-III-B3 to obtain sub 1-B series intermediates sub 1-B2 to sub 1-B10.

| Preparation example | Raw material 1 | Raw material 2 | Sub 1-III_B3 | Output (g) | Yield/% |
|---|---|---|---|---|---|
| Sub 1-B2 | 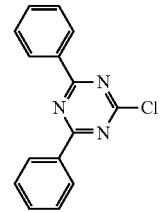 [SMILES: Clc1nc(-c2ccccc2)nc(-c2ccccc2)n1] | 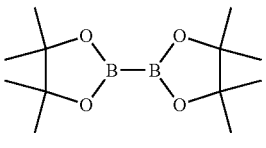 4-2 | 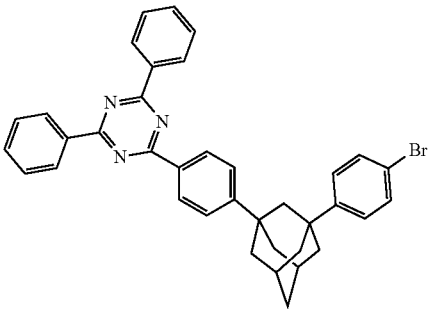 [SMILES: Brc1ccc(C23CC4CC(C2)CC(c2ccc(-c5nc(-c6ccccc6)nc(-c6ccccc6)n5)cc2)(C4)C3)cc1] | 8.54 | 62 |

-continued

| Preparation example | Raw material 1 | Raw material 2 | Sub 1-III_B3 | Output (g) | Yield/% |
|---|---|---|---|---|---|
| Sub 1-B3 | | 4-3 | | 7.36 | 64 |
| Sub 1-B4 | | 4-4 | | 5.68 | 59 |
| Sub 1-B5 | | 4-5 | | 7.55 | 61 |
| Sub 1-B6 | | 4-6 | | 6.87 | 63 |

-continued

| Preparation example | Raw material 1 | Raw material 2 | Sub 1-III_B3 | Output (g) | Yield/% |
|---|---|---|---|---|---|
| Sub 1-B7 | | 4-7 | | 6.45 | 64 |
| Sub 1-B8 | | 4-8 | | 6.32 | 62 |
| Sub 1-B9 | | 4-9 | | 5.78 | 68 |
| Sub 1-B10 | | 4-10 | | 8.65 | 62 |

Preparation Methods of Some Raw Materials 4-9 and 4-10

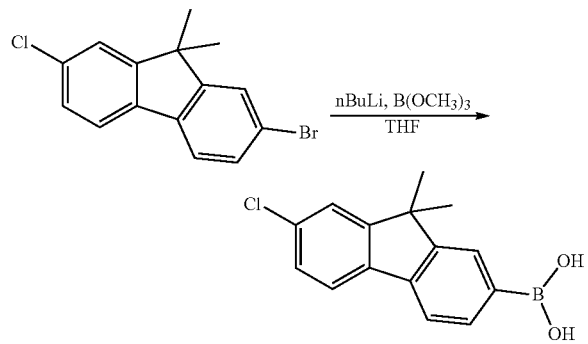

2-bromo-7-chloro-9'9-dimethylfluorene (8.00 g, 26.00 mmol) was added into a round bottom flask, 120 mL of anhydrous tetrahydrofuran (THF) was added into the flask, the system was cooled with liquid nitrogen to −80° C. to −90° C., then n-butyllithium (tetrahydrofuran solution, 33.80 mmol) was added dropwise, and the temperature was preserved for 1 h. Trimethyl borate (4.05 g, 39.01 mmol) was added to the above mixture dropwise, the temperature was kept at −80° C. to −90° C. for 1 h, the system was naturally warmed to room temperature, the reaction was completed. An aqueous solution of hydrochloric acid (20 mL, 40 mmol) was added, followed by stirring for 0.5 h. Dichloromethane and water were added forextraction, the combined organic phases were washed with water to be neutral pH=7, dried with anhydrous MgSO$_4$ for 10 min and filtered, and the filtrate was spin-dried and stirred twice with n-heptane to obtain raw material 4-9 (4.67 g, yield 66%). The preparation methods of other raw materials 4-3 to 4-8 were consistent with the preparation method of 4-9.

The intermediates sub 1-B11 to sub 1-B20 were prepared in the same way as in sub 1-B1, except that raw material 3-1 was used instead of the 2-chloro-4,6-diphenyl-1,3,5-triazine in Preparation Example 1, and raw material 4 was used instead of the p-chlorophenylboronic acid in the synthesis of sub 1-I-B1 in Preparation Example 1, to react with the Sub1-III-B3 to obtain sub 1-B series intermediates sub 1-B11 to sub 1-B21.

| Preparation example | Raw material 4 | Raw material 3-1 | Sub 1-B | Output (g) | Yield/% |
|---|---|---|---|---|---|
| Sub 1-B11 | | | | 6.77 | 62 |
| Sub 1-B12 | | | | 6.20 | 62 |

-continued

| Preparation example | Raw material 4 | Raw material 3-1 | Sub 1-B | Output (g) | Yield/% |
|---|---|---|---|---|---|
| Sub 1-B13 | | | | 5.9 | 60 |
| Sub 1-B14 | | | | 4.68 | 61 |
| Sub 1-B15 | | | | 4.55 | 65 |
| Sub 1-B16 | | | | 4.60 | 69 |

-continued

| Preparation example | Raw material 4 | Raw material 3-1 | Sub 1-B | Output (g) | Yield/% |
|---|---|---|---|---|---|
| Sub 1-B17 | | | | 4.67 | 61 |
| Sub 1-B18 | | | | 4.68 | 63 |
| Sub 1-B19 | | | | 4.80 | 64 |
| Sub 1-B20 | | | | 4.90 | 67 |

-continued

| Preparation example | Raw material 4 | Raw material 3-1 | Sub 1-B | Output (g) | Yield/% |
|---|---|---|---|---|---|
| Sub 1-B21 | | | | 4.13 | 63 |

Intermediates sub 1-B22 to sub 1-B24 were prepare in the same way as in sub 1-B1, except that Sub1-III-B3-x series compounds were used instead of Sub1-III-B3 in Preparation Example 1, and raw material 3-1 was used instead of 2-chloro-4,6-diphenyl-1,3,5-triazine in Preparation Example 1.

| Preparation example | Raw material 3-1 | Sub 1-III-B3-X | Sub 1-B | Output (g) | Yield/% |
|---|---|---|---|---|---|
| Sub 1-B22 | | Sub 1-III-B3-2 | | 4.3 | 62 |
| Sub 1-B23 | | sub 1-III-B3-3 | | 5.23 | 61 |

-continued

| Preparation example | Raw material 3-1 | Sub 1-III-B3-X | Sub 1-B | Output (g) | Yield/% |
|---|---|---|---|---|---|
| Sub 1-B24 | (2,6-diphenylpyrimidin-4-yl chloride structure) | sub 1-III-B3-4 | (product structure) | 5.69 | 63 |

Intermediates sub 1-C2 to sub 1-C5 were prepared in the same way as in sub 1-C1, except that raw material 3 was used instead of 2-chloro-4,6-diphenyl-1,3,5-triazine in Preparation Example 1, raw material 4 was used instead of p-chlorophenylboronic acid in the synthesis of sub 1-I-B1 in Preparation Example 1, and the raw material reacts with Sub 1-III-B3 and then reacts with raw material 4-2 to convert the bromine into borate ester to obtain sub 1-B series intermediates sub 1-C2 to sub 1-C4.

| Preparation example | Raw material 3 | Raw material | Sub 1-B | Output (g) | Yield/% |
|---|---|---|---|---|---|
| Sub 1-C2 | (structure) | 4-2 | (structure) 4 | 8.90 | 61 |
| Sub 1-C3 | 3-1 (structure) | | (structure) | 7.81 | 63 |

| Preparation example | Raw material 3 | Raw material | Sub 1-B 4 | Output (g) | Yield/% |
|---|---|---|---|---|---|
| Sub 1-C4 | 3-2 | | | 6.43 | 61 |

Preparation Methods of the Above Intermediates 3-1 and 3-2

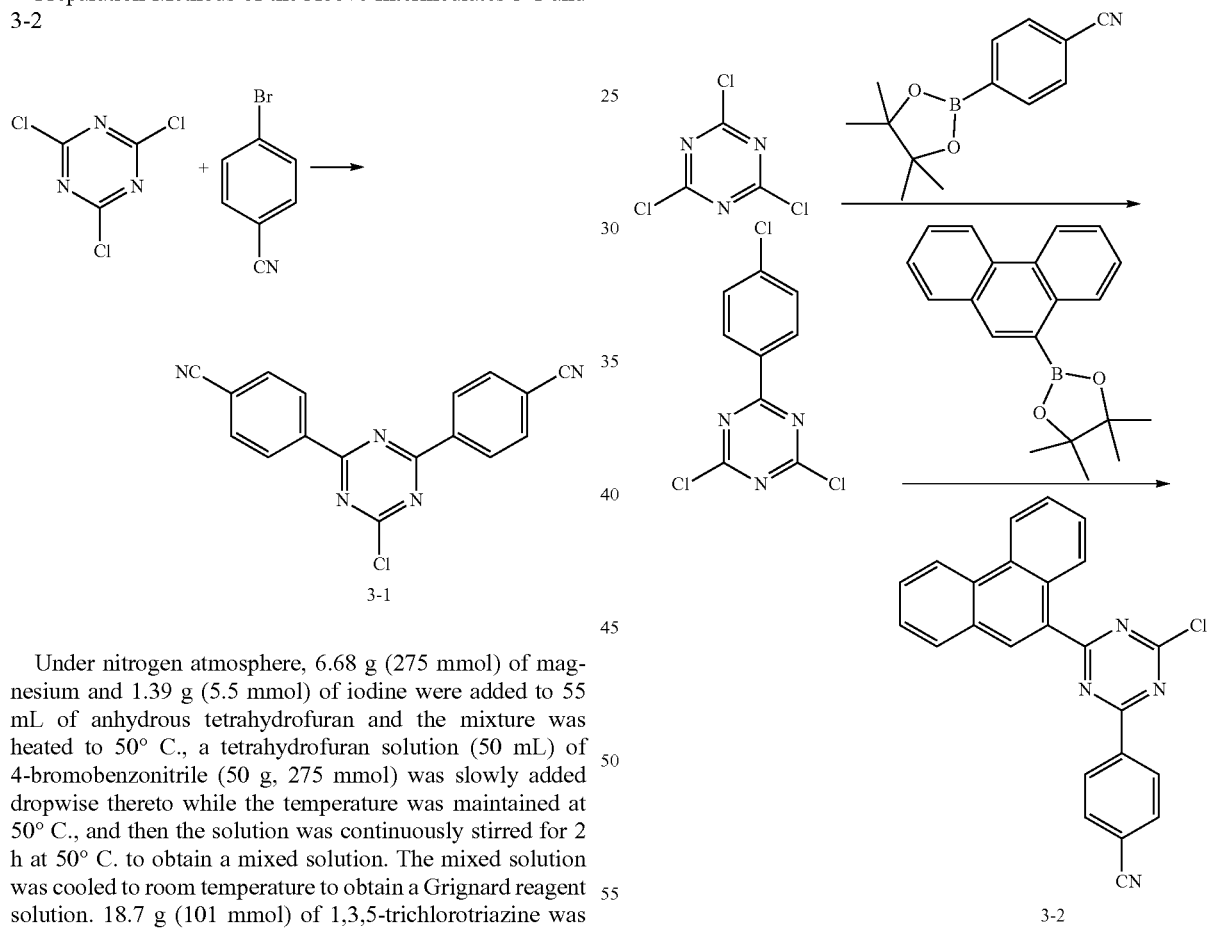

3-1

3-2

Under nitrogen atmosphere, 6.68 g (275 mmol) of magnesium and 1.39 g (5.5 mmol) of iodine were added to 55 mL of anhydrous tetrahydrofuran and the mixture was heated to 50° C., a tetrahydrofuran solution (50 mL) of 4-bromobenzonitrile (50 g, 275 mmol) was slowly added dropwise thereto while the temperature was maintained at 50° C., and then the solution was continuously stirred for 2 h at 50° C. to obtain a mixed solution. The mixed solution was cooled to room temperature to obtain a Grignard reagent solution. 18.7 g (101 mmol) of 1,3,5-trichlorotriazine was dissolved in 100 mL of anhydrous hydrogen furan. The obtained solution was slowly added dropwise to the Grignard reagent solution, and then the mixture was heated to reflux and stirred for about 7 hours. After the reaction was completed, the reaction was quenched by adding water, the mixture was extracted with dichloromethane and distilled water, the separated organic layer was concentrated in vacuo to obtain the residue, and then the obtained residue was purified by silica gel column chromatography (eluted by a mixture of dichloromethane and n-heptane) to obtain 22.4 g of compound 3-1 (yield: 70%).

1,3,5-trichlorotriazine (10.00 g, 54.22 mmol), 4-cyanophenylboronic acid (12.42 g, 54.22 mmol), tetrakis(triphenylphosphine)palladium (1.25 g, 1.08 mmol), potassium carbonate (14.99 g, 108.45 mmol), tetrabutylammonium chloride (0.35 g, 1.08 mmol), toluene (80 mL), ethanol (40 mL) and deionized water (20 mL) were added into a three-necked flask, the mixture was heated to reflux at 78° C. under nitrogen atmosphere and stirred for 8 h. After the reaction completed, the solution was cooled to room temperature, toluene (100 mL) was added to extract the reaction solution. The combined organic phases were dried over anhydrous MgSO₄ and filtered. The filtrate was concentrated in vacuo to obtain a crude product. The crude product was purified by silica gel column chromatography (eluted by a mixture of dichloromethane and n-heptane) to obtain compound 3-2-1# as a solid (8.84 g, yield 65%).

The 3-2-1# (8.00 g, 31.86 mmol), 9-phenanthryl boronic acid pinacol ester (9.78 g, 32.18 mmol), tetrakis(triphenylphosphine)palladium (0.73 g, 0.63 mmol), potassium carbonate (8.81 g, 63.72 mmol), tetrabutylammonium chloride (0.20 g, 0.63 mmol), toluene (64 mL), ethanol (32 mL) and deionized water (16 mL) were added into a three-necked flask, the mixture was heated to reflux at 78° C. under nitrogen atmosphere and stirred for 8 h. After the reaction completed, the solution was cooled to room temperature, toluene (200 mL) was added to extract the reaction solution. The combined organic phases were dried over anhydrous MgSO₄ and filtered. The filtrate was concentrated in vacuo to obtain a crude product. The crude product was purified by silica gel column chromatography (eluted by a mixture of dichloromethane and n-heptane) to obtain compound 3-2 as a solid (7.75 g, yield 62%).

II. Synthesis of Compounds

Synthesis of Compound 1

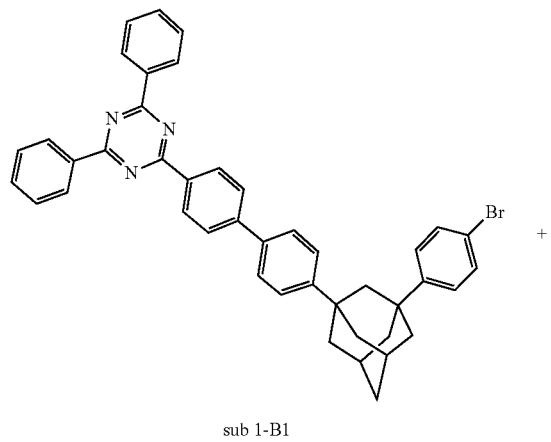

sub 1-B1

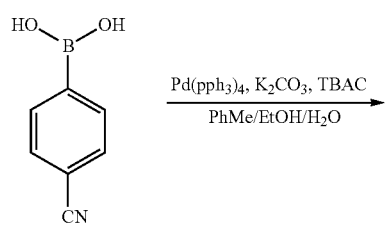

Pd(pph₃)₄, K₂CO₃, TBAC
PhMe/EtOH/H₂O

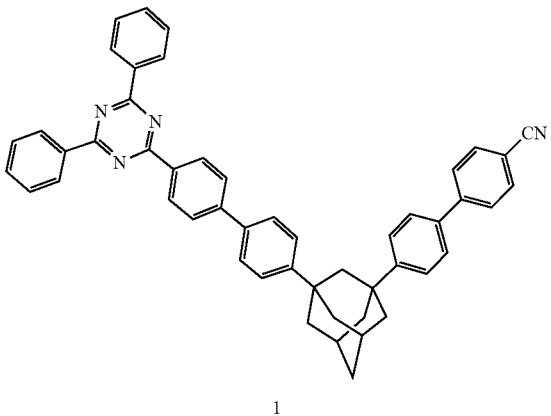

1

The sub 1-B1 (9.00 g, 15.03 mmol), 4-cyanophenylboronic acid (2.65 g, 18.04 mmol), tetrakis(triphenylphosphine)palladium (0.34 g, 0.30 mmol), potassium carbonate (4.57 g, 33.07 mmol), tetrabutylammonium chloride (0.83 g, 3.00 mmol), toluene (72 mL), ethanol (36 mL) and deionized water (18 mL) were added to a three-necked flask, the mixture was heated to reflux at 75-78° C. under nitrogen atmosphere and stirred for 8 h. After the reaction completed, the solution was cooled to room temperature, toluene (100 mL) was added to extract the reaction solution. The combined organic phases were dried over anhydrous MgSO₄ and filtered. The filtrate was concentrated in vacuo to obtain a crude product. The crude product was purified by silica gel column chromatography (eluted by a mixture of dichloromethane and n-heptane) to obtain compound 1 as a solid (7.22 g, yield 69%).

LC-MS (ESI, pos.ion) m/z: 697.3 [M+H]$^+$.

$^1$HNMR (400 MHz, CD$_2$Cl$_2$) δ (ppm): 8.87 (d, 4H), 8.62 (d, 2H), 7.92-7.86 (d, 4H), 7.66-7.56 (m, 6H), 7.47 (d, 2H), 7.37 (d, 2H), 7.32 (d, 2H), 7.25 (d, 4H), 2.30 (s, 2H), 1.92 (s, 6H), 1.80-1.77 (m, 6H).

Synthesis of Compound 2

Compound 2 was prepared in the same way as in Experimental Example 1, except that sub 1-B2 was used instead of sub 1-B1 in Preparation Example 1. LC-MS (ESI, pos.ion) m/z: 621.29 [M+H]$^+$.

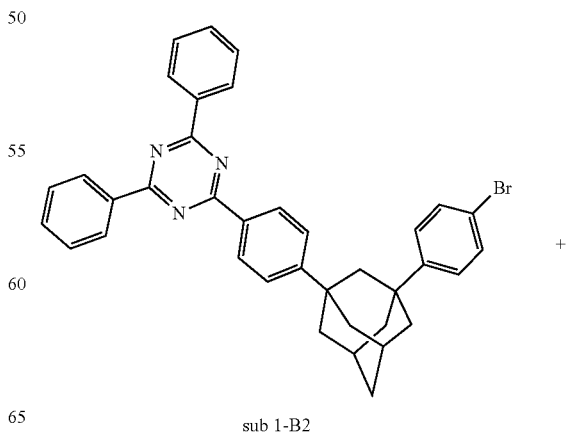

sub 1-B2

-continued

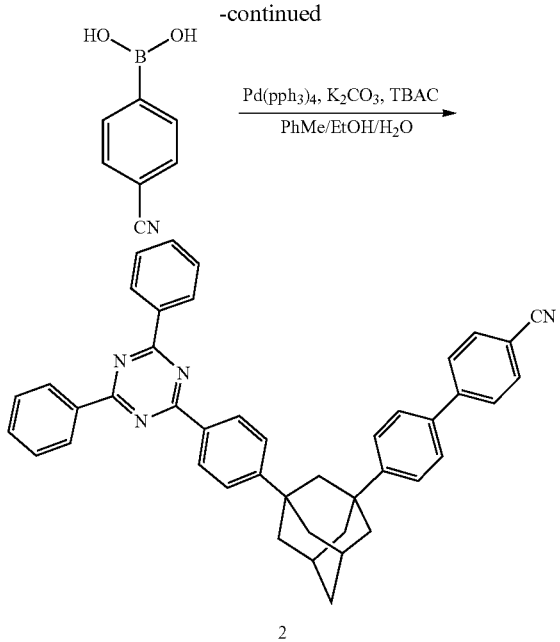

2

$^1$HNMR (400 MHz, CD$_2$Cl$_2$) δ (ppm): 8.81 (d, 4H), 8.24 (d, 2H), 7.93 (d, 2H), 7.66-7.57 (m, 6H), 7.47 (d, 2H), 7.41 (d, 2H), 7.37 (d, 2H), 7.25 (d, 2H), 2.15 (s, 2H), 1.93 (s, 6H), 1.81-1.75 (m, 6H)

Synthesis of Compound 3

Compound 3 was prepared in the same way as in Experimental Example 1, except that sub 1-B3 was used instead of sub 1-B1 in Preparation Example 1, to obtain solid compound 3 (7.86 g, yield 65%).

LC-MS (ESI, pos.ion) m/z: 697.33 [M+H]$^+$.

-continued

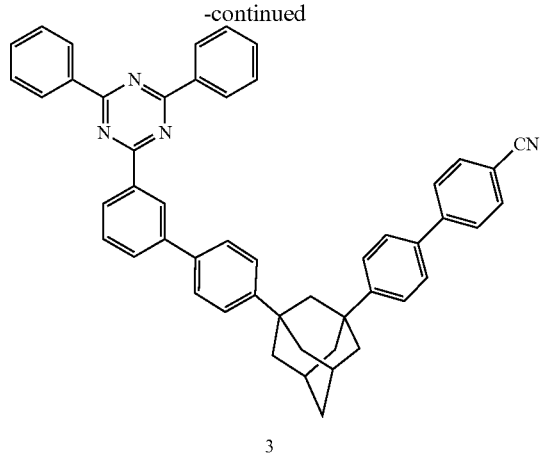

3

Synthesis of Compound 10

Compound 10 was prepared in the same way as in Experimental Example 1, except that sub 1-B4 was used instead of sub 1-B1 in Preparation Example 1, to obtain solid compound 10 (7.55 g, yield 63%). LC-MS (ESI, pos.ion) m/z: 747.34 [M+H]$^+$.

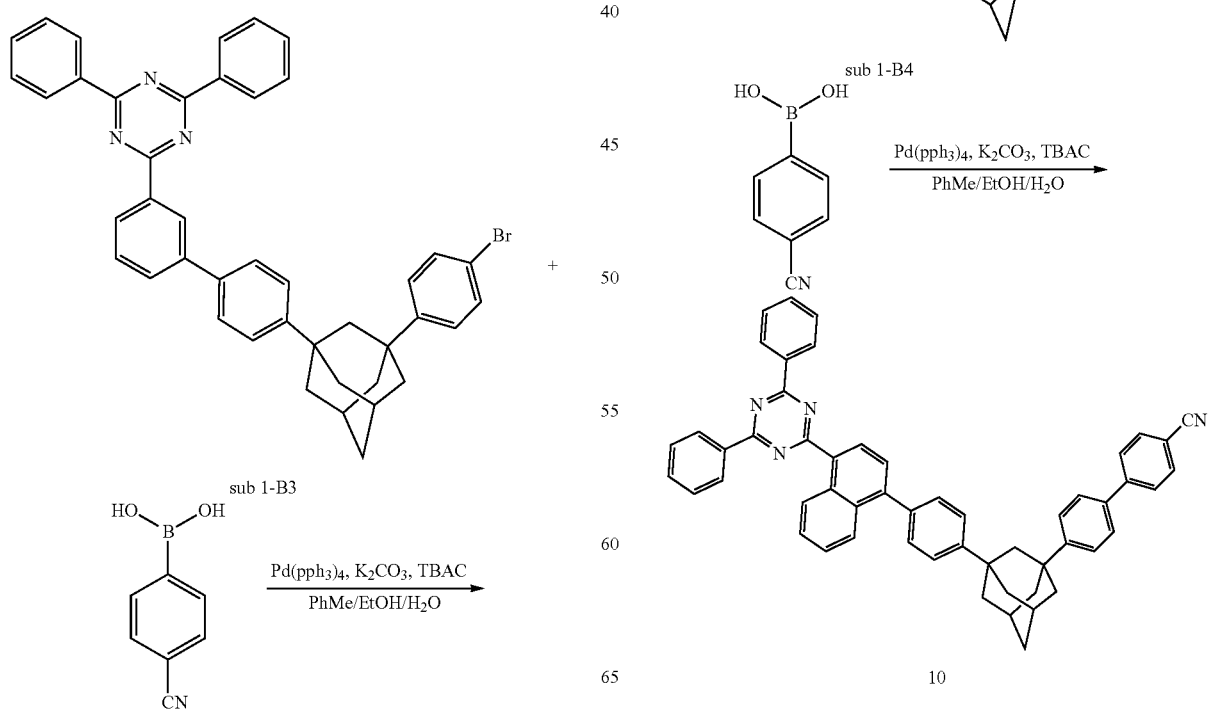

Synthesis of Compound 12

Compound 12 was prepared in the same way as in Experimental Example 1, except that sub 1-B5 was used instead of sub 1-B1 in Preparation Example 1, to obtain solid compound 12 (7.20 g, yield 63%). LC-MS (ESI, pos.ion) m/z: 747.34 [M+H]⁺.

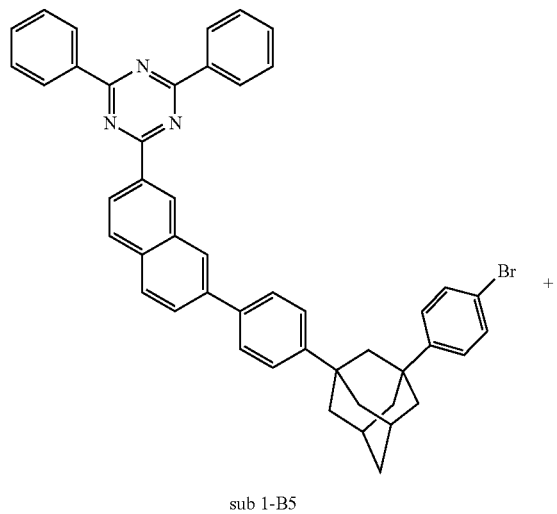

sub 1-B5

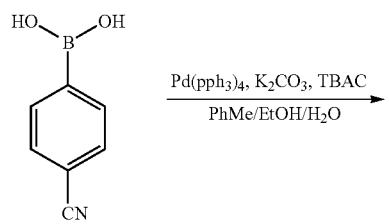

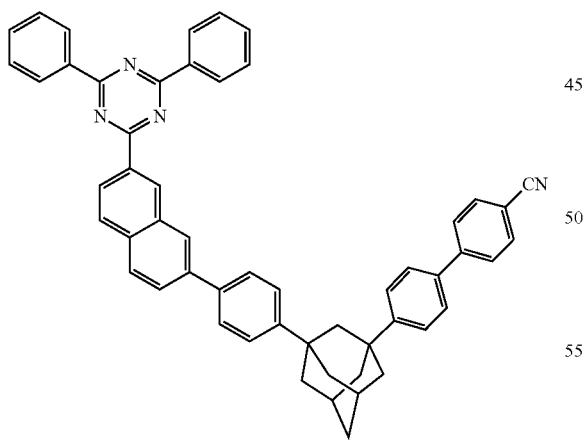

12

Synthesis of Compound 6

Compound 6 was prepared in the same way as in Experimental Example 1, except that sub 1-B6 was used instead of sub 1-B1 in Preparation Example 1, to obtain solid compound 6 (7.16 g, 75%). LC-MS (ESI, pos.ion) m/z: 711.34 [M+H]⁺.

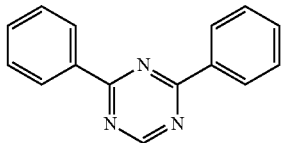

sub 1-B6

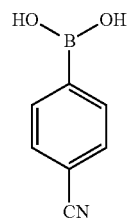

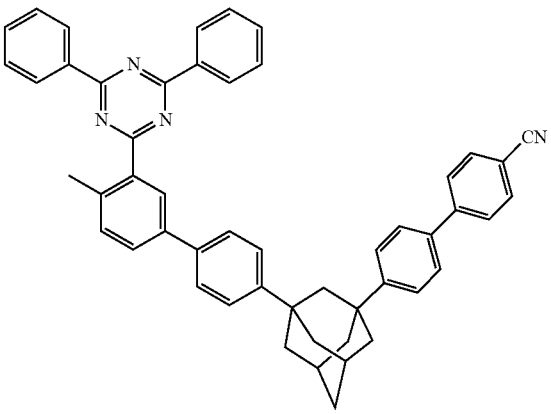

6

Synthesis of Compound 18

Compound 18 was prepared in the same way as in Experimental Example 1, except that sub 1-B7 was used instead of sub 1-B1 in Preparation Example 1, to obtain solid compound 18 (6.86 g, yield 64%). LC-MS (ESI, pos.ion) m/z: 773.36 [M+H]⁺.

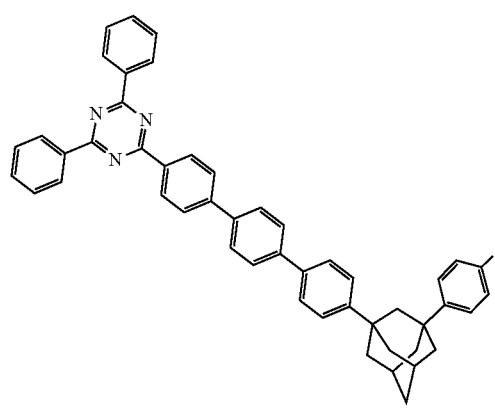

sub 1-B7

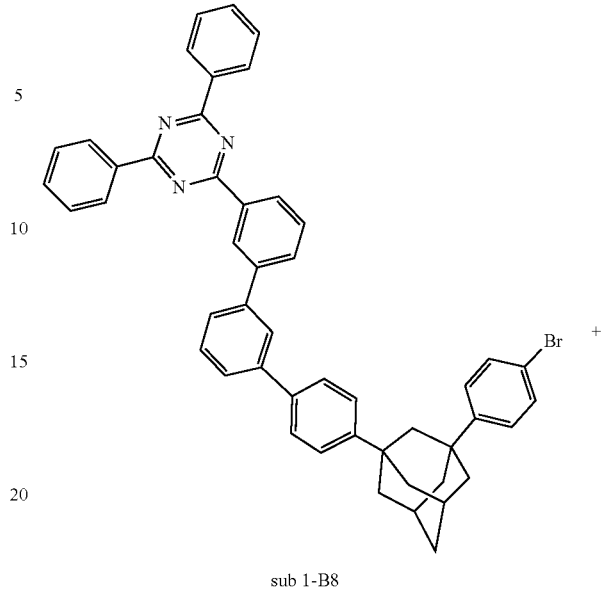

sub 1-B8

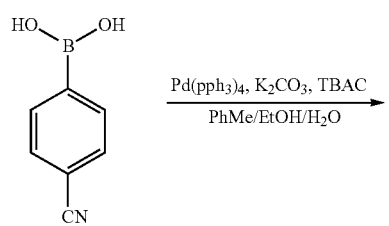

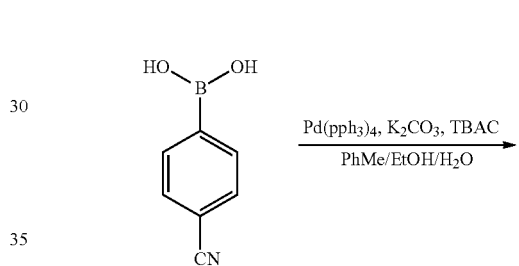

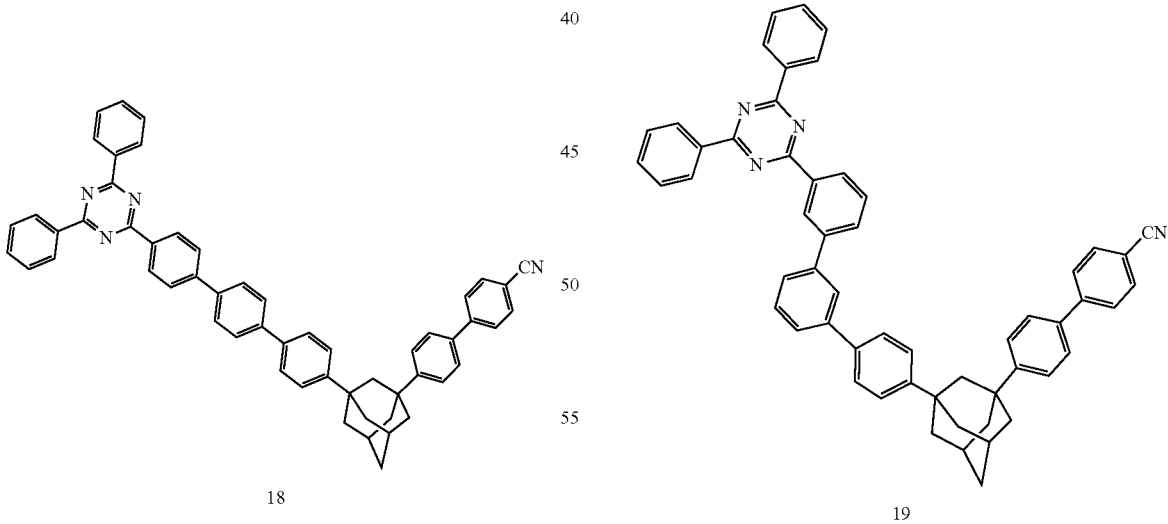

18

19

Synthesis of Compound 19

Compound 19 was prepared in the same way as in Experimental Example 1, except that sub 1-B8 was used instead of sub 1-B1 in Preparation Example 1, to obtain solid compound 19 (5.86 g, yield 65%). LC-MS (ESI, pos.ion) m/z: 773.36 [M+H]⁺.

Synthesis of Compound 27

Compound 27 was prepared in the same way as in Experimental Example 1, except that sub 1-B9 was used instead of sub 1-B1 in Preparation Example 1, to obtain solid compound 27 (7.06 g, yield 72%). LC-MS (ESI, pos.ion) m/z: 813.39 [M+H]⁺.

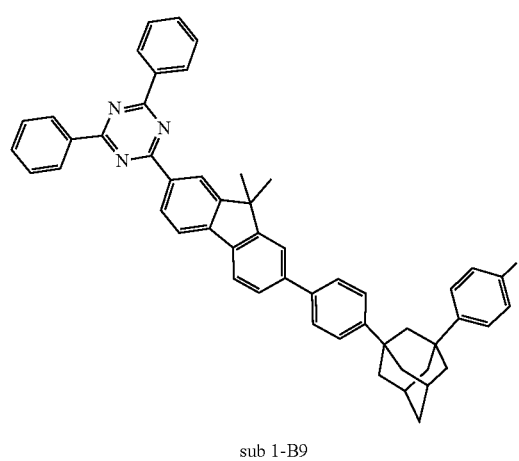

sub 1-B9

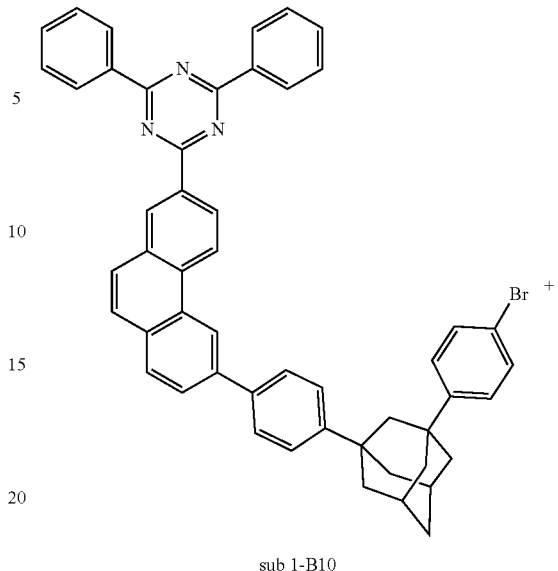

sub 1-B10

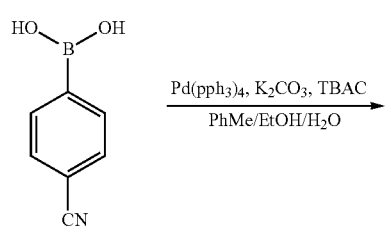

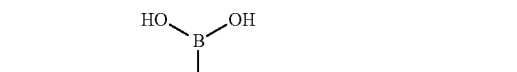

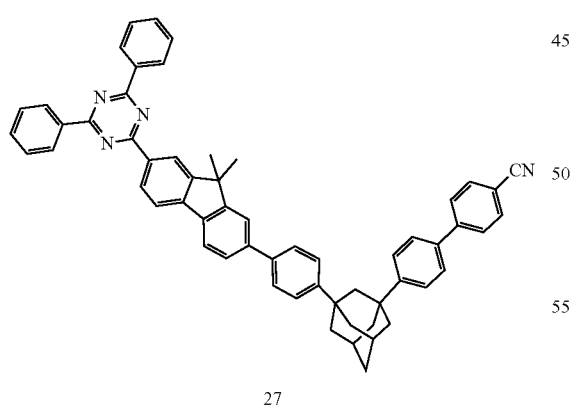

27

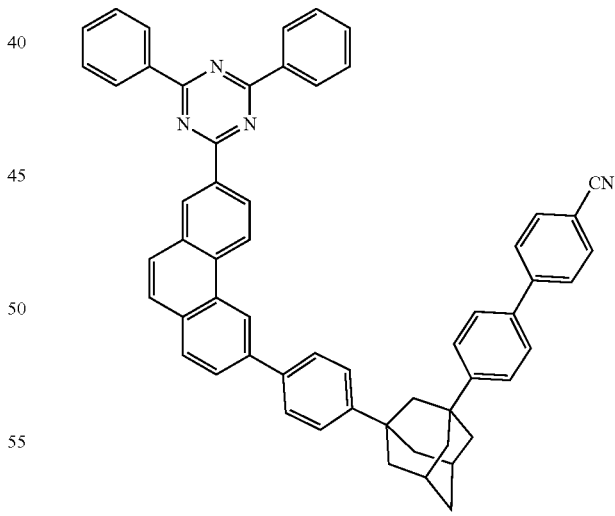

33

Synthesis of Compound 33

Compound 33 was prepared in the same way as in Experimental Example 1, except that sub 1-B10 was used instead of sub 1-B1 in Preparation Example 1, to obtain solid compound 33 (8.54 g, yield 63%). LC-MS (ESI, pos.ion) m/z: 797.36 [M+H]+.

Synthesis of Compound 35

Compound 35 was prepared in the same way as in Experimental Example 1, except that sub 1-B11 was used instead of sub 1-B1 in Preparation Example 1, to obtain solid compound 35 (7.45 g, 60%). LC-MS (ESI, pos.ion) m/z: 671.31 [M+H]+.

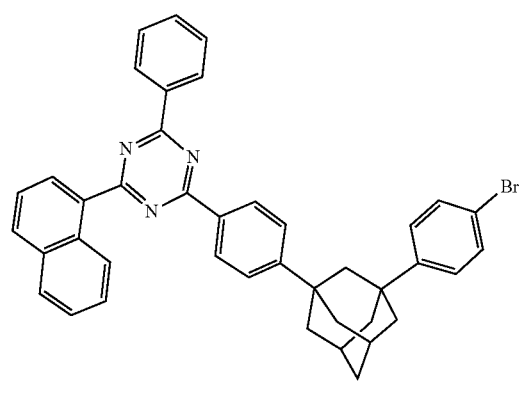

sub 1-B11

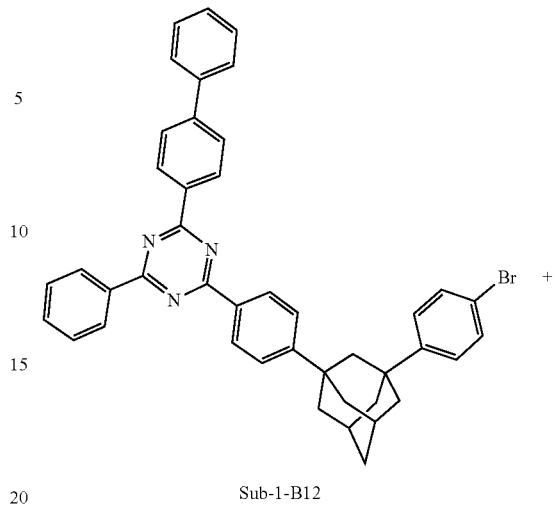

Sub-1-B12

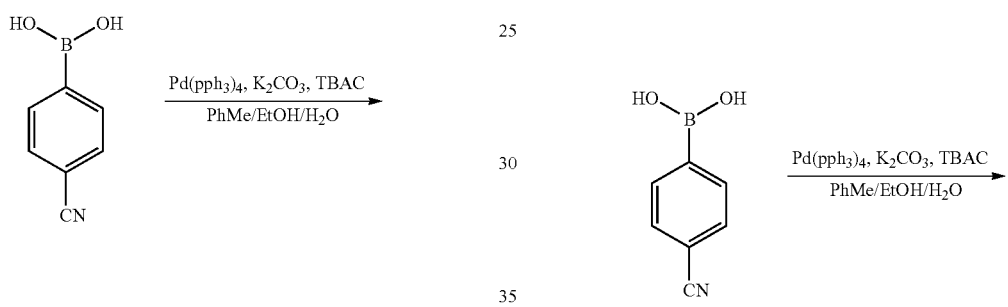

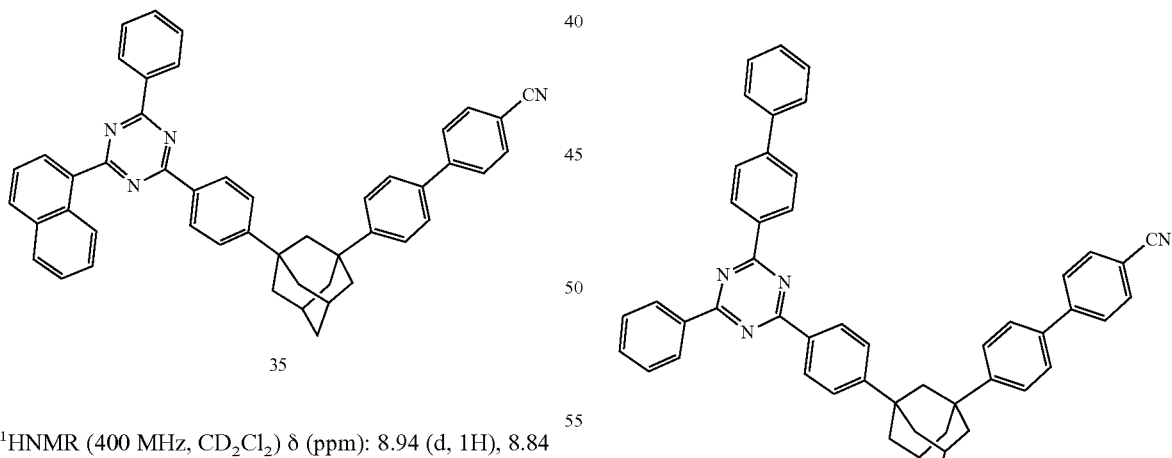

43

¹HNMR (400 MHz, CD₂Cl₂) δ (ppm): 8.94 (d, 1H), 8.84 (d, 2H), 8.79 (d, 2H), 8.53 (d, 1H), 8.24 (d, 2H), 7.92 (d, 2H), 7.68-7.52 (m, 6H), 7.47 (d, 2H), 7.41 (d, 2H), 7.37 (d, 2H), 7.25 (d, 2H), 2.12 (s, 2H), 1.93 (s, 6H), 1.82-1.77 (m, 6H).

Synthesis of Compound 43

Compound 43 was prepared in the same way as in Experimental Example 1, except that sub 1-B12 was used instead of sub 1-B1 in Preparation Example 1, to obtain solid compound 43 (5.94 g, yield 59%). LC-MS (ESI, pos.ion) m/z: 697.33 [M+H]⁺.

Synthesis of Compound 44

Compound 44 was prepared in the same way as in Experimental Example 1, except that sub 1-B13 was used instead of sub 1-B1 in Preparation Example 1, to obtain solid compound 44 (7.12 g, yield 79%). LC-MS (ESI, pos.ion) m/z: 697.33 [M+H]⁺.

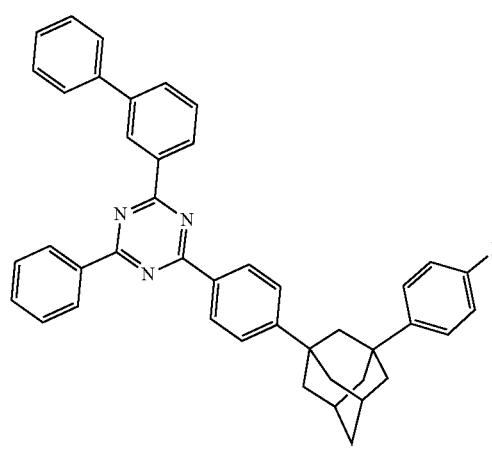

sub 1-B13

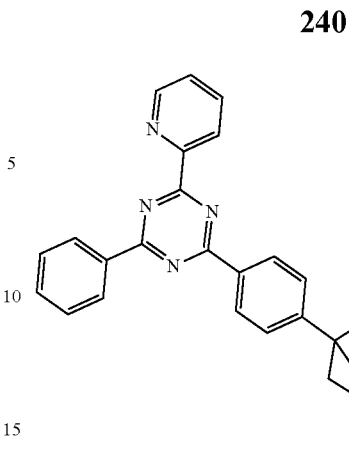

sub 1-B14

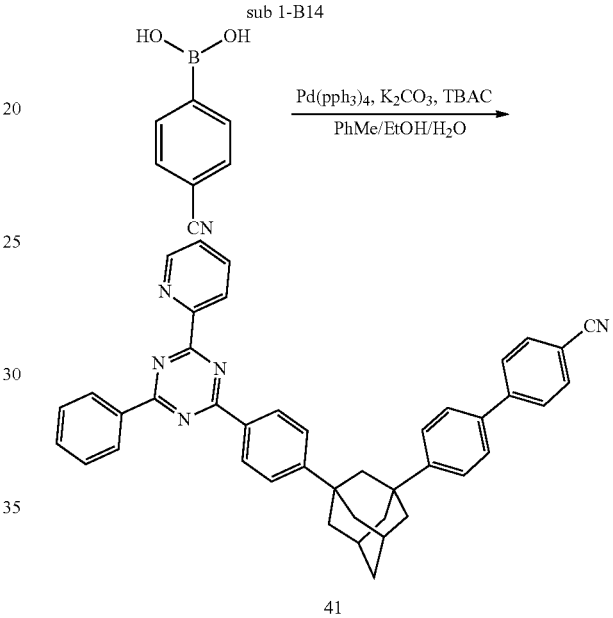

41

Synthesis of Compound 41

Compound 41 was prepared in the same way as in Experimental Example 1, except that sub 1-B14 was used instead of sub 1-B1 in Preparation Example 1, to obtain solid compound 41 (7.05 g, 61%). LC-MS (ESI, pos.ion) m/z: 622.29 [M+H]$^+$.

Synthesis of Compound 59

Compound 59 was prepared in the same way as in Experimental Example 1, except that sub 1-B15 was used instead of sub 1-B1 in Preparation Example 1, to obtain solid compound 59 (9.06 g, yield 67%). LC-MS (ESI, pos.ion) m/z: 620.30 [M+H]$^+$.

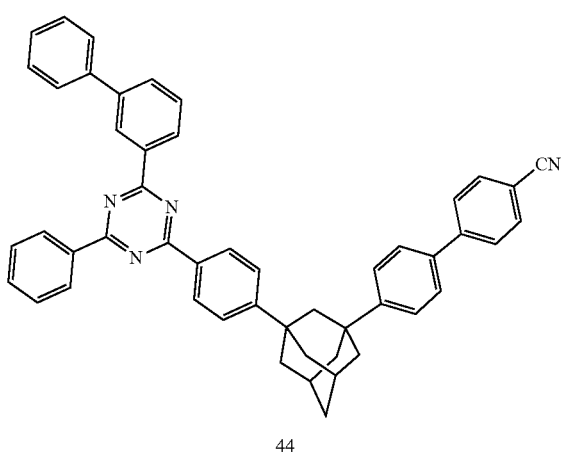

44

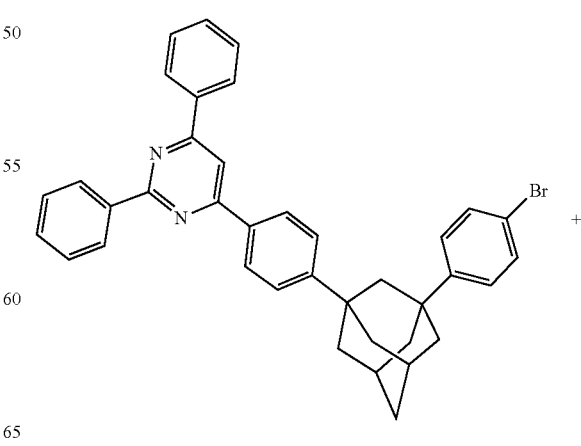

sub 1-B15

-continued

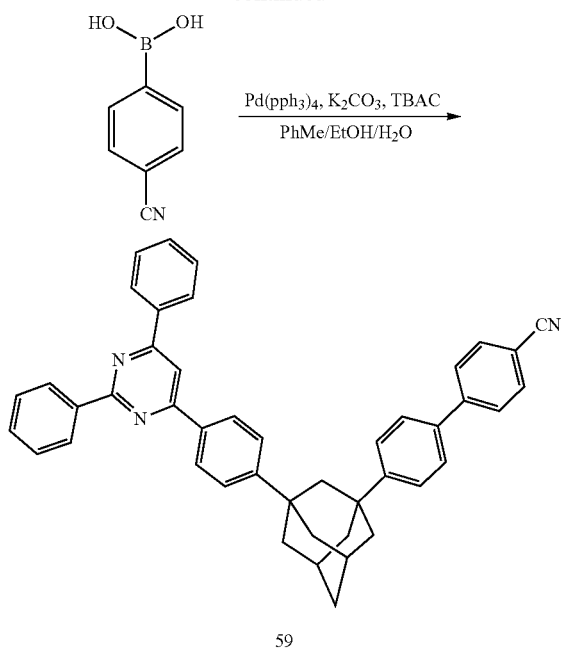

59

Synthesis of Compound 40

Compound 40 was prepared in the same way as in Experimental Example 1, except that sub 1-B16 was used instead of sub 1-B1 in Preparation Example 1, to obtain solid compound 40 (6.55 g, yield 69%). LC-MS (ESI, pos.ion) m/z: 721.33 [M+H]$^+$.

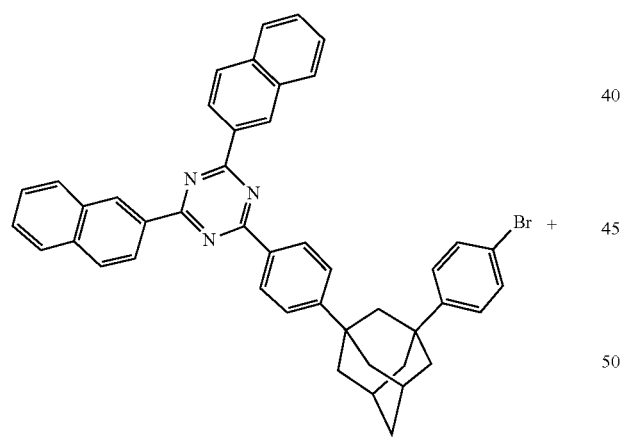

sub 1-B16

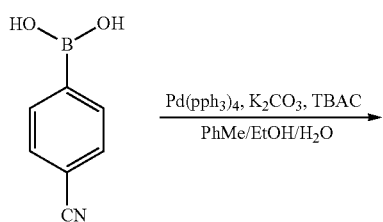

-continued

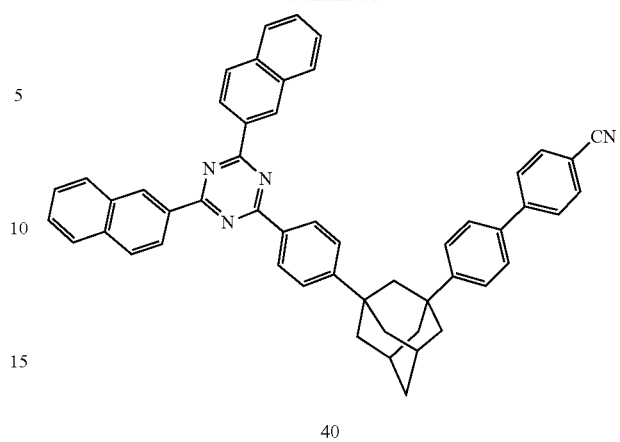

40

Synthesis of Compound 60

Compound 60 was prepared in the same way as in Experimental Example 1, except that sub 1-B17 was used instead of sub 1-B1 in Preparation Example 1, to obtain solid compound 60 (7.12 g, yield 63%). LC-MS (ESI, pos.ion) m/z: 732.42 [M+H]$^+$.

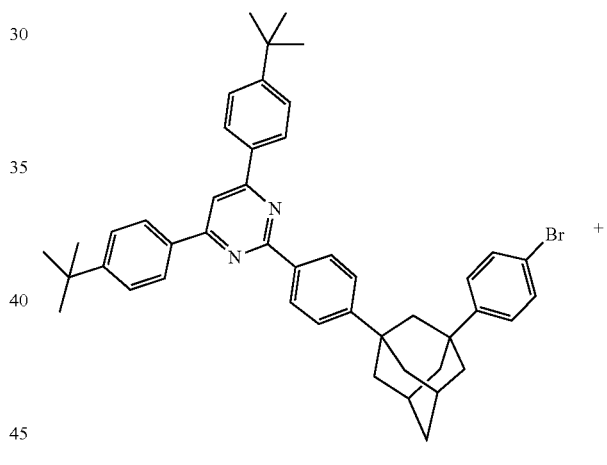

sub 1-B17

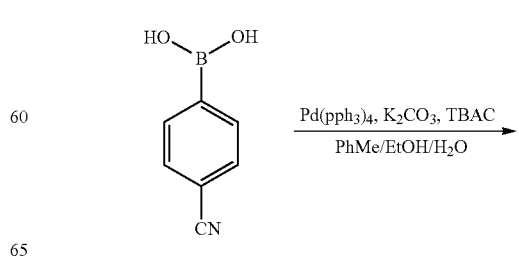

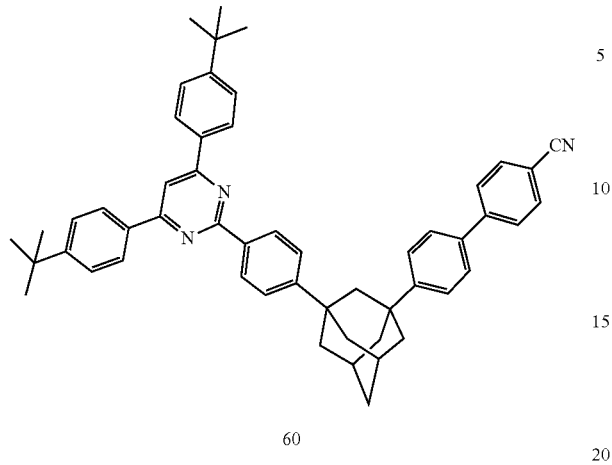

60

Synthesis of Compound 61

Compound 61 was prepared in the same way as in Experimental Example 1, except that sub 1-B18 was used instead of sub 1-B1 in Preparation Example 1, to obtain solid compound 61 (7.00 g, yield 61%). LC-MS (ESI, pos.ion) m/z: 695.33 [M+H]⁺.

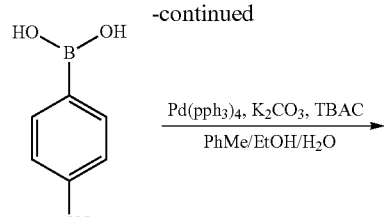

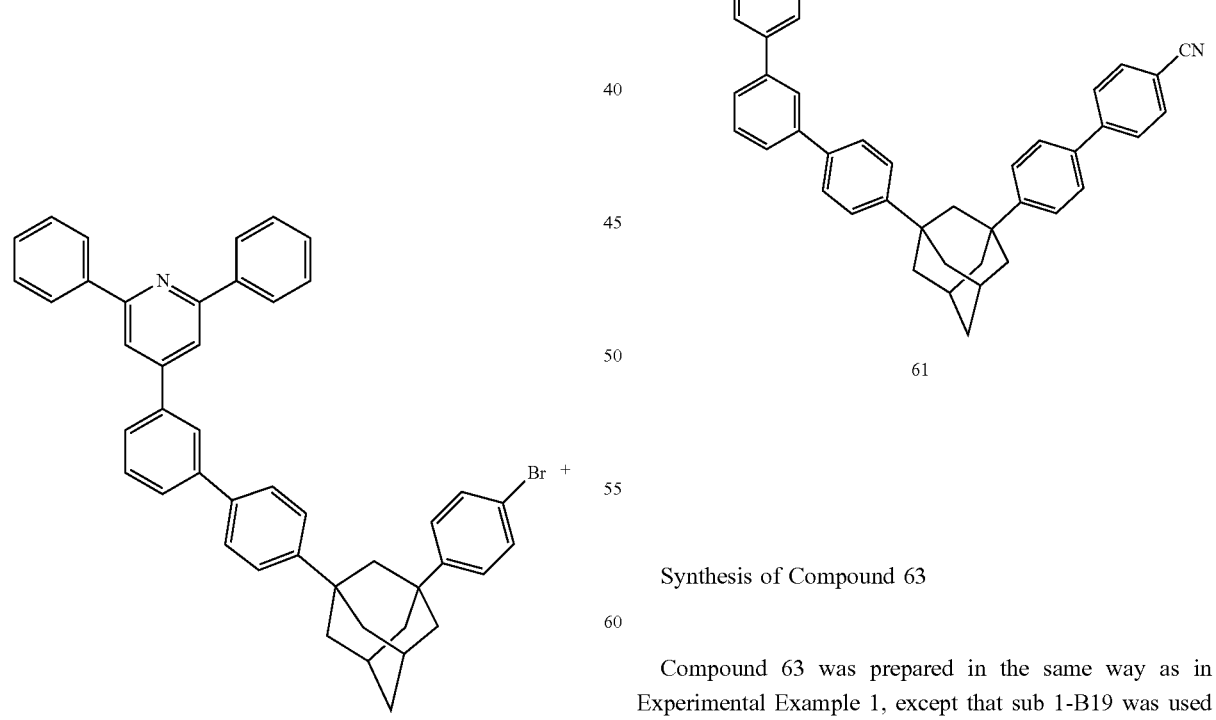

sub 1-B18

61

Synthesis of Compound 63

Compound 63 was prepared in the same way as in Experimental Example 1, except that sub 1-B19 was used instead of sub 1-B1 in Preparation Example 1, to obtain solid compound 63 (7.15 g, yield 72%). LC-MS (ESI, pos.ion) m/z: 899.40 [M+H]⁺.

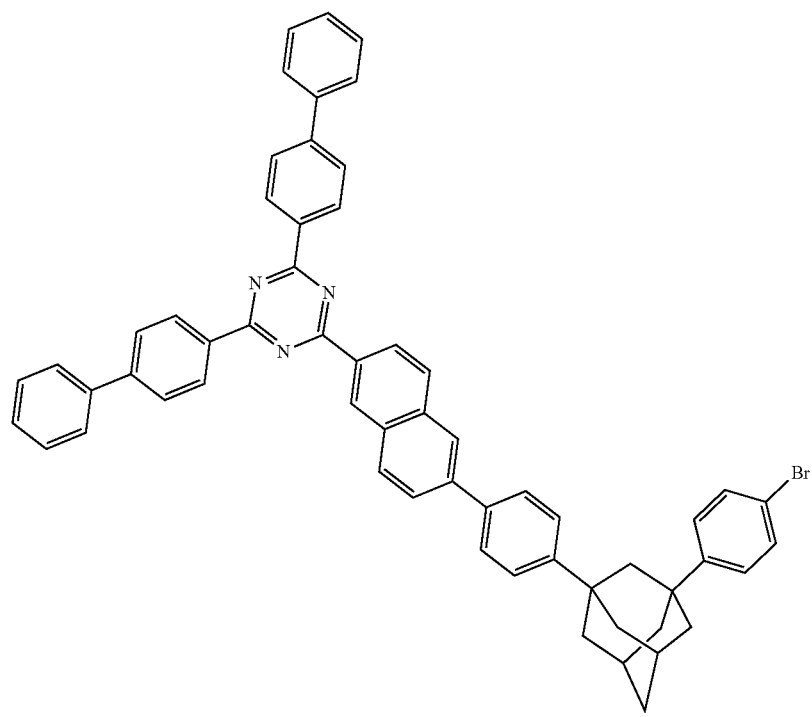 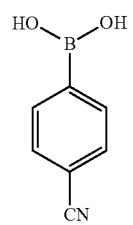
sub 1-B19
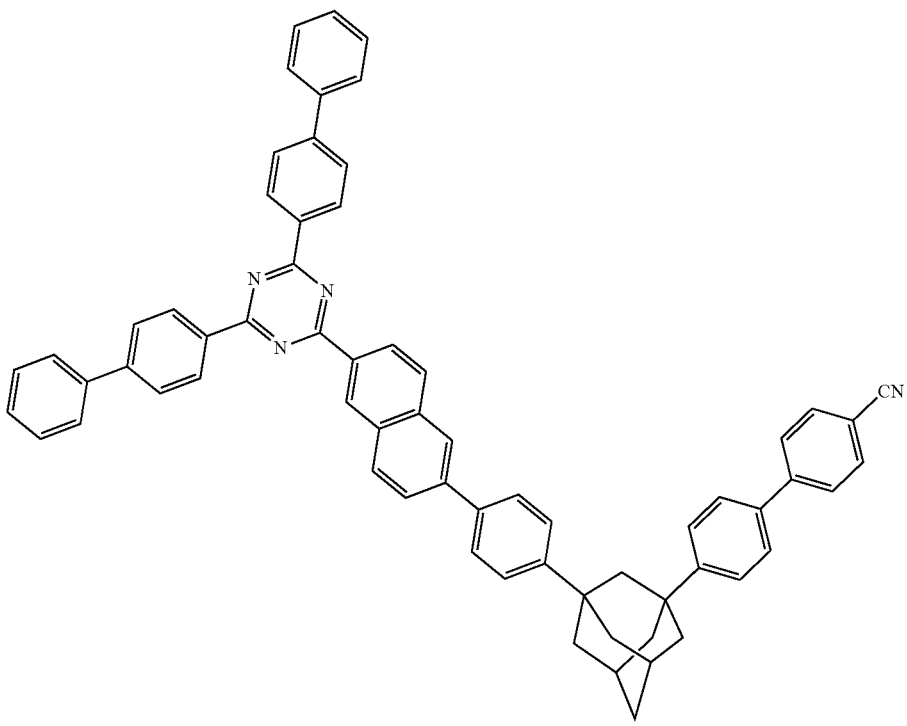
63
Synthesis of Compound 64
Compound 64 was prepared in the same way as in Experimental Example 1, except that sub 1-B20 was used instead of sub 1-B1 in Preparation Example 1, to obtain solid compound 64 (8.30 g, yield 69%). LC-MS (ESI, pos.ion) m/z: 873.39 [M+H]$^+$.

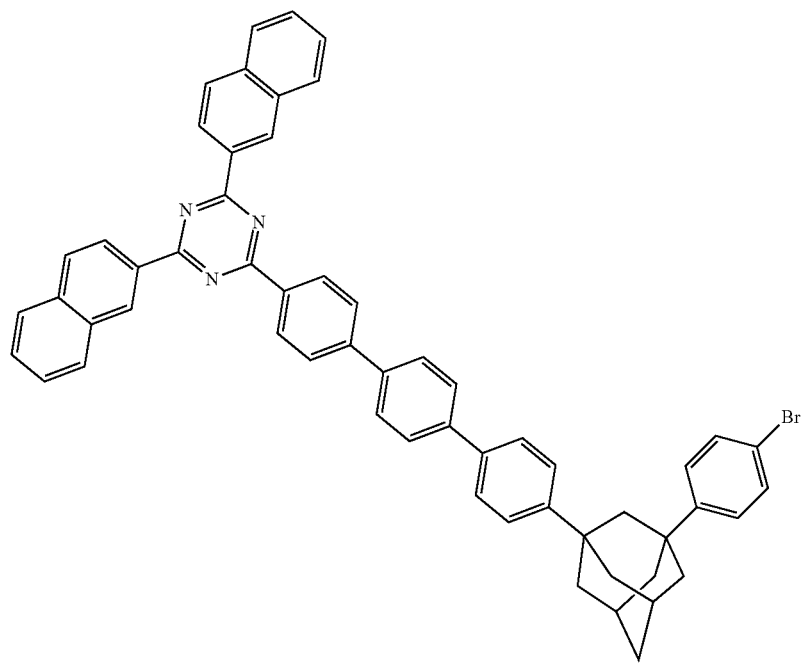
sub 1-B20
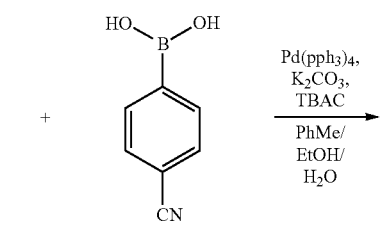
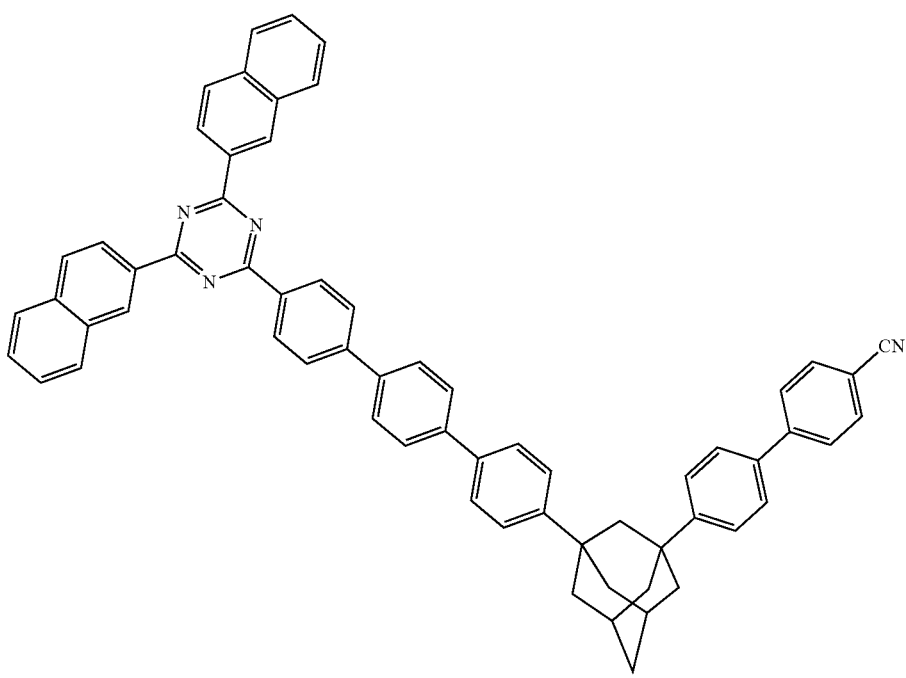
64
Synthesis of Compound 194
Compound 194 was prepared in the same way as in Experimental Example 1, except that sub 1-B21 was used instead of sub 1-B1 in Preparation Example 1, to obtain solid compound 194 (5.37 g, yield 69%). LC-MS (ESI, pos.ion) m/z: 773.36 [M+H]$^+$.

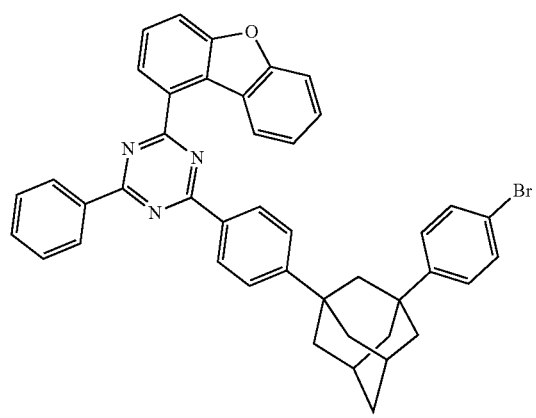

sub 1-B21

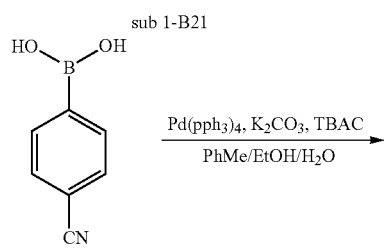

Pd(pph₃)₄, K₂CO₃, TBAC
PhMe/EtOH/H₂O →

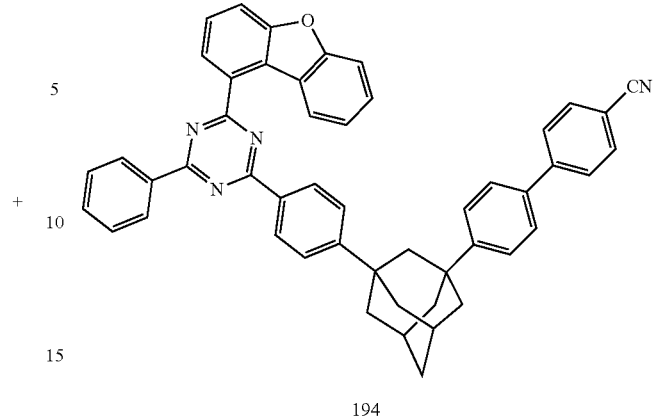

194

Synthesis of Compounds 65, 66, 76, 77, 103, 85, 86, 104, 105, 211, 247, 258 and 259

Compounds 65, 66, 76, 77, 103, 85, 86, 104, 105, 211, 247, 258 and 259 were prepared in the same way as in Experimental Example 1, except that raw material 5 was used instead of the p-cyanophenylboronic acid in Experimental Example 1, to react with the corresponding Sub1-B.

| Number | Raw material 5 | Sub 1-B | Product | Output (g) | Yield/% | Mass spectrum (m/z) [M + H]+ |
|---|---|---|---|---|---|---|
| 65 | | sub 1-B1 | | 8.24 | 64 | 697.33 |
| 66 | | sub 1-B2 | | 7.41 | 73 | 621.29 |

-continued

| Number | Raw material 5 | Sub 1-B | Product | Output (g) | Yield/% | Mass spectrum (m/z) [M + H]+ |
|---|---|---|---|---|---|---|
| 76 | | sub 1-B1 | | 5.70 | 71 | 773.36 |
| 77 | | sub 1-B2 | | 4.89 | 68 | 697.33 |
| 103 | | sub 1-84 | | 5.90 | 65 | 761.36 |
| 85 | | sub 1-B1 | | 6.54 | 65 | 747.34 |
| 86 | | sub 1-B2 | | 5.89 | 63 | 671.31 |

-continued
| Number | Raw material 5 | Sub 1-B | Product | Output (g) | Yield/% | Mass spectrum (m/z) [M + H]+ |
|---|---|---|---|---|---|---|
| 104 | | 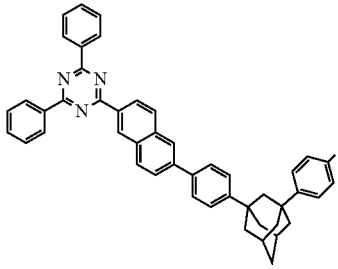 sub 1-B5 | 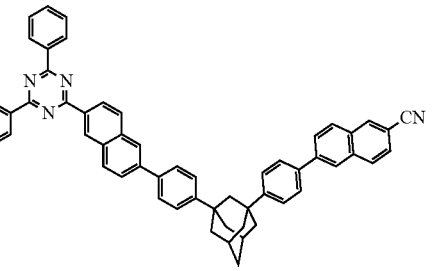 sub 1-B5 | 5.65 | 61 | 797.36 |
| 211 | | 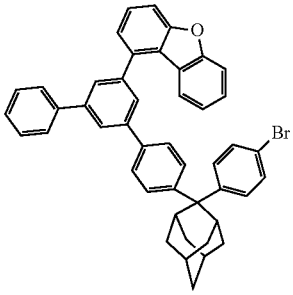 [SMILES: Brc1ccc(C2(c3ccc(-c4cc(-c5ccccc5)cc(-c5cccc6oc7ccccc7c56)c4)cc3)C3CC4CC(C3)CC2C4)cc1] | 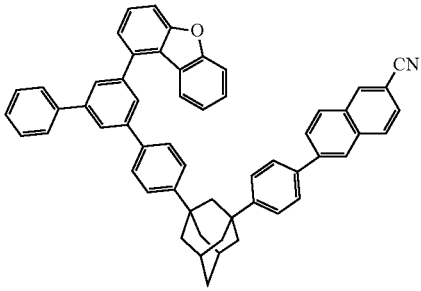 211 | 7.89 | 62 | 761.32 |
| 105 | 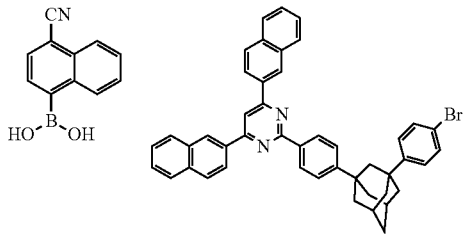 | 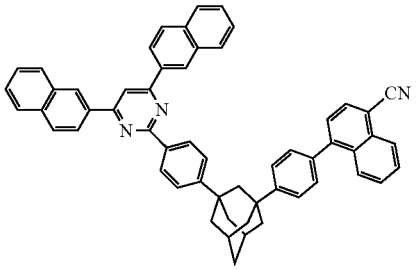 [SMILES: N#Cc1ccc(-c2ccc(C34CC5CC(CC(c6ccc(-c7nc(-c8ccc9ccccc9c8)cc(-c8ccc9ccccc9c8)n7)cc6)(C5)C3)C4)cc2)c2ccccc12] sub 1-B16 | 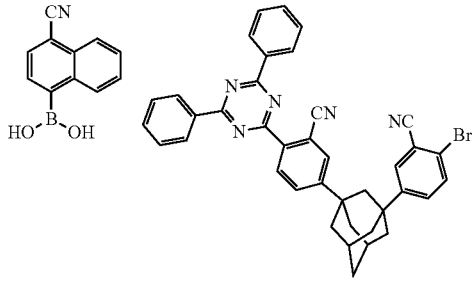 | 7.90 | 67 | 770.35 |
| 247 | 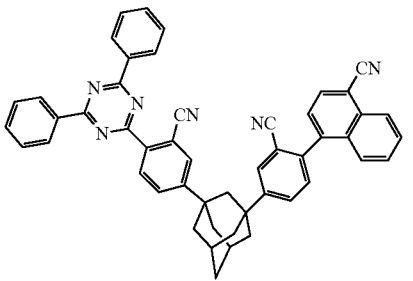 [SMILES: N#Cc1cc(C23CC4CC(C2)CC(c2ccc(-c5ccc(C#N)c6ccccc56)c(C#N)c2)(C4)C3)ccc1-c1nc(-c2ccccc2)nc(-c2ccccc2)n1] | sub 1-B-22 | | 8.12 | 64 | 721.30 |

-continued

| Number | Raw material 5 | Sub 1-B | Product | Output (g) | Yield/% | Mass spectrum (m/z) [M + H]+ |
|---|---|---|---|---|---|---|
| 258 | (CN-phenyl boronic acid) | sub 1-B-23 | 258 | 4.87 | 61 | 811.34 |
| 259 | | sub 1-B-24 | | 4.57 | 60 | 722.32 |

Synthesis of Compounds 266, 267, 268, 269 and 270

Compounds 266, 267, 268, 269, and 270 were prepared in the same way as in Experimental Example 1, except that raw material 5 was used instead of p-cyanophenylboronic acid in Experimental Example 1, to react with sub 1-C.

| Number | Raw material 5 | Sub 1-C | Product | Output (g) | Yield/% | Mass spectrum [M + H] + |
|---|---|---|---|---|---|---|
| 266 | (NC, Cl, CN substituted benzene) | sub 1-C1 | | 6.87 | 64 | 722.32 |

-continued

| Number | Raw material 5 | Sub 1-C | Product | Output (g) | Yield/% | Mass spectrum [M + H]+ |
|---|---|---|---|---|---|---|
| 267 | | sub 1-C2 | | 5.95 | 62 | 745.33 |
| 268 | | sub 1-C3 | | 4.11 | 65 | 777.27 |
| 269 | | | | 5.56 | 61 | 722.30 |
| 270 | | sub 1-C4 | | 6.78 | 60 | 822.35 |

The present disclosure further provides an electronic component for implementing photoelectric conversion or electro-optical conversion. The electronic component includes an anode and a cathode disposed oppositely, and a functional layer disposed between the anode and the cathode; the functional layer includes the organic compound of the present disclosure.

For example, the electronic component is an organic electroluminescent device. As shown in FIG. 1, the organic electroluminescent device includes an anode 100 and a cathode 200 disposed oppositely, and a functional layer 300 disposed between the anode 100 and the cathode 200; the functional layer 300 includes the organic compound provided in the present disclosure.

Optionally, the functional layer 300 includes an electron transport layer 350, and the electron transport layer 350 includes an organic compound provided in the present disclosure. The electron transport layer 350 is composed of the organic compound provided in the present disclosure, or may be composed of the organic compound provided in the present disclosure and other materials.

In an embodiment of the present disclosure, the organic electroluminescent device may include an anode 100, a hole transport layer 321, an electron blocking layer 322, an organic electroluminescent layer 330 as an energy conversion layer, an electron transport layer 350 and a cathode 200 stacked sequentially. The organic compound provided in the present disclosure can be applied to the electron blocking layer 322 of the organic electroluminescent device, which can effectively improve the luminous efficiency and life of the organic electroluminescent device and reduce the driving voltage of the organic electroluminescent device.

Optionally, the anode 100 includes the following anode material, which is optionally a material with a large work function that facilitates injection of holes into the functional layer. Specific examples of the anode material include: metal such as nickel, platinum, vanadium, chromium, copper, zinc and gold, or alloys thereof, metal oxide such as zinc oxide, indium oxide, indium tin oxide (ITO), and indium zinc oxide (IZO); combined metal and oxide such as ZnO:Al or SnO2:Sb; or conductive polymers such as poly(3-methylthiophene), poly[3,4-(ethylene-1,2-dioxyl)thiophene] (PEDT), polypyrrole and polyaniline, but are not limited thereto. Alternatively, a transparent electrode including indium tin oxide (ITO) serves as the anode.

Optionally, the hole transport layer 321 may include one or more hole transport materials. The hole transport materials is selected from carbazole polymers, carbazole-linked triarylamine compounds or other types of compounds, which are not specifically limited in the present disclosure. For example, in an embodiment of the present disclosure, the hole transport layer 321 is composed of compound TPD.

Optionally, the electron blocking layer 322 includes one or more electron blocking materials, and the electron blocking materials is selected from carbazole polymers or other types of compounds, which are not specifically limited in the present disclosure. For example, in some embodiments of the present disclosure, the electron blocking layer 322 is composed of compound TCTA.

Optionally, the organic electroluminescent layer 330 is composed of a single light-emitting material, and may also include a host material and a guest material. Optionally, the organic electroluminescent layer 330 is composed of a host material and a guest material. Holes injected into the organic electroluminescent layer 330 and electrons injected into the organic electroluminescent layer 330 can recombine in the organic electroluminescent layer 330 to form excitons, the excitons transfer energy to the host material, and the host material transfers energy to the guest material, thereby enabling the guest material to emit light.

The host material of the organic electroluminescent layer 330 is a metal chelate compound, a distyryl derivative, an aromatic amine derivative, a dibenzofuran derivative or other types of materials, which are not particularly limited in the present disclosure. In an embodiment of the present disclosure, the host material of the organic electroluminescent layer 330 is CBP.

The guest material of the organic electroluminescent layer 330 is a compound having a condensed aryl ring or a derivative thereof, a compound having a heteroaryl ring or a derivative thereof, an aromatic amine derivative or other materials, which are not particularly limited in the present disclosure. In an embodiment of the present disclosure, the guest material of the organic electroluminescent layer 330 is Ir(piq)$_2$(acac).

Optionally, the cathode 200 includes the following cathode material, which is a material with a small work function that facilitates injection of electrons into the functional layer. Specific examples of the cathode material include: metals such as magnesium, calcium, sodium, potassium, titanium, indium, yttrium, lithium, gadolinium, aluminum, silver, tin and lead, or alloys thereof; or multilayer materials such as LiF/Al, Liq/Al, LiO$_2$/Al, LiF/Ca, LiF/Al and BaF$_2$/Ca, but are not limited thereto. Alternatively, a metal electrode including magnesium and silver serves as the cathode.

Optionally, as shown in FIG. 1, a hole injection layer 310 is further disposed between the anode 100 and the first hole transport layer 321 to enhance the ability to inject holes into the first hole transport layer 321. The hole injection layer 310 is made of benzidine derivatives, starburst arylamine compounds, phthalocyanine derivatives or other materials, which are not particularly limited in the present disclosure. In an embodiment of the present disclosure, the hole injection layer 310 is composed of HAT-CN.

Optionally, as shown in FIG. 1, an electron injection layer 360 is further disposed between the cathode 200 and the electron transport layer 350 to enhance the ability to inject electrons into the electron transport layer 350. The electron injection layer 360 may include inorganic materials such as alkali metal sulfides and alkali metal halides, or may include complexes of alkali metals and organic substances. In an embodiment of the present disclosure, the electron injection layer 360 may include ytterbium (Yb).

Optionally, a hole blocking layer 340 is further disposed between the organic electroluminescent layer 330 and the electron transport layer 350.

Figure 2:
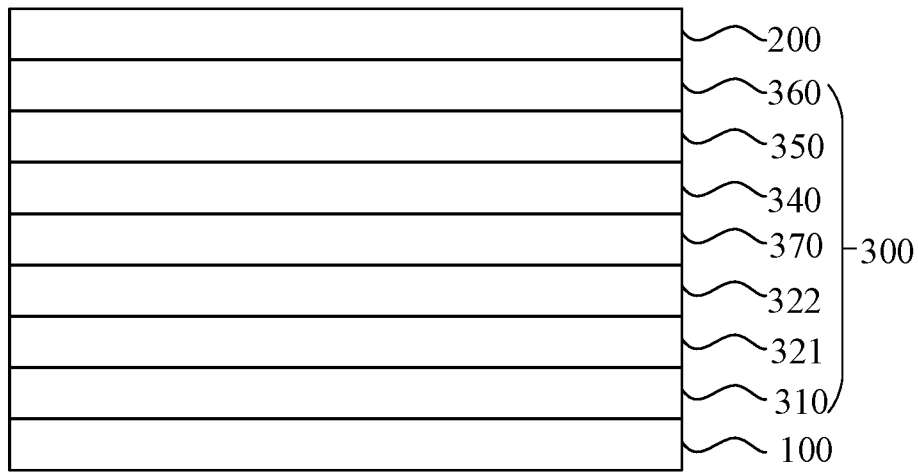
FIG. 2 is a schematic structural diagram of a photoelectric conversion device according to an embodiment of the present disclosure.

For another example, the electronic component is a photoelectric conversion device. As shown in FIG. 2, the photoelectric conversion device may include an anode 100 and a cathode 200 disposed oppositely, and a functional layer 300 disposed between the anode 100 and the cathode 200; the functional layer 300 includes the organic compound provided by the present disclosure.

Optionally, the functional layer 300 includes an electron transport layer 350, and the electron transport layer 350 includes the organic compound provided in the present disclosure. The electron transport layer 350 is composed of the organic compound provided in the present disclosure, or is composed of the organic compound provided in the present disclosure and other materials.

Optionally, as shown in FIG. 2, the photoelectric conversion device may include an anode 100, a hole transport layer 321, an electron blocking layer 322, a photoelectric conversion layer 370 as an energy conversion layer, an electron transport layer 350 and a cathode 200 sequentially stacked. The organic compound provided in the present disclosure can be applied to the electron transport layer 350 of the photoelectric conversion device, which can effectively improve the luminous efficiency and life of the photoelectric conversion device, and increase the open circuit voltage of the photoelectric conversion device.

Optionally, a hole injection layer 310 is further disposed between the anode 100 and the hole transport layer 321.

Optionally, an electron injection layer 360 is further disposed between the cathode 200 and the electron transport layer 350.

Optionally, a hole blocking layer 340 is further disposed between the photoelectric conversion layer 370 and the electron transport layer 350.

Optionally, the photoelectric conversion device is a solar cell, especially an organic thin film solar cell. For example, as shown in FIG. 2, in an embodiment of the present disclosure, the solar cell includes an anode 100, a hole transport layer 321, an electron blocking layer 322, a photoelectric conversion layer 370, an electron transport layer 350 and a cathode 200 sequentially stacked, the electron transport layer 350 including the organic compound of the present disclosure.

An embodiment of the present disclosure further provides an electronic apparatus, which includes any of the electronic components described in the above embodiments. Since the electronic apparatus has any of the electronic components described in the above embodiments, it has the same beneficial effects, and details are not described herein again.

Figure 3:
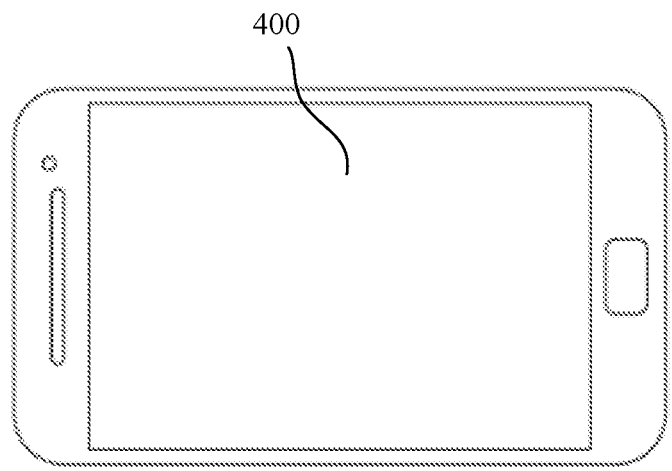
FIG. 3 is a schematic structural diagram of an electronic apparatus according to an embodiment of the present disclosure.

For example, as shown in FIG. 3, the present disclosure provides an electronic apparatus 400, which includes any of the organic electroluminescent devices described in the above embodiments. The electronic apparatus 400 is a display device, a lighting device, an optical communication device or other types of electronic apparatuses, for example, it may include but is not limited to a computer screen, a mobile phone screen, a television, electronic paper, an emergency lamp, an optical module, etc. Since the electronic apparatus 400 has any of the organic electroluminescent devices described in the above embodiments, it has the same beneficial effects, and details are not described herein again.

Figure 4:
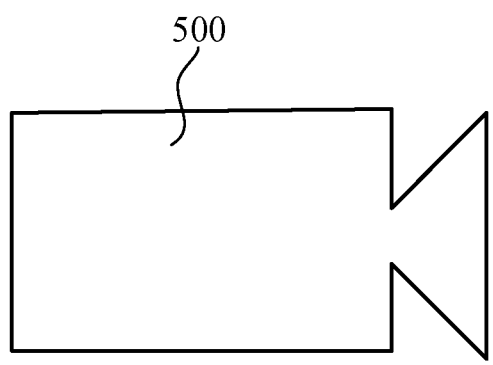
FIG. 4 is a schematic structural diagram of an electronic apparatus according to another embodiment of the present disclosure.

For another example, as shown in FIG. 4, the present disclosure provides an electronic apparatus 500, which includes any of the photoelectric conversion devices described in the above embodiments. The electronic apparatus 500 is a solar-power device, a photodetector, a fingerprint identification device, an optical module, a CCD camera, or other types of electronic apparatuses. Since the electronic apparatus 500 has any of the photoelectric conversion devices described in the above embodiments, it has the same beneficial effects, and details are not described herein again.

Preparation and Performance Evaluation of Organic Electroluminescent Devices

Example 1: Blue Organic Electroluminescent Device

An anode was prepared by the following process: an ITO substrate (manufactured by Corning) with a thickness of 1500 Å was cut into a size of 40 mm×40 mm×0.7 mm, and prepared by photolithography process into an experimental substrate with cathode, anode and insulating layer patterns, and surface treatment was carried out using ultraviolet ozone and $O_2$:$N_2$ plasma to increase the work function of the anode (experimental substrate) and remove scum.

HAT-CN was vacuum-evaporated on the experimental substrate (anode) to form a hole injection layer (HIL) with a thickness of 100 Å, and compound NPB was vacuum-evaporated on the hole injection layer to form a hole transport layer (HTL) with a thickness of 1100 Å.

Compound TCTA was evaporated on the hole transport layer as an electron blocking layer (EBL) with a thickness of 150 Å.

α,β-ADN was used as a host and doped with BD-1 according to a film thickness ratio of 30:3 to form an organic electroluminescent layer (EML) with a thickness of 220 Å.

Compound 1 of the present disclosure was evaporated on the electroluminescent layer to form an electron transport layer (ETL) with a thickness of 300 Å, Yb was evaporated on the electron transport layer to form an electron injection layer (EIL) with a thickness of 10 Å, and then magnesium (Mg) and silver (Ag) were mixed at an evaporation rate of 1:9 and vacuum-evaporated on the electron injection layer to form a cathode with a thickness of 120 Å.

In addition, CP-1 with a thickness of 650 Å was evaporated on the cathode to form a capping layer (CPL), thereby completing the manufacture of an organic electroluminescent device.

Wherein, structural formulae of the HAT-CN, NPB, TCTA, α, β-ADN, BD-1 and CP-1 were as follows:

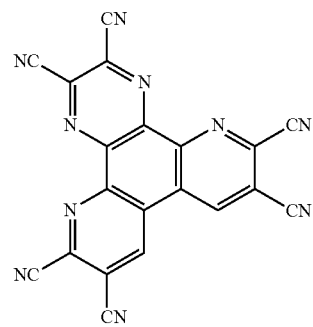

HAT-CN

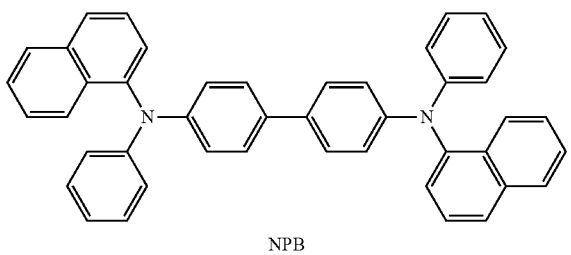

NPB

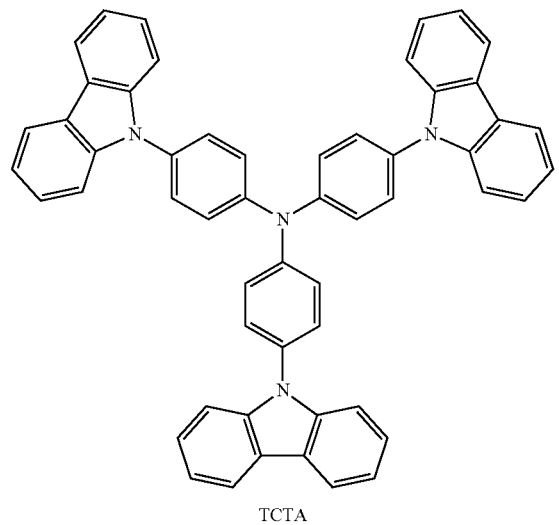

TCTA

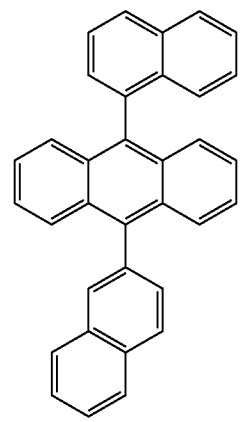

α, β - AND

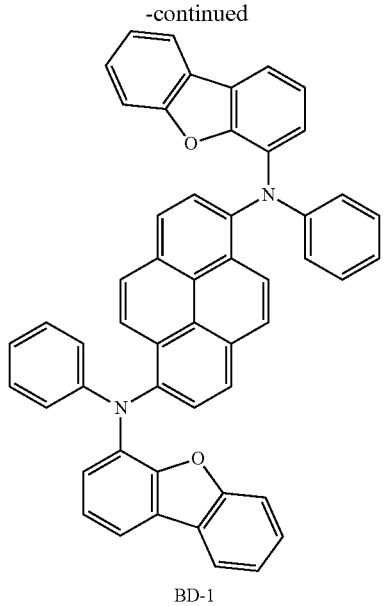

BD-1

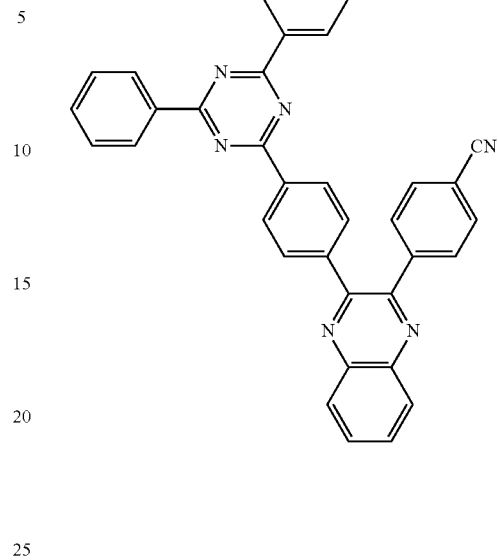

Compound A

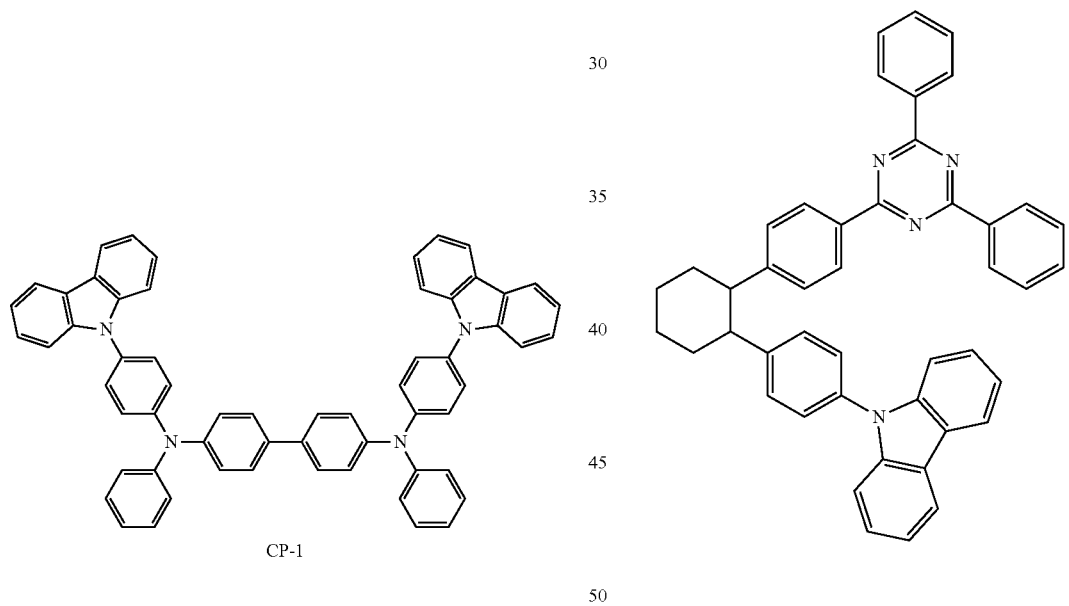

CP-1

Compound B

Examples 2 to 34

Organic electroluminescent devices were manufactured by the same method as that in Example 1, except that compounds shown in Table 1 were used when the electron transport layer (ETL) was formed.

Comparative Examples 1 to 6

In Comparative Examples 1 to 6, organic electroluminescent devices were manufactured by the same method as that in Example 1, except that compound A, compound B, Alq$_3$, compound C, compound D, and compound E were used as the electron transport layer instead of the compound 1.

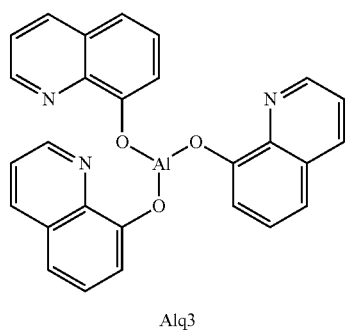

Alq3

Compound C

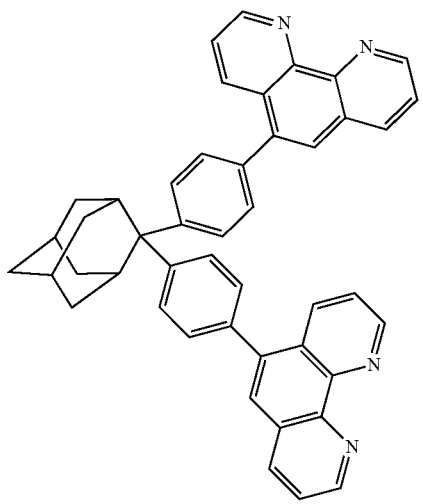

Compound D

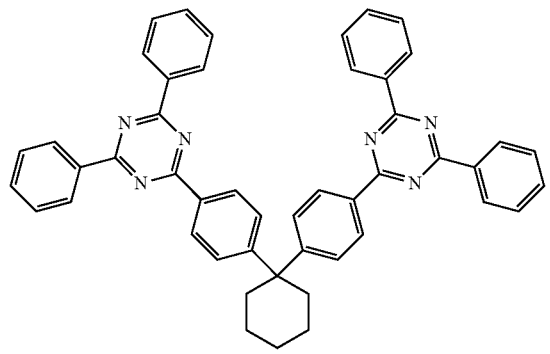

Compound E

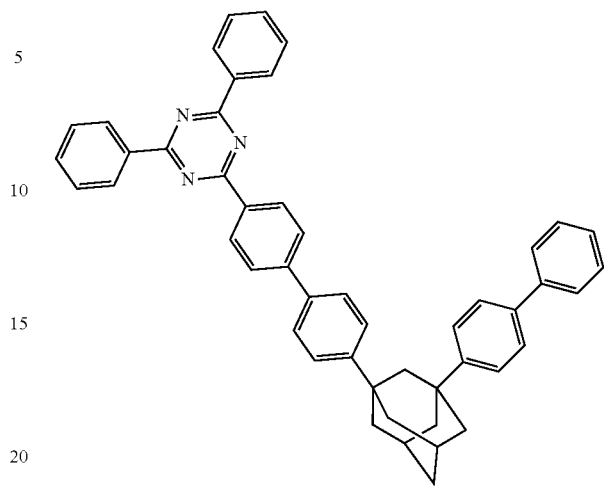

(prepared according to the synthesis method of compound 1)

The performance parameters of the manufactured devices were shown in Table 1, where the IVL data compared the test results under 15 mA/cm$^2$, and the life was tested at a current density of 15 mA/cm$^2$.

TABLE 1

Device performance of Examples 1 to 39 and Comparative Examples 1 to 6

| Example | Electron transport layer | Voltage Volt (V) | Current efficiency Cd/A | External quantum efficiency EQE % | Color coordinates CIEy | LT95 (@ 15 mA/cm$^2$) |
|---|---|---|---|---|---|---|
| Example 1 | Compound 1 | 4.06 | 7.0 | 12.9 | 0.049 | 197 |
| Example 2 | Compound 2 | 4.02 | 6.6 | 12.7 | 0.048 | 204 |
| Example 3 | Compound 3 | 4.05 | 6.6 | 12.7 | 0.049 | 202 |
| Example 4 | Compound 10 | 4.06 | 6.7 | 12.8 | 0.049 | 192 |
| Example 5 | Compound 12 | 4.05 | 6.6 | 12.7 | 0.048 | 195 |
| Example 6 | Compound 6 | 4.05 | 6.9 | 13.0 | 0.048 | 205 |
| Example 7 | Compound 18 | 4.02 | 6.6 | 12.7 | 0.049 | 204 |
| Example 8 | Compound 19 | 4.02 | 6.6 | 12.7 | 0.049 | 200 |
| Example 9 | Compound 27 | 4.05 | 6.6 | 12.7 | 0.048 | 205 |
| Example 10 | Compound 33 | 4.04 | 6.7 | 12.8 | 0.049 | 191 |
| Example 11 | Compound 35 | 4.07 | 6.8 | 13.9 | 0.048 | 191 |
| Example 12 | Compound 43 | 4.04 | 6.8 | 13.0 | 0.049 | 204 |
| Example 13 | Compound 44 | 4.02 | 6.6 | 12.7 | 0.049 | 196 |
| Example 14 | Compound 41 | 4.01 | 6.8 | 12.9 | 0.048 | 191 |
| Example 15 | Compound 59 | 4.07 | 6.3 | 12.4 | 0.048 | 175 |
| Example 16 | Compound 40 | 4.04 | 6.8 | 13.0 | 0.049 | 203 |
| Example 17 | Compound 60 | 4.07 | 6.1 | 12.3 | 0.049 | 172 |
| Example 18 | Compound 61 | 4.04 | 6.0 | 12.3 | 0.048 | 172 |
| Example 19 | Compound 63 | 4.08 | 6.6 | 12.8 | 0.049 | 195 |
| Example 20 | Compound 64 | 4.08 | 6.8 | 13.0 | 0.049 | 197 |
| Example 21 | Compound 194 | 4.03 | 6.7 | 12.8 | 0.048 | 193 |
| Example 22 | Compound 65 | 4.02 | 6.7 | 12.9 | 0.049 | 203 |
| Example 23 | Compound 66 | 4.08 | 6.8 | 12.9 | 0.049 | 199 |
| Example 24 | Compound 76 | 4.05 | 6.8 | 13.0 | 0.048 | 196 |
| Example 25 | Compound 77 | 4.07 | 6.8 | 12.9 | 0.048 | 194 |
| Example 26 | Compound 103 | 4.02 | 6.6 | 12.8 | 0.049 | 199 |
| Example 27 | Compound 85 | 4.00 | 6.7 | 12.8 | 0.049 | 191 |

TABLE 1-continued

Device performance of Examples 1 to 39 and Comparative Examples 1 to 6

| Example | Electron transport layer | Voltage Volt (V) | Current efficiency Cd/A | External quantum efficiency EQE % | Color coordinates CIEy | LT95 (@ 15 mA/cm²) |
|---|---|---|---|---|---|---|
| Example 28 | Compound 86 | 4.03 | 6.7 | 12.8 | 0.048 | 195 |
| Example 29 | Compound 104 | 4.02 | 6.6 | 12.9 | 0.049 | 192 |
| Example 30 | Compound 211 | 4.04 | 6.7 | 12.8 | 0.048 | 191 |
| Example 31 | Compound 105 | 4.02 | 6.0 | 12.3 | 0.049 | 178 |
| Example 32 | Compound 247 | 4.05 | 6.6 | 12.9 | 0.049 | 190 |
| Example 33 | Compound 258 | 4.01 | 6.7 | 12.9 | 0.048 | 190 |
| Example 34 | Compound 259 | 4.00 | 6.1 | 12.3 | 0.049 | 178 |
| Example 35 | Compound 266 | 4.01 | 6.7 | 12.8 | 0.050 | 199 |
| Example 36 | Compound 267 | 4.04 | 6.1 | 12.3 | 0.048 | 175 |
| Example 37 | Compound 268 | 4.03 | 6.6 | 12.3 | 0.049 | 182 |
| Example 38 | Compound 269 | 4.04 | 6.7 | 12.8 | 0.048 | 191 |
| Example 39 | Compound 270 | 4.05 | 6.6 | 12.7 | 0.049 | 188 |
| Comparative Example 1 | Compound A | 4.30 | 5.5 | 10.5 | 0.048 | 121 |
| Comparative Example 2 | Compound B | 4.32 | 5.3 | 10.4 | 0.048 | 120 |
| Comparative Example 3 | Alq3 | 4.36 | 5.2 | 9.1 | 0.049 | 158 |
| Comparative Example 4 | Compound C | 4.35 | 4.5 | 10.8 | 0.050 | 122 |
| Comparative Example 5 | Compound D | 4.33 | 4.9 | 10.6 | 0.052 | 119 |
| Comparative Example 6 | Compound E | 4.33 | 4.9 | 10.9 | 0.051 | 140 |

According to the results of [Table 1] above, it can be seen that, comparing the Examples 1 to 39 prepared using the compounds of the present disclosure with the Comparative Examples 1 to 6, the driving voltage of the devices at a current density of 15 mA/cm² was equivalent, but the device efficiency of the examples was increased by at least 9.1%, and the current efficiency of the devices prepared by most compounds was increased by nearly 20%; the life was prolonged by at least 9%, and the life of the devices prepared by most compounds was prolonged by more than 20%. Comparing the compounds 1 to 39 of the present disclosure with compound E, it can be seen that the link of the cyano to the compound containing adamantane and electron-deficient heteroaryls can increase the dipole moment of molecules, increase the polarity of the material, deepen the LOMO energy level, and improve the electron mobility. Therefore, the compounds with cyano had higher luminous efficiency and longer life.

It should be noted that only one method for preparing a blue organic electroluminescent device is provided above, and the organic compound of the present disclosure can also be used in electron transport layers of organic electroluminescent devices of other colors, such as red organic electroluminescent devices and green organic electroluminescent devices, to bring the same technical effects.

In summary, the organic electroluminescent device manufactured using the compound of the present disclosure in the electron transport layer (ETL) can achieve low driving voltage, high luminous efficiency and long life.

The invention claimed is:

1. An organic compound, wherein the compound has the following structure:

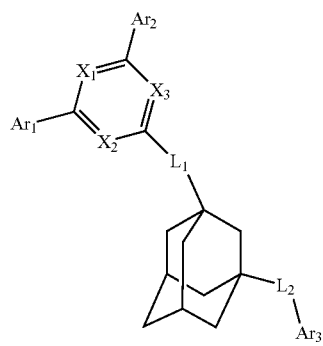

(chemical formula 2)

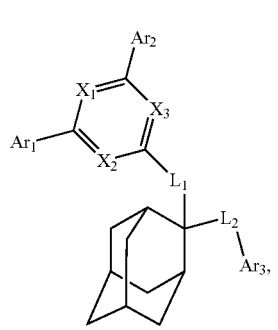

(chemical formula 3)

$Ar_3$ has at least one cyano substituent and ⁜ represents a chemical bond;

$X_1$, $X_2$, and $X_3$ are the same or different, $X_1$ is $C(R^{X1})$ or N, $X_2$ is $C(R^{X2})$ or N, $X_3$ is $C(R^{X3})$ or N, and at least one of $X_1$, $X_2$, and $X_3$ is N;

$R^{X1}$, $R^{X2}$, and $R^{X3}$ are the same or different, and are each independently selected from hydrogen, deuterium, fluorine, chlorine, and cyano;

$L_1$ and $L_2$ are each independently selected from single bond, substituted or unsubstituted phenylene, substituted or unsubstituted biphenylene, substituted or unsubstituted terphenylene, substituted or unsubstituted naphthylene, substituted or unsubstituted quinolylene, substituted or unsubstituted fluorenylene, substituted or unsubstituted phenanthrylene, substituted or unsubstituted isoquinolylene, and a subunit group formed by linking two or three of them through single bond; the substitution of each of $L_1$ and $L_2$ refers to independently substituted by 1, 2, 3 or 4 substituents selected from deuterium, fluorine, chlorine, cyano, methyl, ethyl, isopropyl, tert-butyl, trifluoromethyl, phenyl, naphthyl, and trimethylsilyl;

the $Ar_1$ and $Ar_2$ are the same or different, and are each independently selected from substituted or unsubstituted group $Y_1$, and the group $Y_1$ is selected from the following groups:

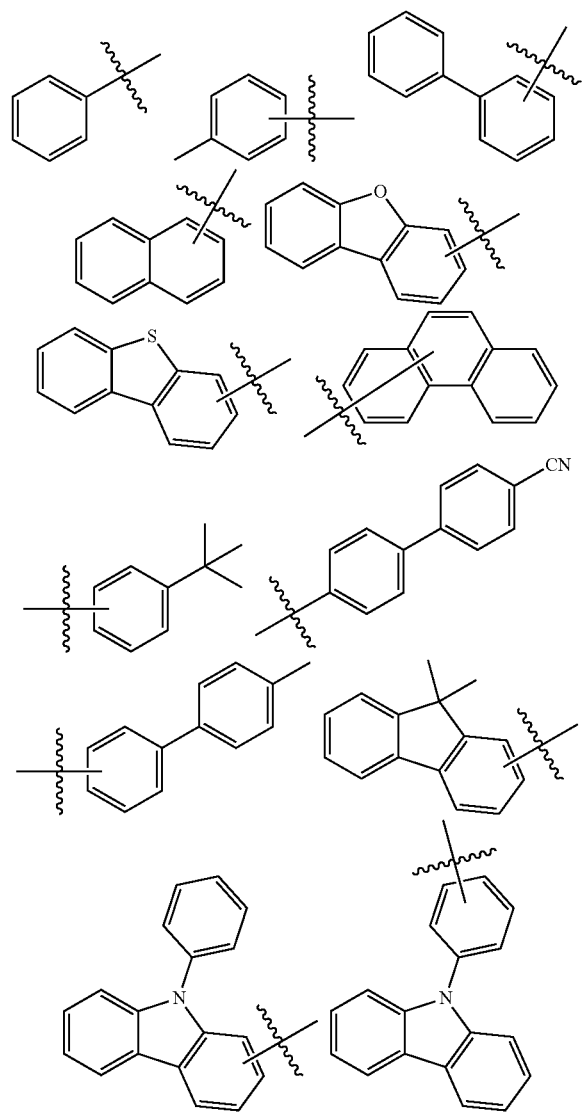

-continued

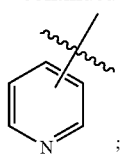

when the group $Y_1$ is substituted, the substituent of $Y_1$ is selected from deuterium, fluorine, chlorine, cyano, alky with 1 to 4 carbon atoms, haloalkyl with 1 to 4 carbon atoms, and aryl with 6 to 12 carbon atoms;

when the $Y_1$ has a plurality of substituents, the substituents are the same or different;

the $Ar_3$ is selected from substituted or unsubstituted group $Z_1$, and the group $Z_1$ is selected from the following groups:

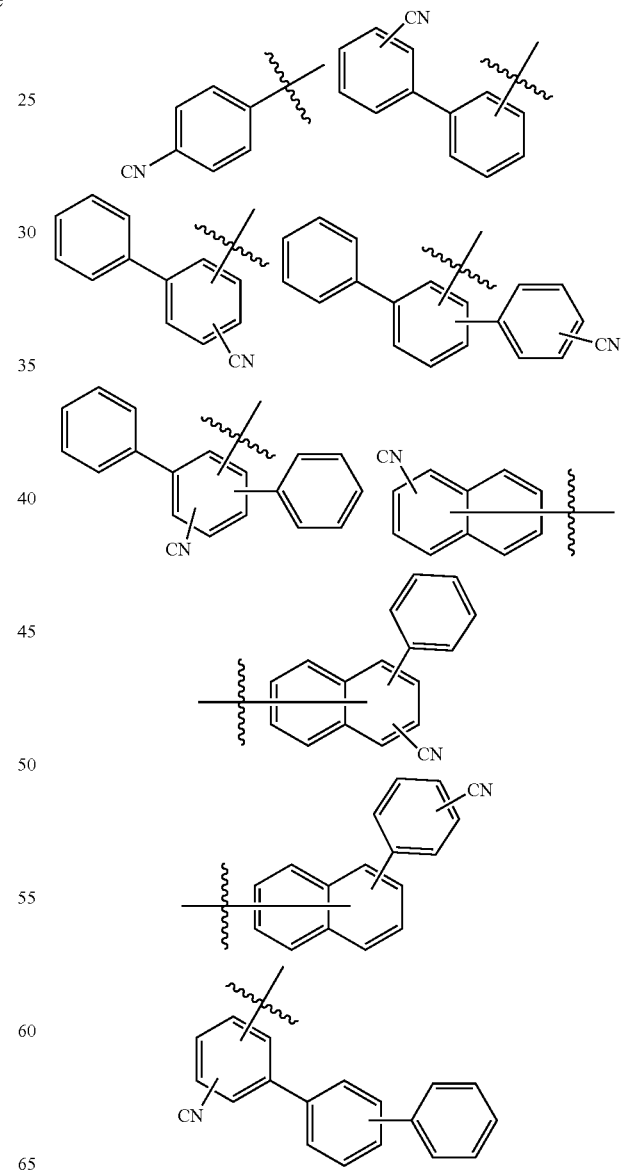

-continued

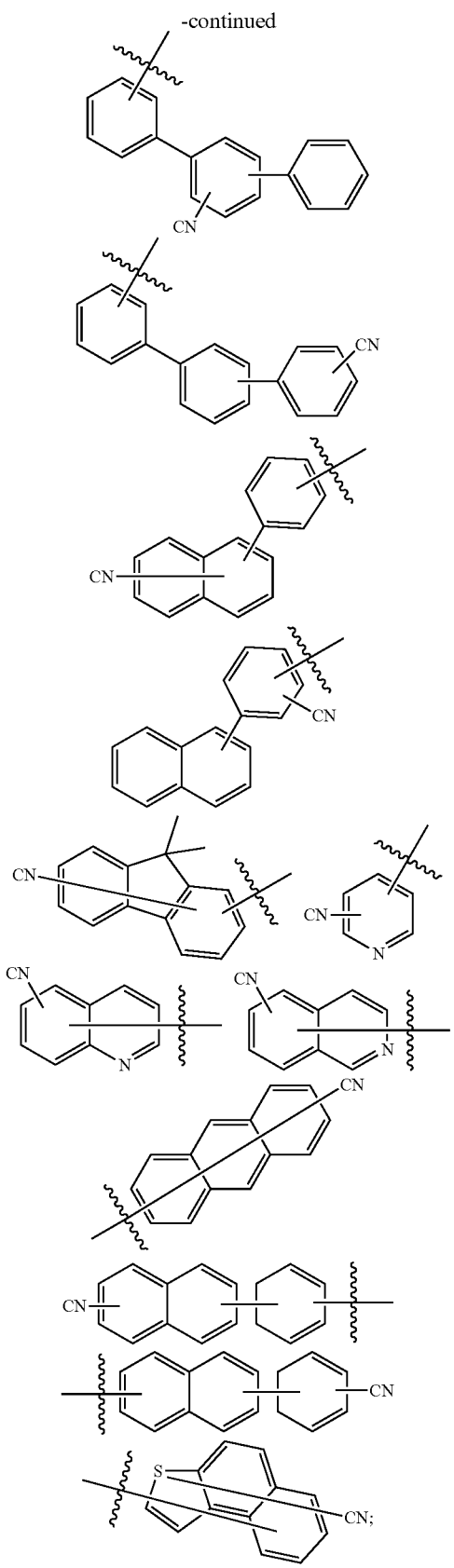

when the group $Z_1$ is substituted, the substituent of $Z_1$ is selected from deuterium, fluorine, chlorine, cyano, alkyl with 1 to 4 carbon atoms, and aryl with 6 to 12 carbon atoms; when the $Z_1$ has a plurality of substituents, the substituents are the same or different.

2. The organic compound according to claim 1, wherein the $L_1$ or $L_2$ is the same or different, and is independently selected from single bond, and substituted or unsubstituted group $W_1$, and the group $W_1$ is selected from the group consisting of the following groups:

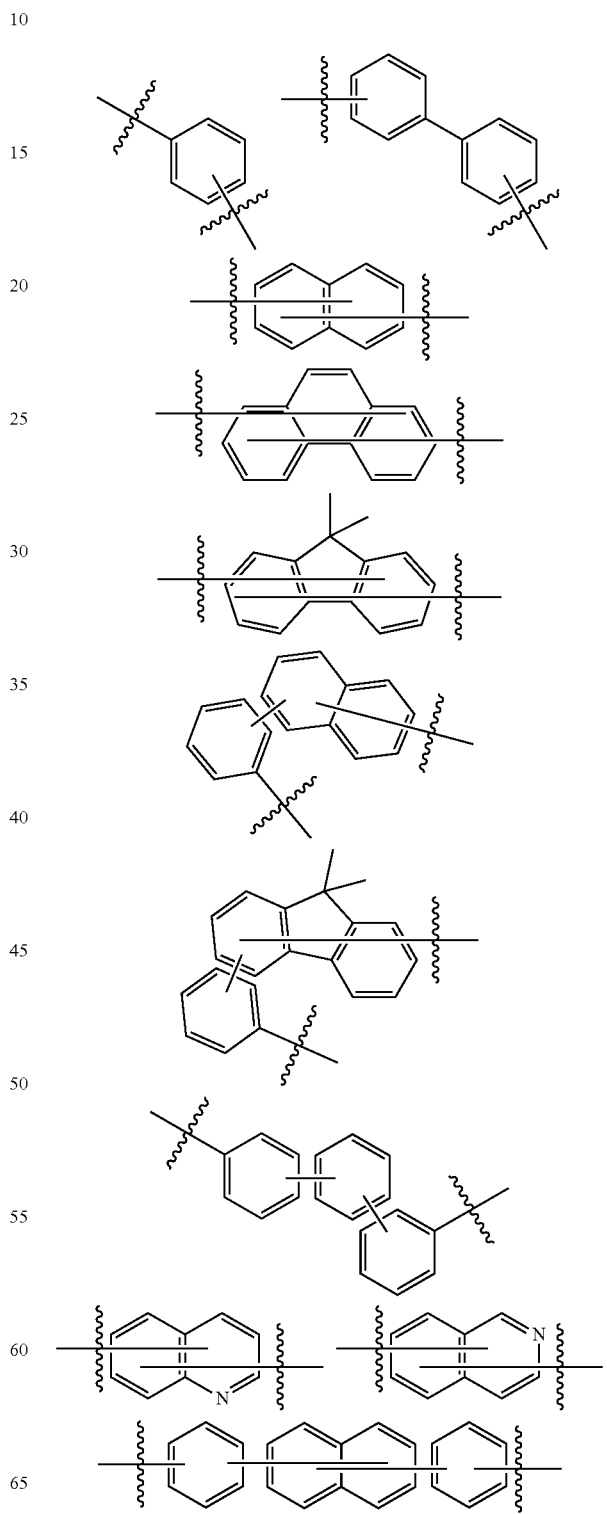

-continued

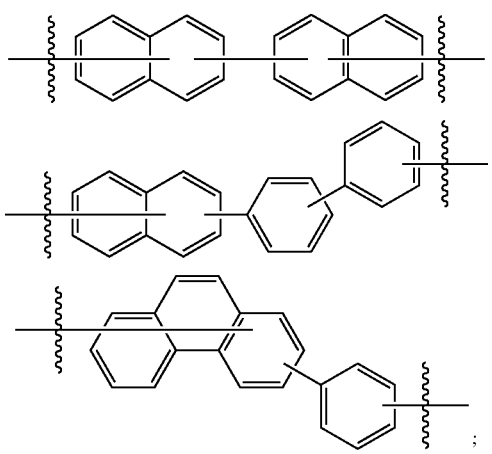

when the $W_1$ group is substituted, the substituent of $W_1$ is selected from deuterium, fluorine, chlorine, cyano, methyl, ethyl, isopropyl, tert-butyl, and alkyl with 6 carbon atoms; when the $W_1$ has a plurality of substituents, the substituents are the same or different.

3. The organic compound according to claim 1, wherein the $L_1$ or $L_2$ is the same or different, and is independently selected from single bond, and the group consisting of the following groups:

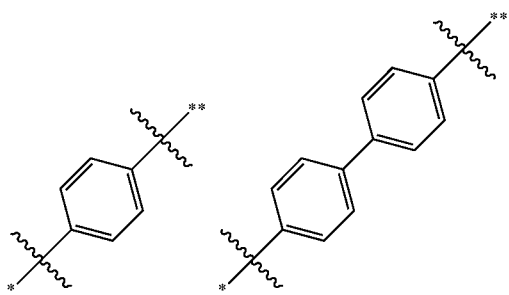

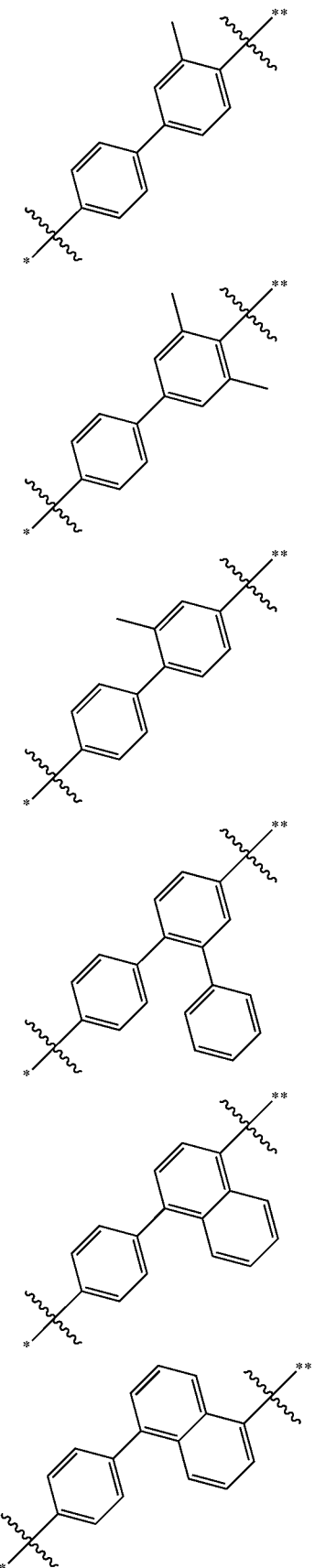

275
-continued
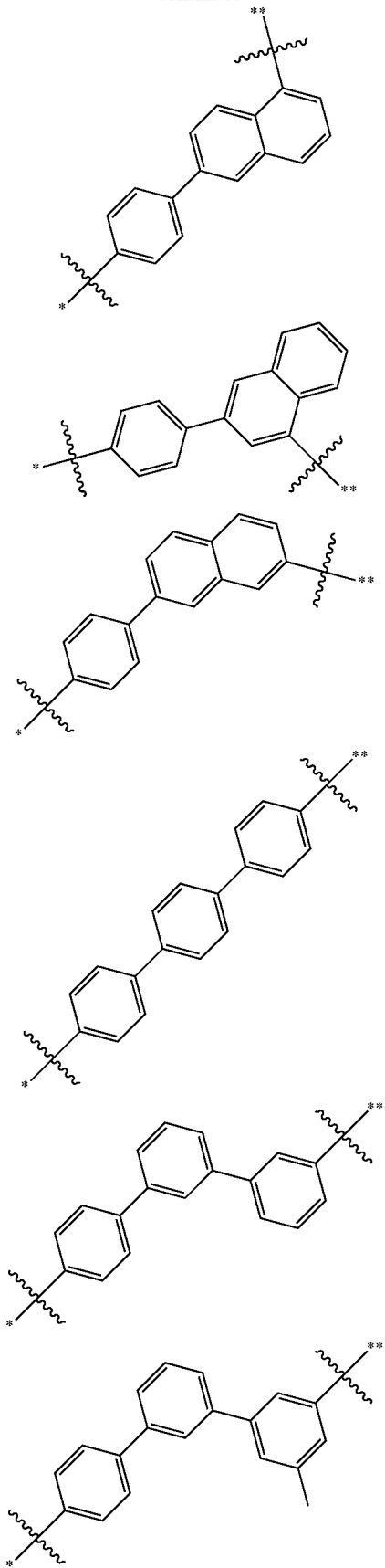
276
-continued
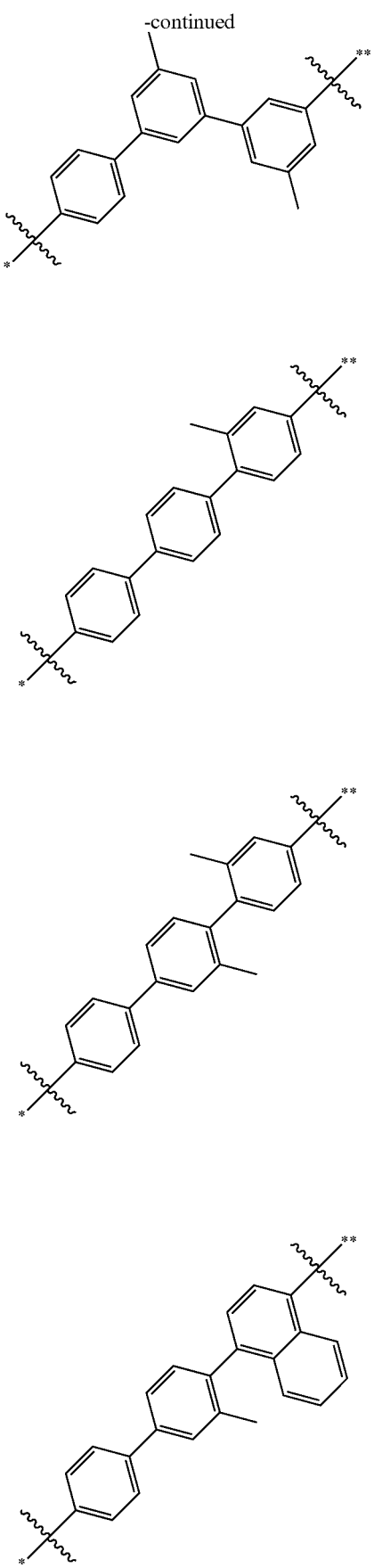

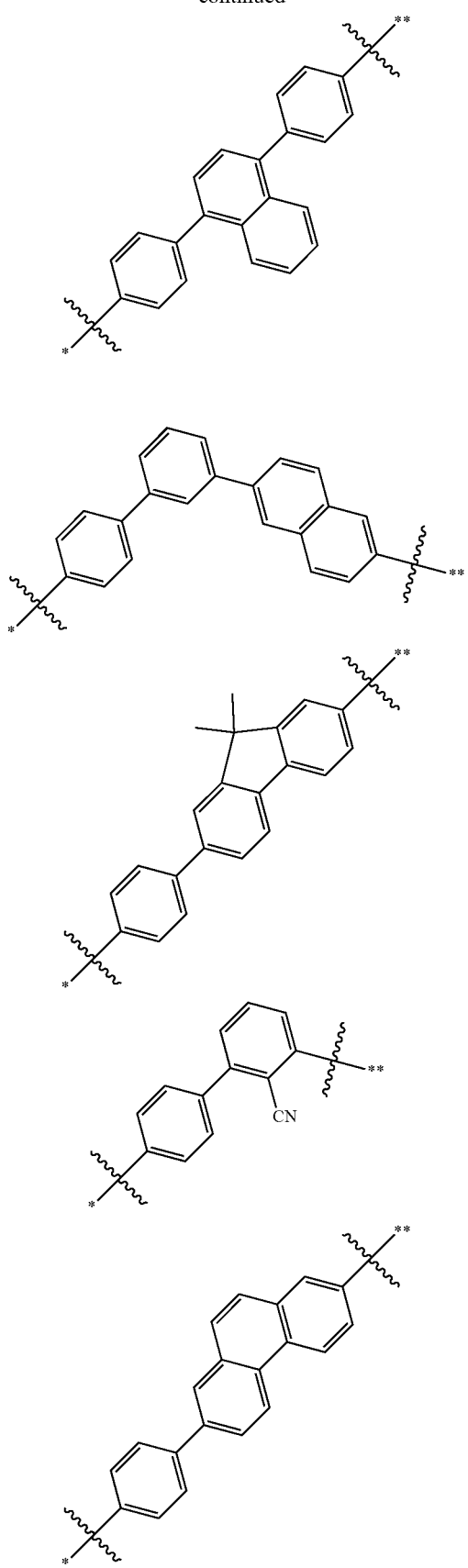
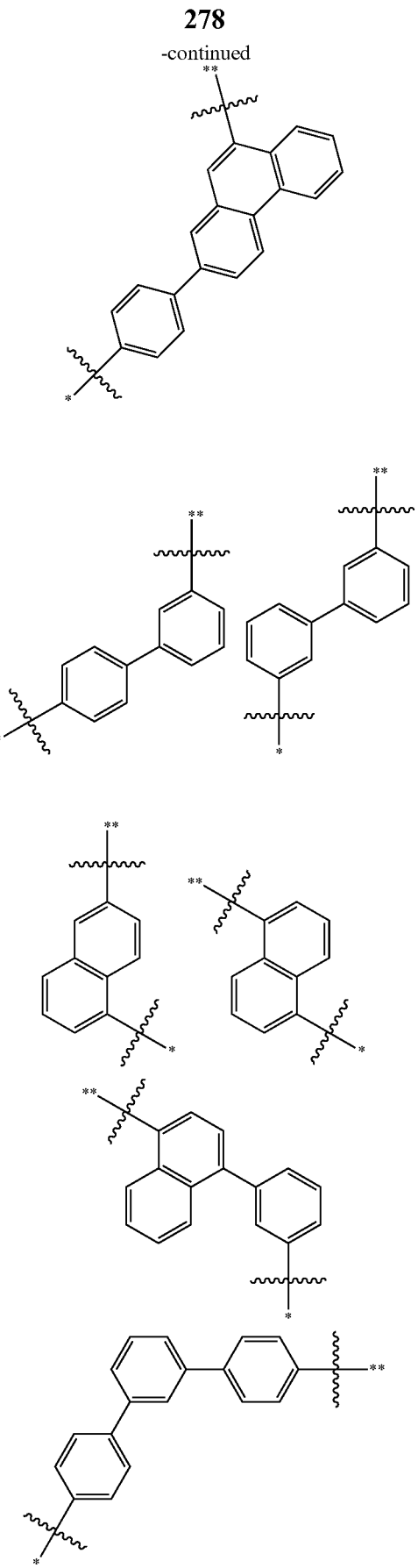

279
-continued
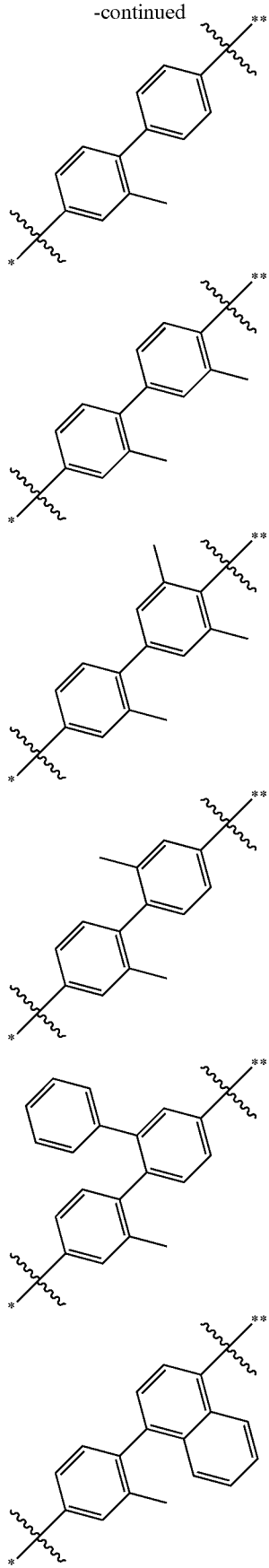
280
-continued
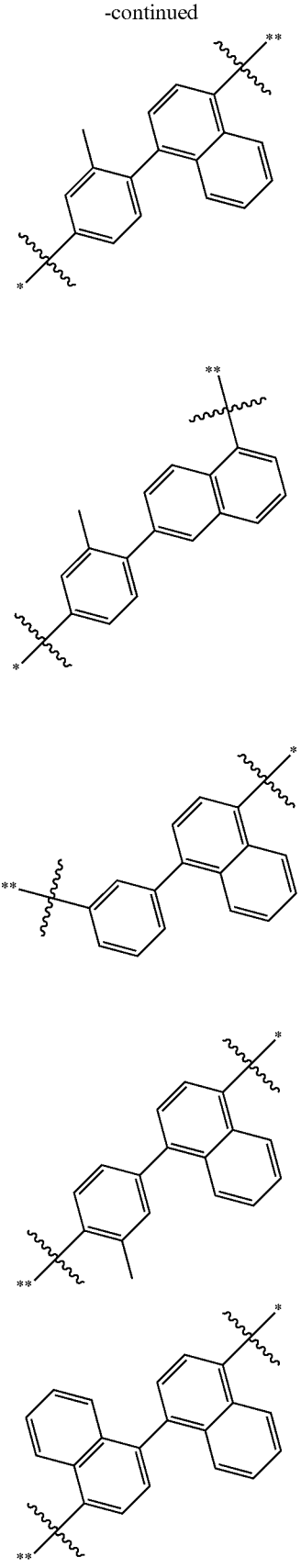

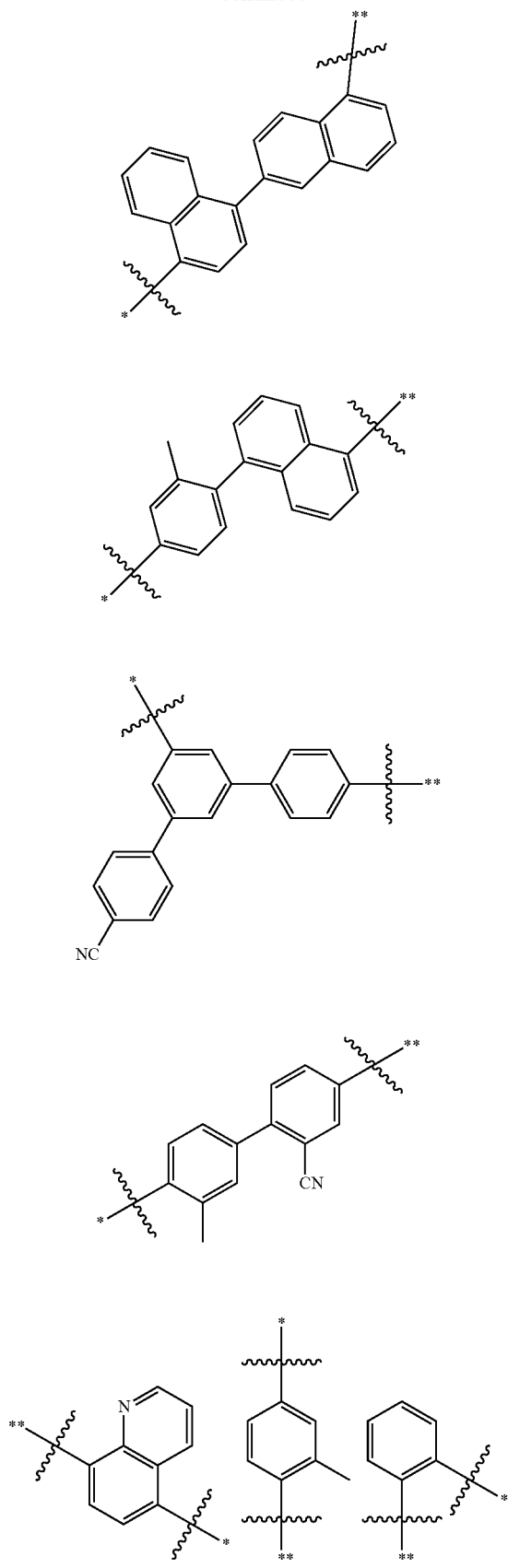
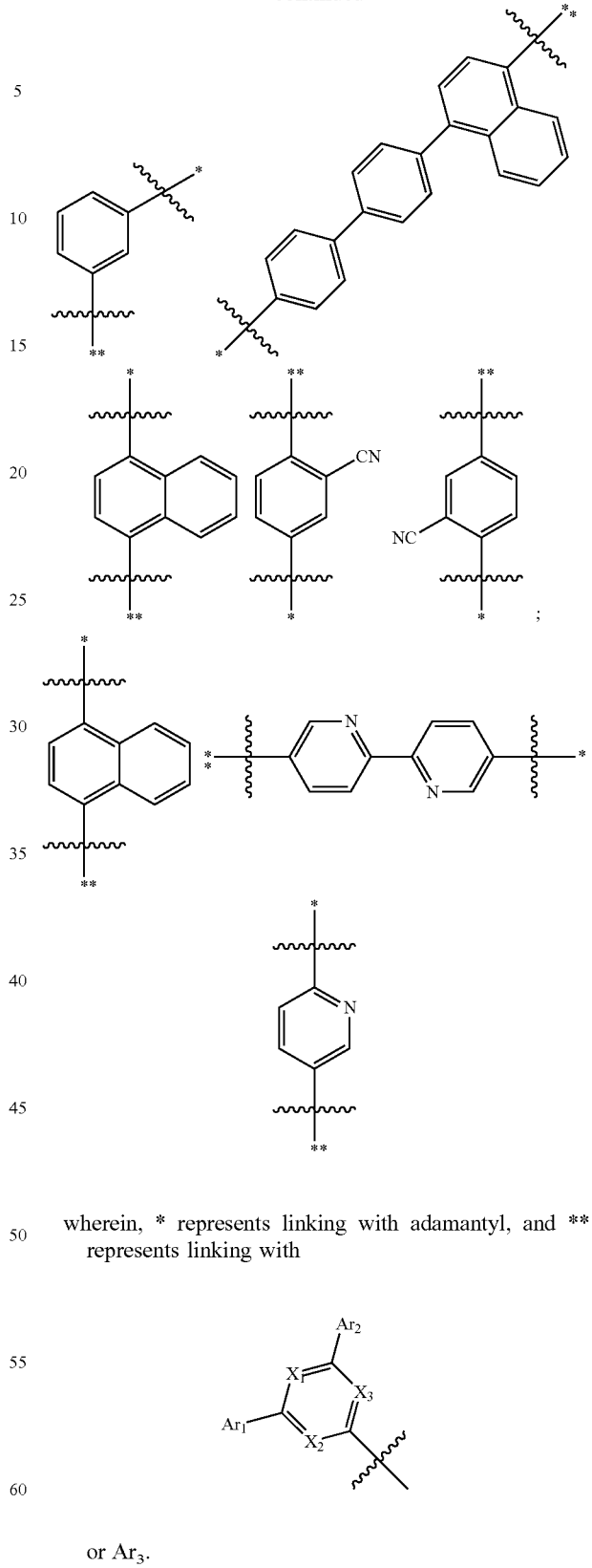
wherein, * represents linking with adamantyl, and ** represents linking with
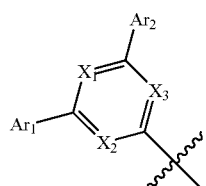
or Ar₃.
4. The organic compound according to claim 1, wherein the L₁ or L₂ is the same or different, and is independently selected from single bond, and the group consisting of the following groups:

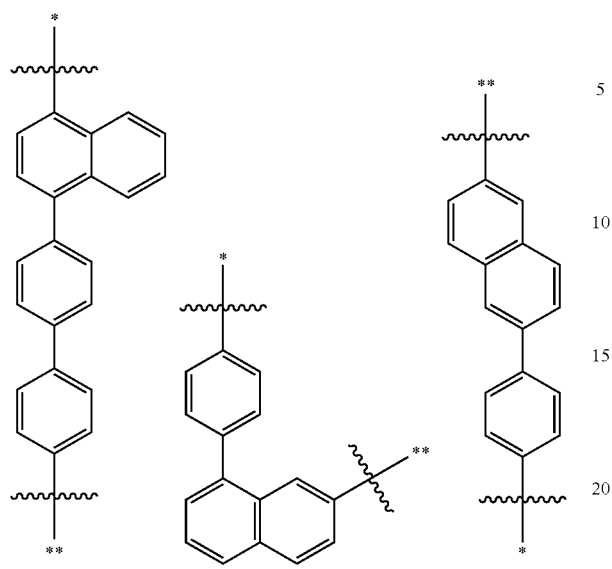
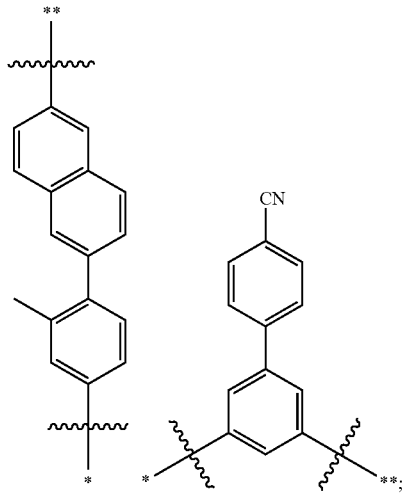
wherein, * represents linking with adamantyl, and ** represents linking with
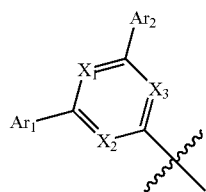
or $Ar_3$.
5. The organic compound according to claim 1, wherein the $Ar_1$ and $Ar_2$ are the same or different, and are each independently selected from the following groups:
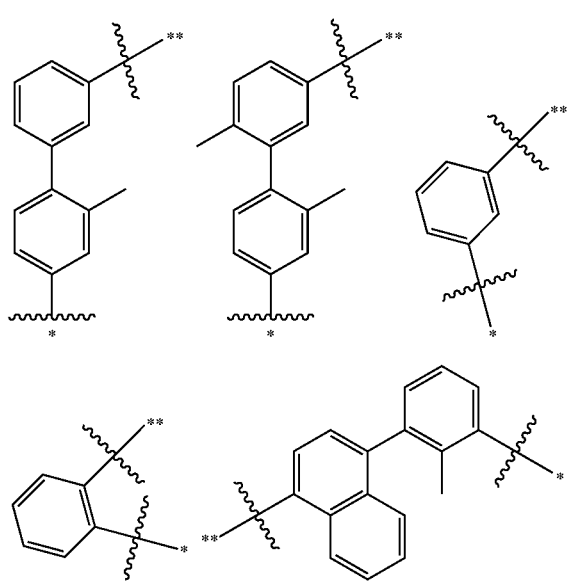
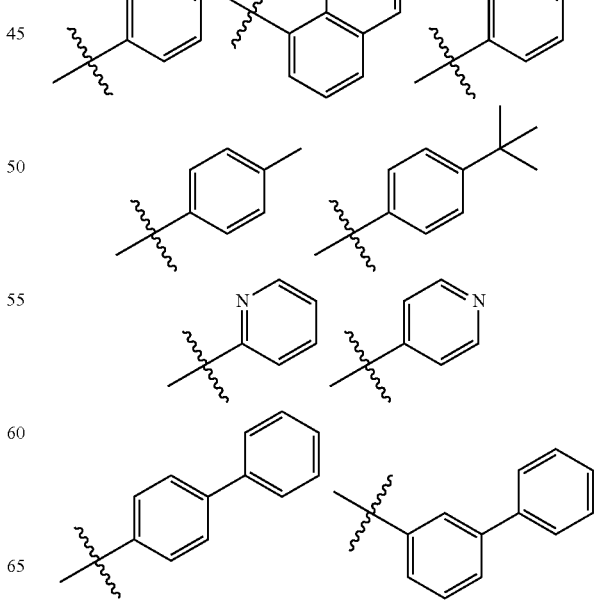

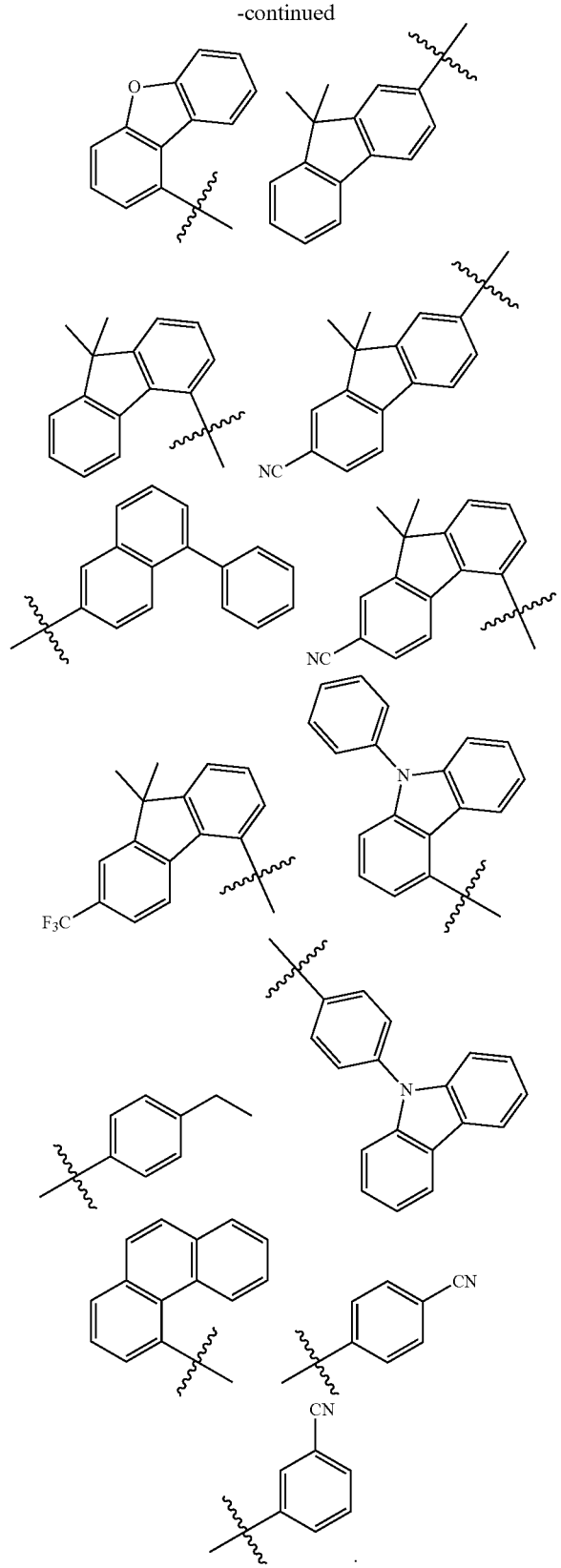
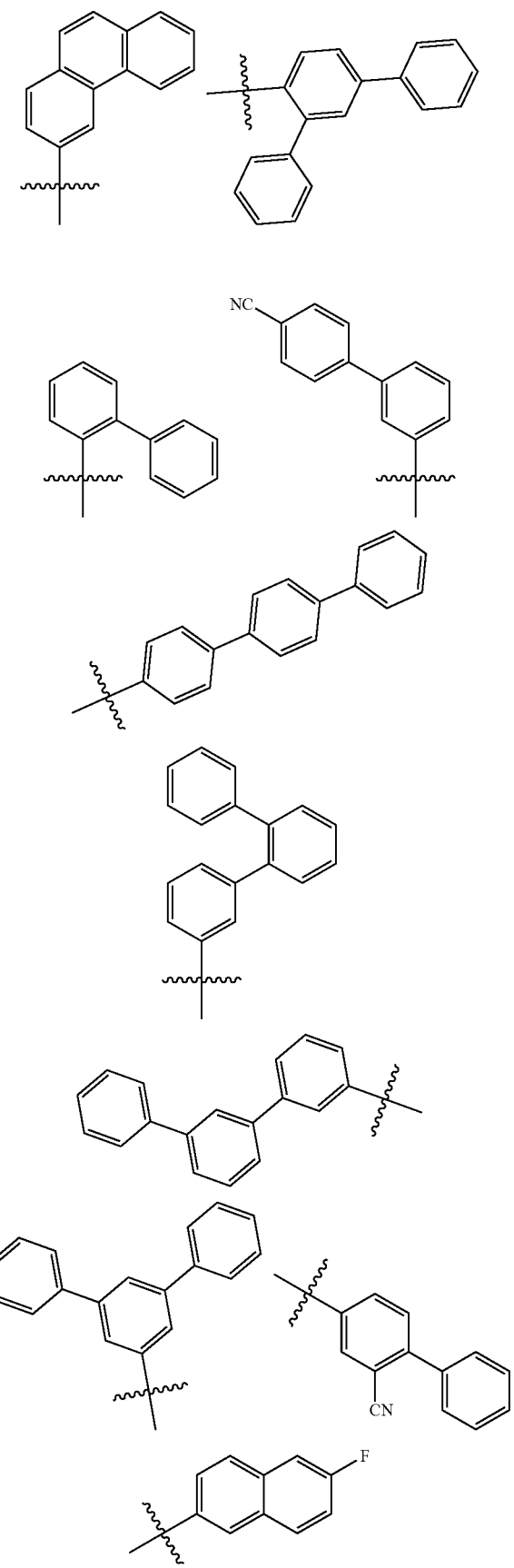
6. The organic compound according to claim 1, wherein the Ar₁ and Ar₂ are the same or different, and are each independently selected from the following groups:

287
-continued
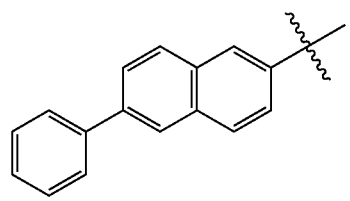
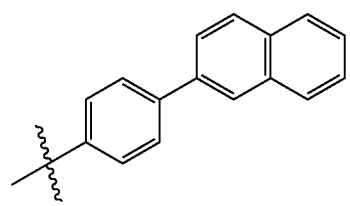
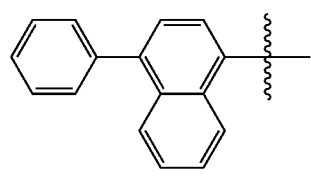
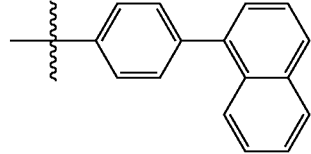
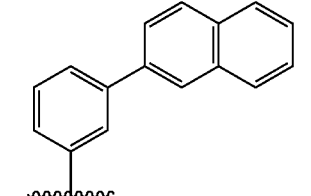
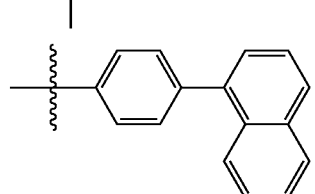
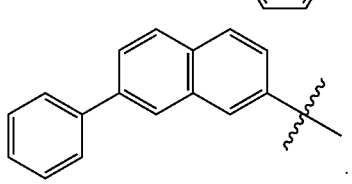
7. The organic compound according to claim 1, wherein the Ar$_3$ is selected from the following groups:
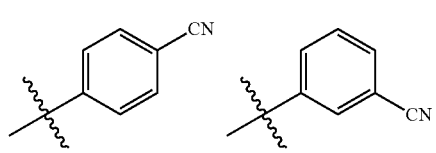
288
-continued
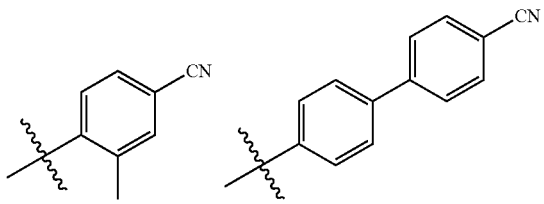
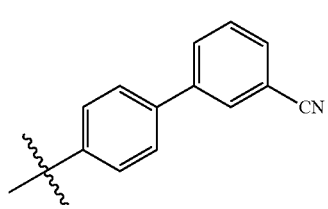
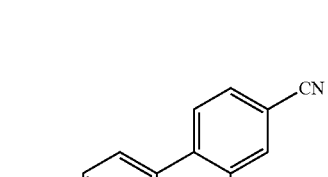
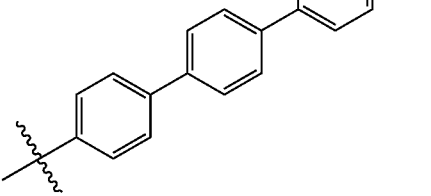
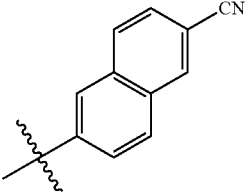
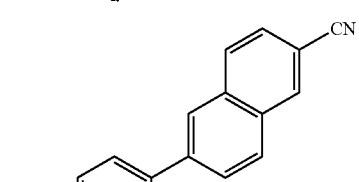
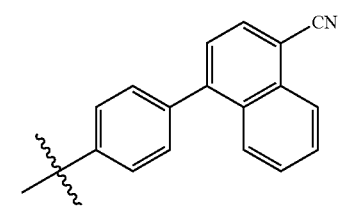

289
-continued
290
-continued
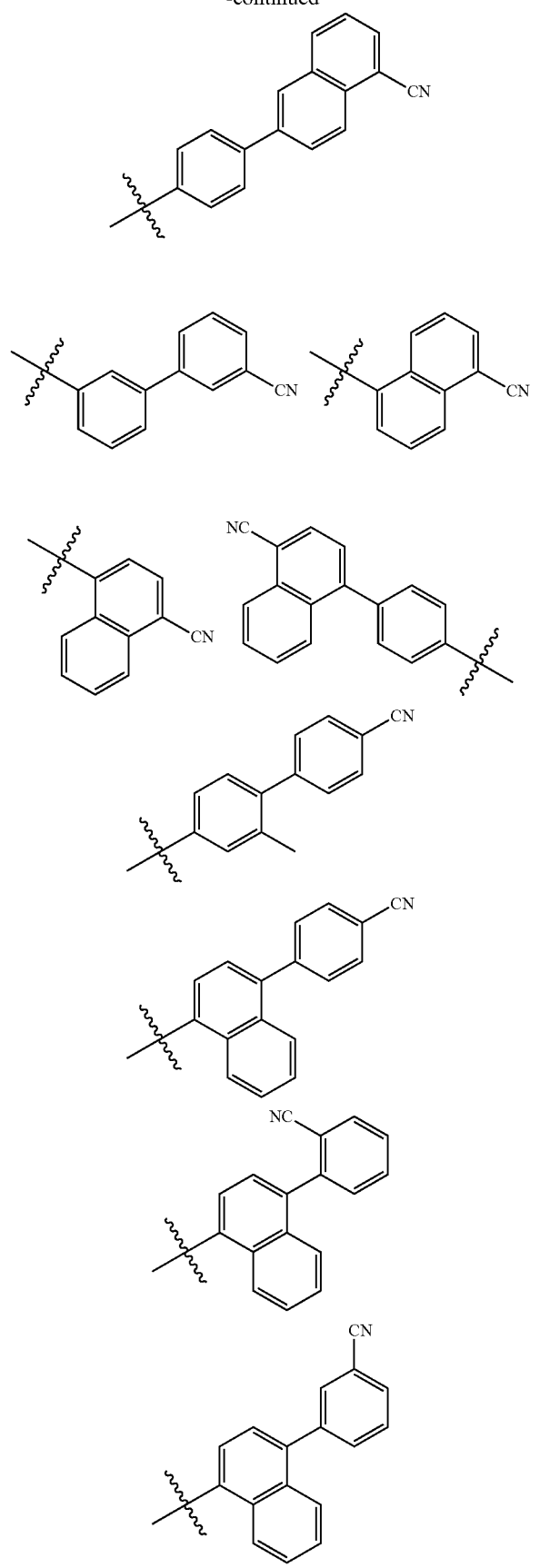
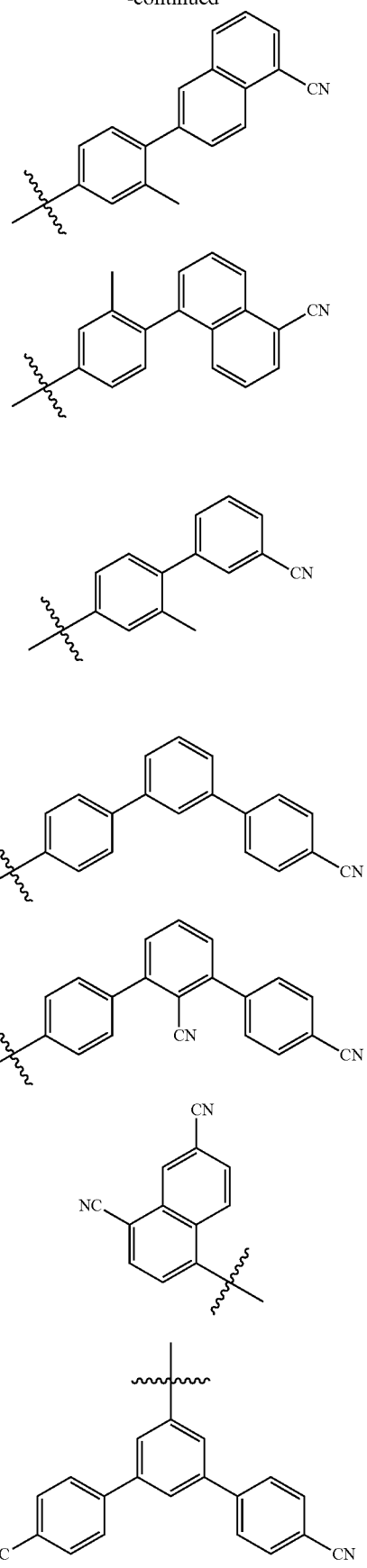

291
-continued
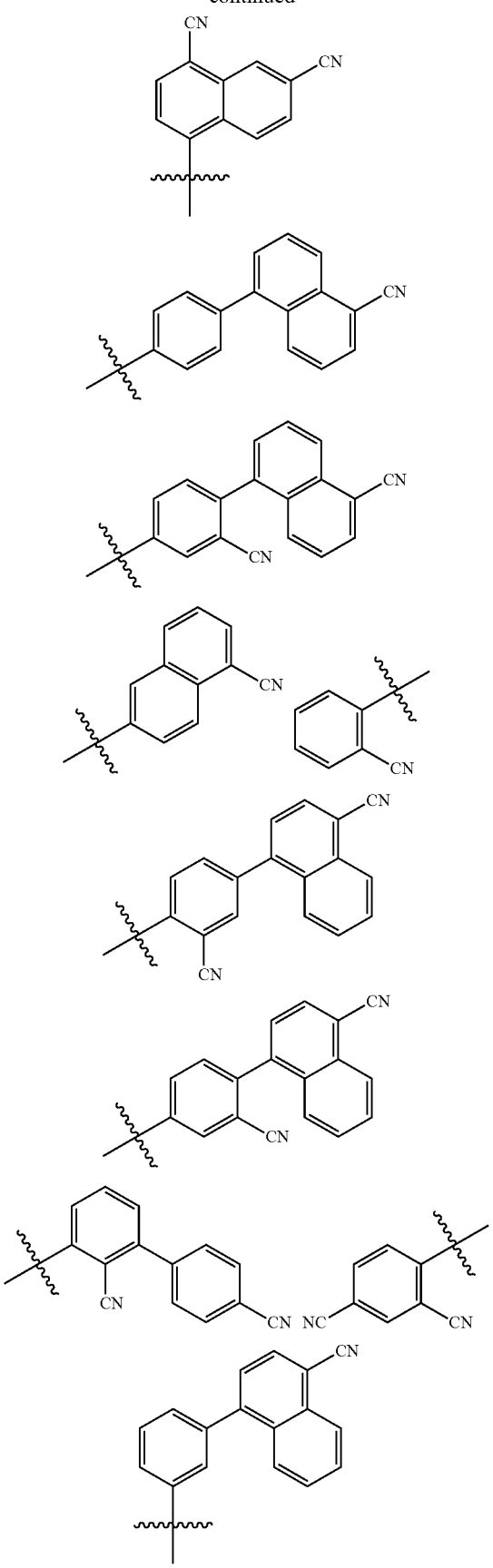
292
-continued
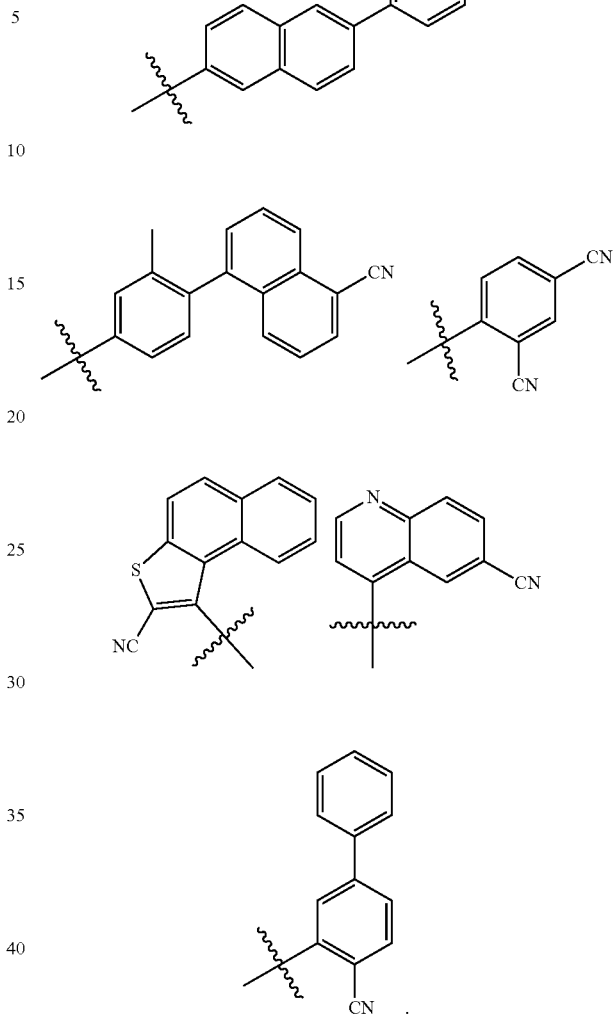
8. The organic compound according to claim 1, wherein the Ara is selected from the following groups:
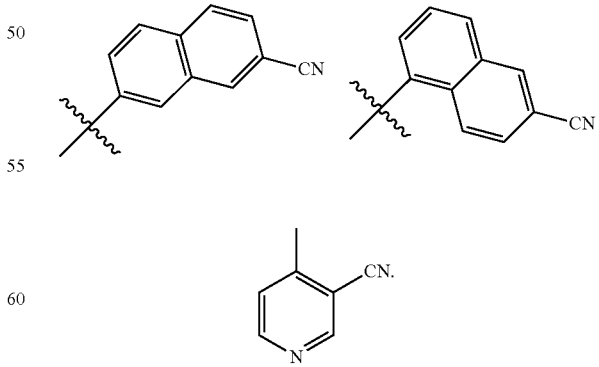
9. The organic compound according to claim 1, wherein the organic compound is selected from the group consisting of the following compounds:

293 294
1
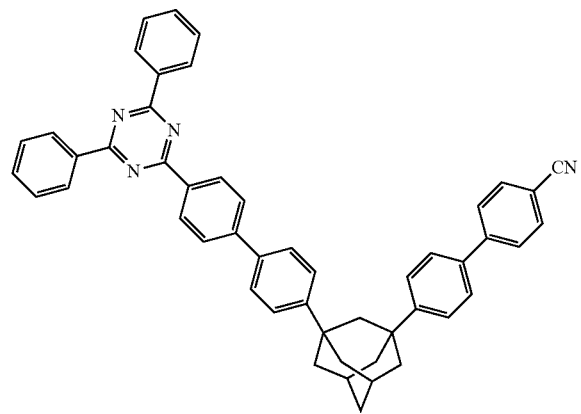
2
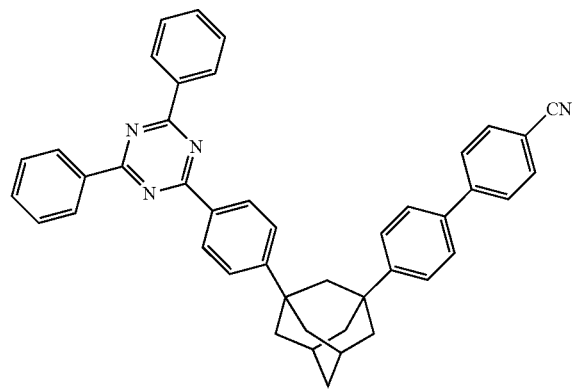
3
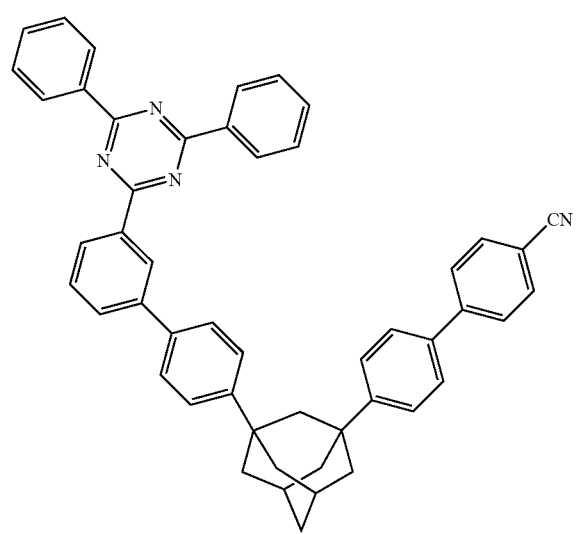
4
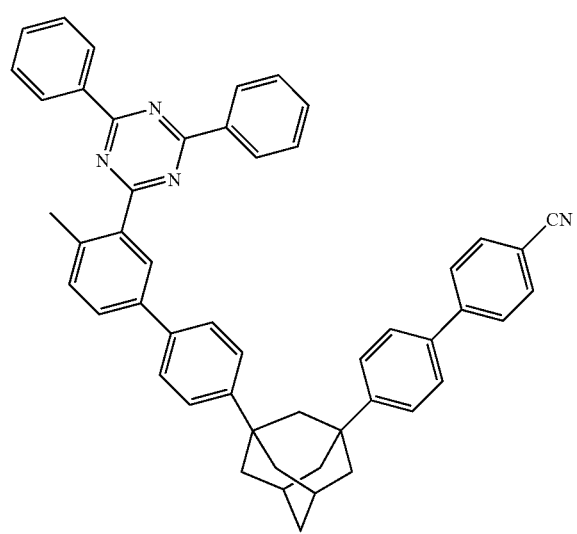
5
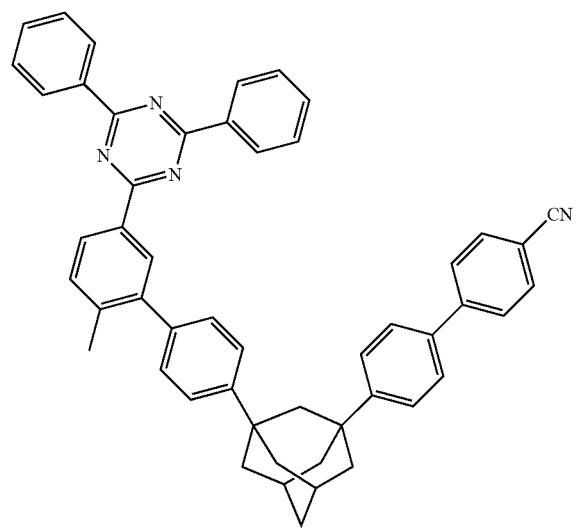
6
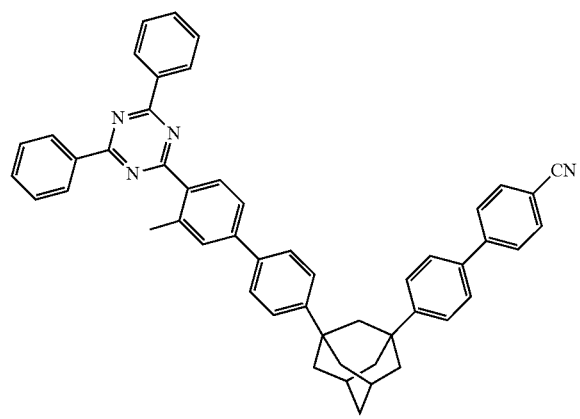

7
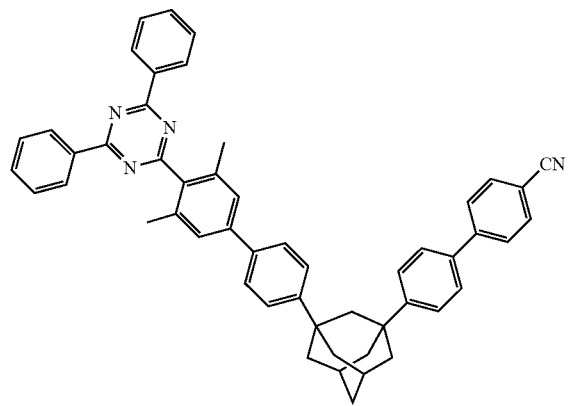
8
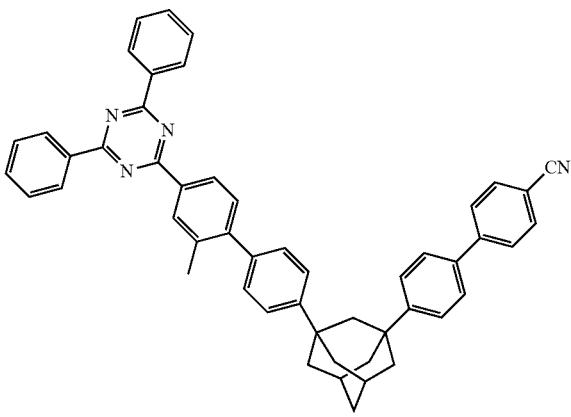
9
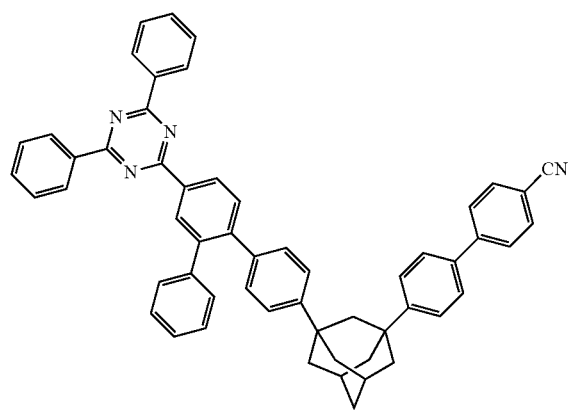
10
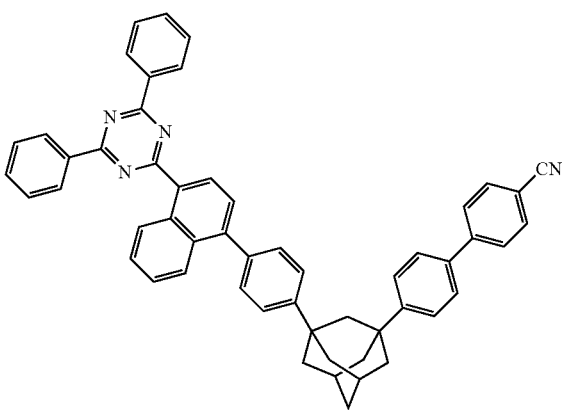
11
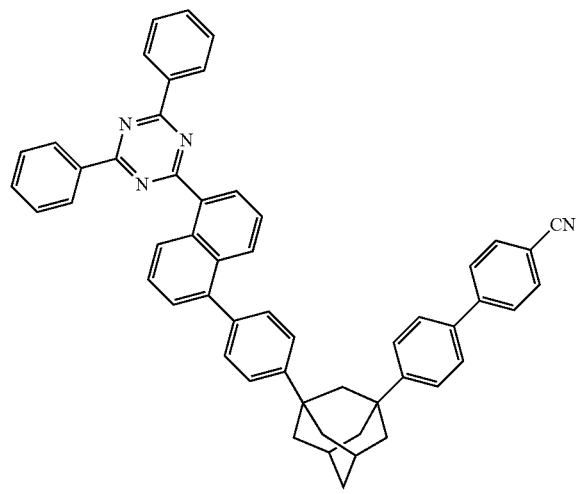
12
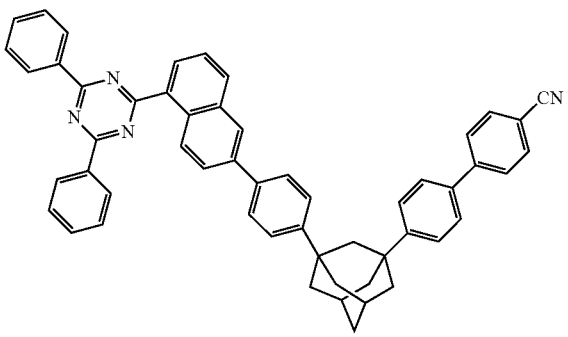

-continued
13
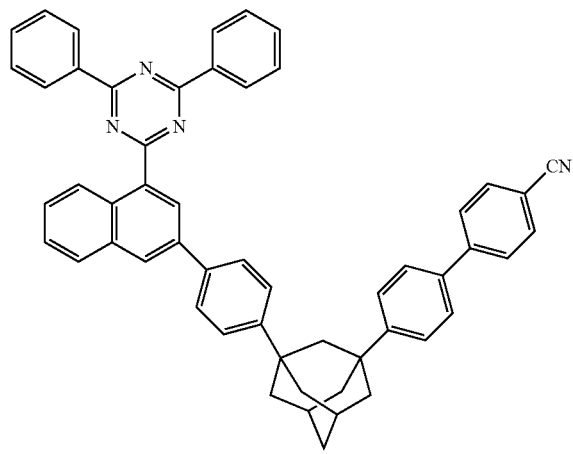
14
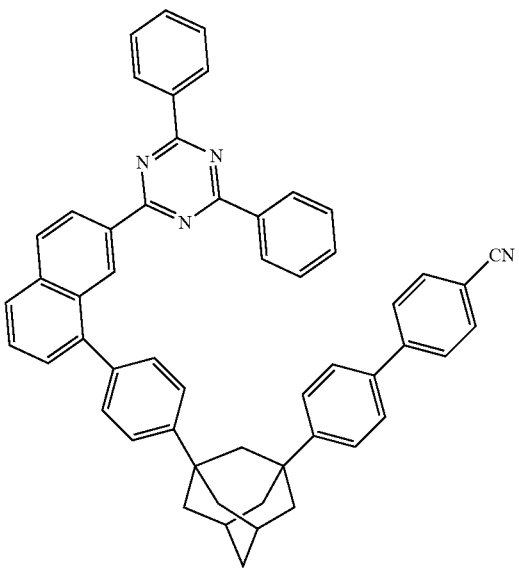
15
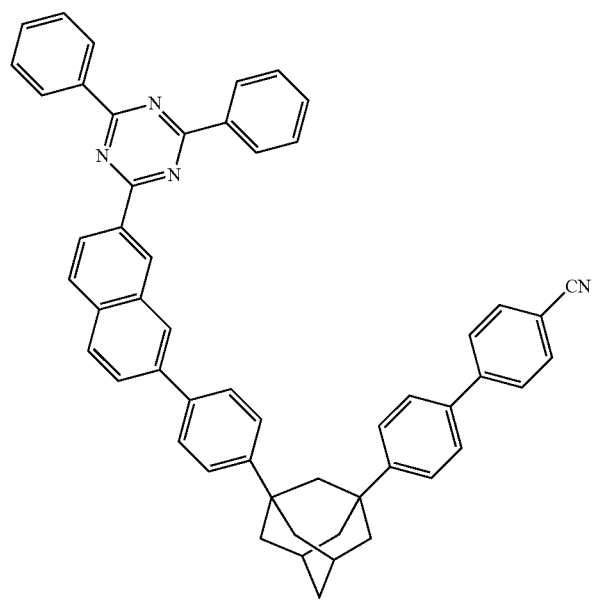
16
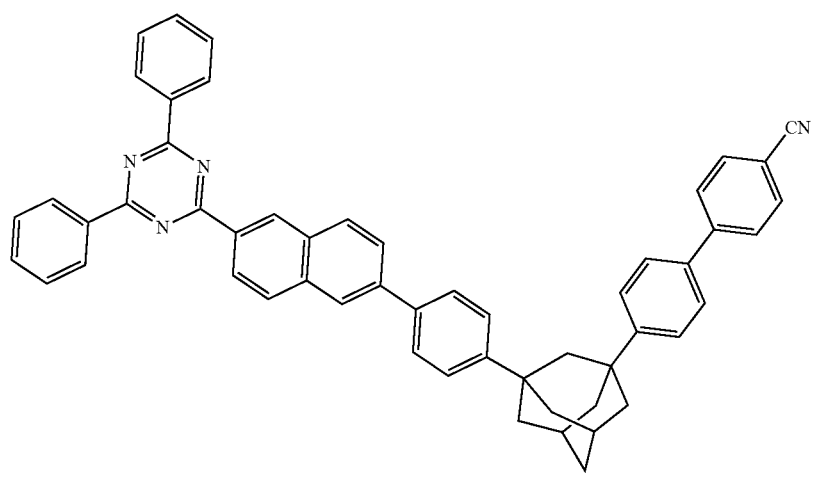

-continued
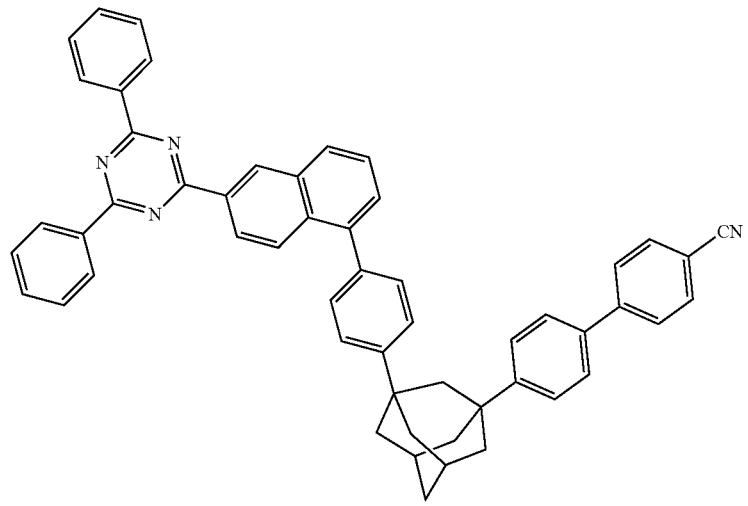
17
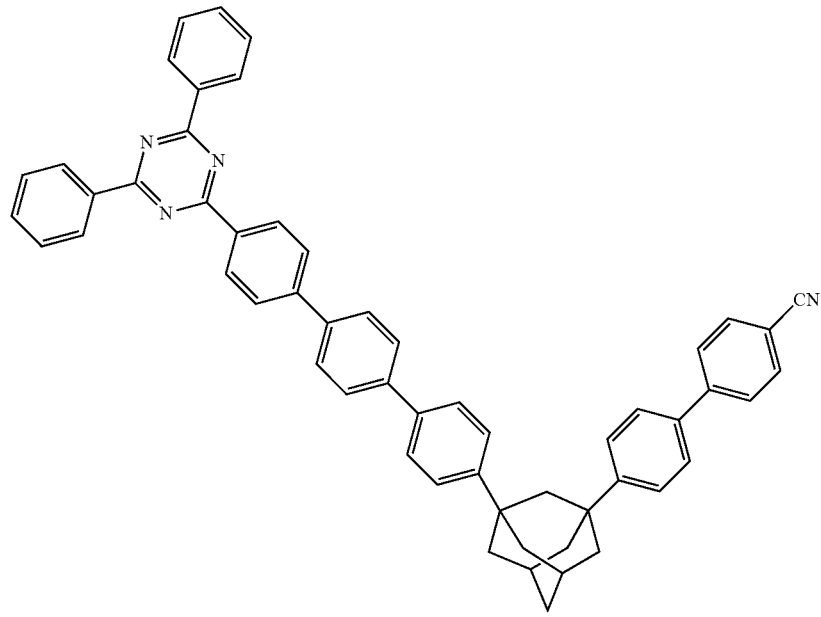
18
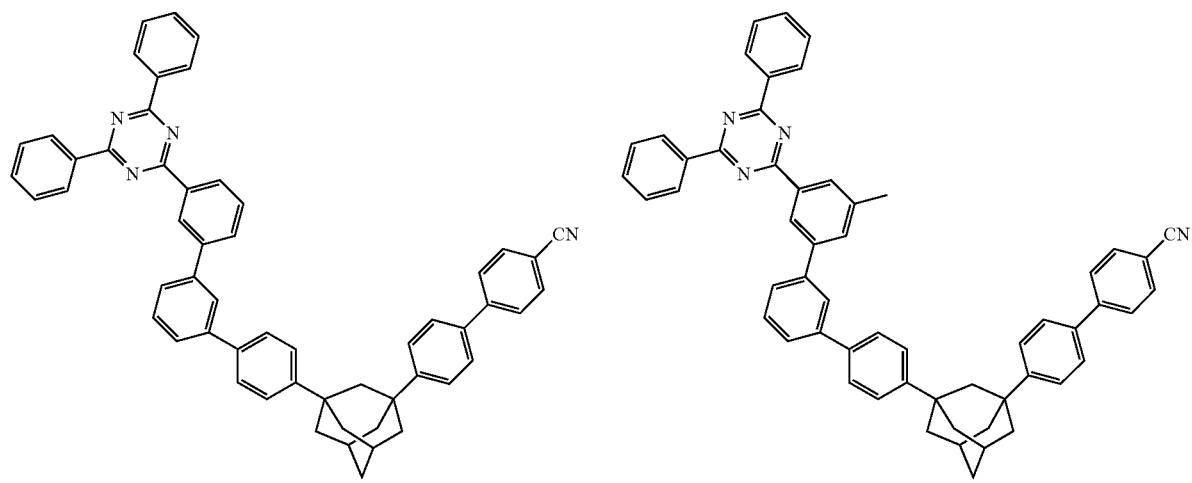
19
20

-continued
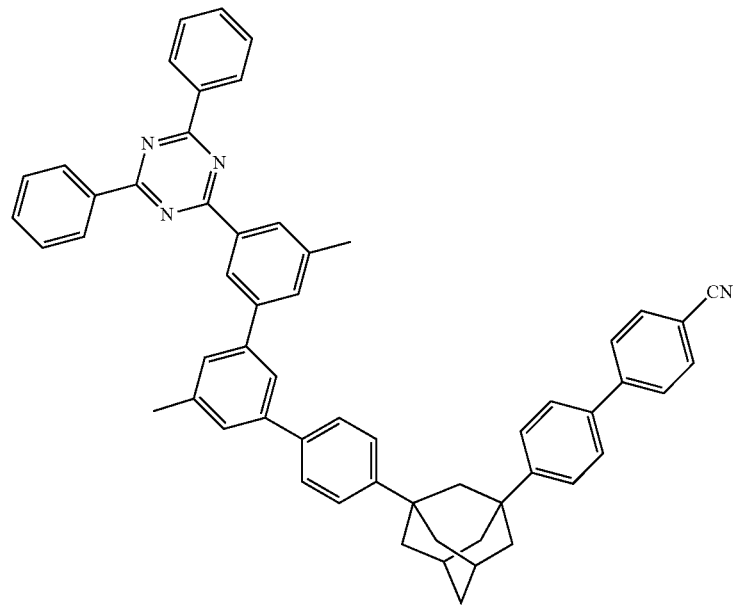
21
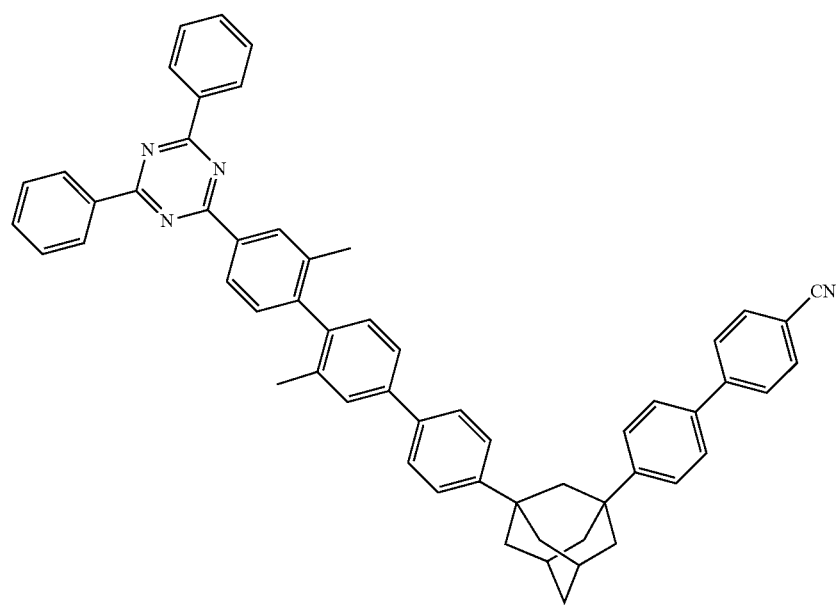
22

23
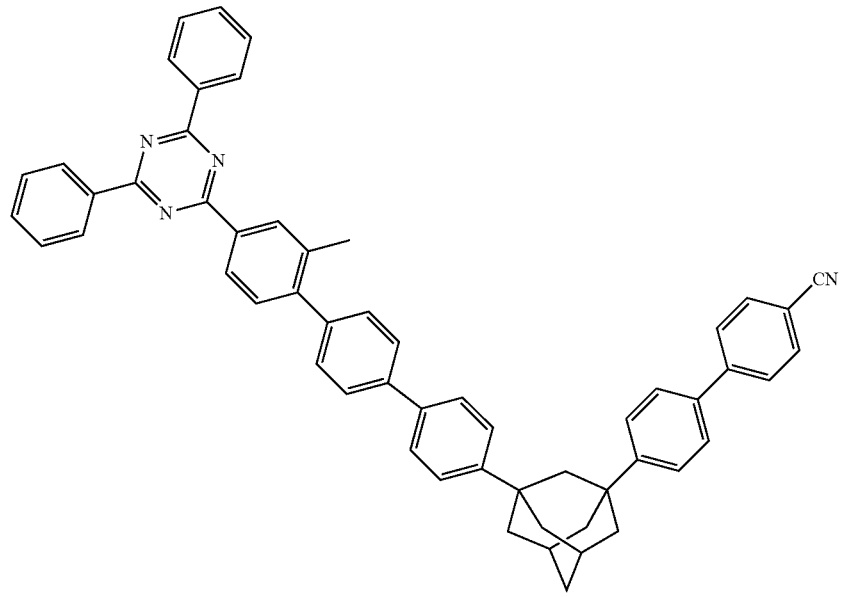
24
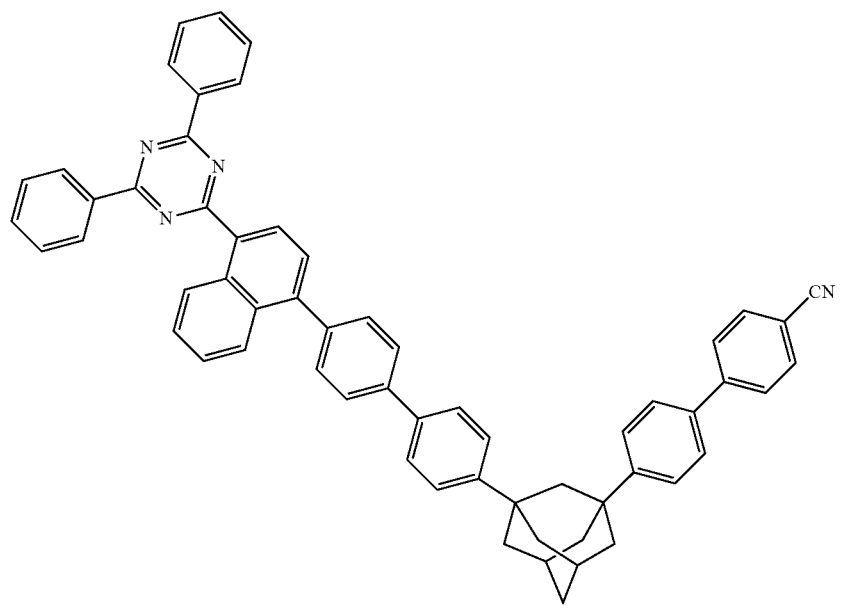

-continued
25
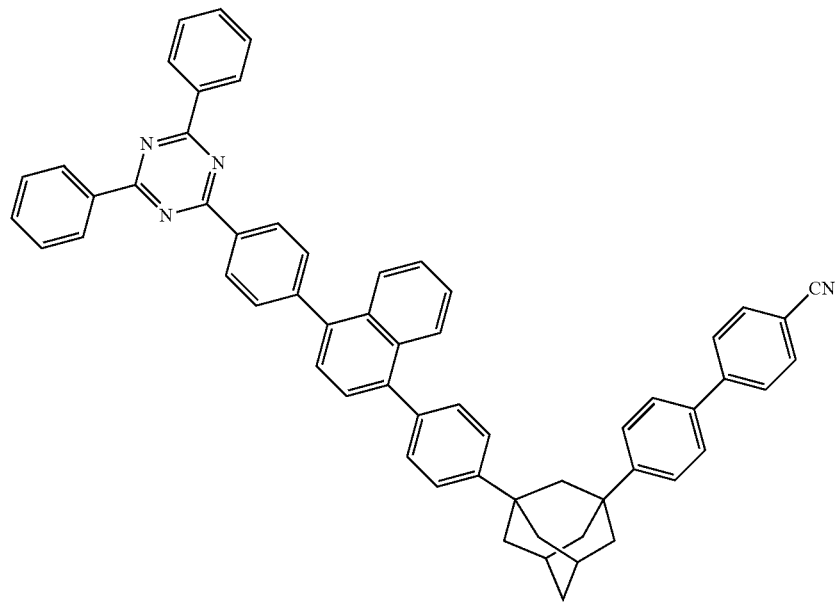
26
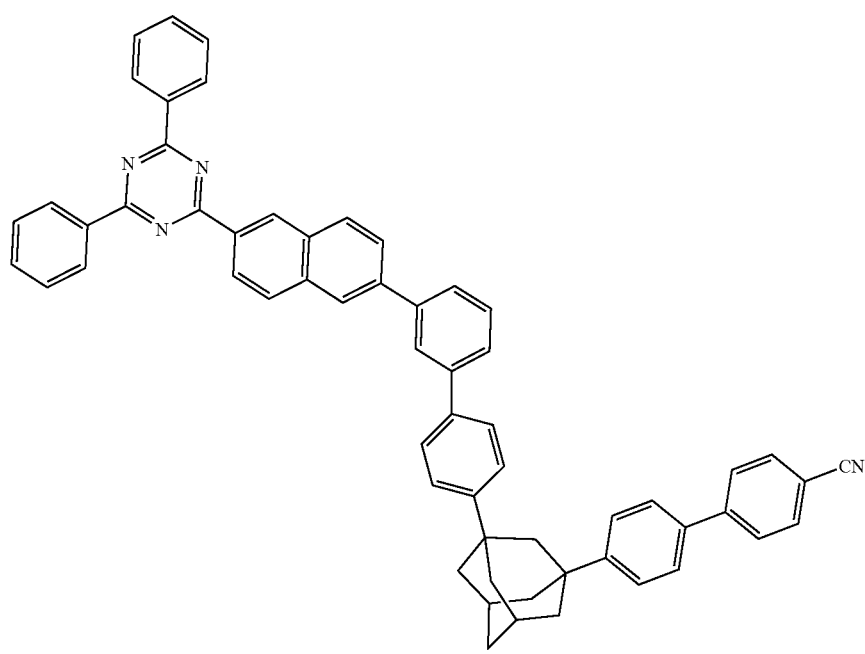

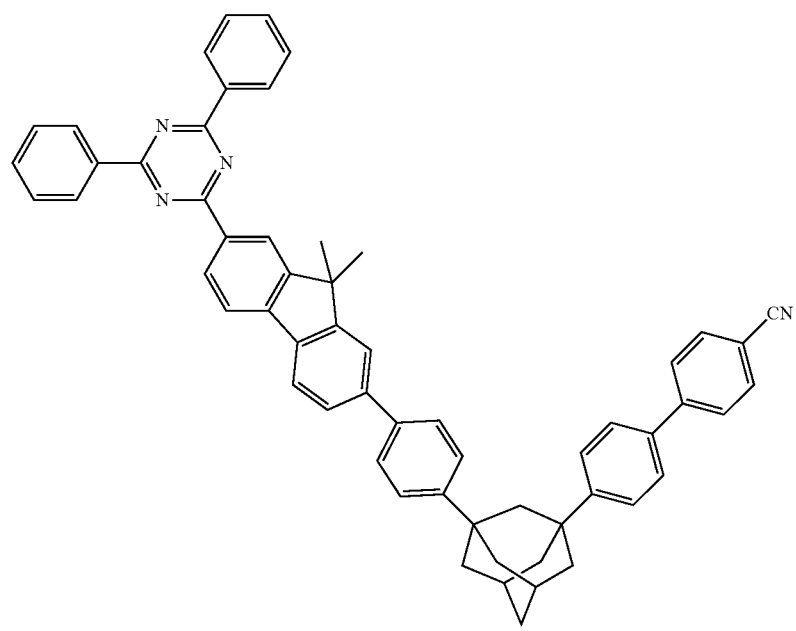
27
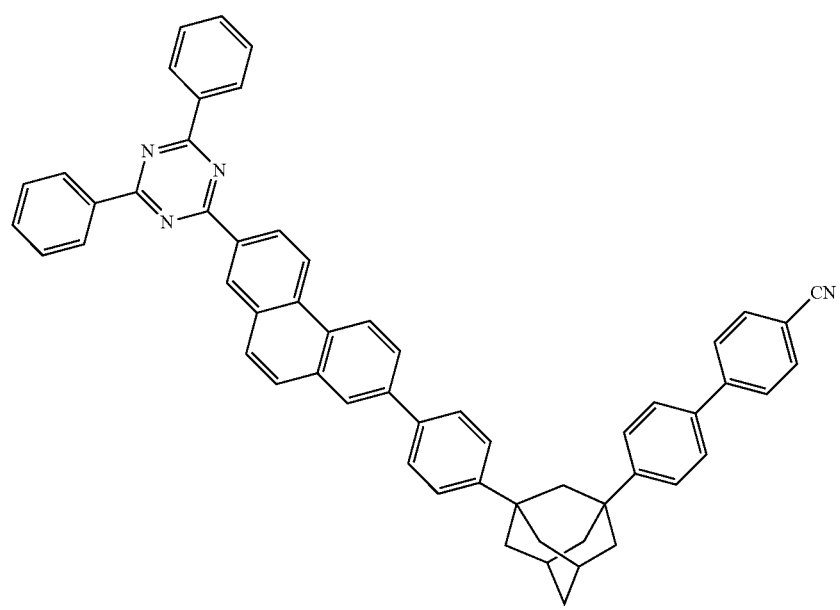
33

-continued
34
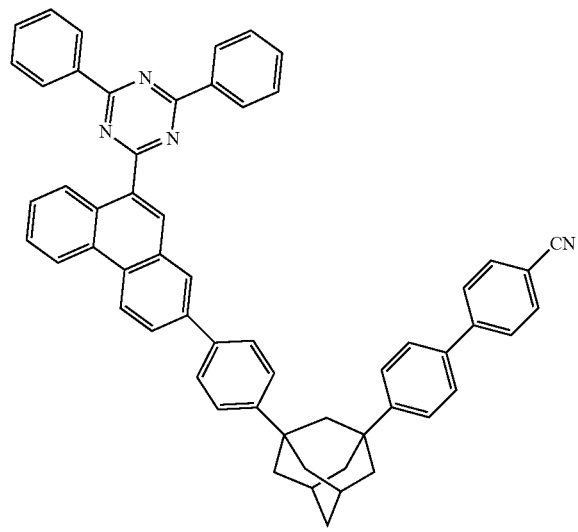
35
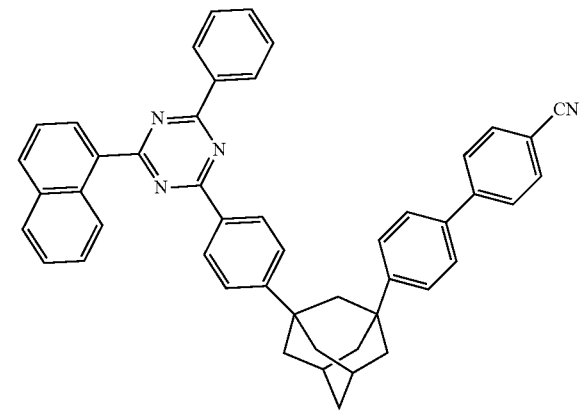
36
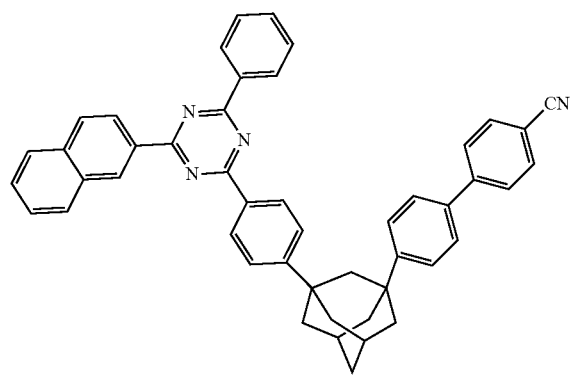
37
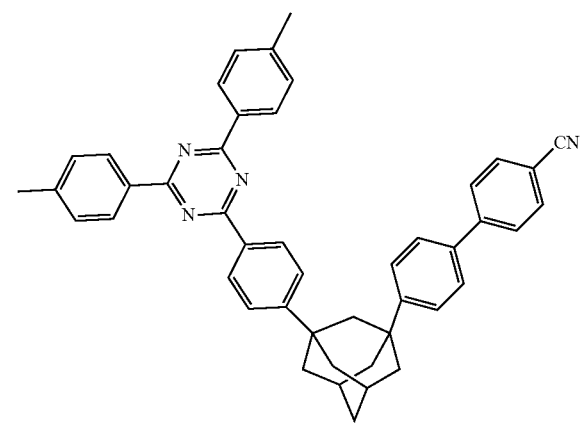
38
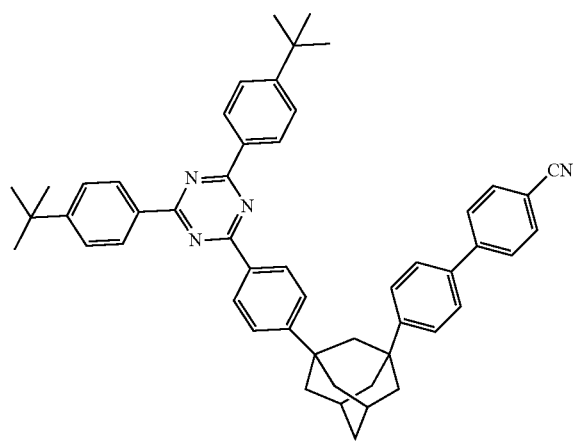
39
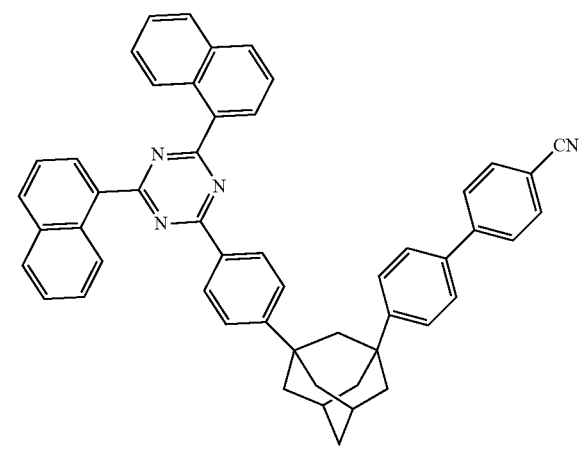

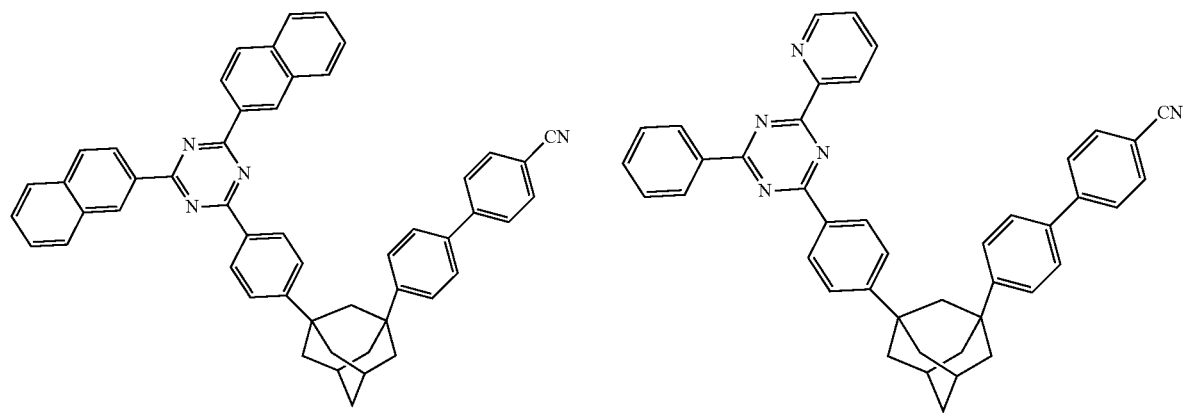
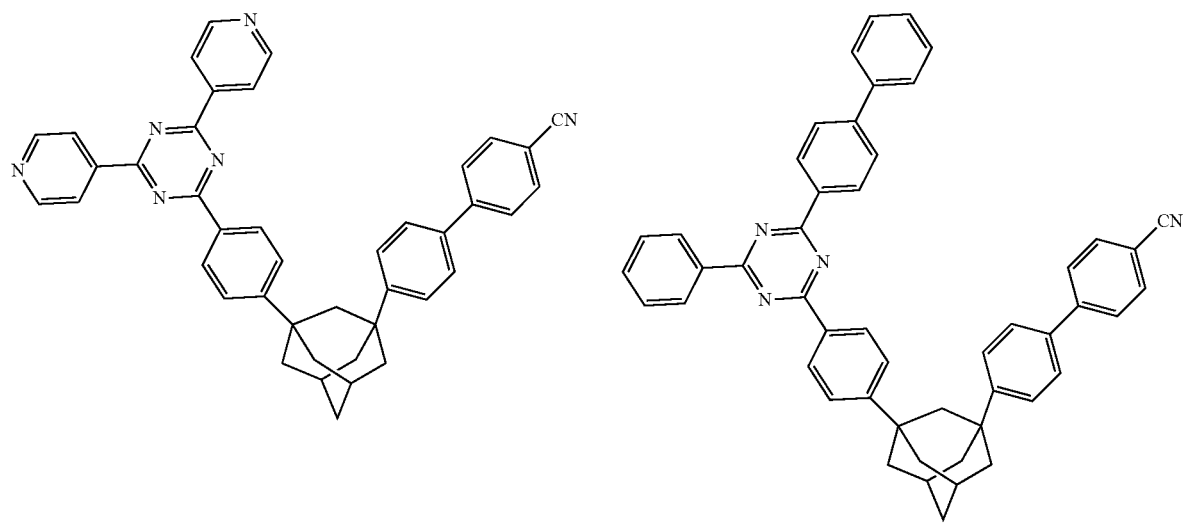
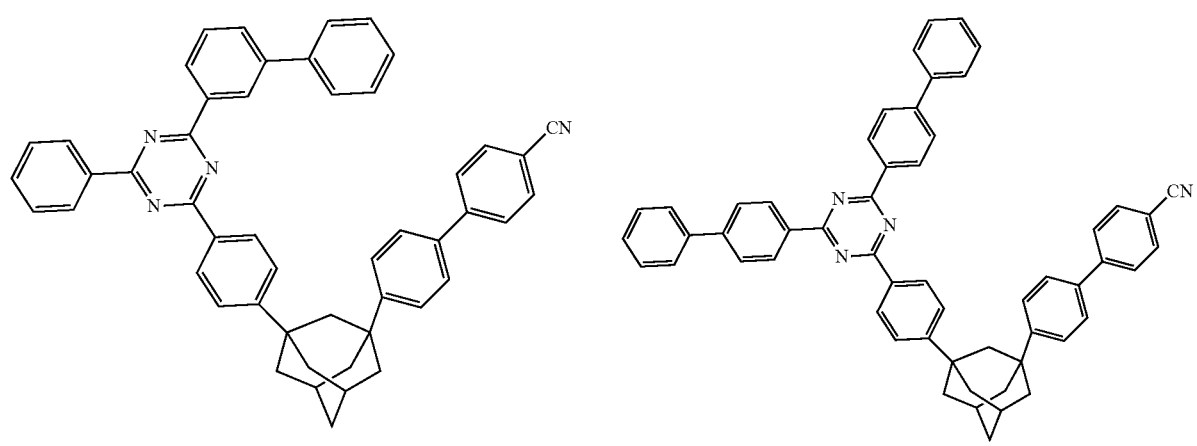

-continued
46
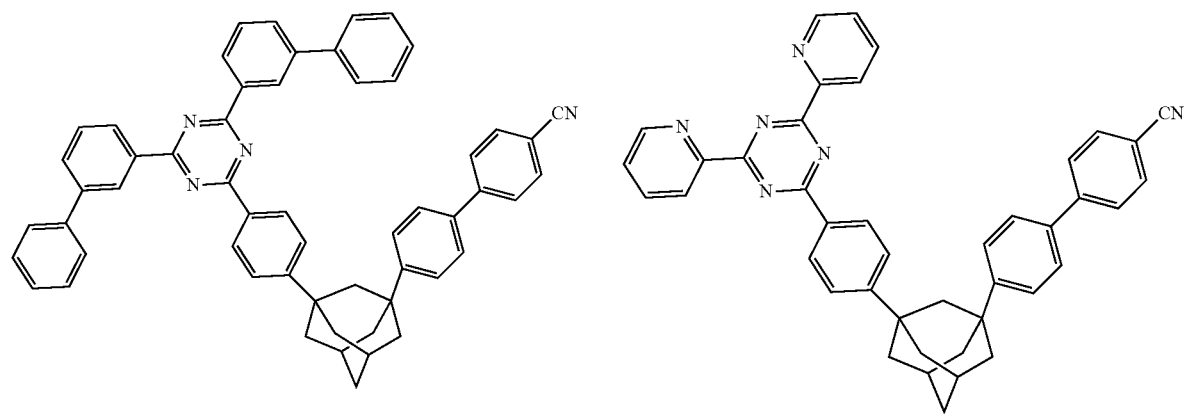
48
49
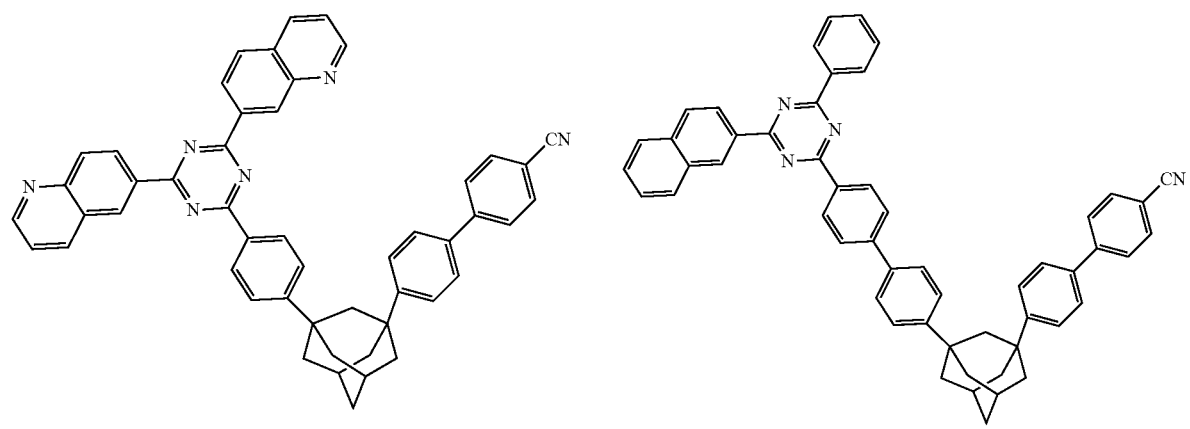
50
51
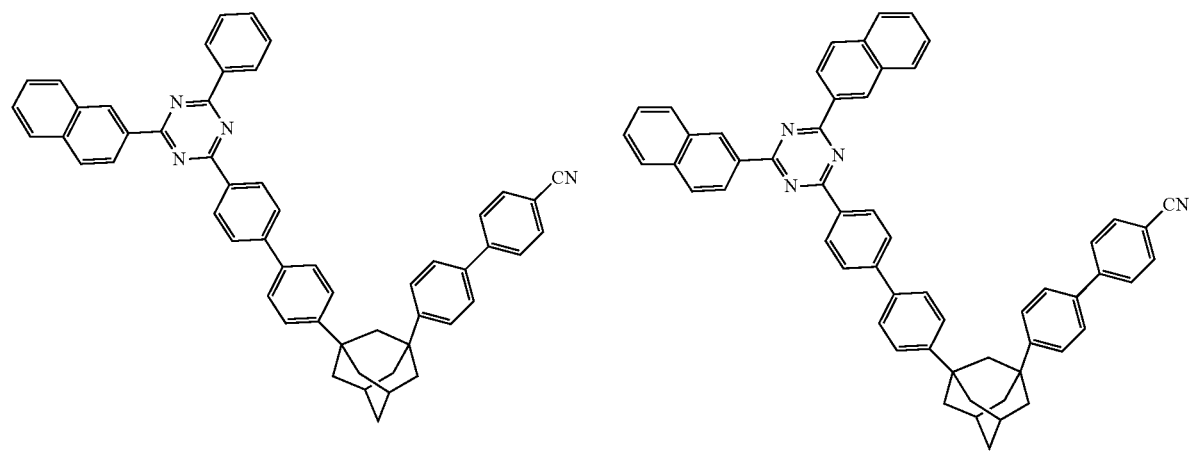
52

53
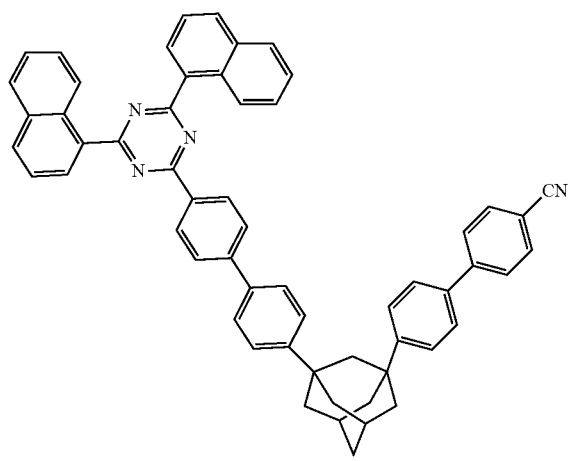
54
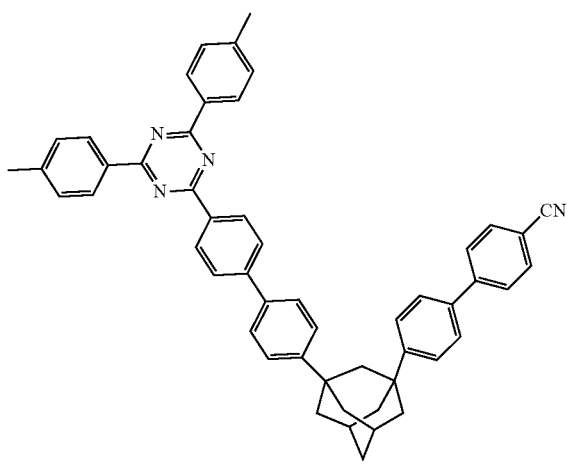
55
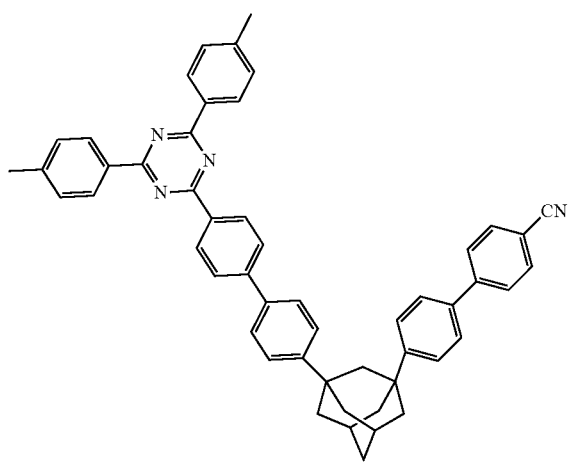
56
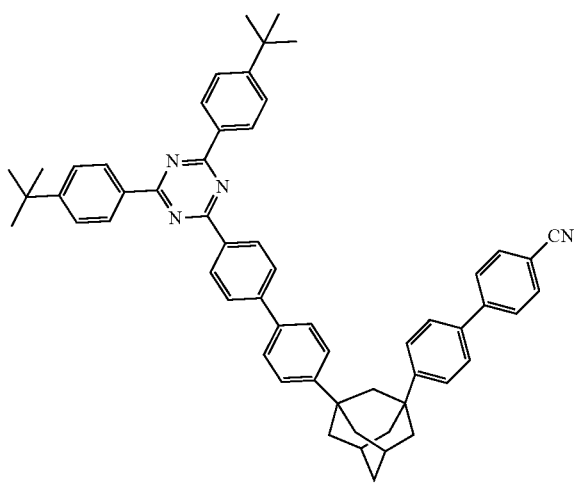
57
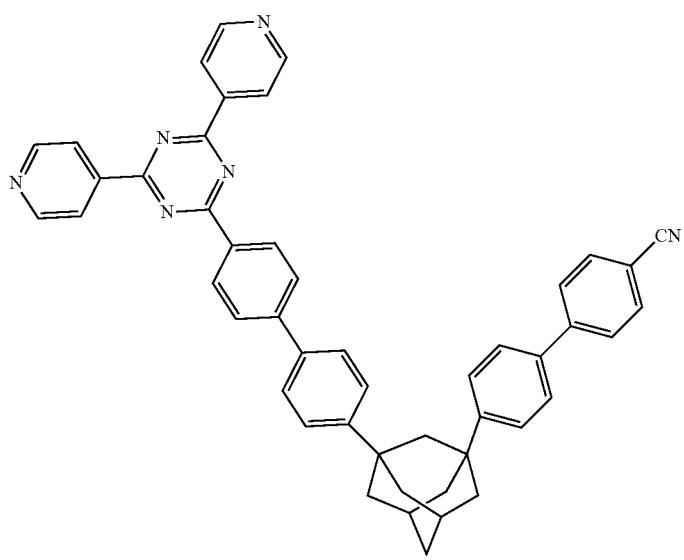

58
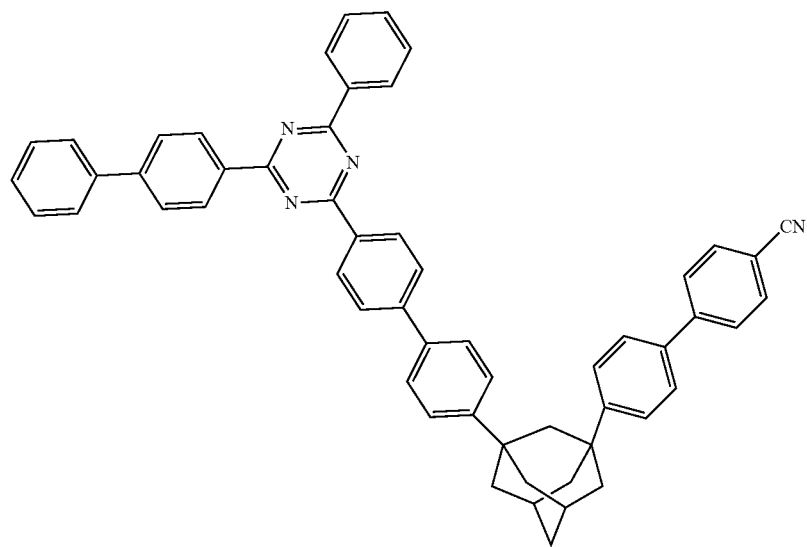
59
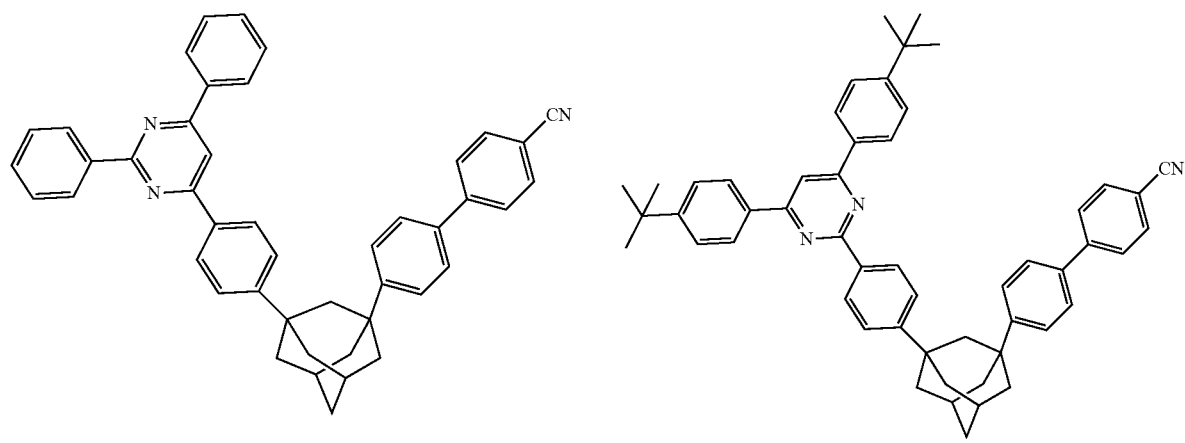
60
61
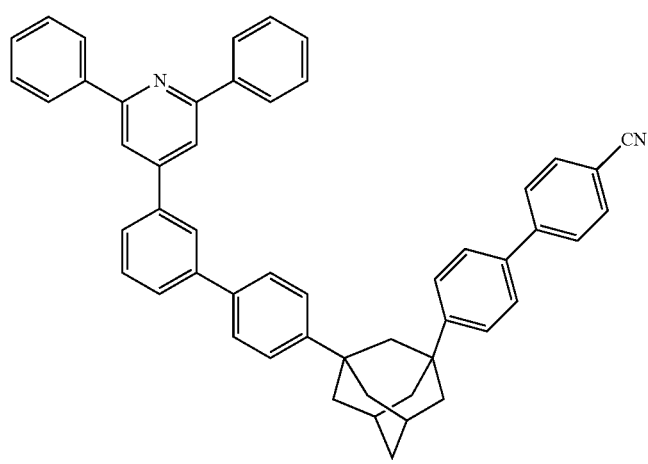

62
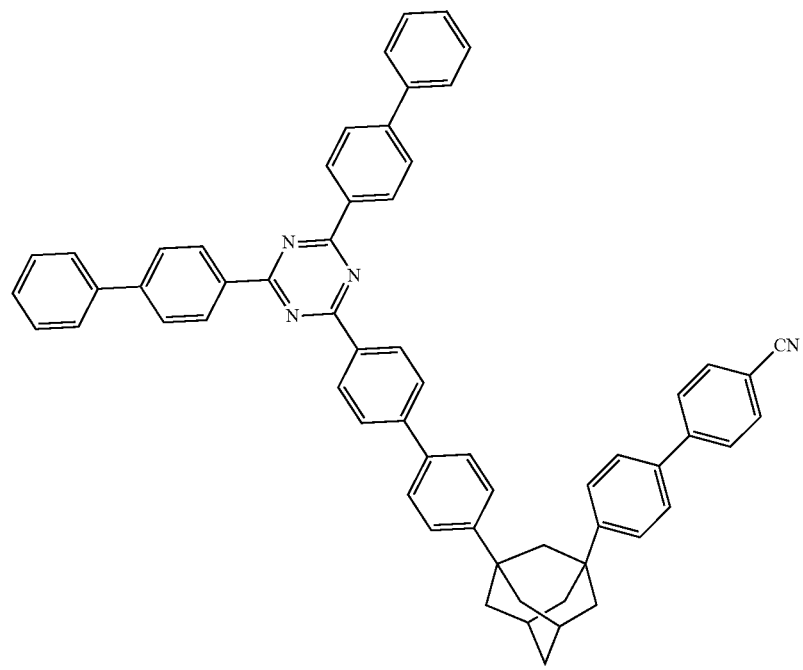
63
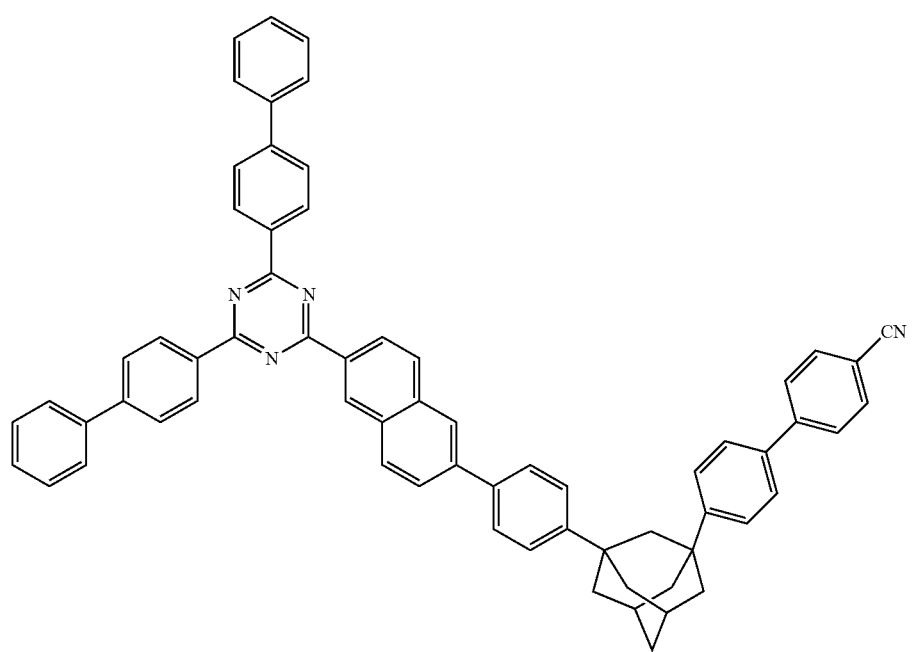

321 322
64
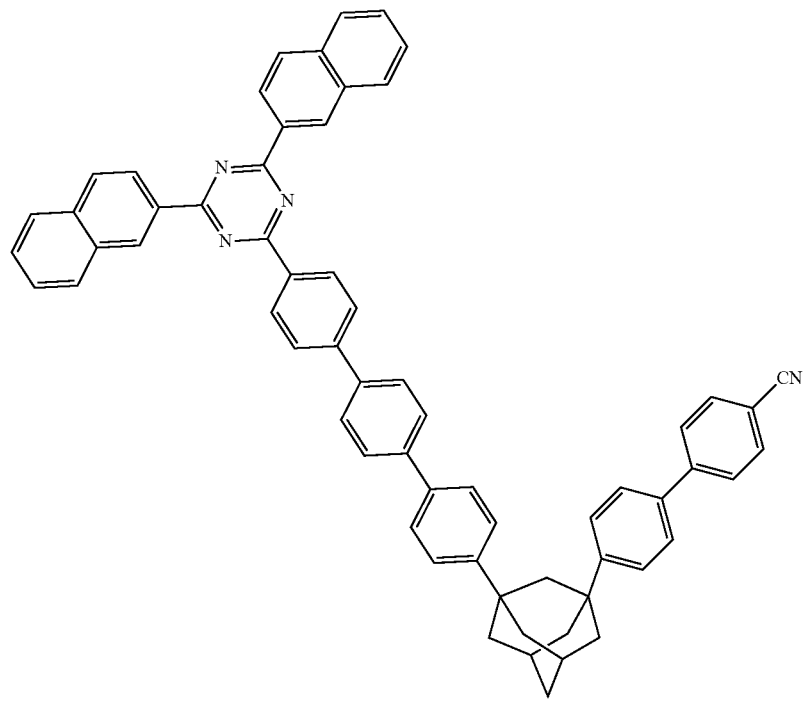
65 66
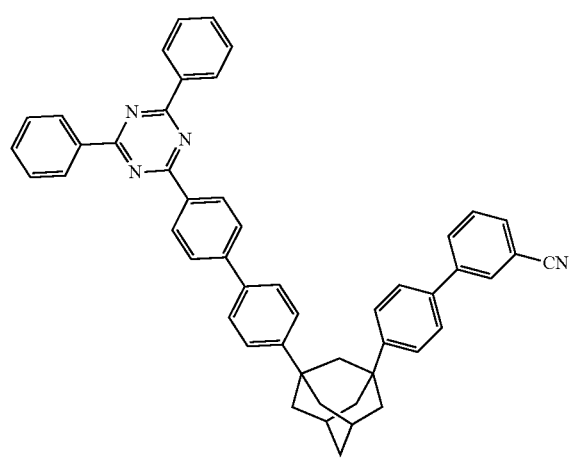 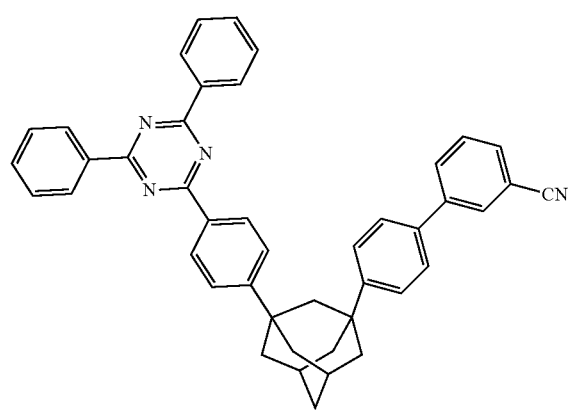

67
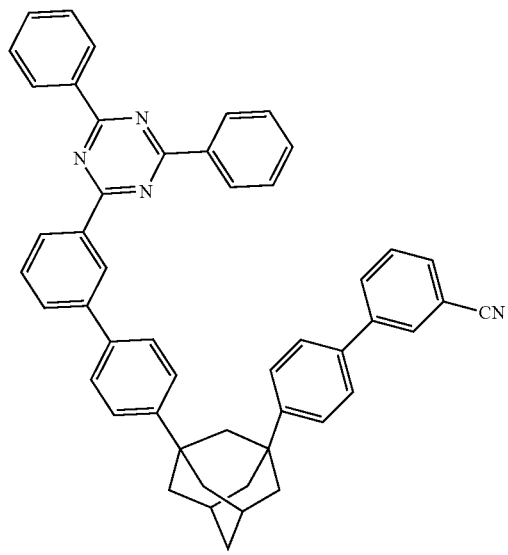
68
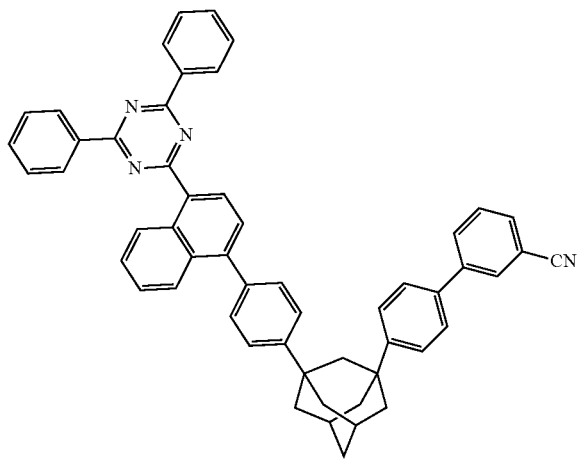
69
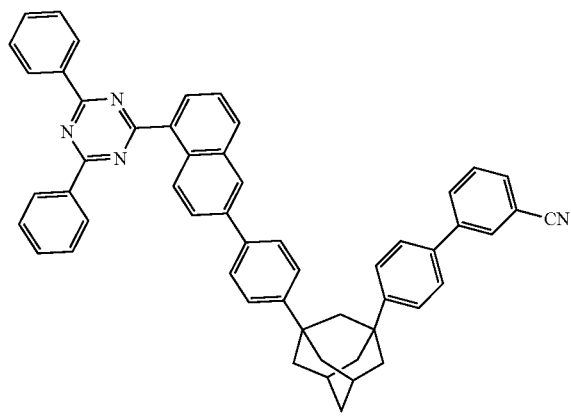
70
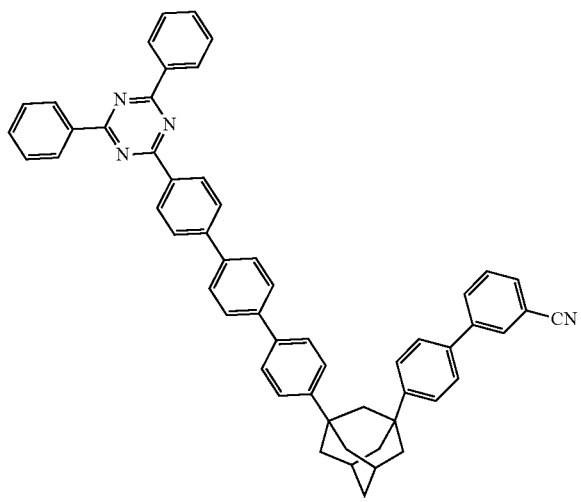
76
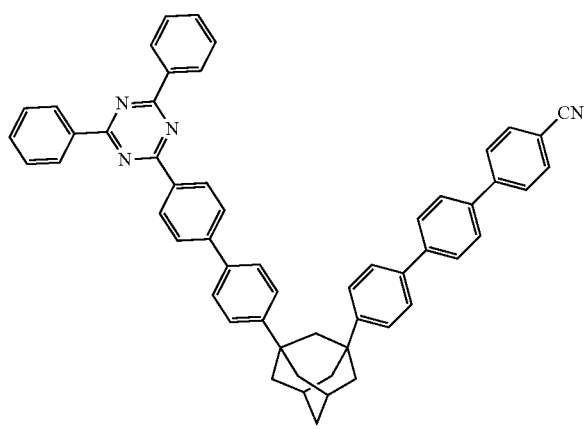
77
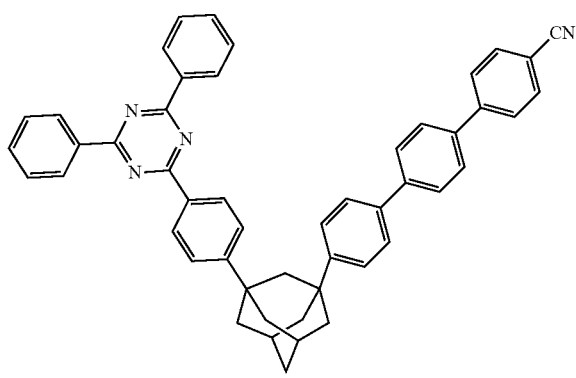

78
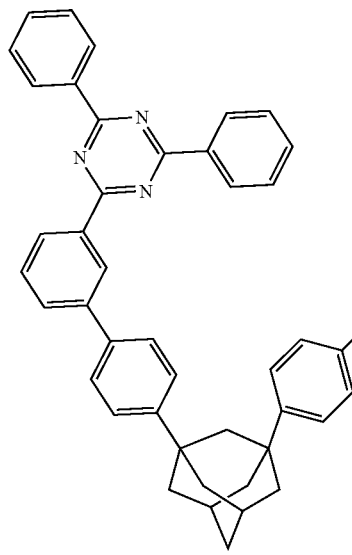
79
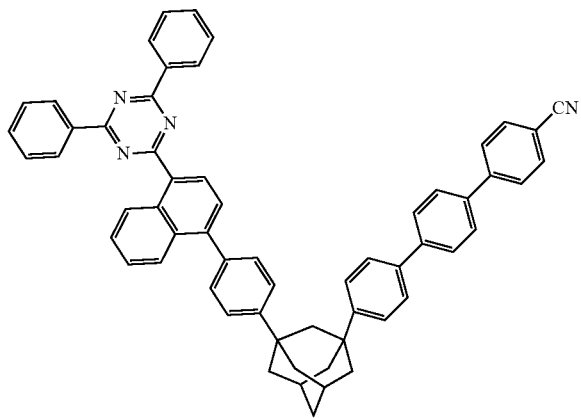
80
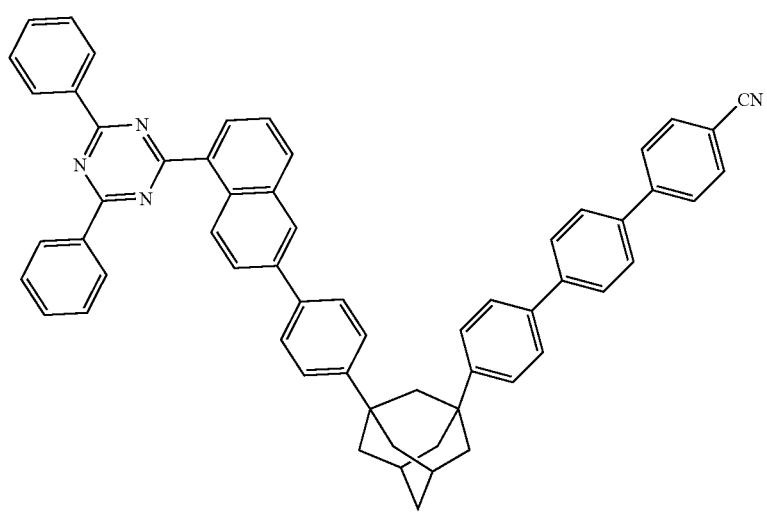

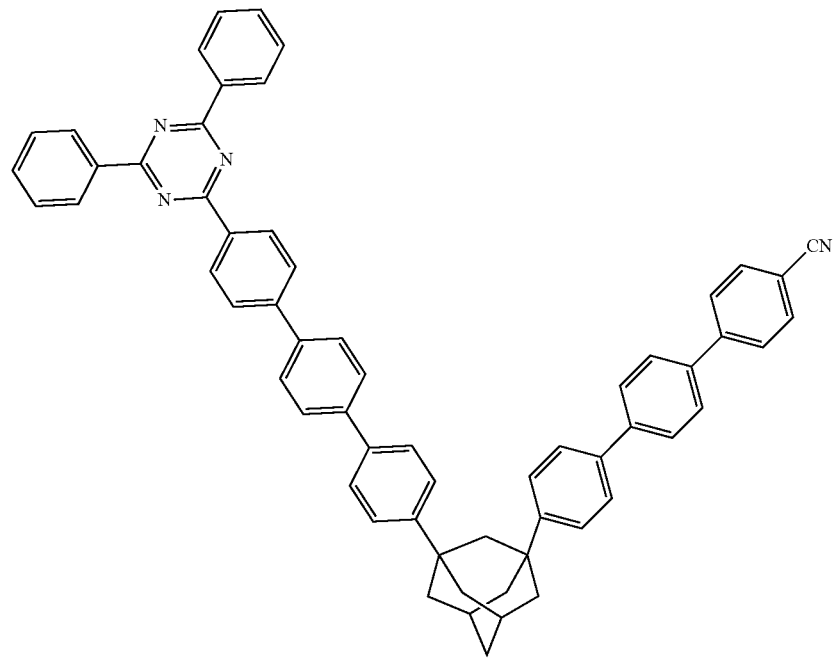
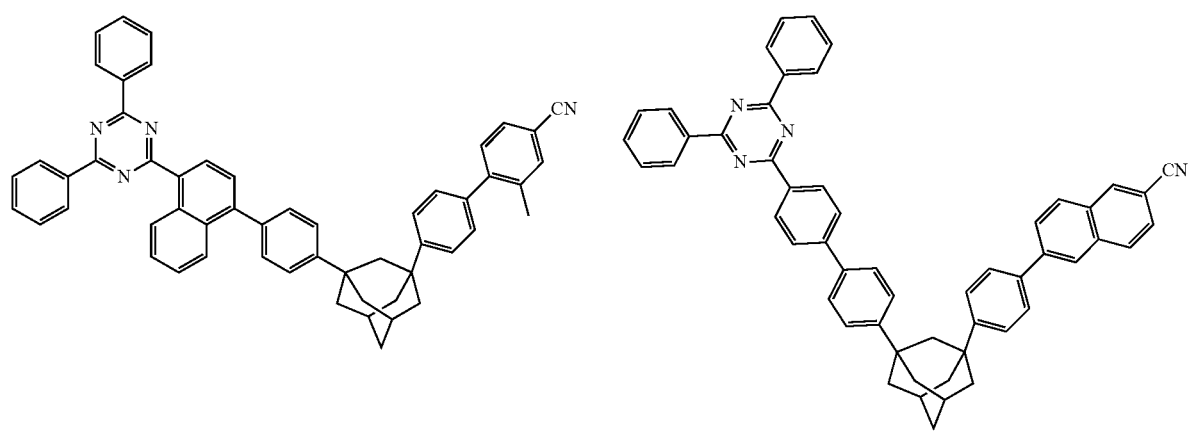

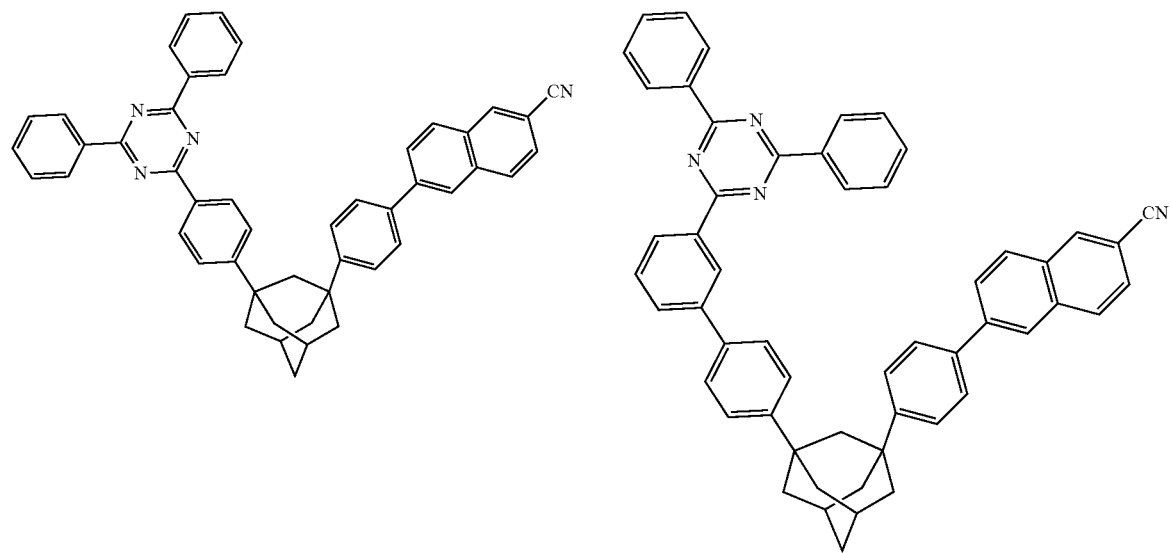
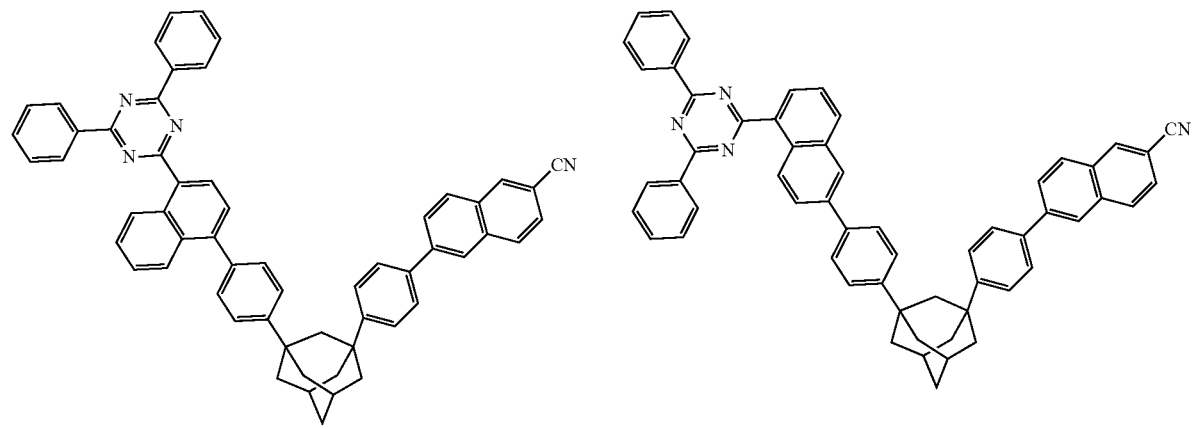

90
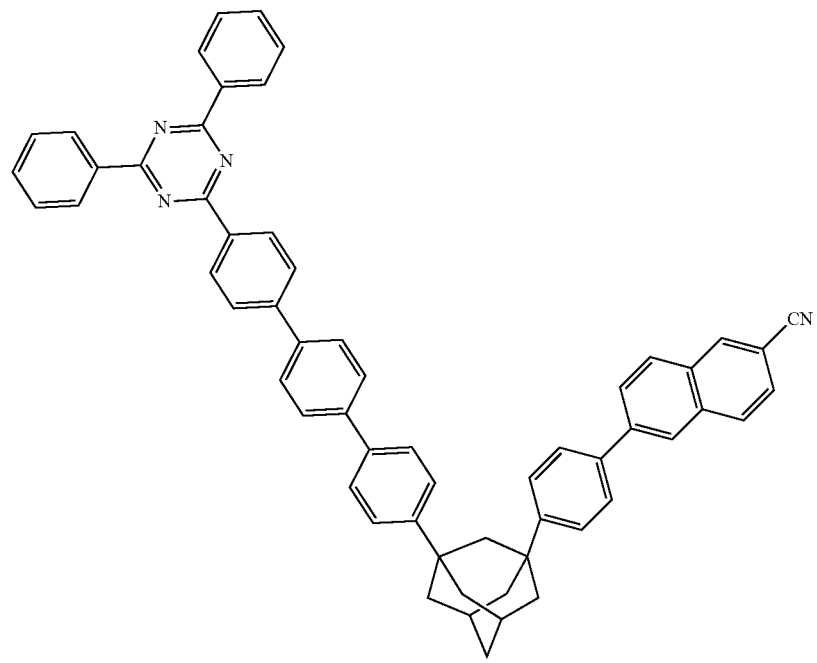
93
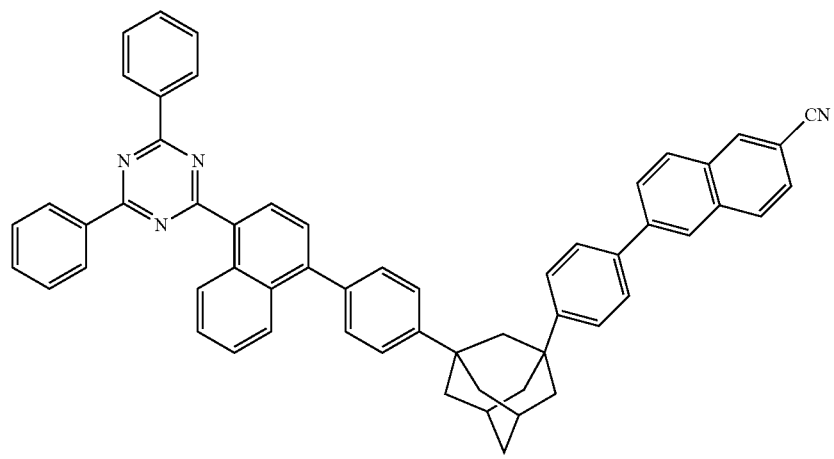
94 95
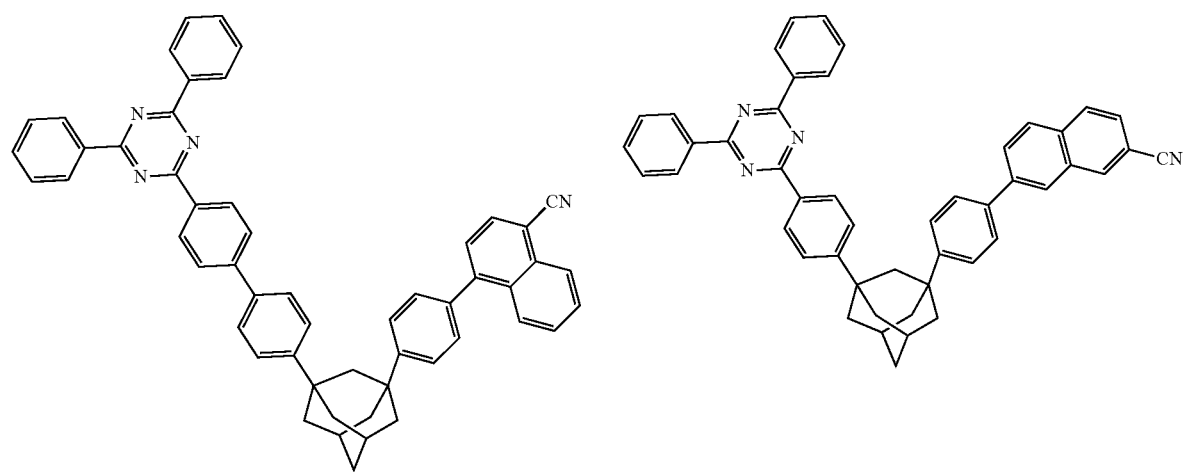

96
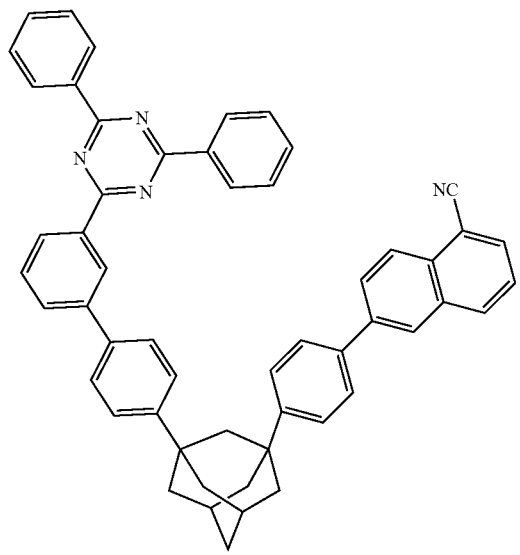
97
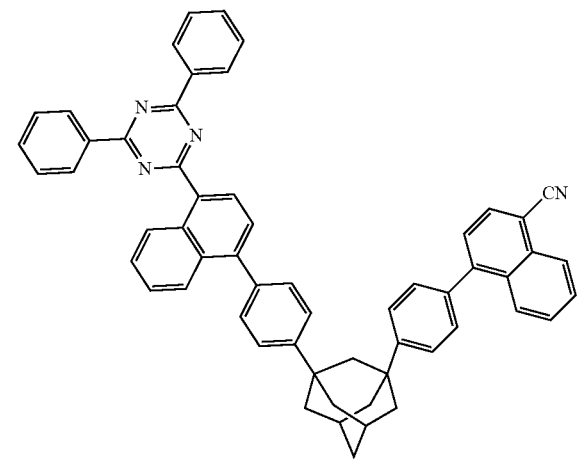
98
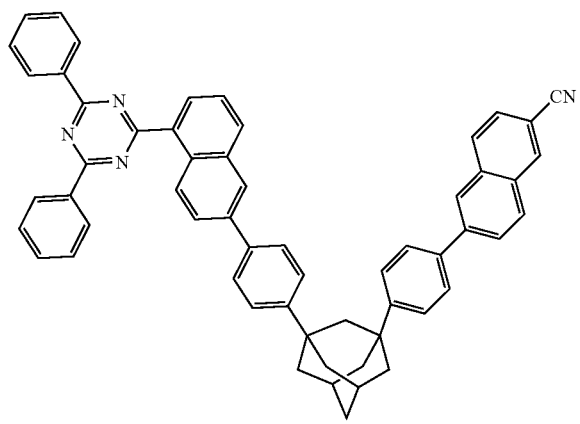
99
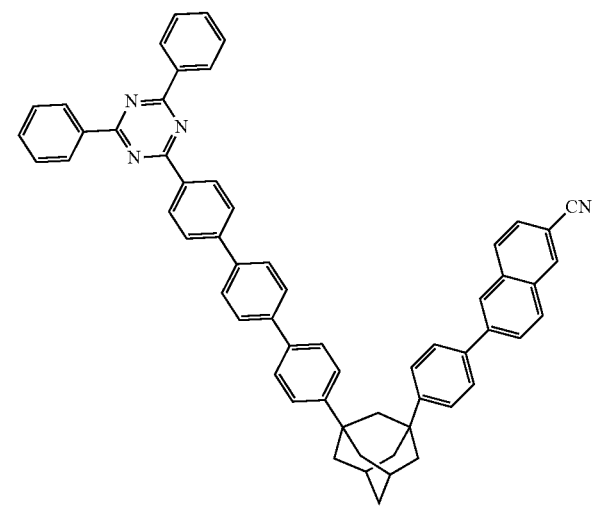
102
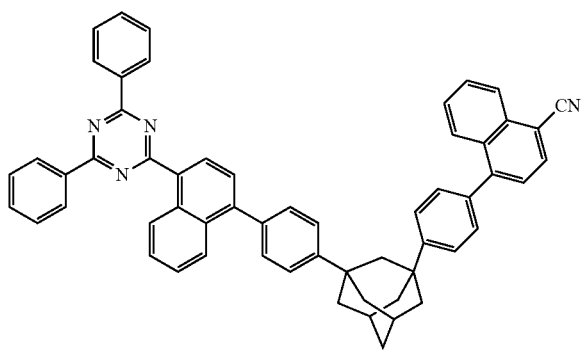
103
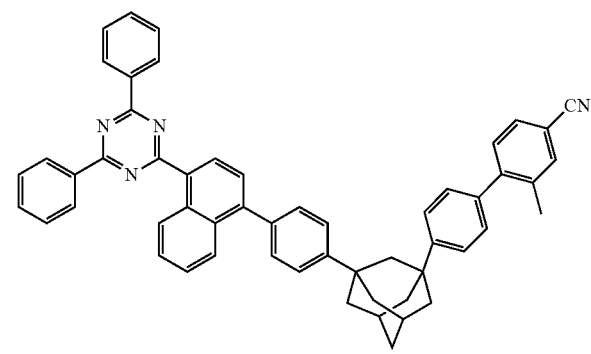

104
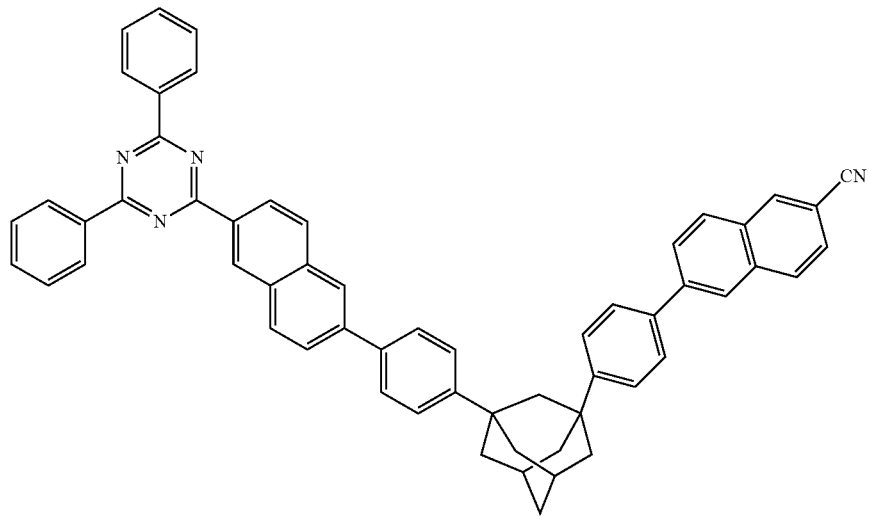
105
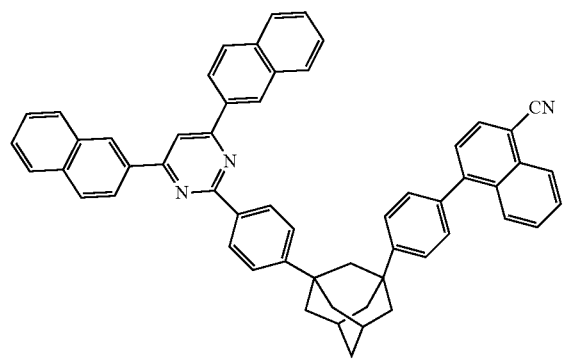
106
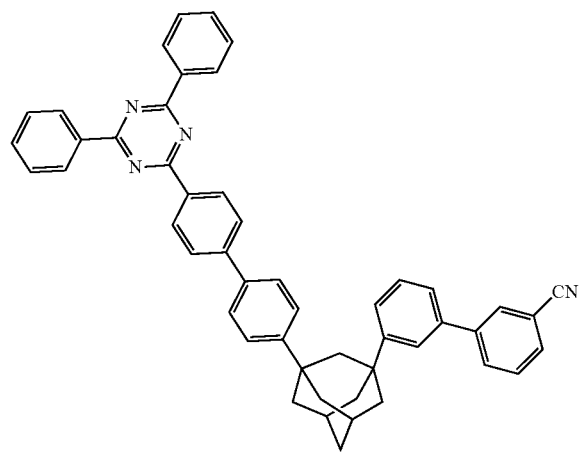
107
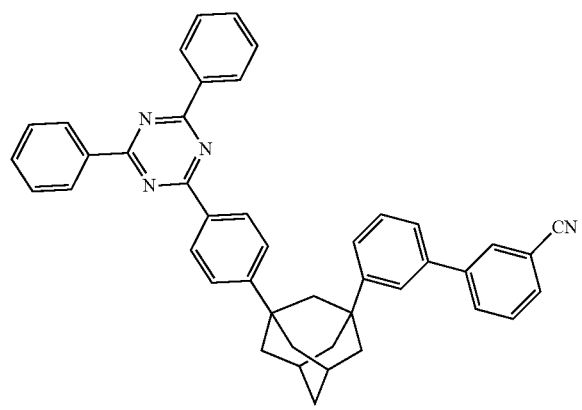
108
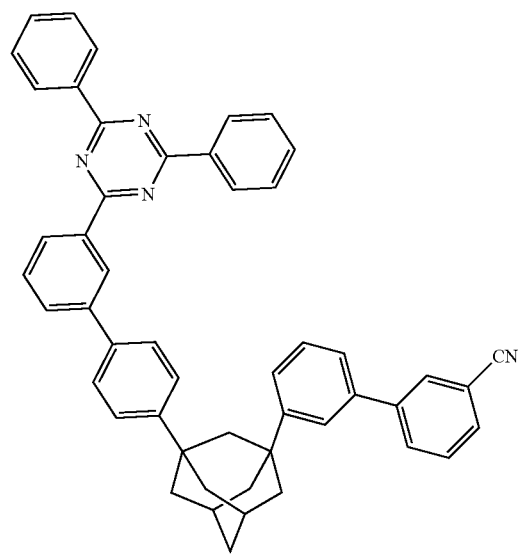

-continued
109
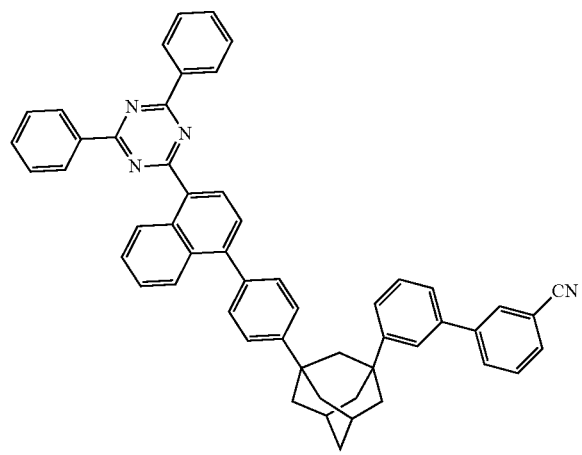
110
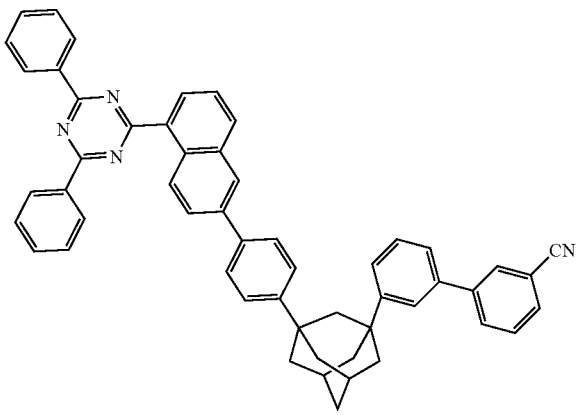
111
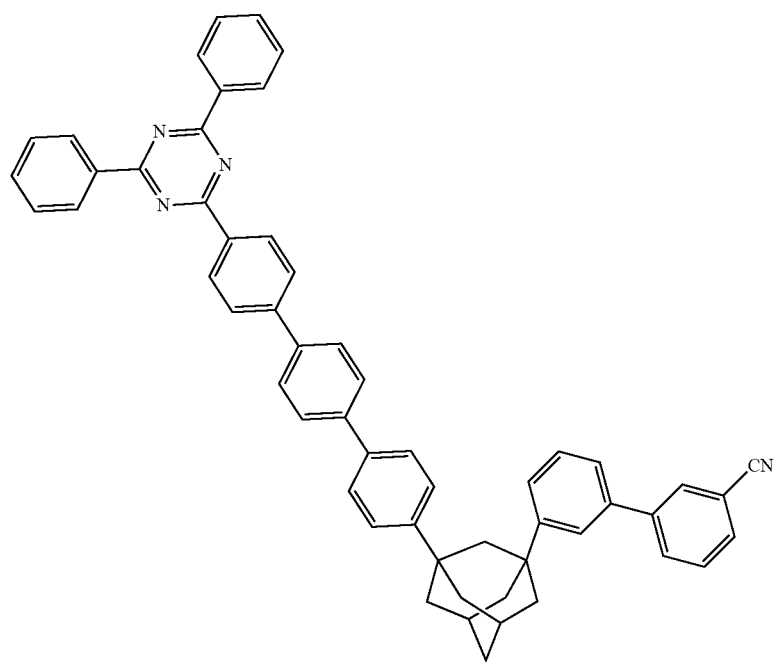
117
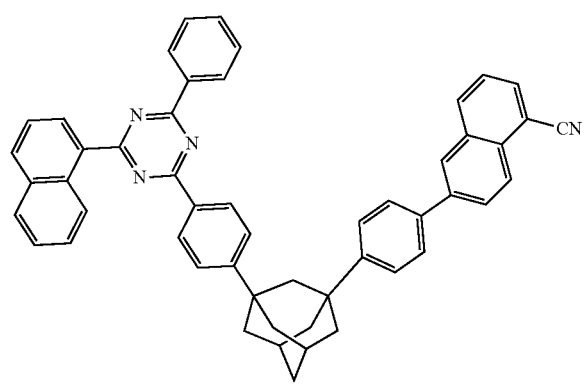
118
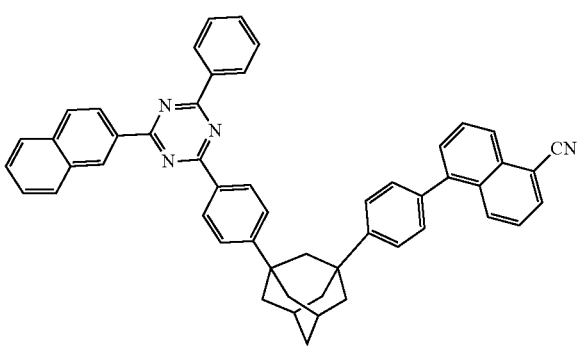

-continued
119
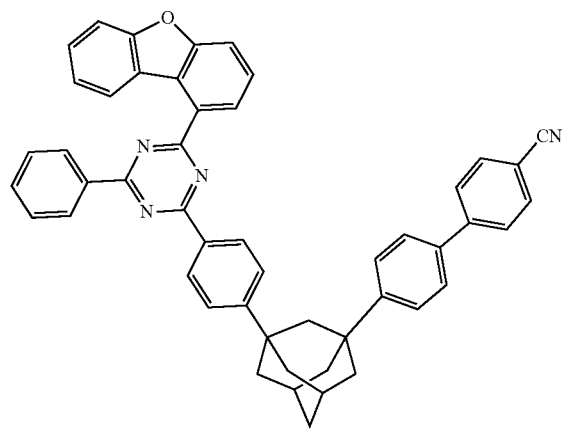
120
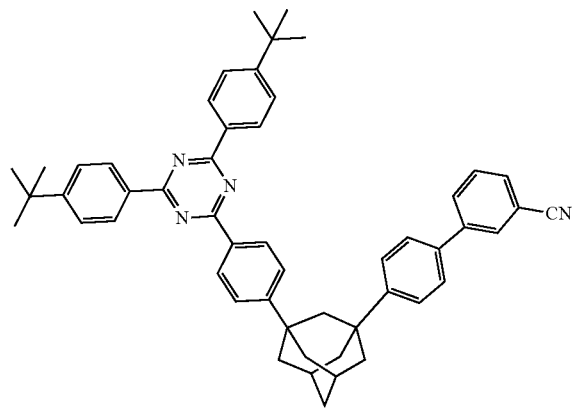
121
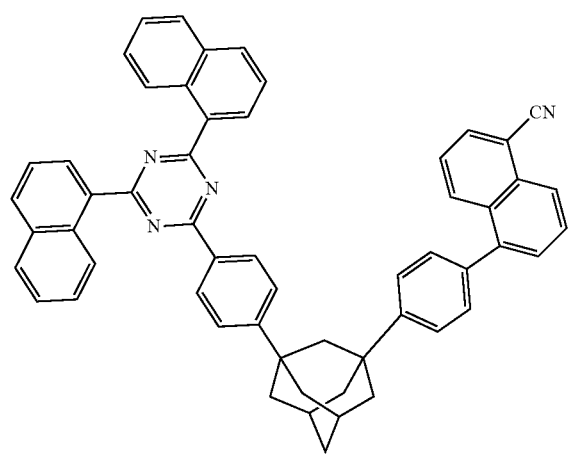
122
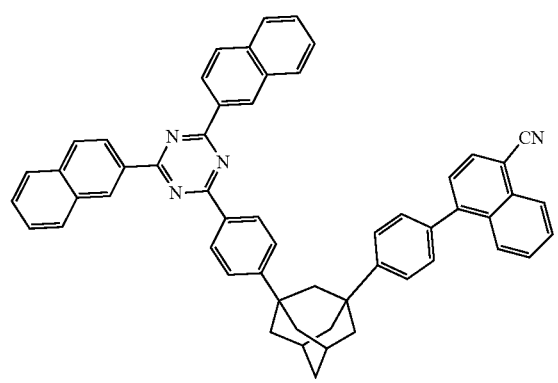
123
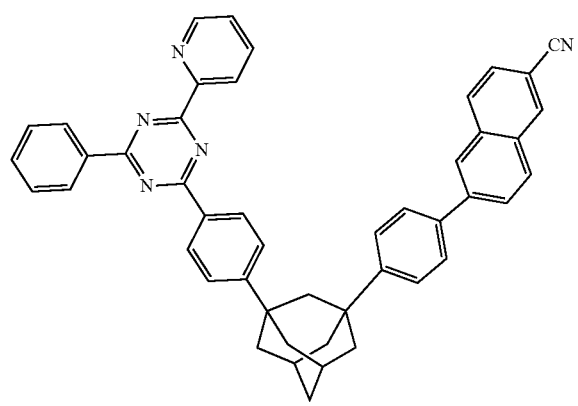
124
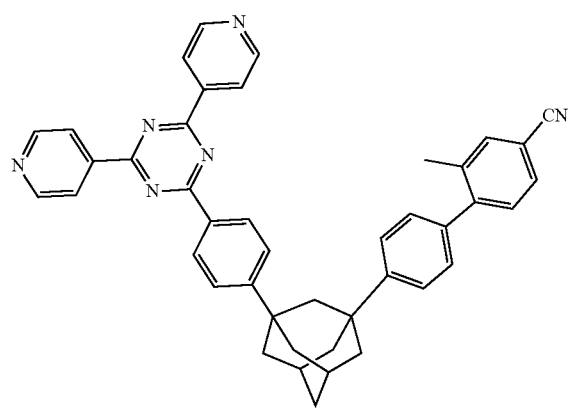

-continued
125
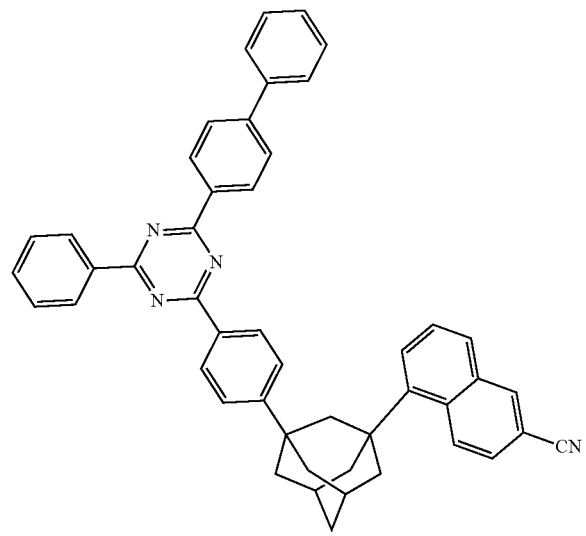
126
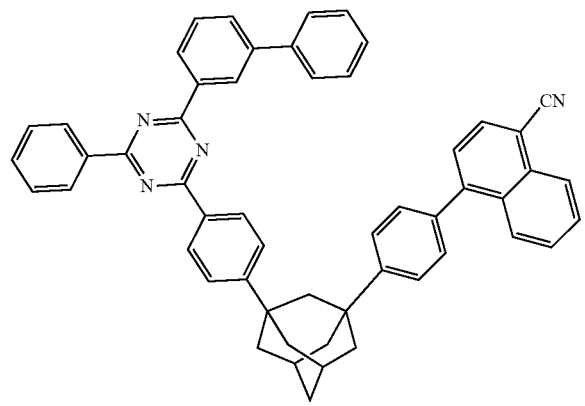
127
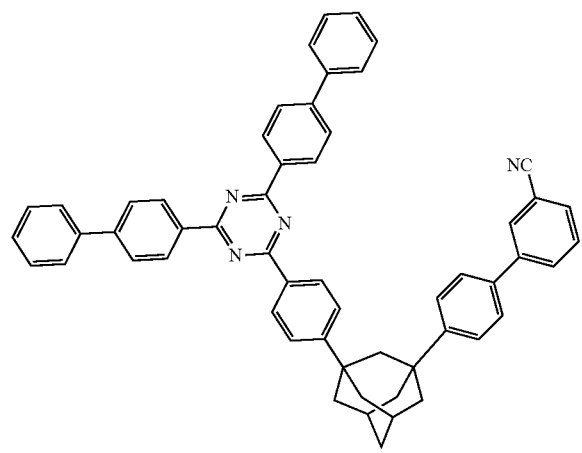
128
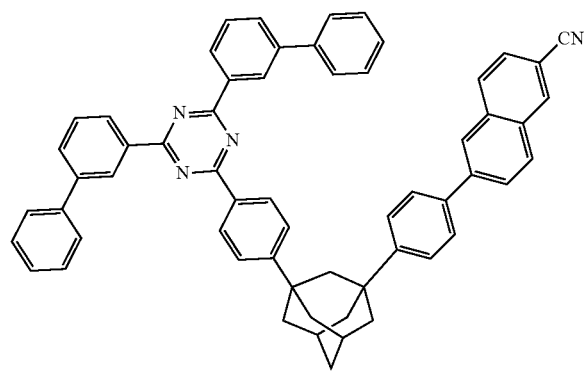
129
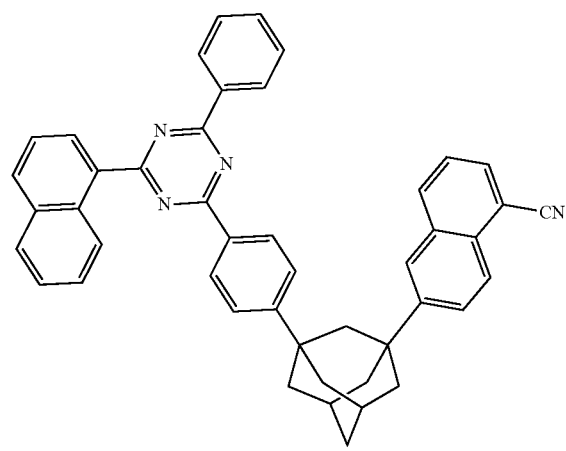
130
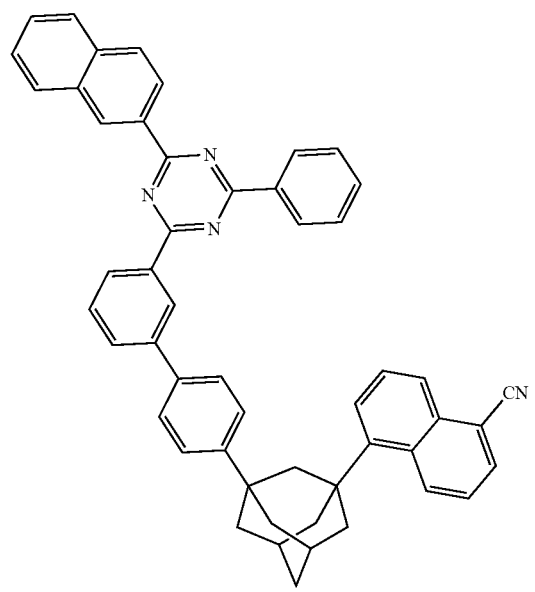

131
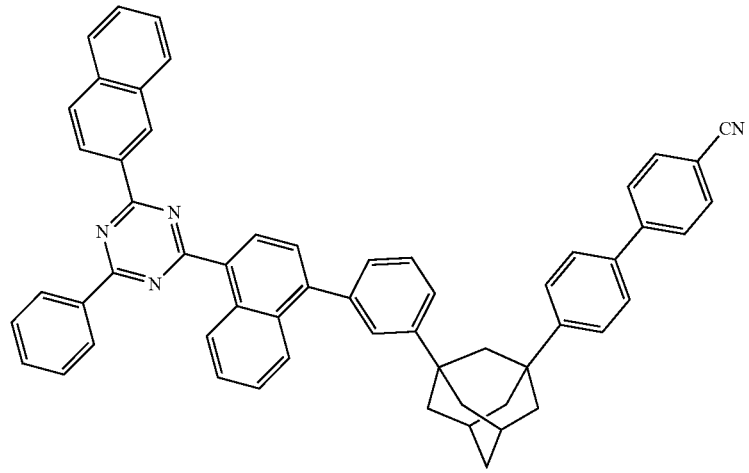
132
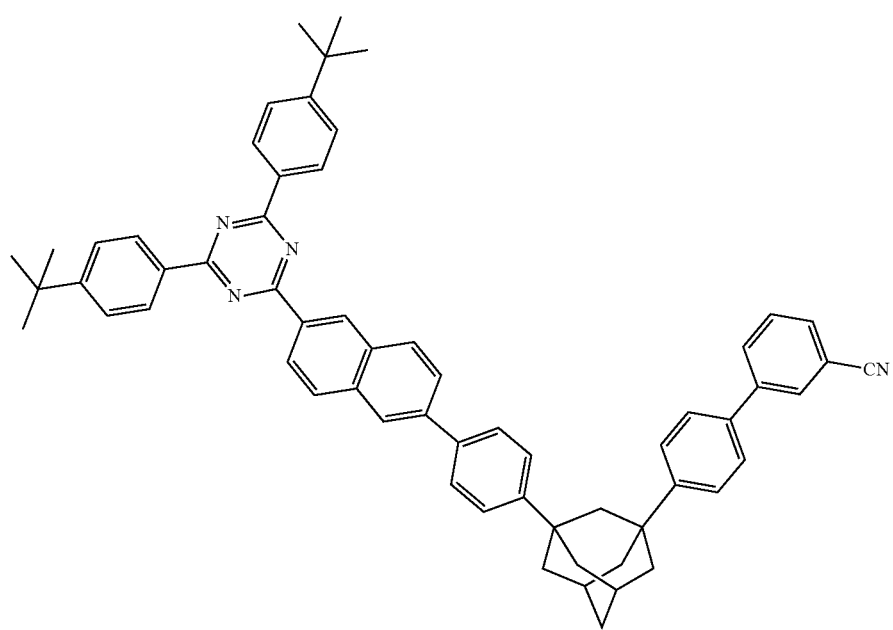

133
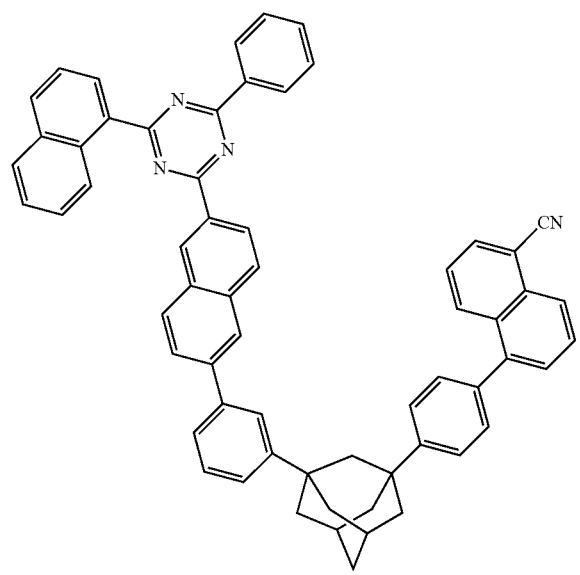
134
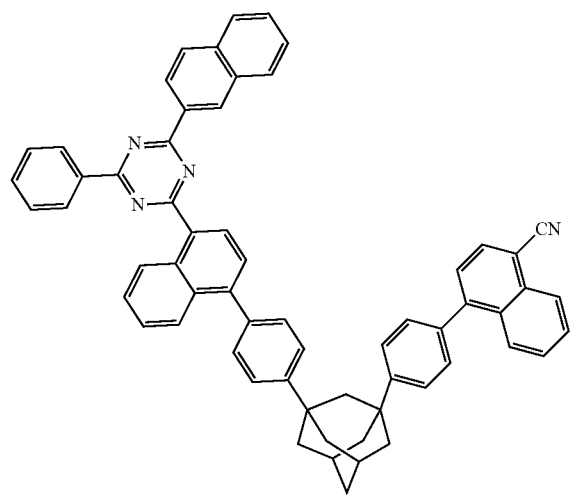
135
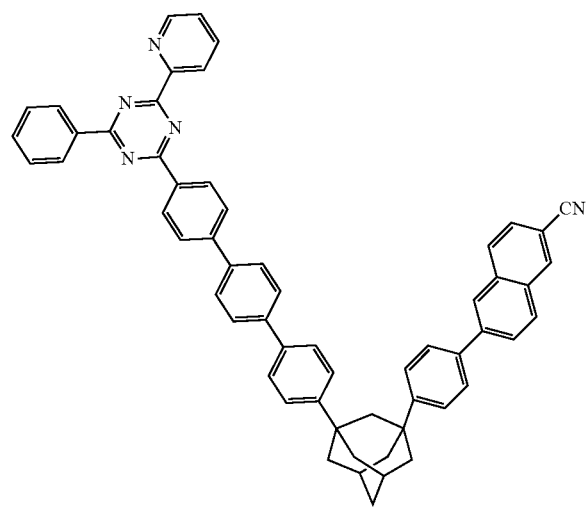
136
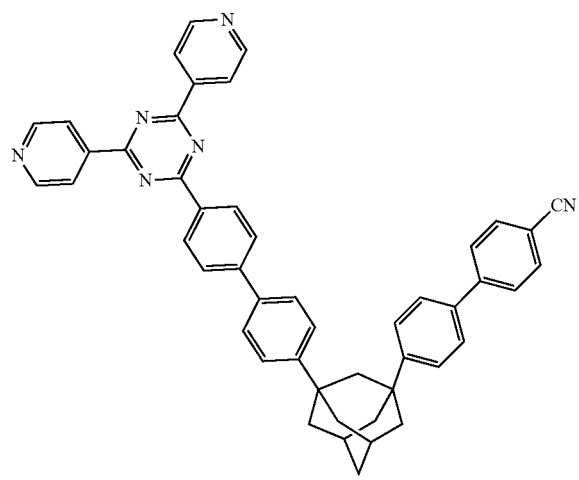

137
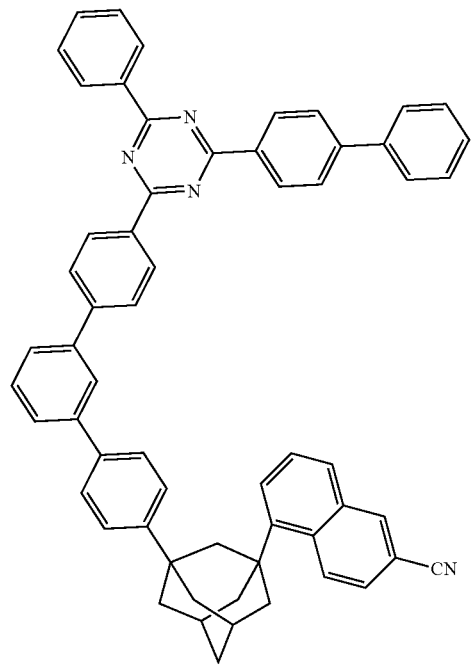
138
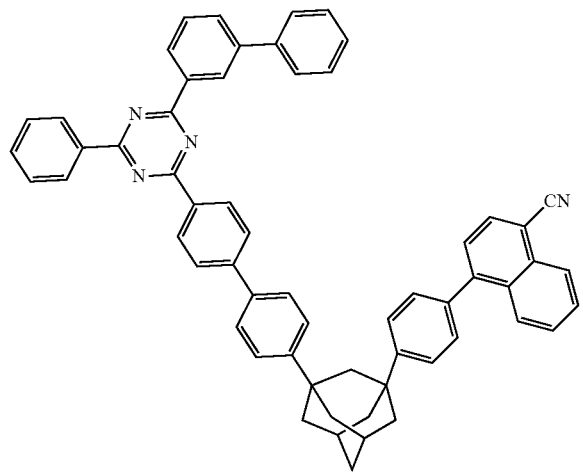
139
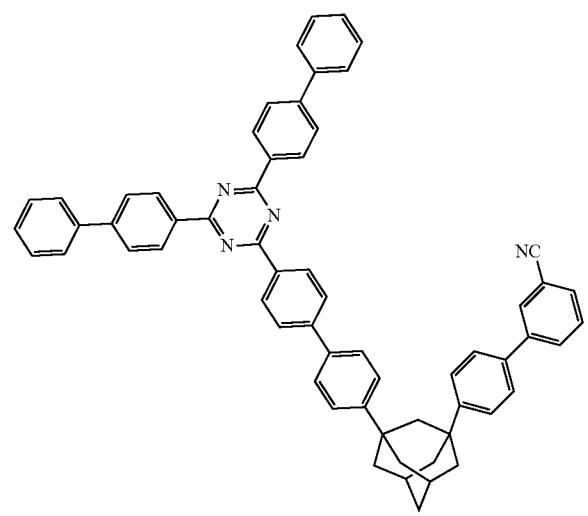
140
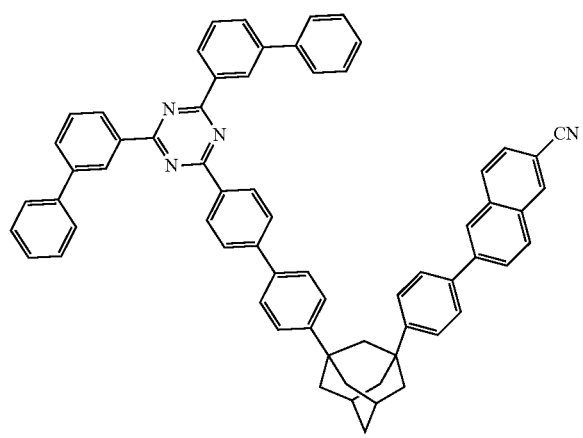

-continued
141
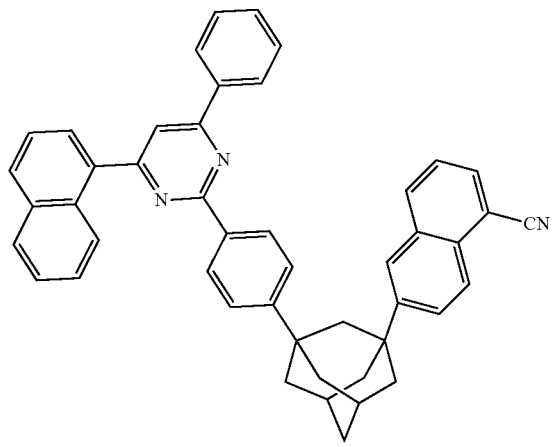
142
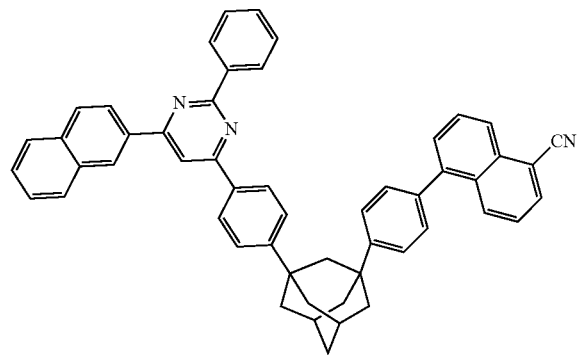
143
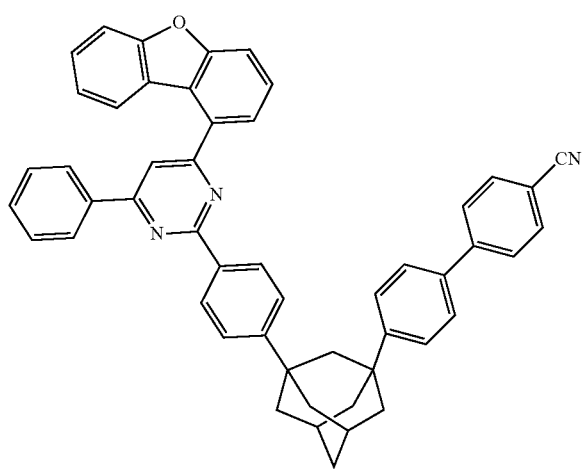
144
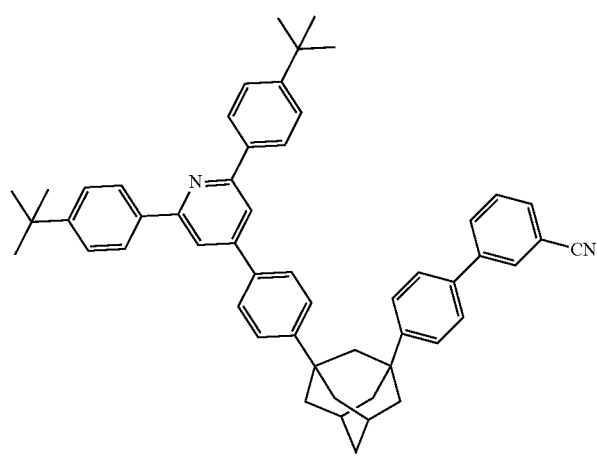
145
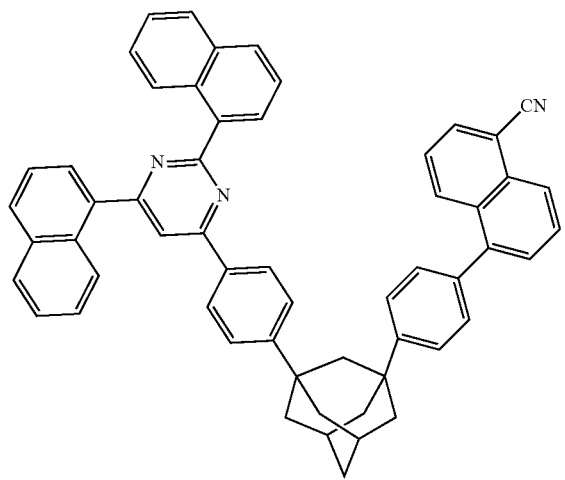
146
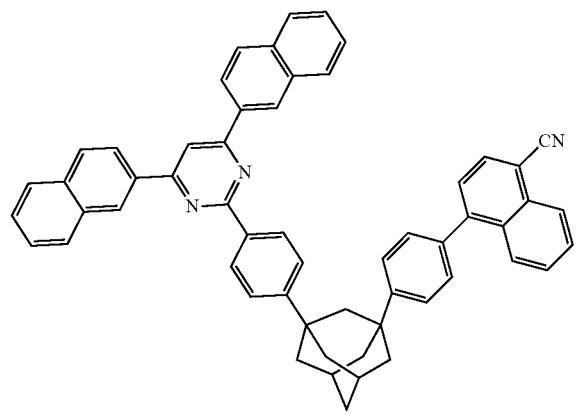

147
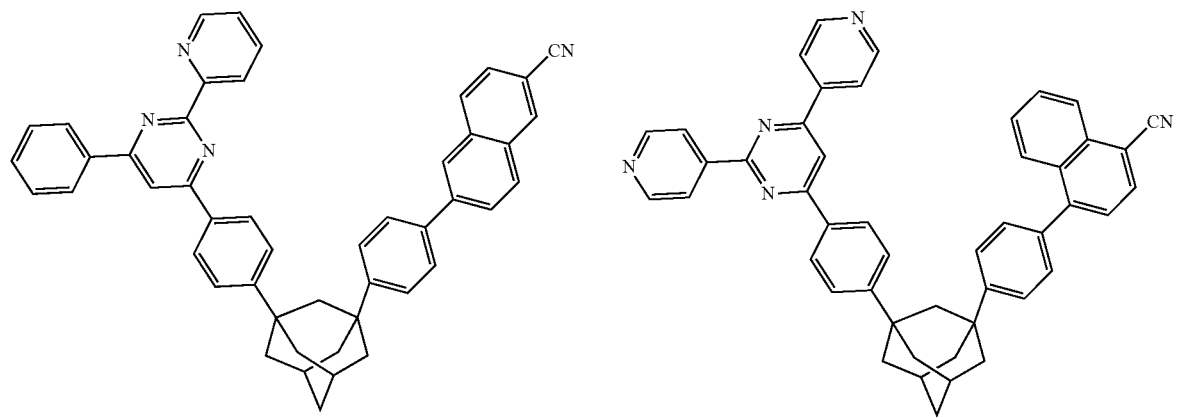
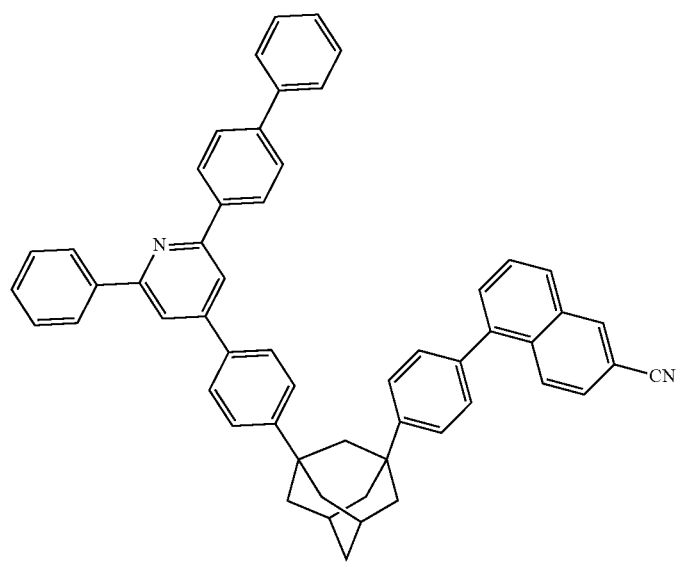
148
149
150
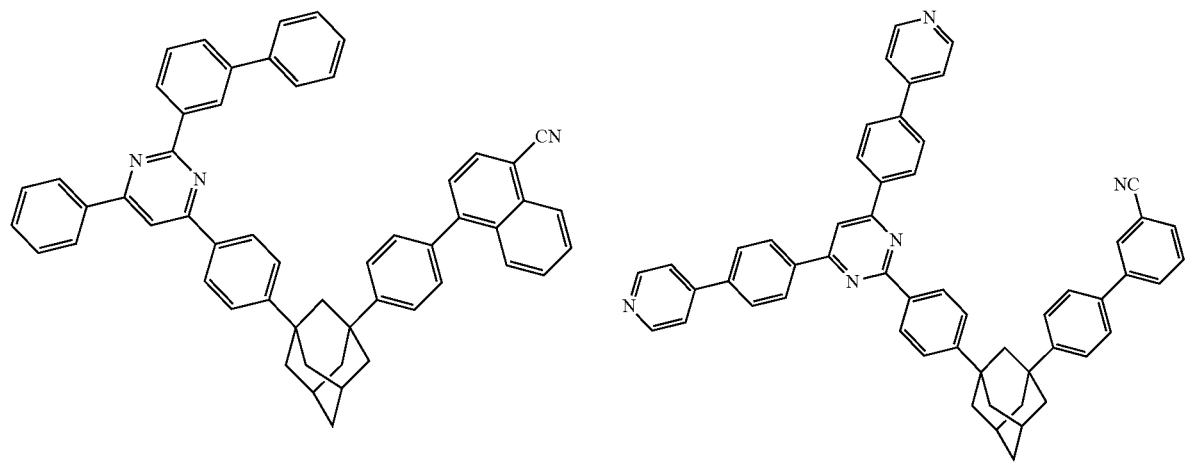
151

-continued
152
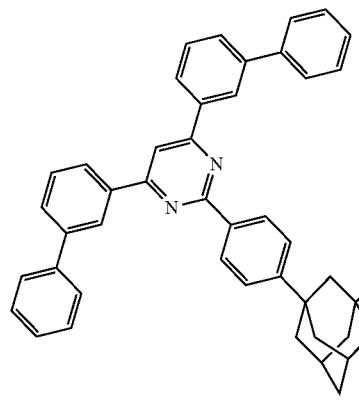
153
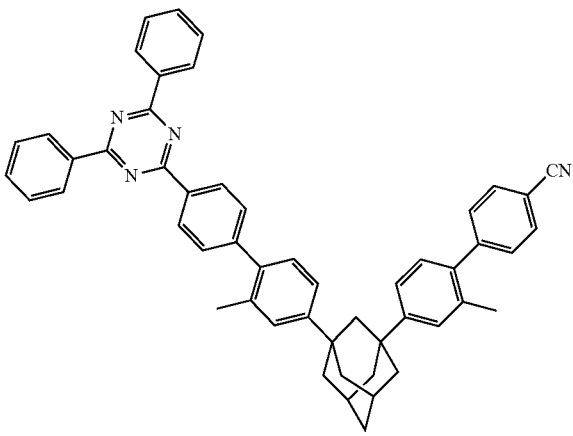
154
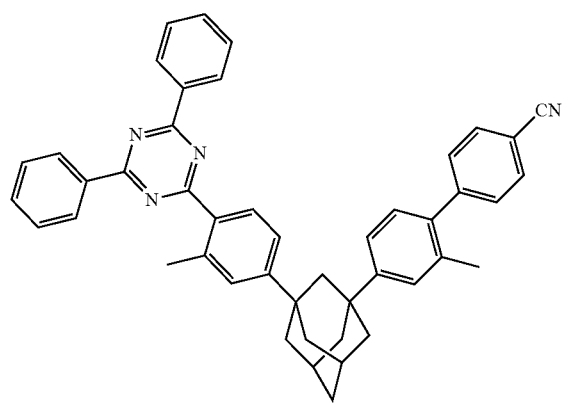
155
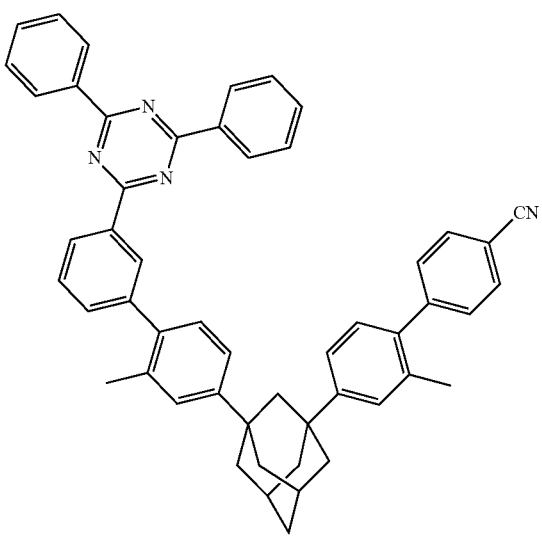
156
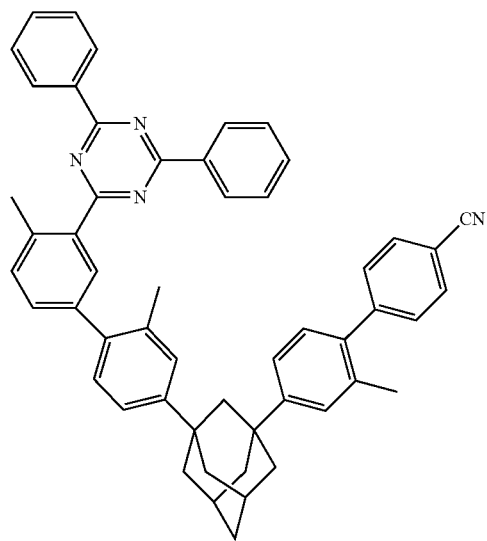
157
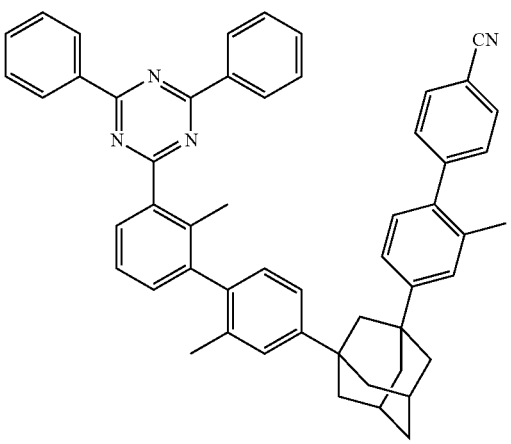

158 159
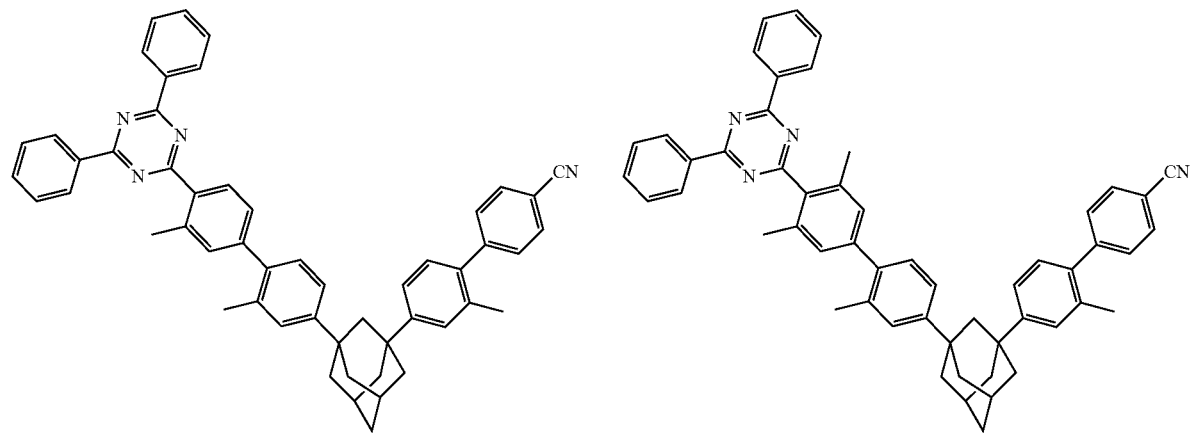
160 161
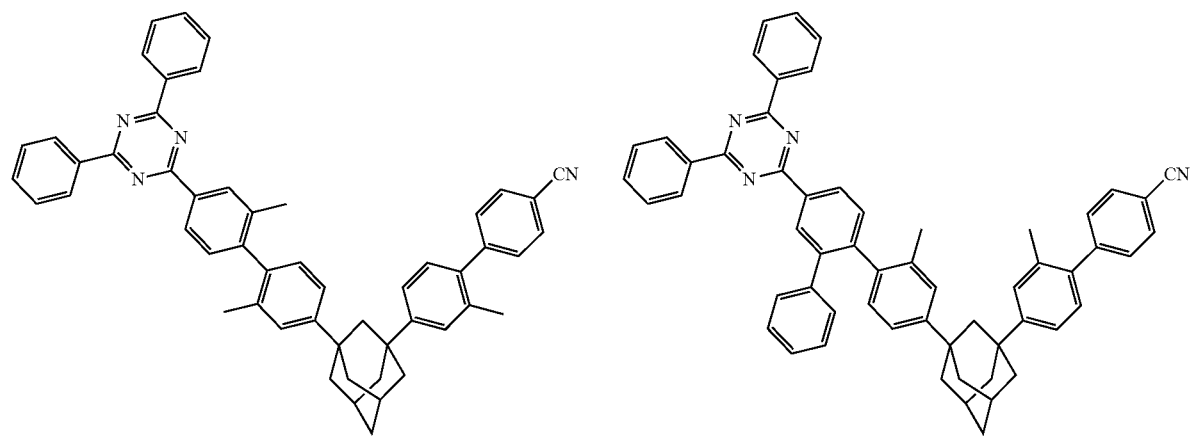
162 163
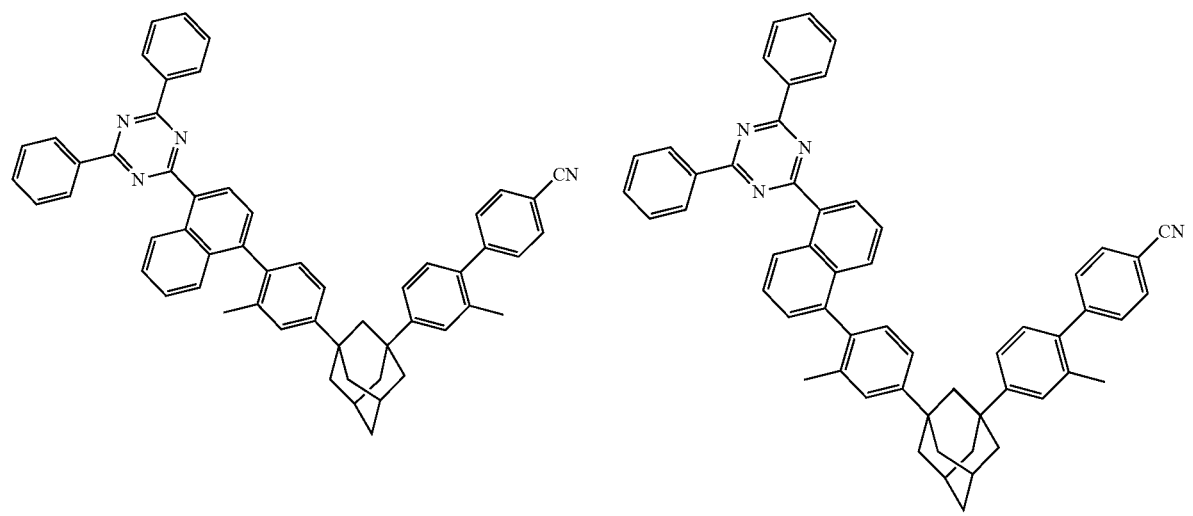

-continued
164
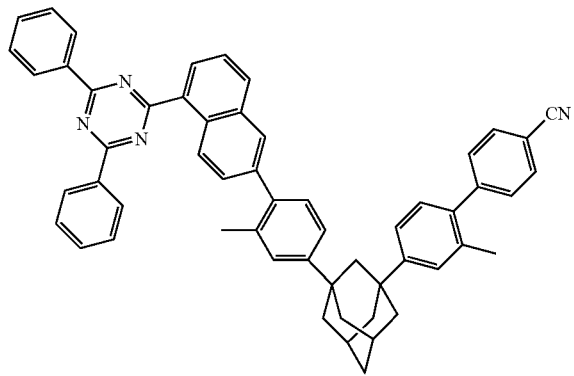
165
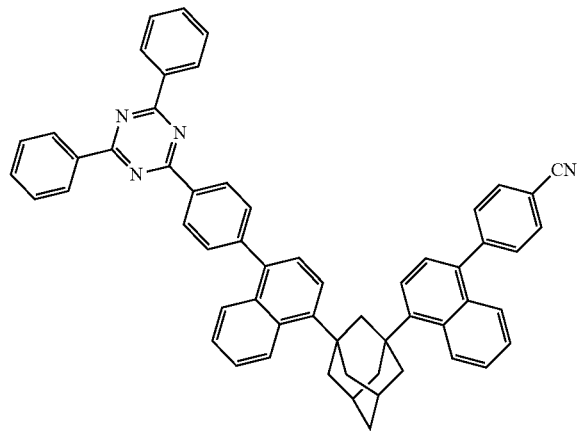
166
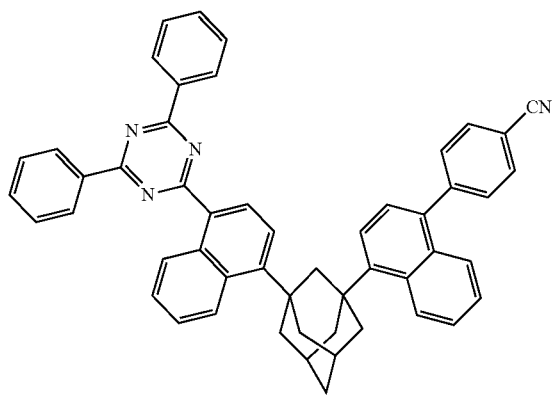
167
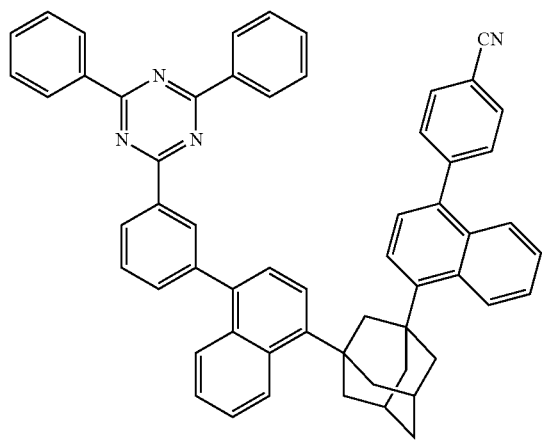
168
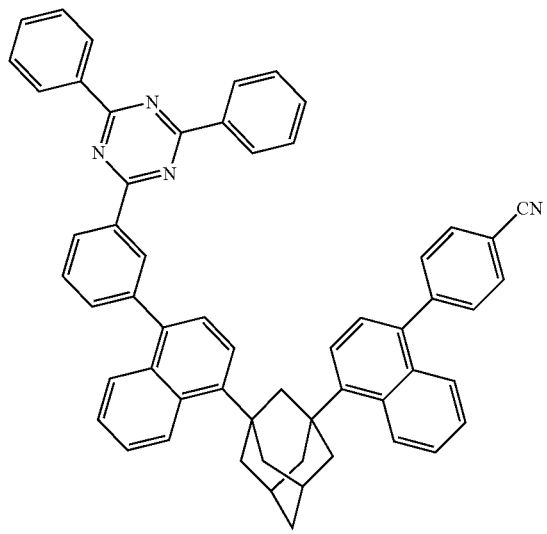
169
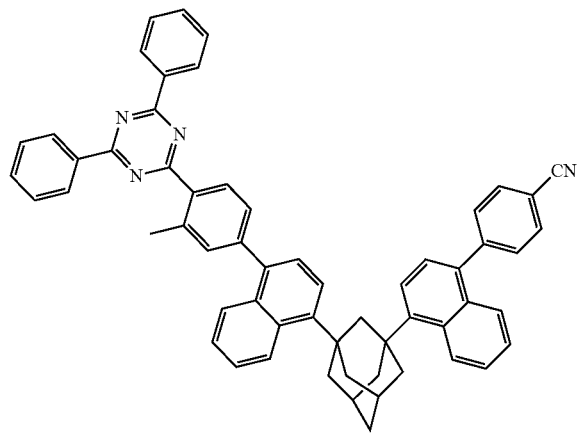

-continued
170
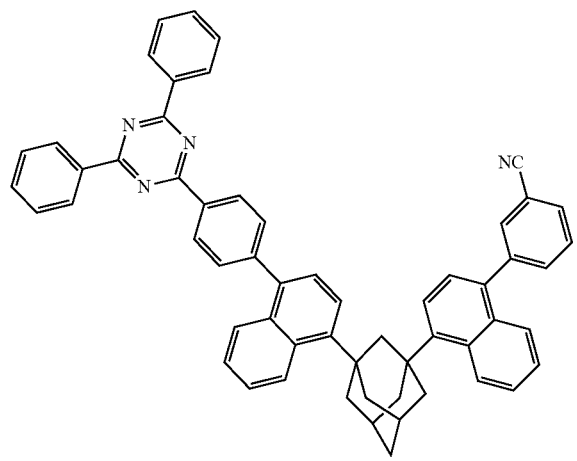
171
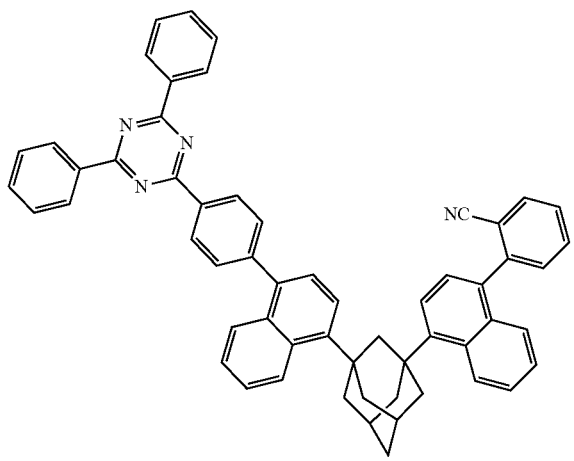
172
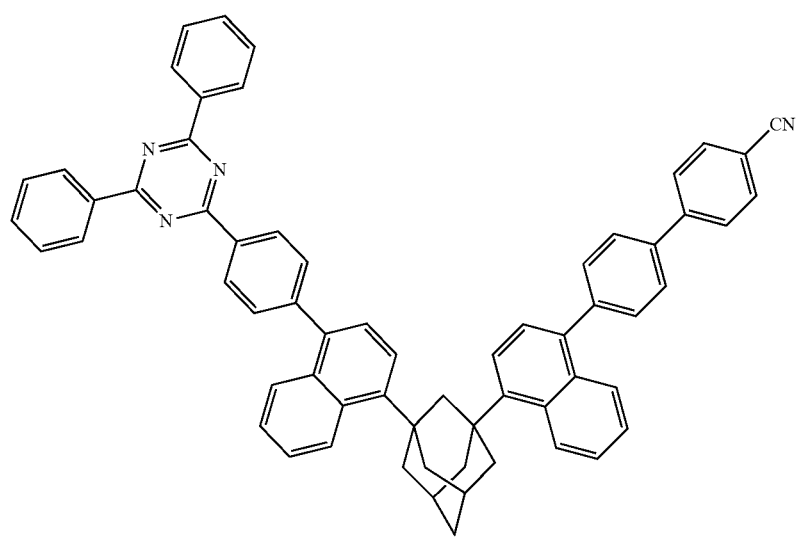
173
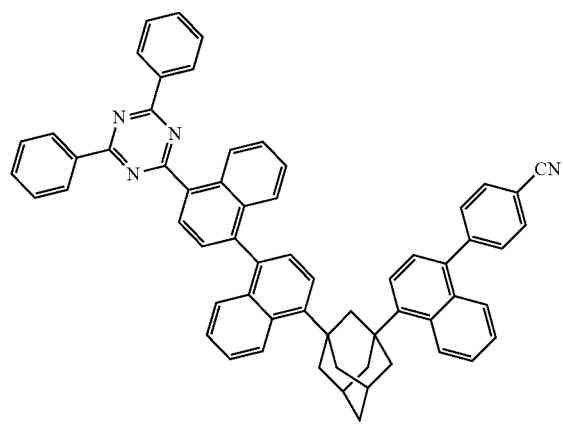
174
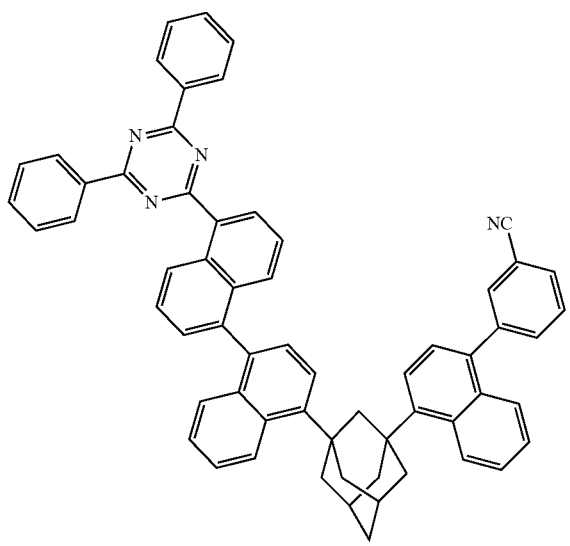

-continued
175
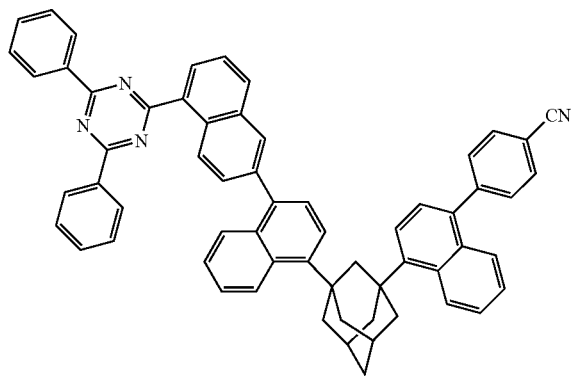
176
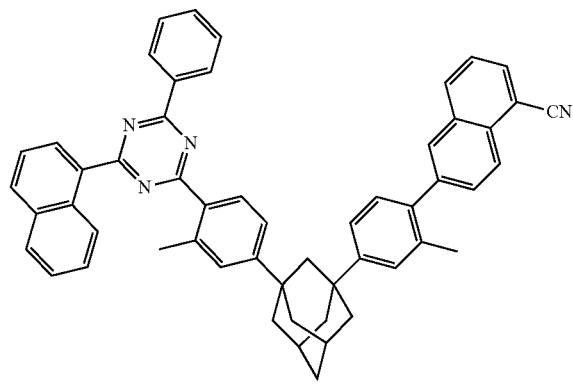
177
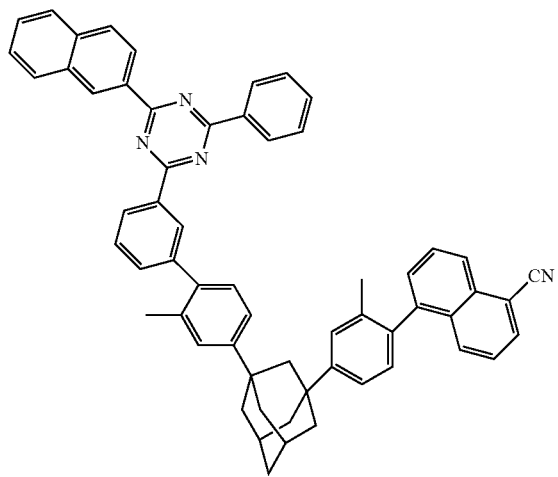
178
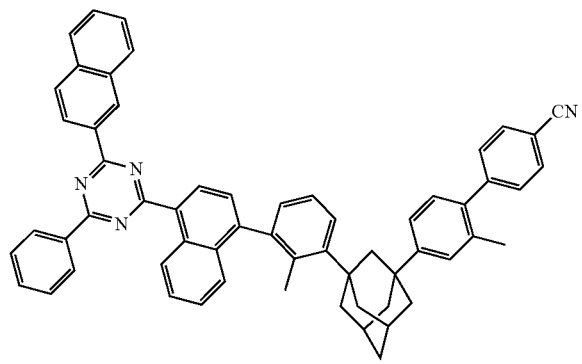
179
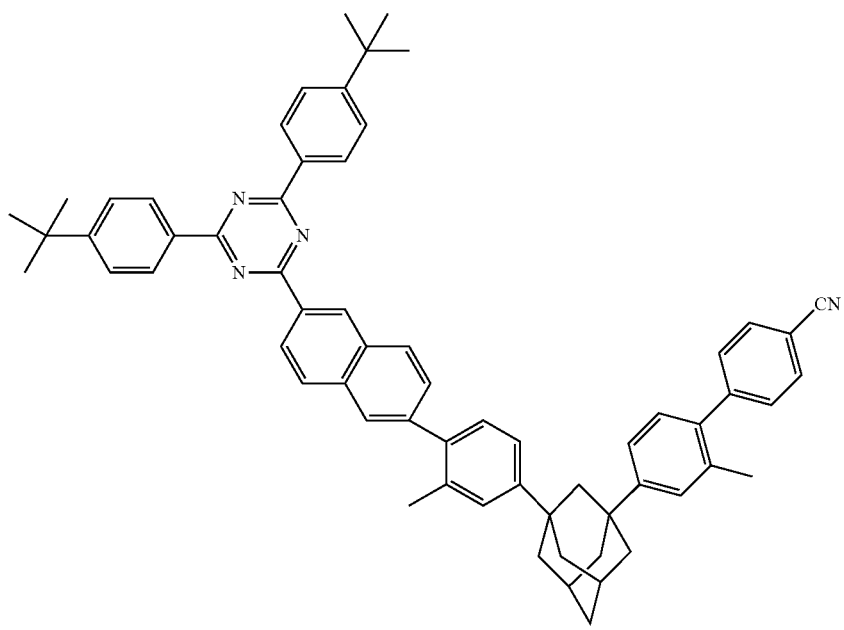

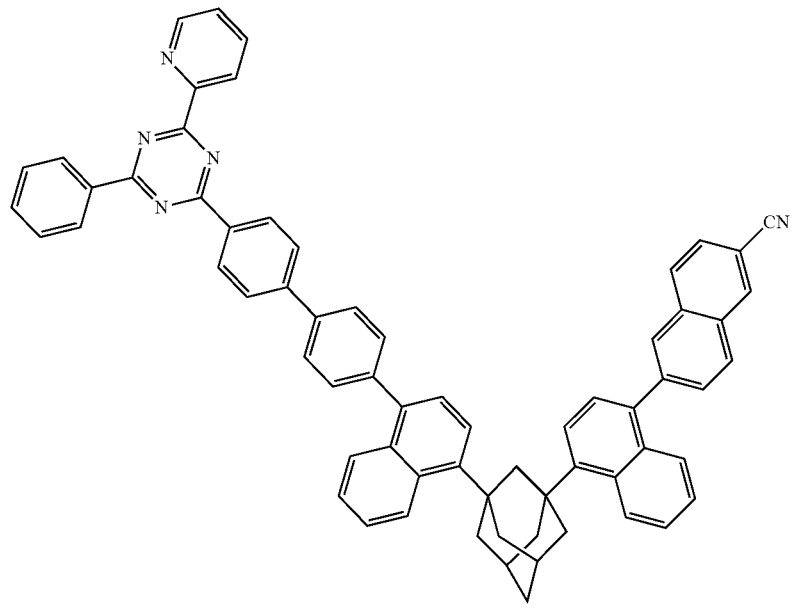
180
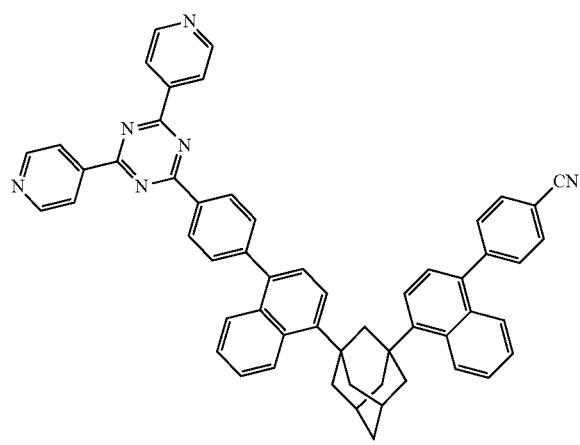
181
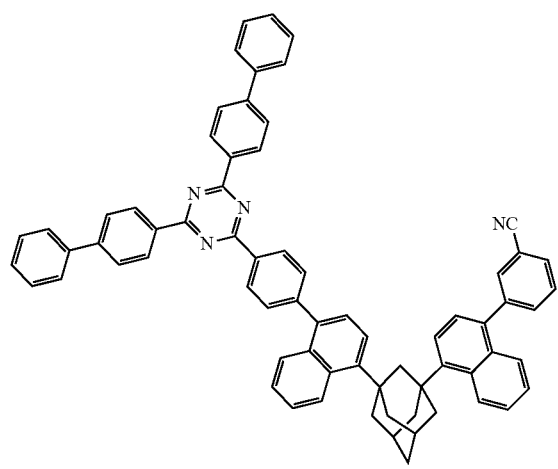
183
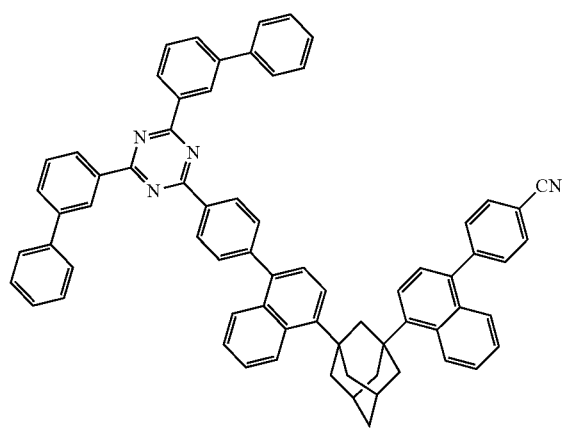
182
184

-continued
185
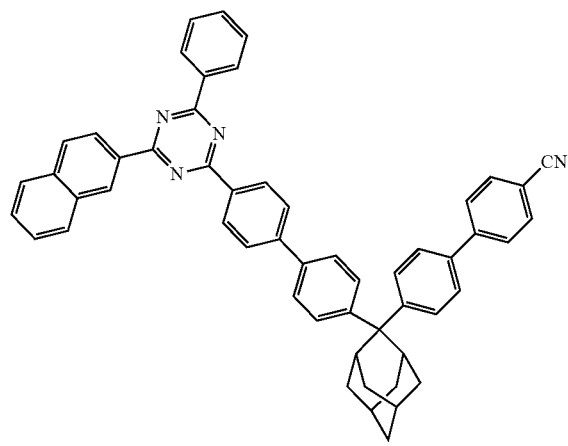
186
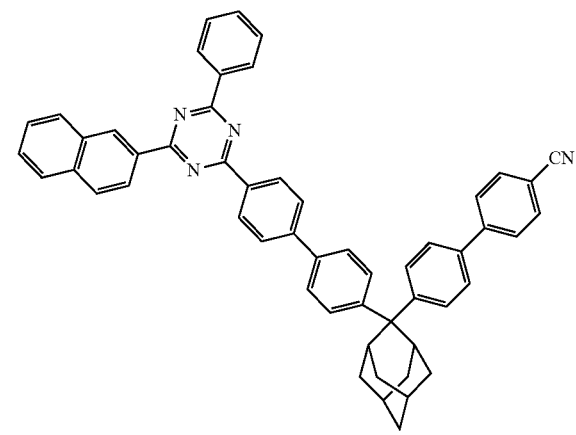
187
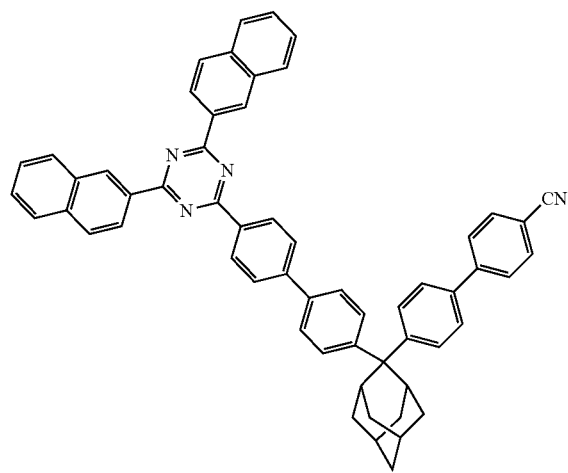
188
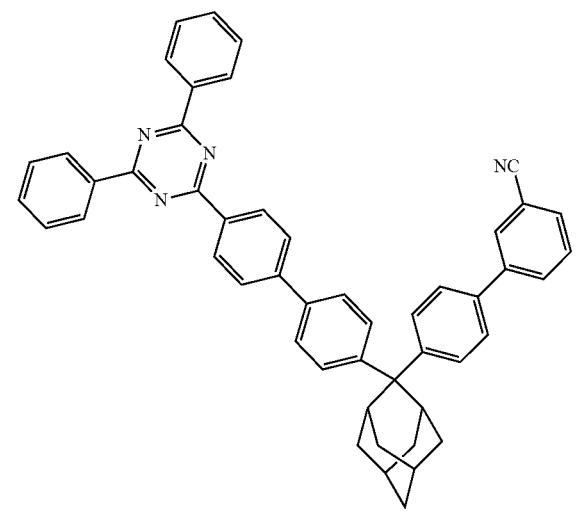
189
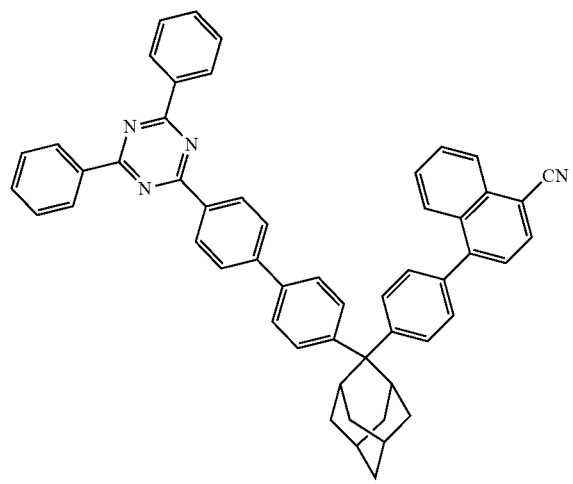
190
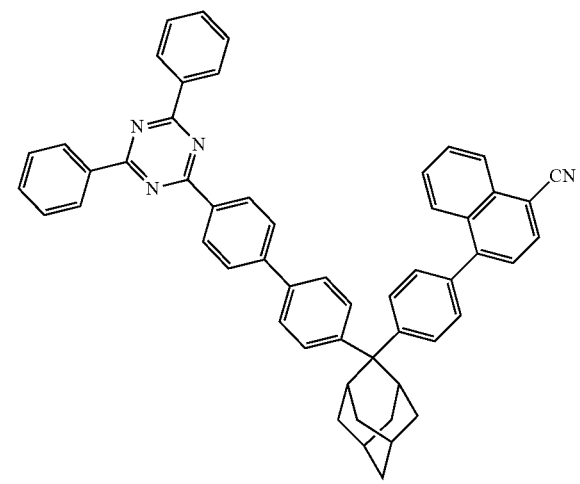

-continued
191
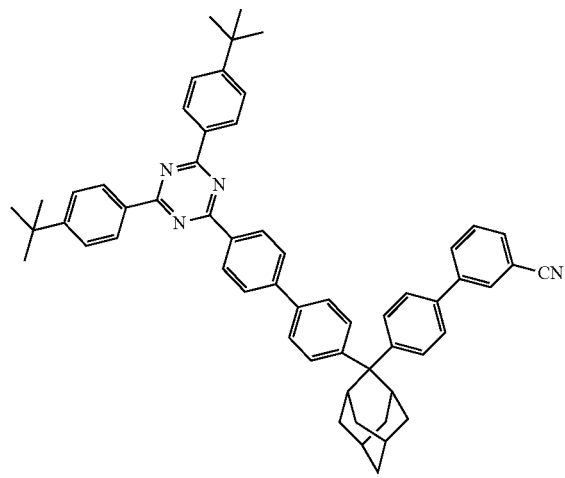
192
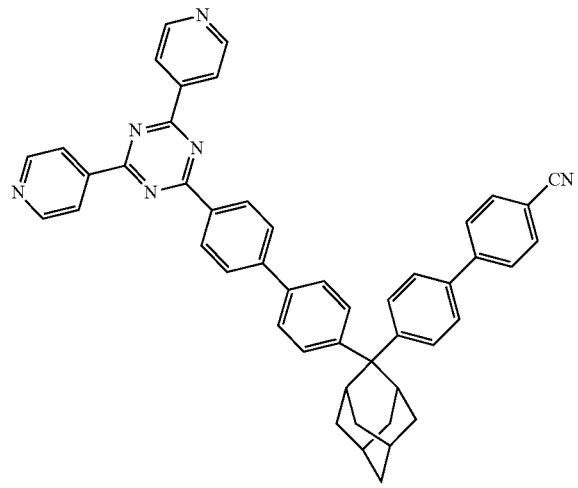
193
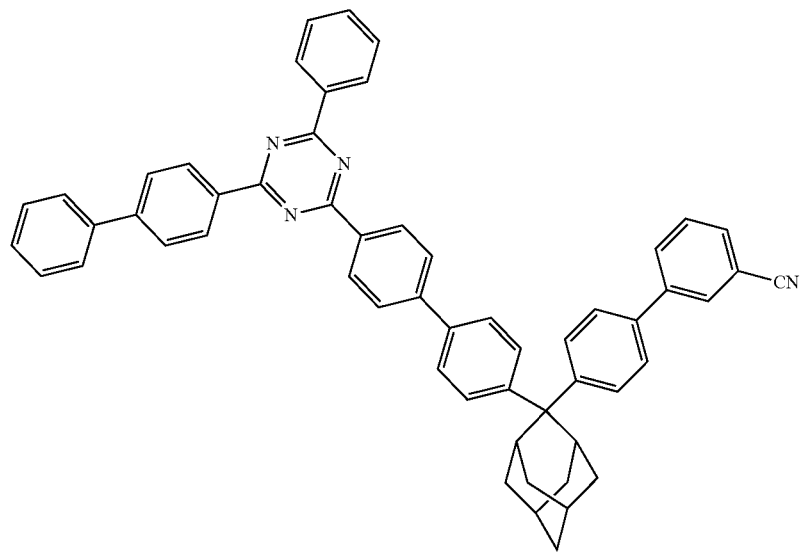
194
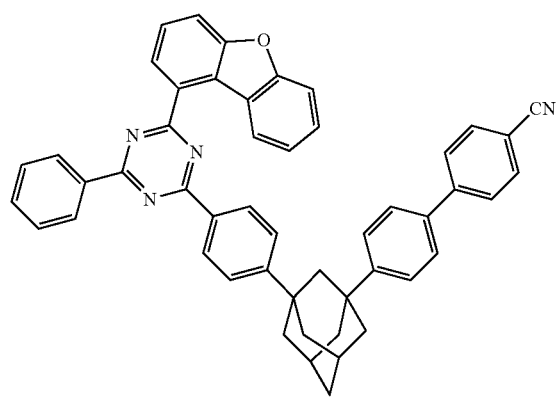
195
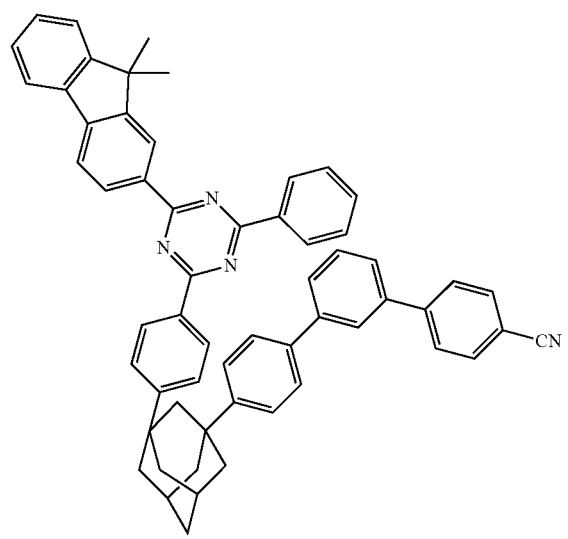

-continued
196
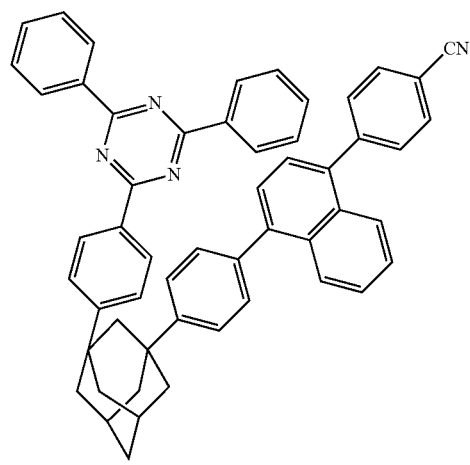
197
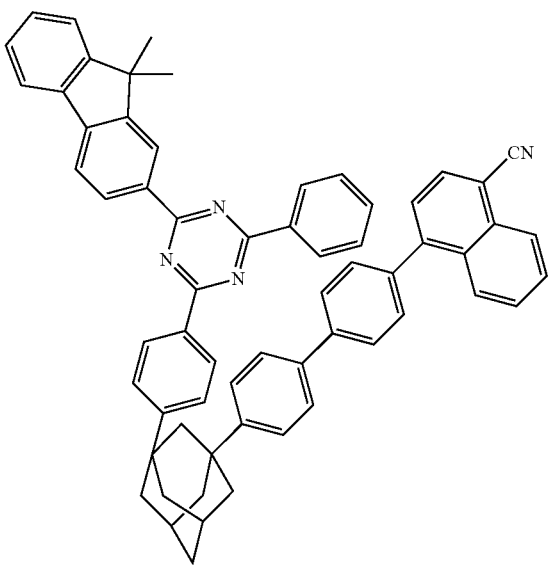
203
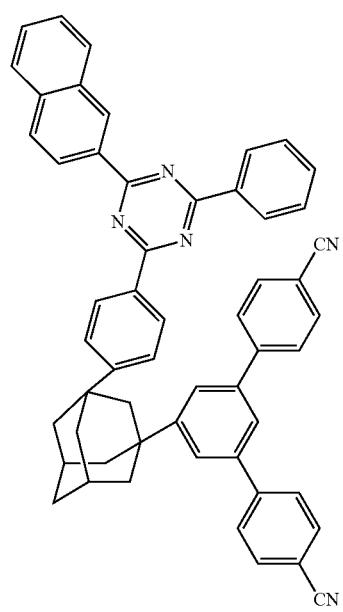
209
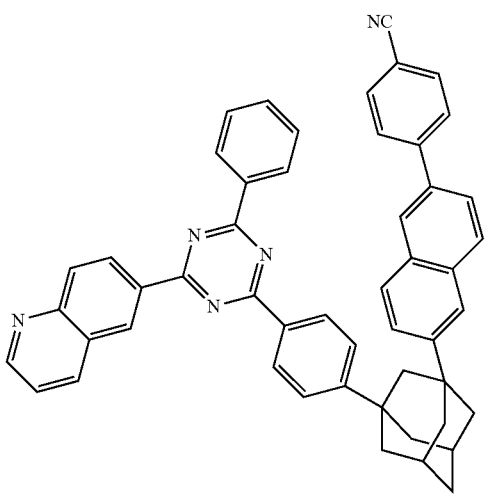

-continued
210
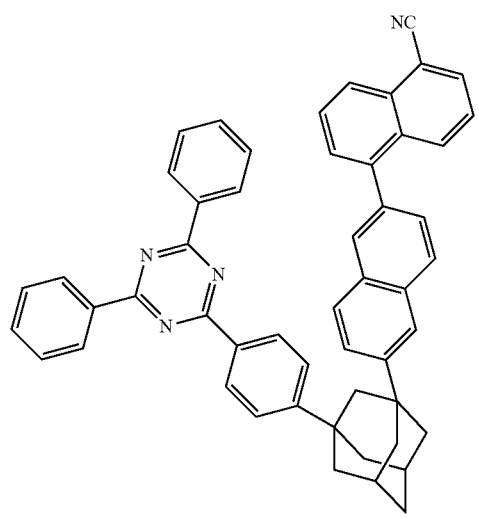
211
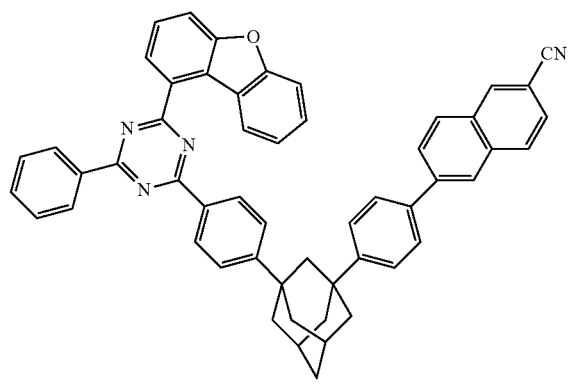
213
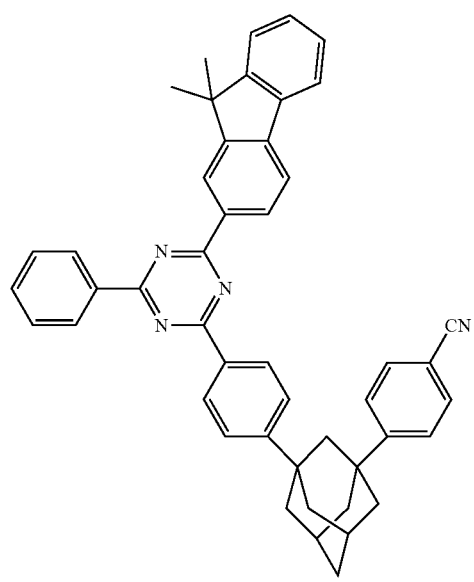
214
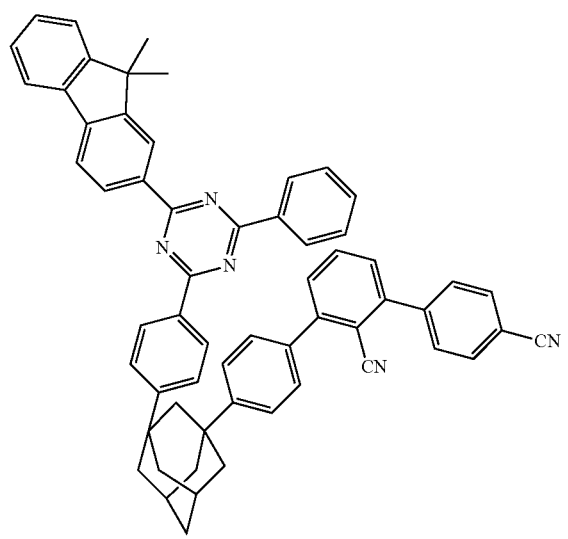

-continued
215
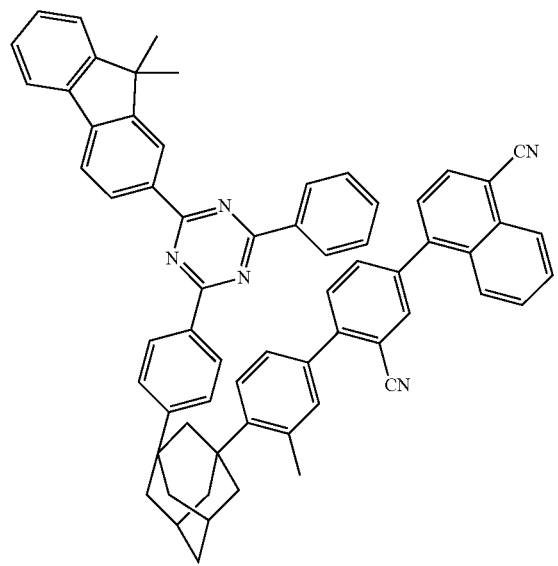
220
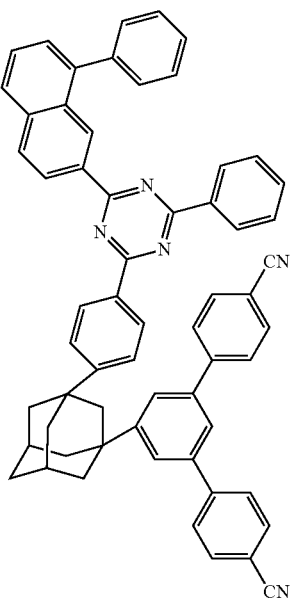
222
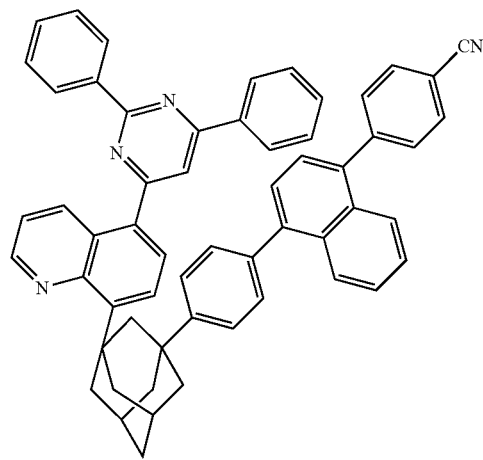
224
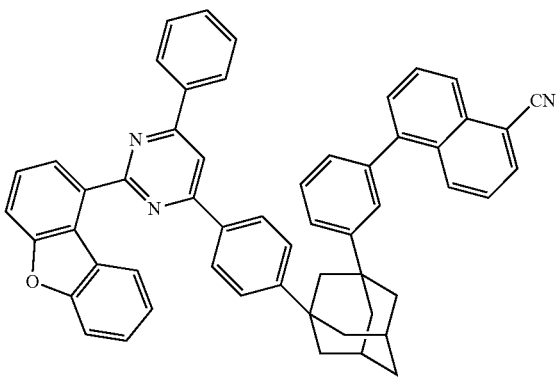

226
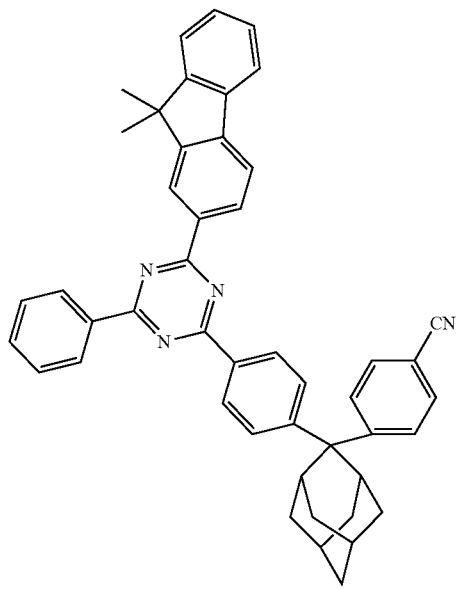
227
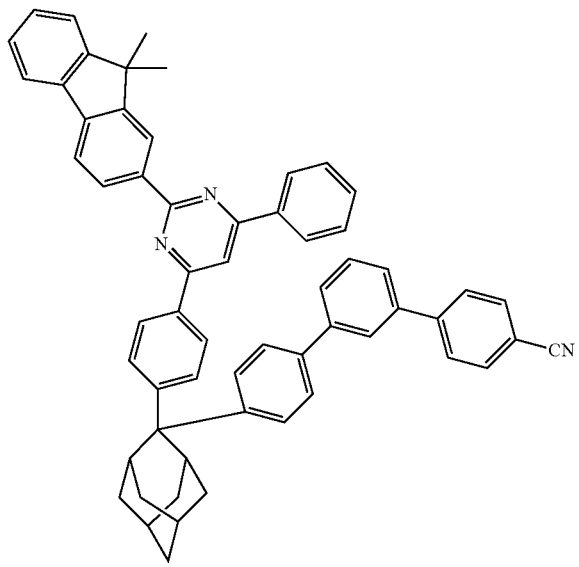
228
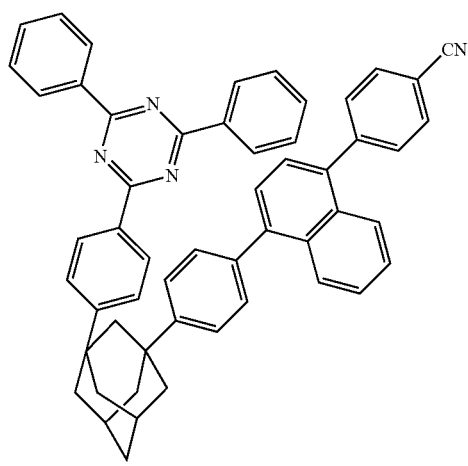
229
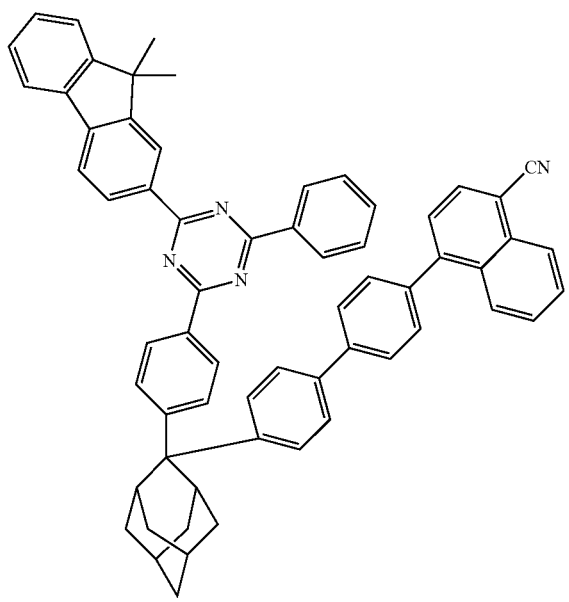

-continued
235
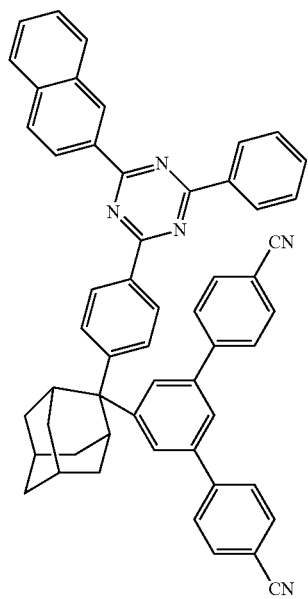
240
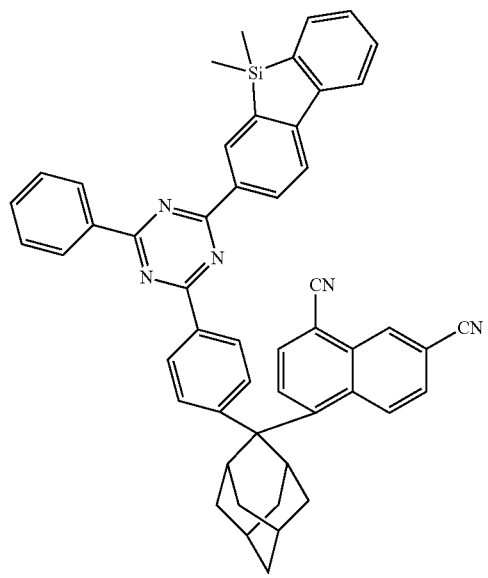
241
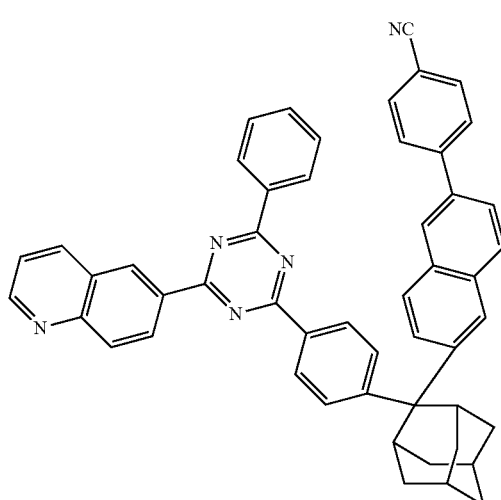
242
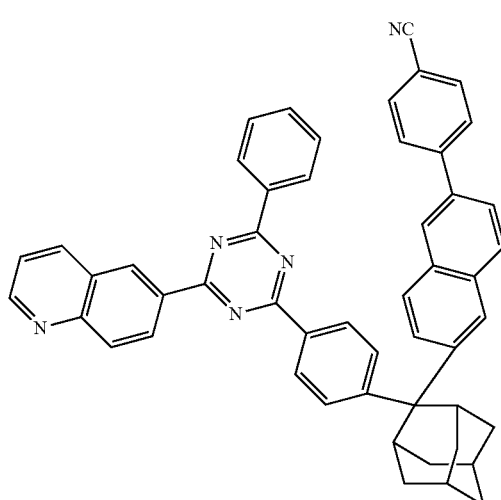
243
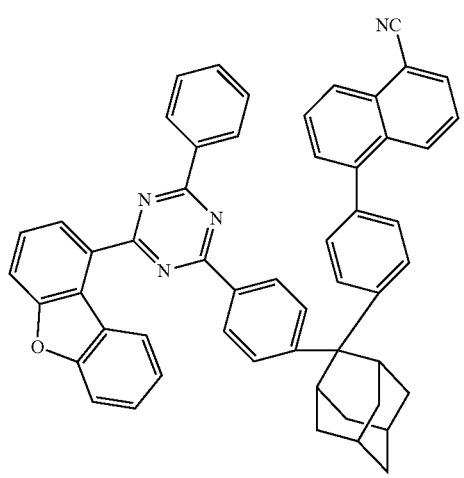
247
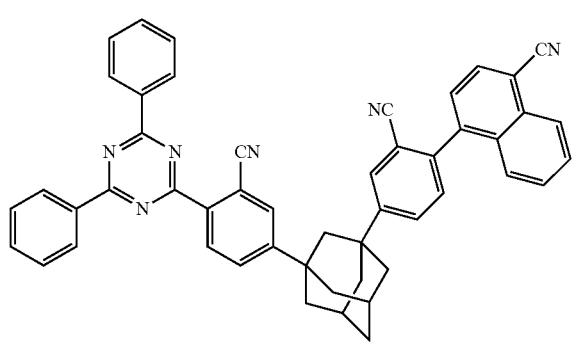

-continued
252
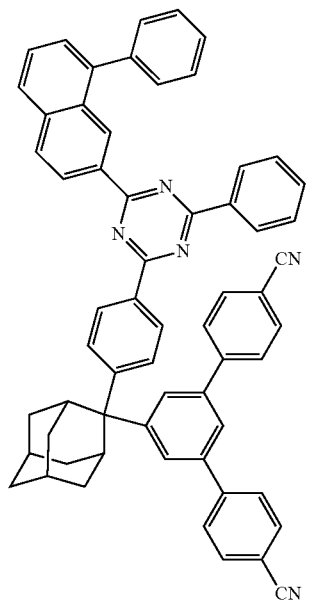
254
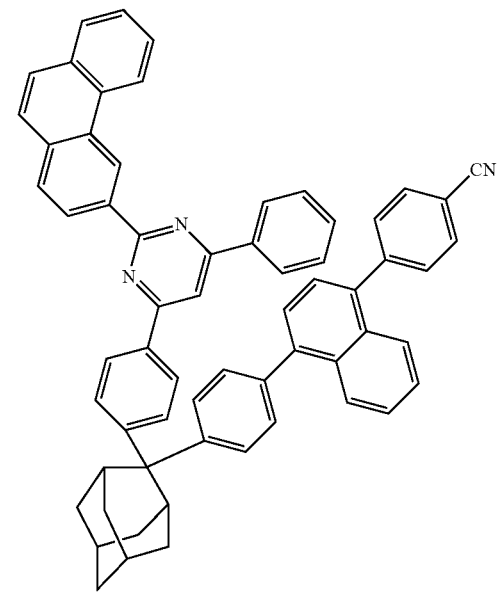
256
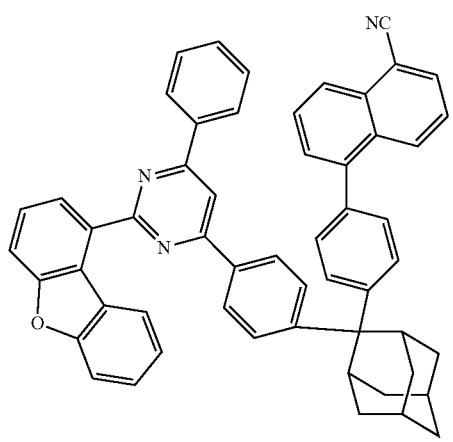
258
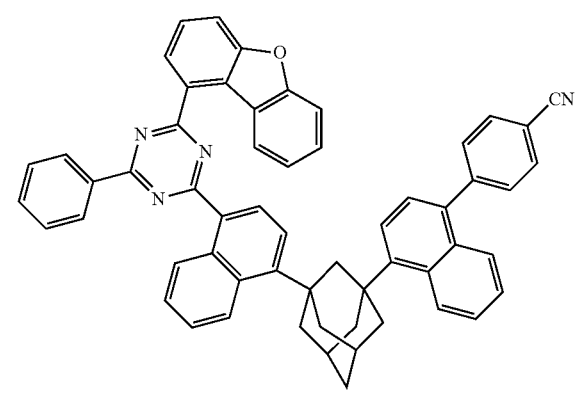
259
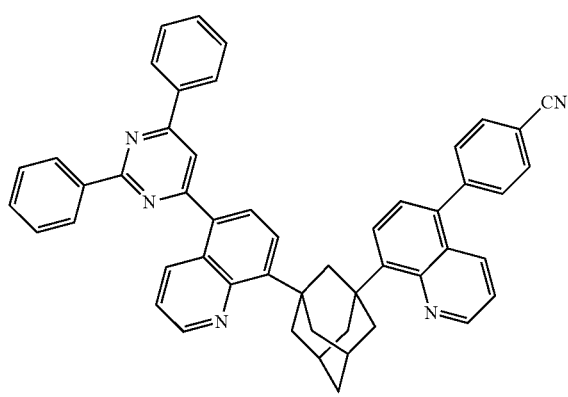
261
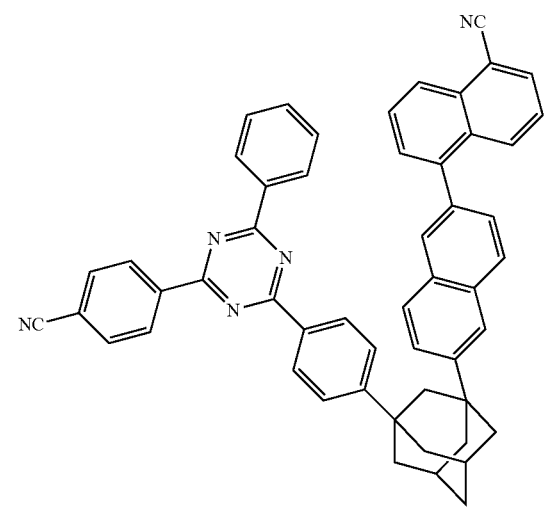

-continued
262
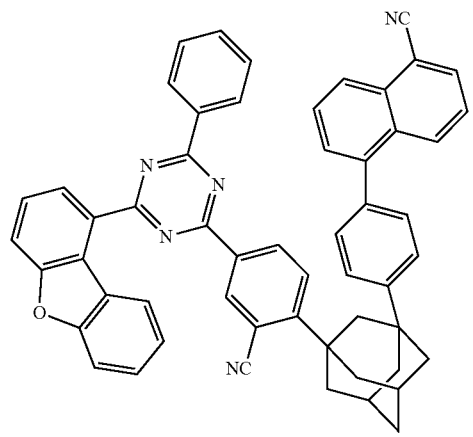
263
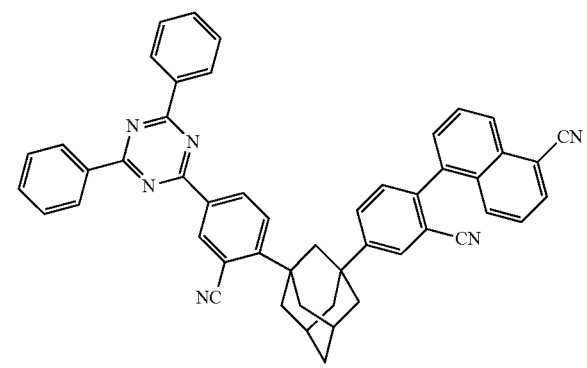
265
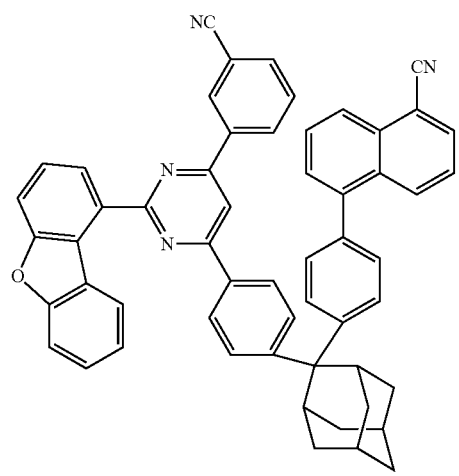
266
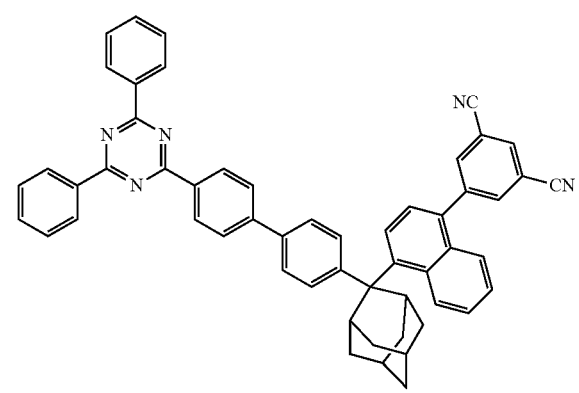
267
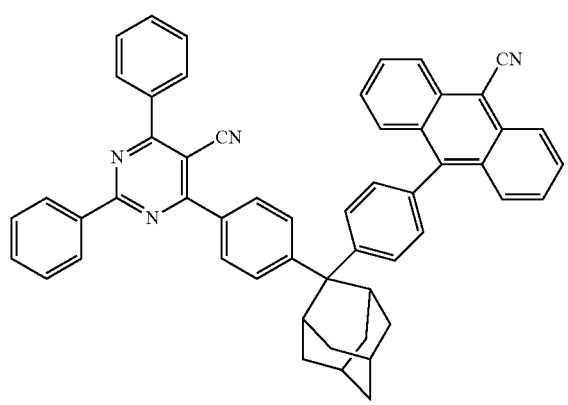
268
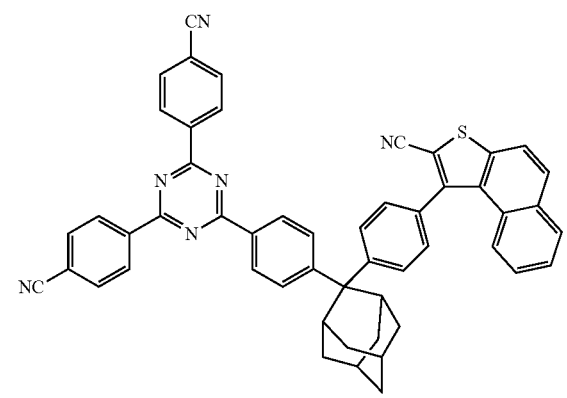

-continued
269
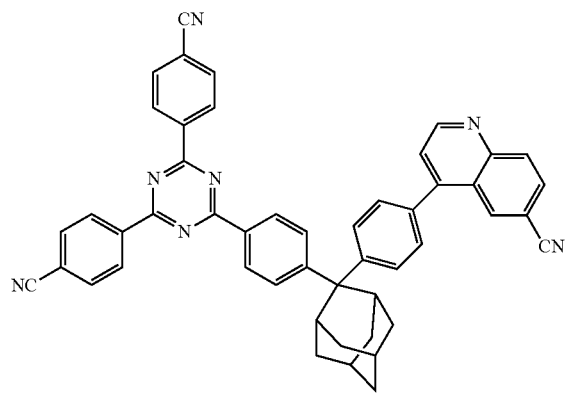
270
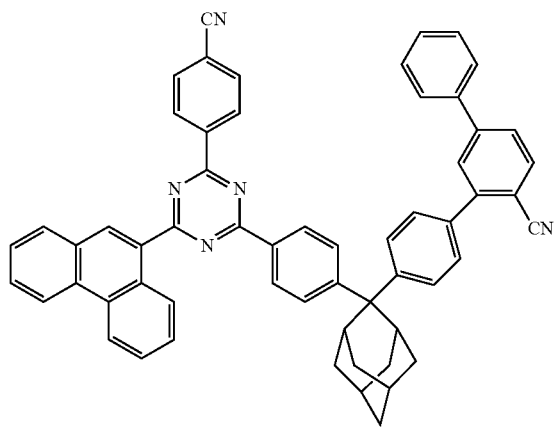
274
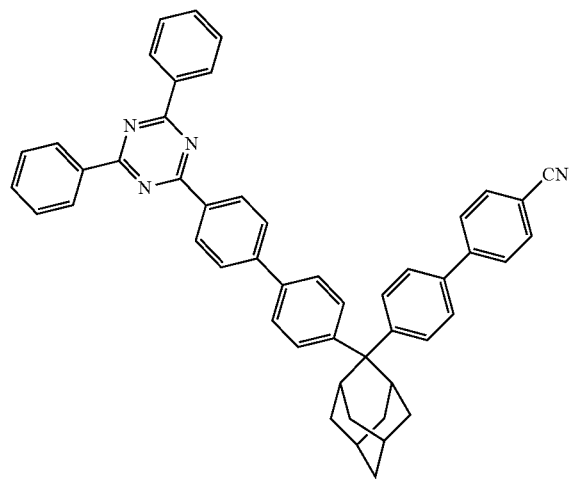
275
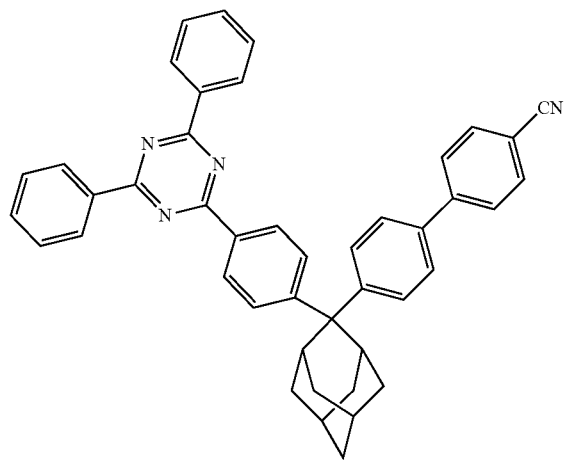
276
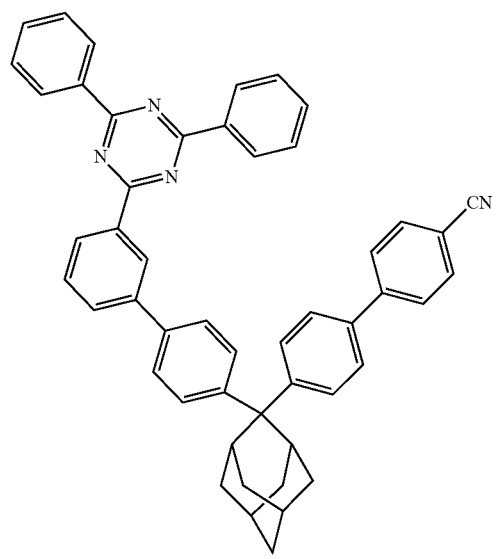
277
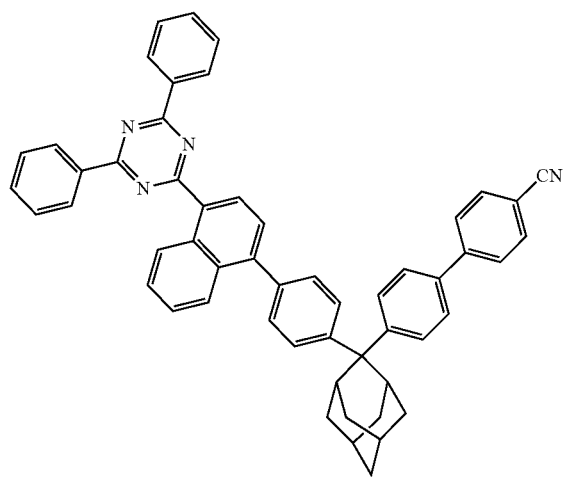

-continued

278
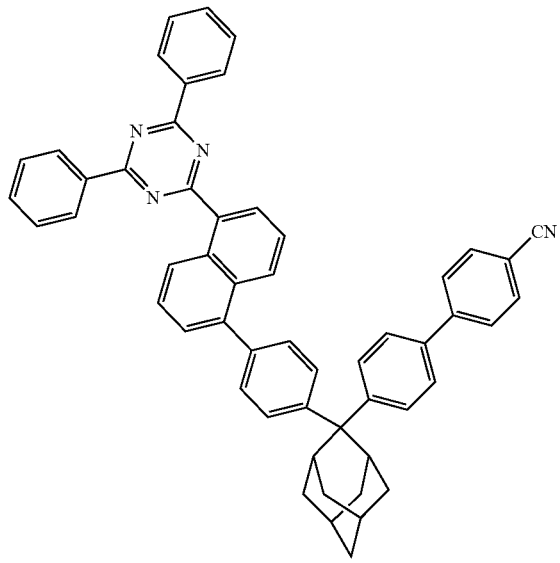

279
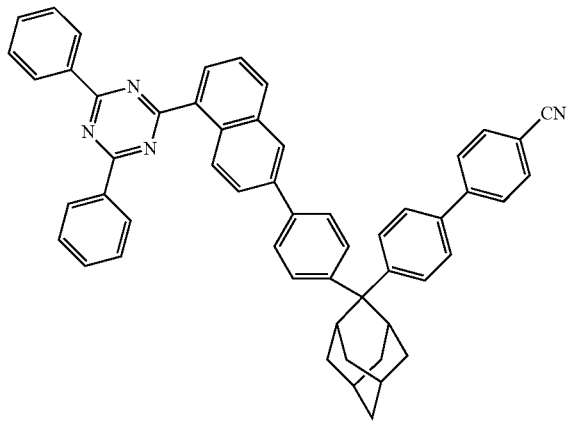

281
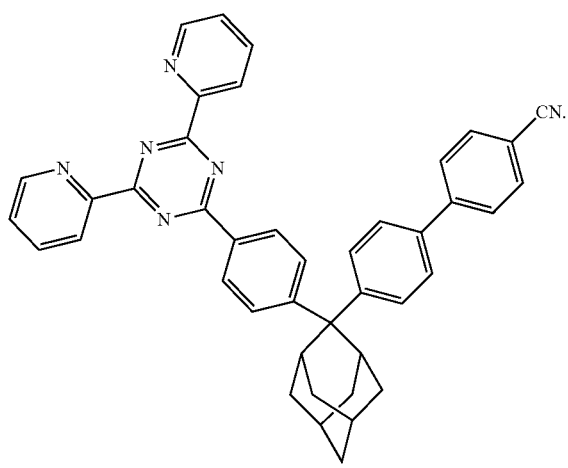

10. An electronic component, comprising an anode, a cathode disposed opposite the anode, and a functional layer disposed between the anode and the cathode;
  wherein the functional layer comprises the organic compound according to claim 1.

11. The electronic component according to claim 10, wherein the functional layer comprises an electron transport layer, and the electron transport layer comprises the organic compound.

12. An electronic apparatus, comprising the electronic component according to claim 10.

13. An electronic apparatus, comprising the electronic component according to claim 11.

* * * * *